US012806270B2

(12) United States Patent
Davila et al.

(10) Patent No.: US 12,806,270 B2
(45) Date of Patent: Nov. 24, 2026

(54) METHODS FOR TREATING CD83-EXPRESSING CANCER

(71) Applicants: H. Lee Moffitt Cancer Center and Research Institute, Inc., Tampa, FL (US); REGENTS OF THE UNIVERSITY OF MINNESOTA, Minneapolis, MN (US)

(72) Inventors: Marco L Davila, Tampa, FL (US); Brian Betts, Blaine, MN (US)

(73) Assignees: H. Lee Moffitt Cancer Center and Research Institute, Inc., Tampa, FL (US); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 463 days.

(21) Appl. No.: 18/547,748

(22) PCT Filed: Feb. 4, 2022

(86) PCT No.: PCT/US2022/070539

§ 371 (c)(1),
(2) Date: Aug. 24, 2023

(87) PCT Pub. No.: WO2022/183160

PCT Pub. Date: Sep. 1, 2022

(65) Prior Publication Data

US 2024/0173411 A1 May 30, 2024

Related U.S. Application Data

(60) Provisional application No. 63/234,366, filed on Aug. 18, 2021, provisional application No. 63/153,481, filed on Feb. 25, 2021.

(51) Int. Cl.

| | |
|---|---|
| ***A61K 40/15*** | (2025.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 16/28*** | (2006.01) |

(52) U.S. Cl.

CPC ........ *A61K 40/421* (2025.01); *A61K 39/3955* (2013.01); *A61K 40/11* (2025.01); *A61K 40/15* (2025.01); *A61K 40/31* (2025.01); *A61K 40/4202* (2025.01); *A61K 40/4211* (2025.01); *A61K 40/4215* (2025.01); *A61K 40/4222* (2025.01); *A61K 40/4224* (2025.01); *C07K 16/2803* (2013.01); *A61K 2239/29* (2023.05); *A61K 2239/48* (2023.05); *C07K 2317/622* (2013.01)

(58) Field of Classification Search

None

See application file for complete search history.

(56) References Cited

U.S. PATENT DOCUMENTS

| | | | | |
|---|---|---|---|---|
| 12,492,254 | B2 * | 12/2025 | Davila ................. | C07K 14/705 |
| 2018/0230225 | A1 | 8/2018 | Fan et al. | |
| 2020/0246382 | A1 | 8/2020 | Perez et al. | |
| 2020/0281973 | A1 | 9/2020 | Dranoff | |
| 2020/0360431 | A1 | 11/2020 | Garfall et al. | |
| 2023/0051885 | A1 * | 2/2023 | Davila ............... | C07K 16/2803 |

FOREIGN PATENT DOCUMENTS

| | | | | |
|---|---|---|---|---|
| WO | 2014/184143 | A1 | 11/2014 | |
| WO | 2015/039523 | A1 | 3/2015 | |
| WO | 2016/168773 | A2 | 10/2016 | |
| WO | WO-2019165156 | A1 * | 8/2019 | ....... C07K 14/70503 |
| WO | 2019/220110 | A1 | 11/2019 | |
| WO | 2020/135426 | A1 | 7/2020 | |
| WO | 2020/232447 | A1 | 11/2020 | |

OTHER PUBLICATIONS

Shrestha et al (Blood, 2019, 134 (Supplement_1): 196).*
Shrestha et al (J. Clinical Invest., 2020, 130:4652-4662).*
Bejcek, Bruce E., et al., "Development and Characterization of Three Recombinant Single Chain Antibody Fragments (scFvs) Directed against the CD19 Antigen," Cancer Research, vol. 55 (1995), pp. 2346-2351.
Fresnak, Andrew D., et al., "Engineered T cells: the promise and challenges of cancer immunotherapy," Nature, vol. 16 (2016), pp. 566-581.
Nicholson, Ian C., et al., "Construction and Characterisation of a Functional CD19 Specific Single Chain Fv Fragment for Immunotherapy of B Lineage Leukaemia and Lymphoma," Molecular Immunolgoy, vol. 34, No. 16-17 (1997), pp. 1157-1165.
Imai, C., et al., "Chimeric receptors with 4-1BB signaling capacity provoke potent cytotoxicity against acute lymphoblastic leukemia," Leukemia, vol. 18 (2004), pp. 676-684.
Maher, John, et al., "Human T-lymphocyte cytotoxicity and proliferation directed by a single chimeric TCR/CD28 receptor," Nature Biotechnology, vol. 20 (2002), pp. 70-75.
Morgan, Richard A., et al., "Case Report of a Serious Adverse Event Following the Administration of T Cells Transduced With a Chimeric Antigen Receptor Recognizing ERBB2," Molecular Therapy, vol. 18, No. 4 (2010), pp. 843-851.
Porter, David L., et al., "Chimeric Antigen Receptor-Modified T Cells in Chronic Lymphoid Leukemia," The New England Journal of Medicine, vol. 365 (2011), pp. 725-733.
Rosenberg, Steven A., et al., "Use of Tumor-Infiltrating Lymphocytes and Interleukin-2 in the Immunotherapy of Patients with Metastatic Melanoma," The New England Journal of Medicine, vol. 319 (1988), pp. 1676-1680.
Woof, Jenny M., et al., "Human Antibody-FC Receptor Interactions Illuminated by Crystal Structures," Immunology, vol. 4 (2004) (11 pgs.).

(Continued)

*Primary Examiner* — Laura B Goddard

(74) *Attorney, Agent, or Firm* — Pabst Patent Group LLP

(57) ABSTRACT

Disclosed herein are methods of providing an anti-tumor immunity in a subject with a CD83-expressing cancer that involves adoptive transfer of the immune effector cells engineered to express chimeric antigen receptor (CAR) polypeptides that selectively bind CD83-expressing cancers. Also disclosed herein are dual-CAR systems to increase safety and/or efficacy of the CAR-T cells.

17 Claims, 21 Drawing Sheets

Specification includes a Sequence Listing.

(56) References Cited

OTHER PUBLICATIONS

International Search Report and Written Opinion, PCT/US2022/070539, mailed Jun. 6, 2022.

Shrestha, Bishwas, et al., "Generation of Antitumor T Cells for Adoptive Cell Therapy With Artificial Antigen Presenting Cells," Journal of Immunotherapy, vol. 43, Issue 3 (2019), pp. 79-88.

* cited by examiner

SEQUENCE LISTING

```
<160> NUMBER OF SEQ ID NOS: 93

<210> SEQ ID NO 1
<211> LENGTH: 12
<212> TYPE: PRT
<213> ORGANISM: Artificial Sequence
<220> FEATURE:
```

<223> OTHER INFORMATION: Synethetic Construct

<400> SEQUENCE: 1

Gly Phe Ser Ile Thr Thr Gly Gly Tyr Trp Trp Thr
1 5 10

<210> SEQ ID NO 2
<211> LENGTH: 17
<212> TYPE: PRT
<213> ORGANISM: Artificial Sequence
<220> FEATURE:
<223> OTHER INFORMATION: Synethetic Construct

<400> SEQUENCE: 2

Gly Tyr Ile Phe Ser Ser Gly Asn Thr Asn Tyr Asn Pro Ser Ile Lys
1 5 10 15

Ser

<210> SEQ ID NO 3
<211> LENGTH: 12
<212> TYPE: PRT
<213> ORGANISM: Artificial Sequence
<220> FEATURE:
<223> OTHER INFORMATION: Synethetic Construct

<400> SEQUENCE: 3

Cys Ala Arg Ala Tyr Gly Lys Leu Gly Phe Asp Tyr
1 5 10

<210> SEQ ID NO 4
<211> LENGTH: 12
<212> TYPE: PRT
<213> ORGANISM: Artificial Sequence
<220> FEATURE:
<223> OTHER INFORMATION: Synethetic Construct

<400> SEQUENCE: 4

Thr Leu Ser Ser Gln His Ser Thr Tyr Thr Ile Gly
1 5 10

<210> SEQ ID NO 5
<211> LENGTH: 11
<212> TYPE: PRT
<213> ORGANISM: Artificial Sequence
<220> FEATURE:
<223> OTHER INFORMATION: Synethetic Construct

<400> SEQUENCE: 5

Val Asn Ser Asp Gly Ser His Ser Lys Gly Asp
1 5 10

<210> SEQ ID NO 6
<211> LENGTH: 9
<212> TYPE: PRT
<213> ORGANISM: Artificial Sequence
<220> FEATURE:
<223> OTHER INFORMATION: Synethetic Construct

<400> SEQUENCE: 6

Gly Ser Ser Asp Ser Ser Gly Tyr Val
1 5

<210> SEQ ID NO 7
<211> LENGTH: 5
<212> TYPE: PRT
<213> ORGANISM: Artificial Sequence
<220> FEATURE:
<223> OTHER INFORMATION: Synethetic Construct

<400> SEQUENCE: 7

Ser Asp Gly Ile Ser
1 5

<210> SEQ ID NO 8
<211> LENGTH: 16
<212> TYPE: PRT
<213> ORGANISM: Artificial Sequence
<220> FEATURE:
<223> OTHER INFORMATION: Synethetic Construct

<400> SEQUENCE: 8

Ile Ile Ser Ser Gly Gly Asn Thr Tyr Tyr Ala Ser Trp Ala Lys Gly
1 5 10 15

<210> SEQ ID NO 9
<211> LENGTH: 8
<212> TYPE: PRT
<213> ORGANISM: Artificial Sequence
<220> FEATURE:
<223> OTHER INFORMATION: Synethetic Construct

<400> SEQUENCE: 9

Val Val Gly Gly Thr Tyr Ser Ile
1 5

<210> SEQ ID NO 10
<211> LENGTH: 13
<212> TYPE: PRT
<213> ORGANISM: Artificial Sequence
<220> FEATURE:
<223> OTHER INFORMATION: Synethetic Construct

<400> SEQUENCE: 10

Gln Ser Ser Gln Ser Val Tyr Asn Asn Asp Phe Leu Ser
1 5 10

<210> SEQ ID NO 11
<211> LENGTH: 7
<212> TYPE: PRT
<213> ORGANISM: Artificial Sequence
<220> FEATURE:
<223> OTHER INFORMATION: Synethetic Construct

<400> SEQUENCE: 11

Tyr Ala Ser Thr Leu Ala Ser
1 5

<210> SEQ ID NO 12
<211> LENGTH: 13
<212> TYPE: PRT
<213> ORGANISM: Artificial Sequence
<220> FEATURE:
<223> OTHER INFORMATION: Synethetic Construct

<400> SEQUENCE: 12

Thr Gly Thr Tyr Gly Asn Ser Ala Trp Tyr Glu Asp Ala
1 5 10

<210> SEQ ID NO 13
<211> LENGTH: 5
<212> TYPE: PRT
<213> ORGANISM: Artificial Sequence
<220> FEATURE:

<223> OTHER INFORMATION: Synethetic Construct

<400> SEQUENCE: 13

Ser Asn Ala Met Ile
1 5

<210> SEQ ID NO 14
<211> LENGTH: 16
<212> TYPE: PRT
<213> ORGANISM: Artificial Sequence
<220> FEATURE:
<223> OTHER INFORMATION: Synethetic Construct

<400> SEQUENCE: 14

Ala Met Asp Ser Asn Ser Arg Thr Tyr Tyr Ala Thr Trp Ala Lys Gly
1 5 10 15

<210> SEQ ID NO 15
<211> LENGTH: 11
<212> TYPE: PRT
<213> ORGANISM: Artificial Sequence
<220> FEATURE:
<223> OTHER INFORMATION: Synethetic Construct

<400> SEQUENCE: 15

Gly Asp Gly Gly Ser Ser Asp Tyr Thr Glu Met
1 5 10

<210> SEQ ID NO 16
<211> LENGTH: 13
<212> TYPE: PRT
<213> ORGANISM: Artificial Sequence
<220> FEATURE:
<223> OTHER INFORMATION: Synethetic Construct

<400> SEQUENCE: 16

Gln Ser Ser Gln Ser Val Tyr Gly Asn Asn Glu Leu Ser
1 5 10

<210> SEQ ID NO 17
<211> LENGTH: 7
<212> TYPE: PRT
<213> ORGANISM: Artificial Sequence
<220> FEATURE:
<223> OTHER INFORMATION: Synethetic Construct

<400> SEQUENCE: 17

Gln Ala Ser Ser Leu Ala Ser
1 5

<210> SEQ ID NO 18
<211> LENGTH: 11
<212> TYPE: PRT
<213> ORGANISM: Artificial Sequence
<220> FEATURE:
<223> OTHER INFORMATION: Synethetic Construct

<400> SEQUENCE: 18

Leu Gly Glu Tyr Ser Ile Ser Ala Asp Asn His
1 5 10

<210> SEQ ID NO 19
<211> LENGTH: 120
<212> TYPE: PRT
<213> ORGANISM: Artificial Sequence
<220> FEATURE:
<223> OTHER INFORMATION: Synethetic Construct

<400> SEQUENCE: 19

Gln Val Gln Leu Lys Glu Ser Gly Pro Gly Leu Val Lys Pro Ser Gln
1 5 10 15

Ser Leu Ser Leu Thr Cys Ser Val Thr Gly Phe Ser Ile Thr Thr Gly
20 25 30

Gly Tyr Trp Trp Thr Trp Ile Arg Gln Phe Pro Gly Gln Lys Leu Glu
35 40 45

Trp Met Gly Tyr Ile Phe Ser Ser Gly Asn Thr Asn Tyr Asn Pro Ser
50 55 60

Ile Lys Ser Arg Ile Ser Ile Thr Arg Asp Thr Ser Lys Asn Gln Phe
65 70 75 80

Phe Leu Gln Leu Asn Ser Val Thr Thr Glu Gly Asp Thr Ala Arg Tyr
85 90 95

Tyr Cys Ala Arg Ala Tyr Gly Lys Leu Gly Phe Asp Tyr Trp Gly Gln
100 105 110

Gly Thr Leu Val Thr Val Ser Ser
115 120

<210> SEQ ID NO 20
<211> LENGTH: 111
<212> TYPE: PRT
<213> ORGANISM: Artificial Sequence
<220> FEATURE:
<223> OTHER INFORMATION: Synethetic Construct

<400> SEQUENCE: 20

Gln Pro Val Leu Thr Gln Ser Pro Ser Ala Ser Ala Ser Leu Gly Asn
1 5 10 15

Ser Val Lys Ile Thr Cys Thr Leu Ser Ser Gln His Ser Thr Tyr Thr
20 25 30

Ile Gly Trp Tyr Gln Gln His Pro Asp Lys Ala Pro Lys Tyr Val Met
35 40 45

Tyr Val Asn Ser Asp Gly Ser His Ser Lys Gly Asp Gly Ile Pro Asp
50 55 60

Arg Phe Ser Gly Ser Ser Ser Gly Ala His Arg Tyr Leu Ser Ile Ser
65 70 75 80

Asn Ile Gln Pro Glu Asp Glu Ala Asp Tyr Phe Cys Gly Ser Ser Asp
85 90 95

Ser Ser Gly Tyr Val Phe Gly Ser Gly Thr Gln Leu Thr Val Leu
100 105 110

<210> SEQ ID NO 21
<211> LENGTH: 454
<212> TYPE: PRT
<213> ORGANISM: Artificial Sequence
<220> FEATURE:
<223> OTHER INFORMATION: Synethetic Construct

<400> SEQUENCE: 21

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Phe Ser Leu Ser
35 40 45

Asn Asn Ala Ile Asn Trp Val Arg Gln Ala Pro Gly Lys Gly Leu Glu
50 55 60

```
Trp Ile Gly Tyr Ile Trp Ser Gly Gly Leu Thr Tyr Tyr Ala Asn Trp
65                  70                  75                  80

Ala Glu Gly Arg Phe Thr Ile Ser Lys Thr Ser Thr Thr Val Asp Leu
                85                  90                  95

Lys Met Thr Ser Pro Thr Ile Glu Asp Thr Ala Thr Tyr Phe Cys Ala
            100                 105                 110

Arg Gly Ile Asn Asn Ser Ala Leu Trp Gly Pro Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
    370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Asn Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450
```

<210> SEQ ID NO 22
<211> LENGTH: 239

<212> TYPE: PRT
<213> ORGANISM: Artificial Sequence
<220> FEATURE:
<223> OTHER INFORMATION: Synethetic Construct

<400> SEQUENCE: 22

```
Met Asp Met Arg Ala Pro Thr Gln Leu Leu Gly Leu Leu Leu Leu Trp
1               5                   10                  15

Leu Pro Gly Ala Arg Cys Ala Asp Val Val Met Thr Gln Thr Pro Ala
            20                  25                  30

Ser Val Ser Ala Ala Val Gly Gly Thr Val Thr Ile Asn Cys Gln Ala
        35                  40                  45

Ser Glu Ser Ile Ser Asn Tyr Leu Ser Trp Tyr Gln Gln Lys Pro Gly
    50                  55                  60

Gln Pro Pro Lys Leu Leu Ile Tyr Arg Thr Ser Thr Leu Ala Ser Gly
65                  70                  75                  80

Val Ser Ser Arg Phe Lys Gly Ser Gly Ser Gly Thr Glu Tyr Thr Leu
                85                  90                  95

Thr Ile Ser Gly Val Gln Cys Asp Asp Val Ala Thr Tyr Tyr Cys Gln
            100                 105                 110

Cys Thr Ser Gly Gly Lys Phe Ile Ser Asp Gly Ala Ala Phe Gly Gly
        115                 120                 125

Gly Thr Glu Val Val Val Lys Gly Asp Pro Val Ala Pro Thr Val Leu
    130                 135                 140

Leu Phe Pro Pro Ser Ser Asp Glu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Ser Arg Lys Asn Cys
225                 230                 235
```

<210> SEQ ID NO 23
<211> LENGTH: 452
<212> TYPE: PRT
<213> ORGANISM: Artificial Sequence
<220> FEATURE:
<223> OTHER INFORMATION: Synthetic Construct

<400> SEQUENCE: 23

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Thr Ile Ser
        35                  40                  45

Asp Tyr Asp Leu Ser Trp Val Arg Gln Ala Pro Gly Glu Gly Leu Lys
    50                  55                  60

Tyr Ile Gly Phe Ile Ala Ile Asp Gly Asn Pro Tyr Tyr Ala Thr Trp
65                  70                  75                  80

Ala Lys Gly Arg Phe Thr Ile Ser Lys Thr Ser Thr Thr Val Asp Leu
                85                  90                  95
```

```
Lys Ile Thr Ala Pro Thr Thr Glu Asp Thr Ala Thr Tyr Phe Cys Ala
            100                 105                 110

Arg Gly Ala Gly Asp Leu Trp Gly Pro Gly Thr Leu Val Thr Val Ser
        115                 120                 125

Ser Gly Gln Pro Lys Ala Pro Ser Val Phe Pro Leu Ala Pro Cys Cys
    130                 135                 140

Gly Asp Thr Pro Ser Ser Thr Val Thr Leu Gly Cys Leu Val Lys Gly
145                 150                 155                 160

Tyr Leu Pro Glu Pro Val Thr Val Thr Trp Asn Ser Gly Thr Leu Thr
                165                 170                 175

Asn Gly Val Arg Thr Phe Pro Ser Val Arg Gln Ser Ser Gly Leu Tyr
            180                 185                 190

Ser Leu Ser Ser Val Val Ser Val Thr Ser Ser Ser Gln Pro Val Thr
        195                 200                 205

Cys Asn Val Ala His Pro Ala Thr Asn Thr Lys Val Asp Lys Thr Val
    210                 215                 220

Ala Pro Ser Thr Cys Ser Lys Pro Thr Cys Pro Pro Pro Glu Leu Leu
225                 230                 235                 240

Gly Gly Pro Ser Val Phe Ile Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Asp Asp Pro Glu Val Gln Phe Thr Trp Tyr Ile Asn Asn Glu Gln
        275                 280                 285

Val Arg Thr Ala Arg Pro Pro Leu Arg Glu Gln Gln Phe Asn Ser Thr
    290                 295                 300

Ile Arg Val Val Ser Thr Leu Pro Ile Ala His Gln Asp Trp Leu Arg
305                 310                 315                 320

Gly Lys Glu Phe Lys Cys Lys Val His Asn Lys Ala Leu Pro Ala Pro
                325                 330                 335

Ile Glu Lys Thr Ile Ser Lys Ala Arg Gly Gln Pro Leu Glu Pro Lys
            340                 345                 350

Val Tyr Thr Met Gly Pro Pro Arg Glu Glu Leu Ser Ser Arg Ser Val
        355                 360                 365

Ser Leu Thr Cys Met Ile Asn Gly Phe Tyr Pro Ser Asp Ile Ser Val
    370                 375                 380

Glu Trp Glu Lys Asn Gly Lys Ala Glu Asp Asn Tyr Lys Thr Thr Pro
385                 390                 395                 400

Ala Val Leu Asp Ser Asp Gly Ser Tyr Phe Leu Tyr Asn Lys Leu Ser
                405                 410                 415

Val Pro Thr Ser Glu Trp Gln Arg Gly Asp Val Phe Thr Cys Ser Val
            420                 425                 430

Met His Glu Ala Leu His Asn His Tyr Thr Gln Lys Ser Ile Ser Arg
        435                 440                 445

Ser Pro Gly Lys
    450
```

<210> SEQ ID NO 24
<211> LENGTH: 238
<212> TYPE: PRT
<213> ORGANISM: Artificial Sequence
<220> FEATURE:
<223> OTHER INFORMATION: Synethetic Construct

<400> SEQUENCE: 24

Met Asp Thr Arg Glu Pro Thr Gln Leu Leu Gly Leu Leu Leu Leu Trp
1               5                   10                  15

Leu Pro Gly Ala Arg Cys Ala Asp Val Val Met Thr Gln Thr Pro Ala
            20                  25                  30

Ser Val Ser Ala Ala Val Gly Gly Thr Val Thr Ile Asn Cys Gln Ser
        35                  40                  45

Ser Lys Asn Val Tyr Asn Asn Asn Trp Leu Ser Trp Phe Gln Gln Lys
    50                  55                  60

Pro Gly Gln Pro Pro Lys Leu Leu Ile Tyr Tyr Ala Ser Thr Leu Ala
65                  70                  75                  80

Ser Gly Val Pro Ser Arg Phe Arg Gly Ser Gly Ser Gly Thr Gln Phe
                85                  90                  95

Thr Leu Thr Ile Ser Asp Val Gln Cys Asp Asp Ala Ala Thr Tyr Tyr
            100                 105                 110

Cys Ala Gly Asp Tyr Ser Ser Ser Ser Asp Asn Gly Phe Gly Gly Gly
        115                 120                 125

Thr Glu Val Val Val Lys Gly Asp Pro Val Ala Pro Thr Val Leu Leu
    130                 135                 140

Phe Pro Pro Ser Ser Asp Glu Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Ser Arg Lys Asn Cys
225                 230                 235

<210> SEQ ID NO 25
<211> LENGTH: 454
<212> TYPE: PRT
<213> ORGANISM: Artificial Sequence
<220> FEATURE:
<223> OTHER INFORMATION: Synethetic Construct

<400> SEQUENCE: 25

Met Glu Thr Gly Leu Arg Trp Leu Leu Leu Val Ala Val Leu Lys Gly
1               5                   10                  15

Val His Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Arg Ser
        35                  40                  45

Ser Tyr Asp Met Ser Trp Val Arg Gln Ala Pro Gly Lys Gly Leu Glu
    50                  55                  60

Trp Val Gly Val Ile Ser Thr Ala Tyr Asn Ser His Tyr Ala Ser Trp
65                  70                  75                  80

Ala Lys Gly Arg Phe Thr Ile Ser Arg Thr Ser Thr Thr Val Asp Leu
                85                  90                  95

Lys Met Thr Ser Leu Thr Thr Glu Asp Thr Ala Thr Tyr Phe Cys Ala
            100                 105                 110

```
Arg Gly Gly Ser Trp Leu Asp Leu Trp Gly Gln Gly Thr Leu Val Thr
        115                 120                 125

Val Ser Ser Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
    370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Asn Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450
```

<210> SEQ ID NO 26
<211> LENGTH: 239
<212> TYPE: PRT
<213> ORGANISM: Artificial Sequence
<220> FEATURE:
<223> OTHER INFORMATION: Synethetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 26

Met Asp Xaa Arg Ala Pro Thr Gln Leu Leu Gly Leu Leu Leu Leu Trp
1 5 10 15

Leu Pro Gly Ala Arg Cys Ala Leu Val Met Thr Gln Thr Pro Ala Ser
20 25 30

Val Ser Ala Ala Val Gly Gly Thr Val Thr Ile Asn Cys Gln Ser Ser
35 40 45

Gln Ser Val Tyr Asp Asn Asp Glu Leu Ser Trp Tyr Gln Gln Lys Pro
50 55 60

Gly Gln Pro Pro Lys Leu Leu Ile Tyr Ala Leu Ala Ser Lys Leu Ala
65 70 75 80

Ser Gly Val Pro Ser Arg Phe Lys Gly Ser Gly Ser Gly Thr Gln Phe
85 90 95

Ala Leu Thr Ile Ser Gly Val Gln Cys Asp Asp Ala Ala Thr Tyr Tyr
100 105 110

Cys Gln Ala Thr His Tyr Ser Ser Asp Trp Tyr Leu Thr Phe Gly Gly
115 120 125

Gly Thr Glu Val Val Val Lys Gly Phe Pro Val Ala Pro Thr Val Leu
130 135 140

Leu Phe Pro Pro Ser Ser Asp Glu Val Ala Thr Gly Thr Val Thr Ile
145 150 155 160

Val Cys Val Ala Asn Lys Tyr Phe Pro Asp Val Thr Val Thr Trp Glu
165 170 175

Val Asp Gly Thr Thr Gln Thr Thr Gly Thr Glu Asn Ser Lys Thr Pro
180 185 190

Gln Asn Ser Ala Asp Cys Thr Tyr Asn Leu Ser Ser Thr Leu Thr Leu
195 200 205

Thr Ser Thr Gln Tyr Asn Ser His Lys Glu Tyr Thr Cys Lys Val Thr
210 215 220

Gln Gly Thr Thr Ser Val Val Gln Ser Phe Ser Arg Lys Asn Cys
225 230 235

<210> SEQ ID NO 27
<211> LENGTH: 456
<212> TYPE: PRT
<213> ORGANISM: Artificial Sequence
<220> FEATURE:
<223> OTHER INFORMATION: Synethetic Construct

<400> SEQUENCE: 27

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Phe Ser Leu Ser
35 40 45

Ser Tyr Asp Met Thr Trp Val Arg Gln Ala Pro Gly Lys Gly Leu Glu
50 55 60

Trp Ile Gly Ile Ile Tyr Ala Ser Gly Thr Thr Tyr Tyr Ala Asn Trp
65 70 75 80

Ala Lys Gly Arg Phe Thr Ile Ser Lys Thr Ser Thr Thr Val Asp Leu
85 90 95

Lys Val Thr Ser Pro Thr Ile Gly Asp Thr Ala Thr Tyr Phe Cys Ala
100 105 110

```
Arg Glu Gly Ala Gly Val Ser Met Thr Leu Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Asn Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455
```

<210> SEQ ID NO 28
<211> LENGTH: 236
<212> TYPE: PRT
<213> ORGANISM: Artificial Sequence
<220> FEATURE:
<223> OTHER INFORMATION: Synethetic Construct

<400> SEQUENCE: 28

```
Met Asp Met Arg Ala Pro Thr Gln Leu Leu Gly Leu Leu Leu Leu Trp
1               5                   10                  15
```

Leu Pro Gly Ala Arg Cys Ala Tyr Asp Met Thr Gln Thr Pro Ala Ser
20 25 30

Val Glu Val Ala Val Gly Gly Thr Val Thr Ile Lys Cys Gln Ala Ser
35 40 45

Gln Ser Ile Ser Thr Tyr Leu Asp Trp Tyr Gln Gln Lys Pro Gly Gln
50 55 60

Pro Pro Lys Leu Leu Ile Tyr Asp Ala Ser Asp Leu Ala Ser Gly Val
65 70 75 80

Pro Ser Arg Phe Lys Gly Ser Gly Ser Gly Thr Gln Phe Thr Leu Thr
85 90 95

Ile Ser Asp Leu Glu Cys Ala Asp Ala Ala Thr Tyr Tyr Cys Gln Gln
100 105 110

Gly Tyr Thr His Ser Asn Val Asp Asn Val Phe Gly Gly Gly Thr Glu
115 120 125

Val Val Val Lys Gly Asp Pro Val Ala Pro Thr Val Leu Leu Phe Pro
130 135 140

Pro Ser Ser Asp Glu Val Ala Thr Gly Thr Val Thr Ile Val Cys Val
145 150 155 160

Ala Asn Lys Tyr Phe Pro Asp Val Thr Val Thr Trp Glu Val Asp Gly
165 170 175

Thr Thr Gln Thr Thr Gly Ile Glu Asn Ser Lys Thr Pro Gln Asn Ser
180 185 190

Ala Asp Cys Thr Tyr Asn Leu Ser Ser Thr Leu Thr Leu Thr Ser Thr
195 200 205

Gln Tyr Asn Ser His Lys Glu Tyr Thr Cys Lys Val Thr Gln Gly Thr
210 215 220

Thr Ser Val Val Gln Ser Phe Ser Arg Lys Asn Cys
225 230 235

<210> SEQ ID NO 29
<211> LENGTH: 459
<212> TYPE: PRT
<213> ORGANISM: Artificial Sequence
<220> FEATURE:
<223> OTHER INFORMATION: Synethetic Construct

<400> SEQUENCE: 29

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Ser Pro
20 25 30

Gly Thr Pro Leu Thr Leu Thr Cys Thr Ala Ser Gly Phe Ser Leu Ser
35 40 45

Ser Tyr Asp Met Ser Trp Val Arg Gln Ala Pro Gly Lys Gly Leu Glu
50 55 60

Tyr Ile Gly Ile Ile Ser Ser Ser Gly Ser Thr Tyr Tyr Ala Ser Trp
65 70 75 80

Ala Lys Gly Arg Phe Thr Ile Ser Lys Thr Ser Thr Thr Val Asp Leu
85 90 95

Glu Val Thr Ser Leu Thr Thr Glu Asp Thr Ala Thr Tyr Phe Cys Ser
100 105 110

Arg Glu His Ala Gly Tyr Ser Gly Asp Thr Gly His Leu Trp Gly Pro
115 120 125

Gly Thr Leu Val Thr Val Ser Ser Gly Gln Pro Lys Ala Pro Ser Val
130 135 140

```
Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
    210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Gly Ile Gly Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Asp Pro Glu Val Gln Phe Thr
        275                 280                 285

Trp Tyr Ile Asn Asn Glu Gln Val Arg Thr Ala Arg Pro Pro Leu Arg
    290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
            340                 345                 350

Gly Gln Pro Leu Glu Pro Lys Val Tyr Thr Met Gly Pro Pro Arg Glu
        355                 360                 365

Glu Leu Ser Ser Arg Ser Val Ser Leu Thr Cys Met Ile Asn Gly Phe
    370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Asn Lys Leu Ser Val Pro Thr Ser Glu Trp Gln Arg Gly
            420                 425                 430

Asp Val Phe Thr Cys Ser Val Met His Glu Ala Leu His Asn His Tyr
        435                 440                 445

Thr Gln Lys Ser Ile Ser Arg Ser Pro Gly Lys
    450                 455
```

<210> SEQ ID NO 30
<211> LENGTH: 236
<212> TYPE: PRT
<213> ORGANISM: Artificial Sequence
<220> FEATURE:
<223> OTHER INFORMATION: Synethetic Construct

<400> SEQUENCE: 30

```
Met Asp Met Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Ala Ile Lys Cys Gln Ala Ser
        35                  40                  45
```

```
Gln Ser Val Ser Ser Tyr Leu Ala Trp Tyr Gln Gln Lys Pro Gly Gln
    50                  55                  60

Pro Pro Lys Pro Leu Ile Tyr Glu Ala Ser Met Leu Ala Ala Gly Val
65                  70                  75                  80

Ser Ser Arg Phe Lys Gly Ser Gly Ser Gly Thr Asp Phe Thr Leu Thr
                85                  90                  95

Ile Ser Asp Leu Glu Cys Asp Asp Ala Ala Thr Tyr Tyr Cys Gln Gln
            100                 105                 110

Gly Tyr Ser Ile Ser Asp Ile Asp Asn Ala Phe Gly Gly Gly Thr Glu
        115                 120                 125

Val Val Val Lys Gly Asp Pro Val Ala Pro Thr Val Leu Leu Phe Pro
    130                 135                 140

Pro Ser Ser Asp Glu Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Ser Arg Lys Asn Cys
225                 230                 235


<210> SEQ ID NO 31
<211> LENGTH: 455
<212> TYPE: PRT
<213> ORGANISM: Artificial Sequence
<220> FEATURE:
<223> OTHER INFORMATION: Synethetic Construct

<400> SEQUENCE: 31

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Asp Gly Ile Ser Trp Val Arg Gln Ala Pro Gly Lys Gly Leu Glu
    50                  55                  60

Trp Ile Gly Ile Ile Ser Ser Gly Gly Asn Thr Tyr Tyr Ala Ser Trp
65                  70                  75                  80

Ala Lys Gly Arg Phe Thr Ile Ser Arg Thr Ser Thr Thr Val Asp Leu
                85                  90                  95

Lys Met Thr Ser Leu Thr Thr Glu Asp Thr Ala Thr Tyr Phe Cys Ala
            100                 105                 110

Arg Val Val Gly Gly Thr Tyr Ser Ile Trp Gly Gln Gly Thr Leu Val
        115                 120                 125

Thr Val Ser Ser Ala Ser Thr Lys Gly Pro Ser Val Tyr Pro Leu Ala
    130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175
```

```
Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Thr Trp Pro
        195                 200                 205

Ser Glu Thr Val Thr Cys Asn Val Ala His Pro Ala Ser Ser Thr Lys
    210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Gln Pro Arg Glu Glu Gln Phe
    290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Pro Lys Glu Gln Met Ala Lys
        355                 360                 365

Asp Lys Val Ser Leu Thr Cys Met Ile Thr Asp Phe Phe Pro Glu Asp
    370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys
    450                 455


<210> SEQ ID NO 32
<211> LENGTH: 240
<212> TYPE: PRT
<213> ORGANISM: Artificial Sequence
<220> FEATURE:
<223> OTHER INFORMATION: Synethetic Construct

<400> SEQUENCE: 32

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Pro Val Gly Gly Thr Val Thr Ile Asn Cys Gln Ser Ser
        35                  40                  45

Gln Ser Val Tyr Asn Asn Asp Phe Leu Ser Trp Tyr Gln Gln Lys Pro
    50                  55                  60

Gly Gln Pro Pro Lys Leu Leu Ile Tyr Tyr Ala Ser Thr Leu Ala Ser
65                  70                  75                  80
```

```
Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Thr Gly Thr Tyr Gly Asn Ser Ala Trp Tyr Glu Asp Ala Phe Gly Gly
        115                 120                 125

Gly Thr Glu Val Val Val Lys Arg Thr Pro Val Ala Pro Thr Val Leu
    130                 135                 140

Leu Phe Pro Pro Ser Ser Ala Glu Leu Ala Thr Gly Thr Ala Thr Ile
145                 150                 155                 160

Val Cys Val Ala Asn Lys Tyr Phe Pro Asp Gly Thr Val Thr Trp Lys
                165                 170                 175

Val Asp Gly Ile Thr Gln Ser Ser Gly Ile Asn Asn Ser Arg Thr Pro
            180                 185                 190

Gln Asn Ser Ala Asp Cys Thr Tyr Asn Leu Ser Ser Thr Leu Thr Leu
        195                 200                 205

Ser Ser Asp Glu Tyr Asn Ser His Asp Glu Tyr Thr Cys Gln Val Ala
    210                 215                 220

Gln Asp Ser Gly Ser Pro Val Val Gln Ser Phe Ser Arg Lys Ser Cys
225                 230                 235                 240


<210> SEQ ID NO 33
<211> LENGTH: 460
<212> TYPE: PRT
<213> ORGANISM: Artificial Sequence
<220> FEATURE:
<223> OTHER INFORMATION: Synethetic Construct

<400> SEQUENCE: 33

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Asn Ala Met Ile Trp Val Arg Gln Ala Pro Arg Glu Gly Leu Glu
    50                  55                  60

Trp Ile Gly Ala Met Asp Ser Asn Ser Arg Thr Tyr Tyr Ala Thr Trp
65                  70                  75                  80

Ala Lys Gly Arg Phe Thr Ile Ser Arg Thr Ser Ser Ile Thr Val Asp
                85                  90                  95

Leu Lys Ile Thr Ser Pro Thr Thr Glu Asp Thr Ala Thr Tyr Phe Cys
            100                 105                 110

Ala Arg Gly Asp Gly Gly Ser Ser Asp Tyr Thr Glu Met Trp Gly Pro
        115                 120                 125

Gly Thr Leu Val Thr Val Ser Ser Ala Ser Thr Lys Gly Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205
```

Ser Thr Trp Pro Ser Glu Thr Val Thr Cys Asn Val Ala His Pro Ala
210 215 220

Ser Ser Thr Lys Val Asp Lys Lys Ile Val Pro Arg Asp Cys Gly Cys
225 230 235 240

Lys Pro Cys Ile Cys Thr Val Pro Glu Val Ser Ser Val Phe Ile Phe
245 250 255

Pro Pro Lys Pro Lys Asp Val Leu Thr Ile Thr Leu Thr Pro Lys Val
260 265 270

Thr Cys Val Val Val Asp Ile Ser Lys Asp Asp Pro Glu Val Gln Phe
275 280 285

Ser Trp Phe Val Asp Asp Val Glu Val His Thr Ala Gln Thr Gln Pro
290 295 300

Arg Glu Glu Gln Phe Asn Ser Thr Phe Arg Ser Val Ser Glu Leu Pro
305 310 315 320

Ile Met His Gln Asp Trp Leu Asn Gly Lys Glu Phe Lys Cys Arg Val
325 330 335

Asn Ser Ala Ala Phe Pro Ala Pro Ile Glu Lys Thr Ile Ser Lys Thr
340 345 350

Lys Gly Arg Pro Lys Ala Pro Gln Val Tyr Thr Ile Pro Pro Pro Lys
355 360 365

Glu Gln Met Ala Lys Asp Lys Val Ser Leu Thr Cys Met Ile Thr Asp
370 375 380

Phe Phe Pro Glu Asp Ile Thr Val Glu Trp Gln Trp Asn Gly Gln Pro
385 390 395 400

Ala Glu Asn Tyr Lys Asn Thr Gln Pro Ile Met Asp Thr Asp Gly Ser
405 410 415

Tyr Phe Val Tyr Ser Lys Leu Asn Val Gln Lys Ser Asn Trp Glu Ala
420 425 430

Gly Asn Thr Phe Thr Cys Ser Val Leu His Glu Gly Leu His Asn His
435 440 445

His Thr Glu Lys Ser Leu Ser His Ser Pro Gly Lys
450 455 460

<210> SEQ ID NO 34
<211> LENGTH: 239
<212> TYPE: PRT
<213> ORGANISM: Artificial Sequence
<220> FEATURE:
<223> OTHER INFORMATION: Synethetic Construct

<400> SEQUENCE: 34

Met Asp Thr Arg Ala Pro Thr Gln Leu Leu Gly Leu Leu Leu Leu Trp
1 5 10 15

Leu Pro Gly Ala Thr Phe Ala Gln Ala Val Val Thr Gln Thr Thr Ser
20 25 30

Pro Val Ser Ala Pro Val Gly Gly Thr Val Thr Ile Asn Cys Gln Ser
35 40 45

Ser Gln Ser Val Tyr Gly Asn Asn Glu Leu Ser Trp Tyr Gln Gln Lys
50 55 60

Pro Gly Gln Pro Pro Lys Leu Leu Ile Tyr Gln Ala Ser Ser Leu Ala
65 70 75 80

Ser Gly Val Pro Ser Arg Phe Lys Gly Ser Gly Ser Gly Thr Gln Phe
85 90 95

Thr Leu Thr Ile Ser Asp Leu Glu Cys Asp Asp Ala Ala Thr Tyr Tyr
100 105 110

```
Cys Leu Gly Glu Tyr Ser Ile Ser Ala Asp Asn His Phe Gly Gly Gly
        115                 120                 125

Thr Glu Val Val Val Lys Arg Thr Pro Val Ala Pro Thr Val Leu Leu
    130                 135                 140

Phe Pro Pro Ser Ser Ala Glu Leu Ala Thr Gly Thr Ala Thr Ile Val
145                 150                 155                 160

Cys Val Ala Asn Lys Tyr Phe Pro Asp Gly Thr Val Thr Trp Lys Val
                165                 170                 175

Asp Gly Ile Thr Gln Ser Ser Gly Ile Asn Asn Ser Arg Thr Pro Gln
            180                 185                 190

Asn Ser Ala Asp Cys Thr Tyr Asn Leu Ser Ser Thr Leu Thr Leu Ser
        195                 200                 205

Ser Asp Glu Tyr Asn Ser His Asp Glu Tyr Thr Cys Gln Val Ala Gln
    210                 215                 220

Asp Ser Gly Ser Pro Val Val Gln Ser Phe Ser Arg Lys Ser Cys
225                 230                 235


<210> SEQ ID NO 35
<211> LENGTH: 221
<212> TYPE: PRT
<213> ORGANISM: Artificial Sequence
<220> FEATURE:
<223> OTHER INFORMATION: Synethetic Construct

<400> SEQUENCE: 35

Gln Val Gln Leu Val Gln Ser Gly Gly Ala Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Ala Val Ser Tyr Asp Gly Ser Asn Lys Tyr Tyr Ala Asp Phe Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Arg Gly Gly Leu Asp Ile Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Ala Ala Ala
    210                 215                 220


<210> SEQ ID NO 36
<211> LENGTH: 110
```

<212> TYPE: PRT
<213> ORGANISM: Artificial Sequence
<220> FEATURE:
<223> OTHER INFORMATION: Synethetic Construct

<400> SEQUENCE: 36

```
Leu Thr Gln Pro Pro Pro Ala Ser Gly Thr Pro Gly Gln Gln Arg Val
1               5                   10                  15

Thr Ile Ser Cys Ser Gly Ser Ser Ser Asn Ile Gly Ser Asn Thr Val
            20                  25                  30

Asn Trp Tyr Gln Gln Leu Pro Gly Thr Ala Pro Lys Leu Leu Ile Tyr
        35                  40                  45

Tyr Gly Asn Asp Gln Arg Pro Ser Gly Val Pro Asp Arg Phe Ser Ala
    50                  55                  60

Ser Lys Ser Gly Thr Ser Ala Ser Leu Ala Ile Ser Gly Leu Gln Ser
65                  70                  75                  80

Glu Asp Glu Ala His Tyr Tyr Cys Ala Ala Trp Asp Gly Ser Leu Asn
                85                  90                  95

Gly Gly Val Ile Phe Gly Gly Gly Thr Lys Val Thr Leu Gly
            100                 105                 110
```

<210> SEQ ID NO 37
<211> LENGTH: 109
<212> TYPE: PRT
<213> ORGANISM: Artificial Sequence
<220> FEATURE:
<223> OTHER INFORMATION: Synethetic Construct

<400> SEQUENCE: 37

```
Val Thr Gln Pro Pro Ser Ala Ser Gly Thr Pro Gly Gln Arg Val Thr
1               5                   10                  15

Ile Ser Cys Ser Gly Ser Ser Ser Asn Ile Gly Thr Asn Pro Val Asn
            20                  25                  30

Trp Tyr Gln Gln Leu Pro Gly Thr Ala Pro Lys Leu Leu Ile Tyr Thr
        35                  40                  45

Thr Asp Gln Arg Pro Ser Gly Val Pro Asp Arg Phe Ser Gly Ser Lys
    50                  55                  60

Ser Gly Thr Ser Ala Ser Leu Ala Ile Ser Gly Leu Gln Ser Glu Asp
65                  70                  75                  80

Glu Ala Asp Tyr Tyr Cys Ala Ala Trp Asp Asp Ser Leu Ser Gly Leu
                85                  90                  95

Tyr Val Phe Gly Thr Gly Thr Lys Val Thr Val Leu Gly
            100                 105
```

<210> SEQ ID NO 38
<211> LENGTH: 109
<212> TYPE: PRT
<213> ORGANISM: Artificial Sequence
<220> FEATURE:
<223> OTHER INFORMATION: Synethetic Construct

<400> SEQUENCE: 38

```
Met Thr His Thr Pro Leu Ser Leu Ser Val Thr Pro Gly Gln Pro Ala
1               5                   10                  15

Ser Ile Ser Cys Lys Ser Ser Gln Ser Leu Leu His Ser Asp Gly Lys
            20                  25                  30

Thr Tyr Leu Tyr Trp Tyr Leu Gln Arg Pro Gly Gln Ser Pro Gln Pro
        35                  40                  45
```

Leu Ile Tyr Glu Val Ser Asn Arg Phe Ser Gly Val Pro Asp Arg Phe
50 55 60

Ser Gly Ser Gly Ser Gly Thr Asp Phe Thr Leu Lys Ile Ser Arg Val
65 70 75 80

Gln Ala Glu Asp Val Gly Val Tyr Tyr Cys Met Gln Ser Leu Gln Leu
85 90 95

Trp Thr Phe Gly Gln Gly Thr Lys Val Glu Ile Lys Arg
100 105

<210> SEQ ID NO 39
<211> LENGTH: 110
<212> TYPE: PRT
<213> ORGANISM: Artificial Sequence
<220> FEATURE:
<223> OTHER INFORMATION: Synethetic Construct

<400> SEQUENCE: 39

Met Thr Gln Ser Pro Leu Ser Leu Pro Val Thr Leu Gly Gln Pro Ala
1 5 10 15

Ser Ile Ser Cys Arg Ser Ser Gln Ser Leu Ile His Ser Asp Gly Asn
20 25 30

Thr Tyr Leu Asp Trp Phe Gln Gln Arg Pro Gly Gln Ser Pro Arg Arg
35 40 45

Leu Ile Tyr Lys Val Ser Asn Arg Asp Ser Gly Val Pro Asp Arg Phe
50 55 60

Ser Gly Ser Gly Ser Gly Thr Asp Phe Thr Leu Arg Ile Ser Arg Val
65 70 75 80

Glu Ala Glu Asp Ile Gly Val Tyr Tyr Cys Met Gln Ala Thr His Trp
85 90 95

Pro Arg Thr Phe Gly Gln Gly Thr Lys Val Glu Ile Lys Arg
100 105 110

<210> SEQ ID NO 40
<211> LENGTH: 110
<212> TYPE: PRT
<213> ORGANISM: Artificial Sequence
<220> FEATURE:
<223> OTHER INFORMATION: Synethetic Construct

<400> SEQUENCE: 40

Met Thr Gln Ser Pro Leu Ser Leu Pro Val Thr Leu Gly Gln Pro Ala
1 5 10 15

Ser Ile Ser Cys Arg Ser Ser Gln Ser Leu Val Asp Ser Ala Gly Asn
20 25 30

Thr Phe Leu His Trp Phe His Gln Arg Pro Gly Gln Ser Pro Arg Arg
35 40 45

Leu Ile Tyr Lys Val Ser Asn Arg Asp Ser Gly Val Pro Asp Arg Phe
50 55 60

Ser Gly Ser Gly Ser Gly Thr Asp Phe Thr Leu Lys Ile Ser Arg Val
65 70 75 80

Glu Ala Glu Asp Val Gly Val Tyr Tyr Cys Met Gln Gly Thr His Trp
85 90 95

Pro Arg Thr Phe Gly Gln Gly Thr Lys Val Glu Ile Lys Arg
100 105 110

<210> SEQ ID NO 41
<211> LENGTH: 110
<212> TYPE: PRT

<213> ORGANISM: Artificial Sequence
<220> FEATURE:
<223> OTHER INFORMATION: Synethetic Construct

<400> SEQUENCE: 41

Leu Thr Gln Ser Pro Leu Ser Leu Pro Val Thr Leu Gly Gln Pro Ala
1 5 10 15

Ser Ile Ser Cys Lys Ser Ser Gln Ser Leu Val Asp Ser Asp Gly Asn
20 25 30

Thr Tyr Leu Asn Trp Phe Gln Gln Arg Pro Gly Gln Ser Pro Arg Arg
35 40 45

Leu Ile Tyr Lys Val Ser Asn Arg Asp Ser Gly Val Pro Asp Arg Phe
50 55 60

Ser Gly Ser Gly Ser Gly Thr Asp Phe Thr Leu Lys Ile Ser Arg Val
65 70 75 80

Glu Ala Glu Asp Val Gly Val Tyr Tyr Cys Met Gln Gly Thr His Trp
85 90 95

Pro Arg Thr Phe Gly Gln Gly Thr Lys Val Glu Ile Lys Arg
100 105 110

<210> SEQ ID NO 42
<211> LENGTH: 110
<212> TYPE: PRT
<213> ORGANISM: Artificial Sequence
<220> FEATURE:
<223> OTHER INFORMATION: Synethetic Construct

<400> SEQUENCE: 42

Met Thr Gln Ser Pro Leu Ser Leu Pro Val Thr Leu Gly Gln Pro Ala
1 5 10 15

Ser Ile Ser Cys Arg Ser Ser Gln Ser Leu Val His Ser Asp Gly Asn
20 25 30

Met Tyr Leu Asn Trp Phe Gln Gln Arg Pro Gly Gln Ser Pro Arg Arg
35 40 45

Leu Ile Tyr Lys Val Ser Asn Arg Asp Ser Gly Val Pro Asp Arg Phe
50 55 60

Ser Gly Ser Gly Ser Gly Thr Asp Phe Thr Leu Lys Ile Ser Arg Val
65 70 75 80

Glu Ala Glu Asp Val Gly Val Tyr Tyr Cys Met Gln Ala Thr Gln Pro
85 90 95

Thr Trp Thr Phe Gly Gln Gly Thr Lys Leu Glu Ile Lys Arg
100 105 110

<210> SEQ ID NO 43
<211> LENGTH: 92
<212> TYPE: PRT
<213> ORGANISM: Artificial Sequence
<220> FEATURE:
<223> OTHER INFORMATION: Synethetic Construct

<400> SEQUENCE: 43

Met Thr Gln Ser Pro Ser Ser Leu Ser Ala Ser Val Gly Asp Arg Val
1 5 10 15

Thr Ile Thr Cys Gln Ala Ser Gln Asp Ile Ser Asn Tyr Leu Asn Trp
20 25 30

Tyr Gln Gln Lys Pro Gly Lys Ala Pro Lys Leu Leu Ile Tyr Asp Ala
35 40 45

Ser Asn Leu Glu Thr Gly Val Pro Ser Arg Phe Ser Gly Ser Gly Ser
50 55 60

Gly Thr Asp Phe Thr Phe Thr Ile Ser Ser Ala Thr Tyr Tyr Cys Gln
65 70 75 80

Gln Thr Tyr Gln Gly Thr Lys Leu Glu Ile Lys Arg
85 90

<210> SEQ ID NO 44
<211> LENGTH: 105
<212> TYPE: PRT
<213> ORGANISM: Artificial Sequence
<220> FEATURE:
<223> OTHER INFORMATION: Synethetic Construct

<400> SEQUENCE: 44

Met Thr Gln Ser Pro Ser Ser Leu Ser Ala Ser Val Gly His Pro Val
1 5 10 15

Thr Ile Thr Cys Arg Ala Ser Gln Ser Leu Ile Ser Tyr Leu Asn Trp
20 25 30

Tyr His Gln Lys Pro Gly Lys Ala Pro Lys Leu Leu Ile Tyr Ala Ala
35 40 45

Ser Ile Leu Gln Ser Gly Val Pro Ser Arg Phe Ser Gly Ser Gly Ser
50 55 60

Gly Thr Asp Phe Thr Leu Thr Ile Ser Ser Leu Gln Pro Glu Asn Phe
65 70 75 80

Ala Ser Tyr Tyr Cys Gln His Thr Asp Ser Phe Pro Arg Thr Phe Gly
85 90 95

His Gly Thr Lys Val Glu Ile Lys Arg
100 105

<210> SEQ ID NO 45
<211> LENGTH: 108
<212> TYPE: PRT
<213> ORGANISM: Artificial Sequence
<220> FEATURE:
<223> OTHER INFORMATION: Synethetic Construct

<400> SEQUENCE: 45

Leu Thr Gln Pro Pro Ser Ala Ser Gly Thr Pro Gly Gln Gly Val Thr
1 5 10 15

Ile Ser Cys Arg Gly Ser Thr Ser Asn Ile Gly Asn Asn Val Val Asn
20 25 30

Trp Tyr Gln His Val Pro Gly Ser Ala Pro Lys Leu Leu Ile Trp Ser
35 40 45

Asn Ile Gln Arg Pro Ser Gly Ile Pro Asp Arg Phe Ser Gly Ser Lys
50 55 60

Ser Gly Thr Ser Ala Ser Leu Ala Ile Ser Gly Leu Gln Ser Glu Asp
65 70 75 80

Gln Ala Val Tyr Tyr Cys Ala Val Trp Asp Asp Gly Leu Ala Gly Trp
85 90 95

Val Phe Gly Gly Gly Thr Thr Val Thr Val Leu Ser
100 105

<210> SEQ ID NO 46
<211> LENGTH: 105
<212> TYPE: PRT
<213> ORGANISM: Artificial Sequence
<220> FEATURE:
<223> OTHER INFORMATION: Synethetic Construct

<400> SEQUENCE: 46

Met Thr Gln Ala Pro Val Val Ser Val Ala Leu Glu Gln Thr Val Arg
1 5 10 15

Ile Thr Cys Gln Gly Asp Ser Leu Ala Ile Tyr Tyr Asp Phe Trp Tyr
20 25 30

Gln His Lys Pro Gly Gln Ala Pro Val Leu Val Ile Tyr Gly Lys Asn
35 40 45

Asn Arg Pro Ser Gly Ile Pro His Arg Phe Ser Gly Ser Ser Ser Asn
50 55 60

Thr Asp Ser Leu Thr Ile Thr Gly Ala Gln Ala Glu Asp Glu Ala Asp
65 70 75 80

Tyr Tyr Cys Asn Ser Arg Asp Ser Ser Gly Asn His Trp Val Phe Gly
85 90 95

Gly Gly Thr Asn Leu Thr Val Leu Gly
100 105

<210> SEQ ID NO 47
<211> LENGTH: 111
<212> TYPE: PRT
<213> ORGANISM: Artificial Sequence
<220> FEATURE:
<223> OTHER INFORMATION: Synethetic Construct

<400> SEQUENCE: 47

Leu Thr Gln Ser Pro Leu Ser Leu Pro Val Thr Leu Gly Gln Pro Ala
1 5 10 15

Ser Ile Ser Cys Lys Ser Asn Gln Ser Leu Val His Ser Asp Gly Asn
20 25 30

Thr Tyr Leu Asn Trp Phe Gln Gln Arg Pro Gly Gln Ser Pro Arg Arg
35 40 45

Leu Ile Tyr Lys Val Ser Asn Arg Asp Ser Gly Val Pro Asp Arg Phe
50 55 60

Ser Gly Ser Gly Ser Gly Thr Asp Phe Thr Leu Lys Ile Asn Arg Val
65 70 75 80

Glu Ala Glu Asp Val Gly Val Tyr Tyr Cys Met Gln Gly Thr Gln Trp
85 90 95

Pro Arg Thr Phe Gly Gly Gln Gly Thr Lys Leu Asp Ile Lys Arg
100 105 110

<210> SEQ ID NO 48
<211> LENGTH: 119
<212> TYPE: PRT
<213> ORGANISM: Artificial Sequence
<220> FEATURE:
<223> OTHER INFORMATION: Synethetic Construct

<400> SEQUENCE: 48

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Val Asp Thr Ser Lys Asn Gln Phe
65 70 75 80

```
Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser
        115


<210> SEQ ID NO 49
<211> LENGTH: 119
<212> TYPE: PRT
<213> ORGANISM: Artificial Sequence
<220> FEATURE:
<223> OTHER INFORMATION: Synethetic Construct

<400> SEQUENCE: 49

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln His Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser
        115


<210> SEQ ID NO 50
<211> LENGTH: 119
<212> TYPE: PRT
<213> ORGANISM: Artificial Sequence
<220> FEATURE:
<223> OTHER INFORMATION: Synethetic Construct

<400> SEQUENCE: 50

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser
        115
```

<210> SEQ ID NO 51
<211> LENGTH: 119
<212> TYPE: PRT
<213> ORGANISM: Artificial Sequence
<220> FEATURE:
<223> OTHER INFORMATION: Synethetic Construct

<400> SEQUENCE: 51

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Arg Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser
115

<210> SEQ ID NO 52
<211> LENGTH: 119
<212> TYPE: PRT
<213> ORGANISM: Artificial Sequence
<220> FEATURE:
<223> OTHER INFORMATION: Synethetic Construct

<400> SEQUENCE: 52

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Arg Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser
115

<210> SEQ ID NO 53
<211> LENGTH: 120
<212> TYPE: PRT
<213> ORGANISM: Artificial Sequence
<220> FEATURE:
<223> OTHER INFORMATION: Synethetic Construct

<400> SEQUENCE: 53

Gln Val Gln Leu Gln Glu Ser Gly Pro Gly Leu Val Lys Pro Ser Glu
1 5 10 15

```
Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Ile Ser Ile Thr Arg Asp Thr Ser Lys Asn Gln Phe
65                  70                  75                  80

Phe Leu Gln Leu Asn Ser Val Thr Thr Glu Gly Asp Thr Ala Arg Tyr
                85                  90                  95

Tyr Cys Ala Arg Ala Tyr Gly Lys Leu Gly Phe Asp Tyr Trp Gly Gln
            100                 105                 110

Gly Thr Leu Val Thr Val Ser Ser
        115                 120


<210> SEQ ID NO 54
<211> LENGTH: 111
<212> TYPE: PRT
<213> ORGANISM: Artificial Sequence
<220> FEATURE:
<223> OTHER INFORMATION: Synethetic Construct

<400> SEQUENCE: 54

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Gly Trp His Gln Gln Gln Pro Glu Lys Gly Pro Arg Tyr Leu Met
        35                  40                  45

Lys Val Asn Ser Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Ser Ser Asp
                85                  90                  95

Ser Ser Gly Tyr Val Phe Gly Ser Gly Thr Lys Val Thr Val Leu
            100                 105                 110


<210> SEQ ID NO 55
<211> LENGTH: 111
<212> TYPE: PRT
<213> ORGANISM: Artificial Sequence
<220> FEATURE:
<223> OTHER INFORMATION: Synethetic Construct

<400> SEQUENCE: 55

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Gln His Ser Thr Tyr Thr
            20                  25                  30

Ile Gly Trp Tyr Gln Gln Arg Pro Gly Arg Ser Pro Gln Tyr Ile Met
        35                  40                  45

Lys Val Asn Ser Asp Gly Ser His Ser Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80
```

```
Asn Leu Gln Ser Asp Asp Glu Ala Glu Tyr His Cys Gly Ser Ser Asp
                85                  90                  95

Ser Ser Gly Tyr Val Phe Gly Ser Gly Thr Lys Val Thr Val Leu
            100                 105                 110


<210> SEQ ID NO 56
<211> LENGTH: 15
<212> TYPE: PRT
<213> ORGANISM: Artificial Sequence
<220> FEATURE:
<223> OTHER INFORMATION: Synethetic Construct

<400> SEQUENCE: 56

Gly Gly Gly Gly Ser Gly Gly Gly Gly Ser Gly Gly Gly Gly Ser
1               5                   10                  15


<210> SEQ ID NO 57
<211> LENGTH: 247
<212> TYPE: PRT
<213> ORGANISM: Artificial Sequence
<220> FEATURE:
<223> OTHER INFORMATION: Synethetic Construct

<400> SEQUENCE: 57

Gln Pro Val Leu Thr Gln Ser Pro Ser Ala Ser Ala Ser Leu Gly Asn
1               5                   10                  15

Ser Val Lys Ile Thr Cys Thr Leu Ser Ser Gln His Ser Thr Tyr Thr
            20                  25                  30

Ile Gly Trp Tyr Gln Gln His Pro Asp Lys Ala Pro Lys Tyr Val Met
        35                  40                  45

Tyr Val Asn Ser Asp Gly Ser His Ser Lys Gly Asp Gly Ile Pro Asp
    50                  55                  60

Arg Phe Ser Gly Ser Ser Ser Gly Ala His Arg Tyr Leu Ser Ile Ser
65                  70                  75                  80

Asn Ile Gln Pro Glu Asp Glu Ala Asp Tyr Phe Cys Gly Ser Ser Asp
                85                  90                  95

Ser Ser Gly Tyr Val Phe Gly Ser Gly Thr Gln Leu Thr Val Leu Arg
            100                 105                 110

Ala Ala Ala Ser Ser Gly Gly Gly Gly Ser Gly Gly Gly Gly Ser Gly
        115                 120                 125

Gly Gly Gly Ser Gln Pro Val Leu Thr Gln Ser Pro Ser Ala Ser Ala
    130                 135                 140

Ser Leu Gly Asn Ser Val Lys Ile Thr Cys Thr Leu Ser Ser Gln His
145                 150                 155                 160

Ser Thr Tyr Thr Ile Gly Trp Tyr Gln Gln His Pro Asp Lys Ala Pro
                165                 170                 175

Lys Tyr Val Met Tyr Val Asn Ser Asp Gly Ser His Ser Lys Gly Asp
            180                 185                 190

Gly Ile Pro Asp Arg Phe Ser Gly Ser Ser Ser Gly Ala His Arg Tyr
        195                 200                 205

Leu Ser Ile Ser Asn Ile Gln Pro Glu Asp Glu Ala Asp Tyr Phe Cys
    210                 215                 220

Gly Ser Ser Asp Ser Ser Gly Tyr Val Phe Gly Ser Gly Thr Gln Leu
225                 230                 235                 240

Thr Val Leu Arg Ala Ala Ala
                245
```

<210> SEQ ID NO 58
<211> LENGTH: 253
<212> TYPE: PRT
<213> ORGANISM: Artificial Sequence
<220> FEATURE:
<223> OTHER INFORMATION: Synethetic Construct

<400> SEQUENCE: 58

Gln Val Gln Leu Lys Glu Ser Gly Pro Gly Leu Val Lys Pro Ser Gln
1               5                   10                  15

Ser Leu Ser Leu Thr Cys Ser Val Thr Gly Phe Ser Ile Thr Thr Gly
            20                  25                  30

Gly Tyr Trp Trp Thr Trp Ile Arg Gln Phe Pro Gly Gln Lys Leu Glu
        35                  40                  45

Trp Met Gly Tyr Ile Phe Ser Ser Gly Asn Thr Asn Tyr Asn Pro Ser
    50                  55                  60

Ile Lys Ser Arg Ile Ser Ile Thr Arg Asp Thr Ser Lys Asn Gln Phe
65                  70                  75                  80

Phe Leu Gln Leu Asn Ser Val Thr Thr Glu Gly Asp Thr Ala Arg Tyr
                85                  90                  95

Tyr Cys Ala Arg Ala Tyr Gly Lys Leu Gly Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Val Gln Leu Lys Glu Ser Gly Pro
    130                 135                 140

Gly Leu Val Lys Pro Ser Gln Ser Leu Ser Leu Thr Cys Ser Val Thr
145                 150                 155                 160

Gly Phe Ser Ile Thr Thr Gly Gly Tyr Trp Trp Thr Trp Ile Arg Gln
                165                 170                 175

Phe Pro Gly Gln Lys Leu Glu Trp Met Gly Tyr Ile Phe Ser Ser Gly
            180                 185                 190

Asn Thr Asn Tyr Asn Pro Ser Ile Lys Ser Arg Ile Ser Ile Thr Arg
        195                 200                 205

Asp Thr Ser Lys Asn Gln Phe Phe Leu Gln Leu Asn Ser Val Thr Thr
    210                 215                 220

Glu Gly Asp Thr Ala Arg Tyr Tyr Cys Ala Arg Ala Tyr Gly Lys Leu
225                 230                 235                 240

Gly Phe Asp Tyr Trp Gly Gln Gly Thr Leu Val Thr Val
                245                 250

<210> SEQ ID NO 59
<211> LENGTH: 245
<212> TYPE: PRT
<213> ORGANISM: Artificial Sequence
<220> FEATURE:
<223> OTHER INFORMATION: Synethetic Construct

<400> SEQUENCE: 59

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gln Leu Val Leu Thr Gln Ser Pro Ser Ala
130 135 140

Ser Ala Ser Leu Gly Ala Ser Val Lys Leu Thr Cys Thr Leu Ser Ser
145 150 155 160

Gln His Ser Thr Tyr Thr Ile Gly Trp His Gln Gln Gln Pro Glu Lys
165 170 175

Gly Pro Arg Tyr Leu Met Lys Val Asn Ser Asp Gly Ser His Ser Lys
180 185 190

Gly Asp Gly Ile Pro Asp Arg Phe Ser Gly Ser Ser Ser Gly Ala Glu
195 200 205

Arg Tyr Leu Thr Ile Ser Ser Leu Gln Ser Glu Asp Glu Ala Asp Tyr
210 215 220

Tyr Cys Gly Ser Ser Asp Ser Ser Gly Tyr Val Phe Gly Ser Gly Thr
225 230 235 240

Lys Val Thr Val Leu
245

<210> SEQ ID NO 60
<211> LENGTH: 245
<212> TYPE: PRT
<213> ORGANISM: Artificial Sequence
<220> FEATURE:
<223> OTHER INFORMATION: Synethetic Construct

<400> SEQUENCE: 60

Gln Val Gln Leu Gln Glu Ser Gly Pro Gly Leu Val Lys Pro Ser Gln
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln His Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Leu Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gln Leu Val Leu Thr Gln Ser Pro Ser Ala
130 135 140

Ser Ala Ser Leu Gly Ala Ser Val Lys Leu Thr Cys Thr Leu Ser Ser
145 150 155 160

Gln His Ser Thr Tyr Thr Ile Gly Trp His Gln Gln Gln Pro Glu Lys
165 170 175

Gly Pro Arg Tyr Leu Met Lys Val Asn Ser Asp Gly Ser His Ser Lys
180 185 190

Gly Asp Gly Ile Pro Asp Arg Phe Ser Gly Ser Ser Ser Gly Ala Glu
195 200 205

Arg Tyr Leu Thr Ile Ser Ser Leu Gln Ser Glu Asp Glu Ala Asp Tyr
210 215 220

Tyr Cys Gly Ser Ser Asp Ser Ser Gly Tyr Val Phe Gly Ser Gly Thr
225 230 235 240

Lys Val Thr Val Leu
245

<210> SEQ ID NO 61
<211> LENGTH: 245
<212> TYPE: PRT
<213> ORGANISM: Artificial Sequence
<220> FEATURE:
<223> OTHER INFORMATION: Synethetic Construct

<400> SEQUENCE: 61

Gln Val Gln Leu Gln Glu Ser Gly Pro Gly Leu Val Lys Pro Ser Gln
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gln Leu Val Leu Thr Gln Ser Pro Ser Ala
130 135 140

Ser Ala Ser Leu Gly Ala Ser Val Lys Leu Thr Cys Thr Leu Ser Ser
145 150 155 160

Gln His Ser Thr Tyr Thr Ile Gly Trp His Gln Gln Gln Pro Glu Lys
165 170 175

Gly Pro Arg Tyr Leu Met Lys Val Asn Ser Asp Gly Ser His Ser Lys
180 185 190

Gly Asp Gly Ile Pro Asp Arg Phe Ser Gly Ser Ser Ser Gly Ala Glu
195 200 205

Arg Tyr Leu Thr Ile Ser Ser Leu Gln Ser Glu Asp Glu Ala Asp Tyr
210 215 220

Tyr Cys Gly Ser Ser Asp Ser Ser Gly Tyr Val Phe Gly Ser Gly Thr
225 230 235 240

Lys Val Thr Val Leu
245

<210> SEQ ID NO 62
<211> LENGTH: 245
<212> TYPE: PRT
<213> ORGANISM: Artificial Sequence
<220> FEATURE:

<223> OTHER INFORMATION: Synethetic Construct

<400> SEQUENCE: 62

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Arg Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gln Leu Val Leu Thr Gln Ser Pro Ser Ala
130 135 140

Ser Ala Ser Leu Gly Ala Ser Val Lys Leu Thr Cys Thr Leu Ser Ser
145 150 155 160

Gln His Ser Thr Tyr Thr Ile Gly Trp His Gln Gln Gln Pro Glu Lys
165 170 175

Gly Pro Arg Tyr Leu Met Lys Val Asn Ser Asp Gly Ser His Ser Lys
180 185 190

Gly Asp Gly Ile Pro Asp Arg Phe Ser Gly Ser Ser Ser Gly Ala Glu
195 200 205

Arg Tyr Leu Thr Ile Ser Ser Leu Gln Ser Glu Asp Glu Ala Asp Tyr
210 215 220

Tyr Cys Gly Ser Ser Asp Ser Ser Gly Tyr Val Phe Gly Ser Gly Thr
225 230 235 240

Lys Val Thr Val Leu
245

<210> SEQ ID NO 63
<211> LENGTH: 245
<212> TYPE: PRT
<213> ORGANISM: Artificial Sequence
<220> FEATURE:
<223> OTHER INFORMATION: Synethetic Construct

<400> SEQUENCE: 63

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Arg Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gln Leu Val Leu Thr Gln Ser Pro Ser Ala
130 135 140

Ser Ala Ser Leu Gly Ala Ser Val Lys Leu Thr Cys Thr Leu Ser Ser
145 150 155 160

Gln His Ser Thr Tyr Thr Ile Gly Trp His Gln Gln Gln Pro Glu Lys
165 170 175

Gly Pro Arg Tyr Leu Met Lys Val Asn Ser Asp Gly Ser His Ser Lys
180 185 190

Gly Asp Gly Ile Pro Asp Arg Phe Ser Gly Ser Ser Ser Gly Ala Glu
195 200 205

Arg Tyr Leu Thr Ile Ser Ser Leu Gln Ser Glu Asp Glu Ala Asp Tyr
210 215 220

Tyr Cys Gly Ser Ser Asp Ser Ser Gly Tyr Val Phe Gly Ser Gly Thr
225 230 235 240

Lys Val Thr Val Leu
245

<210> SEQ ID NO 64
<211> LENGTH: 246
<212> TYPE: PRT
<213> ORGANISM: Artificial Sequence
<220> FEATURE:
<223> OTHER INFORMATION: Synethetic Construct

<400> SEQUENCE: 64

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Ile Ser Ile Thr Arg Asp Thr Ser Lys Asn Gln Phe
65 70 75 80

Phe Leu Gln Leu Asn Ser Val Thr Thr Glu Gly Asp Thr Ala Arg Tyr
85 90 95

Tyr Cys Ala Arg Ala Tyr Gly Lys Leu Gly Phe Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gln Leu Val Leu Thr Gln Ser Pro Ser
130 135 140

Ala Ser Ala Ser Leu Gly Ala Ser Val Lys Leu Thr Cys Thr Leu Ser
145 150 155 160

Ser Gln His Ser Thr Tyr Thr Ile Gly Trp His Gln Gln Gln Pro Glu
165 170 175

Lys Gly Pro Arg Tyr Leu Met Lys Val Asn Ser Asp Gly Ser His Ser
180 185 190

Lys Gly Asp Gly Ile Pro Asp Arg Phe Ser Gly Ser Ser Ser Gly Ala
195 200 205

```
Glu Arg Tyr Leu Thr Ile Ser Ser Leu Gln Ser Glu Asp Glu Ala Asp
    210                 215                 220

Tyr Tyr Cys Gly Ser Ser Asp Ser Ser Gly Tyr Val Phe Gly Ser Gly
225                 230                 235                 240

Thr Lys Val Thr Val Leu
                245


<210> SEQ ID NO 65
<211> LENGTH: 245
<212> TYPE: PRT
<213> ORGANISM: Artificial Sequence
<220> FEATURE:
<223> OTHER INFORMATION: Synethetic Construct

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Leu Pro Val Leu Thr Gln Pro Pro Ser Ala
    130                 135                 140

Ser Ala Leu Leu Gly Ala Ser Ile Lys Leu Thr Cys Thr Leu Ser Ser
145                 150                 155                 160

Gln His Ser Thr Tyr Thr Ile Gly Trp Tyr Gln Gln Arg Pro Gly Arg
                165                 170                 175

Ser Pro Gln Tyr Ile Met Lys Val Asn Ser Asp Gly Ser His Ser Lys
            180                 185                 190

Gly Asp Gly Ile Pro Asp Arg Phe Met Gly Ser Ser Ser Gly Ala Asp
        195                 200                 205

Arg Tyr Leu Thr Phe Ser Asn Leu Gln Ser Asp Asp Glu Ala Glu Tyr
    210                 215                 220

His Cys Gly Ser Ser Asp Ser Ser Gly Tyr Val Phe Gly Ser Gly Thr
225                 230                 235                 240

Lys Val Thr Val Leu
                245


<210> SEQ ID NO 66
<211> LENGTH: 245
<212> TYPE: PRT
<213> ORGANISM: Artificial Sequence
<220> FEATURE:
<223> OTHER INFORMATION: Synethetic Construct
```

<400> SEQUENCE: 66

Gln Val Gln Leu Gln Glu Ser Gly Pro Gly Leu Val Lys Pro Ser Gln
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln His Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Leu Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Ala Tyr Gly Lys Leu Gly Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Leu Pro Val Leu Thr Gln Pro Pro Ser Ala
130 135 140

Ser Ala Leu Leu Gly Ala Ser Ile Lys Leu Thr Cys Thr Leu Ser Ser
145 150 155 160

Gln His Ser Thr Tyr Thr Ile Gly Trp Tyr Gln Gln Arg Pro Gly Arg
165 170 175

Ser Pro Gln Tyr Ile Met Lys Val Asn Ser Asp Gly Ser His Ser Lys
180 185 190

Gly Asp Gly Ile Pro Asp Arg Phe Met Gly Ser Ser Ser Gly Ala Asp
195 200 205

Arg Tyr Leu Thr Phe Ser Asn Leu Gln Ser Asp Asp Glu Ala Glu Tyr
210 215 220

His Cys Gly Ser Ser Asp Ser Ser Gly Tyr Val Phe Gly Ser Gly Thr
225 230 235 240

Lys Val Thr Val Leu
245

<210> SEQ ID NO 67
<211> LENGTH: 245
<212> TYPE: PRT
<213> ORGANISM: Artificial Sequence
<220> FEATURE:
<223> OTHER INFORMATION: Synethetic Construct

<400> SEQUENCE: 67

Gln Val Gln Leu Gln Glu Ser Gly Pro Gly Leu Val Lys Pro Ser Gln
1 5 10 15

Thr Leu Ser Leu Thr Cys Thr Val Ser Gly Phe Ser Ile Thr Thr Gly
20 25 30

Gly Tyr Trp Trp Thr Trp Ile Arg Gln Pro Pro Gly Lys Gly Leu Glu
35 40 45

Trp Ile Gly Tyr Ile Phe Ser Ser Gly Asn Thr Asn Tyr Asn Pro Ser
50 55 60

Ile Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

```
Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Leu Pro Val Leu Thr Gln Pro Pro Ser Ala
    130                 135                 140

Ser Ala Leu Leu Gly Ala Ser Ile Lys Leu Thr Cys Thr Leu Ser Ser
145                 150                 155                 160

Gln His Ser Thr Tyr Thr Ile Gly Trp Tyr Gln Gln Arg Pro Gly Arg
                165                 170                 175

Ser Pro Gln Tyr Ile Met Lys Val Asn Ser Asp Gly Ser His Ser Lys
            180                 185                 190

Gly Asp Gly Ile Pro Asp Arg Phe Met Gly Ser Ser Ser Gly Ala Asp
        195                 200                 205

Arg Tyr Leu Thr Phe Ser Asn Leu Gln Ser Asp Asp Glu Ala Glu Tyr
    210                 215                 220

His Cys Gly Ser Ser Asp Ser Ser Gly Tyr Val Phe Gly Ser Gly Thr
225                 230                 235                 240

Lys Val Thr Val Leu
                245


<210> SEQ ID NO 68
<211> LENGTH: 245
<212> TYPE: PRT
<213> ORGANISM: Artificial Sequence
<220> FEATURE:
<223> OTHER INFORMATION: Synethetic Construct

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Leu Pro Val Leu Thr Gln Pro Pro Ser Ala
    130                 135                 140

Ser Ala Leu Leu Gly Ala Ser Ile Lys Leu Thr Cys Thr Leu Ser Ser
145                 150                 155                 160

Gln His Ser Thr Tyr Thr Ile Gly Trp Tyr Gln Gln Arg Pro Gly Arg
                165                 170                 175

Ser Pro Gln Tyr Ile Met Lys Val Asn Ser Asp Gly Ser His Ser Lys
            180                 185                 190

Gly Asp Gly Ile Pro Asp Arg Phe Met Gly Ser Ser Ser Gly Ala Asp
        195                 200                 205
```

```
Arg Tyr Leu Thr Phe Ser Asn Leu Gln Ser Asp Asp Glu Ala Glu Tyr
    210                 215                 220

His Cys Gly Ser Ser Asp Ser Ser Gly Tyr Val Phe Gly Ser Gly Thr
225                 230                 235                 240

Lys Val Thr Val Leu
                245


<210> SEQ ID NO 69
<211> LENGTH: 245
<212> TYPE: PRT
<213> ORGANISM: Artificial Sequence
<220> FEATURE:
<223> OTHER INFORMATION: Synethetic Construct

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Arg Tyr Tyr
                85                  90                  95

Cys Ala Arg Ala Tyr Gly Lys Leu Gly Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Leu Pro Val Leu Thr Gln Pro Pro Ser Ala
    130                 135                 140

Ser Ala Leu Leu Gly Ala Ser Ile Lys Leu Thr Cys Thr Leu Ser Ser
145                 150                 155                 160

Gln His Ser Thr Tyr Thr Ile Gly Trp Tyr Gln Gln Arg Pro Gly Arg
                165                 170                 175

Ser Pro Gln Tyr Ile Met Lys Val Asn Ser Asp Gly Ser His Ser Lys
            180                 185                 190

Gly Asp Gly Ile Pro Asp Arg Phe Met Gly Ser Ser Ser Gly Ala Asp
        195                 200                 205

Arg Tyr Leu Thr Phe Ser Asn Leu Gln Ser Asp Asp Glu Ala Glu Tyr
    210                 215                 220

His Cys Gly Ser Ser Asp Ser Ser Gly Tyr Val Phe Gly Ser Gly Thr
225                 230                 235                 240

Lys Val Thr Val Leu
                245


<210> SEQ ID NO 70
<211> LENGTH: 246
<212> TYPE: PRT
<213> ORGANISM: Artificial Sequence
<220> FEATURE:
<223> OTHER INFORMATION: Synethetic Construct

<400> SEQUENCE: 70

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Ile Thr Thr Gly
            20                  25                  30

Gly Tyr Trp Trp Thr Trp Ile Arg Gln Pro Pro Gly Lys Gly Leu Glu
        35                  40                  45

Trp Ile Gly Tyr Ile Phe Ser Ser Gly Asn Thr Asn Tyr Asn Pro Ser
    50                  55                  60

Ile Lys Ser Arg Ile Ser Ile Thr Arg Asp Thr Ser Lys Asn Gln Phe
65                  70                  75                  80

Phe Leu Gln Leu Asn Ser Val Thr Thr Glu Gly Asp Thr Ala Arg Tyr
                85                  90                  95

Tyr Cys Ala Arg Ala Tyr Gly Lys Leu Gly Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Leu Pro Val Leu Thr Gln Pro Pro Ser
    130                 135                 140

Ala Ser Ala Leu Leu Gly Ala Ser Ile Lys Leu Thr Cys Thr Leu Ser
145                 150                 155                 160

Ser Gln His Ser Thr Tyr Thr Ile Gly Trp Tyr Gln Gln Arg Pro Gly
                165                 170                 175

Arg Ser Pro Gln Tyr Ile Met Lys Val Asn Ser Asp Gly Ser His Ser
            180                 185                 190

Lys Gly Asp Gly Ile Pro Asp Arg Phe Met Gly Ser Ser Ser Gly Ala
        195                 200                 205

Asp Arg Tyr Leu Thr Phe Ser Asn Leu Gln Ser Asp Asp Glu Ala Glu
    210                 215                 220

Tyr His Cys Gly Ser Ser Asp Ser Ser Gly Tyr Val Phe Gly Ser Gly
225                 230                 235                 240

Thr Lys Val Thr Val Leu
                245


<210> SEQ ID NO 71
<211> LENGTH: 246
<212> TYPE: PRT
<213> ORGANISM: Artificial Sequence
<220> FEATURE:
<223> OTHER INFORMATION: Synethetic Construct

<400> SEQUENCE: 71

Gln Val Gln Leu Lys Glu Ser Gly Pro Gly Leu Val Lys Pro Ser Gln
1               5                   10                  15

Ser Leu Ser Leu Thr Cys Ser Val Thr Gly Phe Ser Ile Thr Thr Gly
            20                  25                  30

Gly Tyr Trp Trp Thr Trp Ile Arg Gln Phe Pro Gly Gln Lys Leu Glu
        35                  40                  45

Trp Met Gly Tyr Ile Phe Ser Ser Gly Asn Thr Asn Tyr Asn Pro Ser
    50                  55                  60

Ile Lys Ser Arg Ile Ser Ile Thr Arg Asp Thr Ser Lys Asn Gln Phe
65                  70                  75                  80

Phe Leu Gln Leu Asn Ser Val Thr Thr Glu Gly Asp Thr Ala Arg Tyr
                85                  90                  95

Tyr Cys Ala Arg Ala Tyr Gly Lys Leu Gly Phe Asp Tyr Trp Gly Gln
            100                 105                 110

Gly Thr Leu Val Thr Val Ser Ser Gly Gly Gly Gly Ser Gly Gly Gly
        115                 120                 125
```

```
Gly Ser Gly Gly Gly Gly Ser Gln Pro Val Leu Thr Gln Ser Pro Ser
    130                 135                 140

Ala Ser Ala Ser Leu Gly Asn Ser Val Lys Ile Thr Cys Thr Leu Ser
145                 150                 155                 160

Ser Gln His Ser Thr Tyr Thr Ile Gly Trp Tyr Gln Gln His Pro Asp
                165                 170                 175

Lys Ala Pro Lys Tyr Val Met Tyr Val Asn Ser Asp Gly Ser His Ser
            180                 185                 190

Lys Gly Asp Gly Ile Pro Asp Arg Phe Ser Gly Ser Ser Ser Gly Ala
        195                 200                 205

His Arg Tyr Leu Ser Ile Ser Asn Ile Gln Pro Glu Asp Glu Ala Asp
    210                 215                 220

Tyr Phe Cys Gly Ser Ser Asp Ser Ser Gly Tyr Val Phe Gly Ser Gly
225                 230                 235                 240

Thr Gln Leu Thr Val Leu
                245


<210> SEQ ID NO 72
<211> LENGTH: 5
<212> TYPE: PRT
<213> ORGANISM: Artificial Sequence
<220> FEATURE:
<223> OTHER INFORMATION: Synethetic Construct

<400> SEQUENCE: 72

Ser Tyr Trp Met Asn
1               5


<210> SEQ ID NO 73
<211> LENGTH: 17
<212> TYPE: PRT
<213> ORGANISM: Artificial Sequence
<220> FEATURE:
<223> OTHER INFORMATION: Synethetic Construct

<400> SEQUENCE: 73

Gln Ile Trp Pro Gly Asp Gly Asp Thr Asn Tyr Asn Gly Lys Phe Lys
1               5                   10                  15

Gly


<210> SEQ ID NO 74
<211> LENGTH: 15
<212> TYPE: PRT
<213> ORGANISM: Artificial Sequence
<220> FEATURE:
<223> OTHER INFORMATION: Synethetic Construct

<400> SEQUENCE: 74

Arg Glu Thr Thr Thr Val Gly Arg Tyr Tyr Tyr Ala Met Asp Tyr
1               5                   10                  15


<210> SEQ ID NO 75
<211> LENGTH: 15
<212> TYPE: PRT
<213> ORGANISM: Artificial Sequence
<220> FEATURE:
<223> OTHER INFORMATION: Synethetic Construct

<400> SEQUENCE: 75

Lys Ala Ser Gln Ser Val Asp Tyr Asp Gly Asp Ser Tyr Leu Asn
1               5                   10                  15
```

<210> SEQ ID NO 76
<211> LENGTH: 7
<212> TYPE: PRT
<213> ORGANISM: Artificial Sequence
<220> FEATURE:
<223> OTHER INFORMATION: Synethetic Construct

<400> SEQUENCE: 76

Asp Ala Ser Asn Leu Val Ser
1               5

<210> SEQ ID NO 77
<211> LENGTH: 9
<212> TYPE: PRT
<213> ORGANISM: Artificial Sequence
<220> FEATURE:
<223> OTHER INFORMATION: Synethetic Construct

<400> SEQUENCE: 77

Gln Gln Ser Thr Glu Asp Pro Trp Thr
1               5

<210> SEQ ID NO 78
<211> LENGTH: 124
<212> TYPE: PRT
<213> ORGANISM: Artificial Sequence
<220> FEATURE:
<223> OTHER INFORMATION: Synethetic Construct

<400> SEQUENCE: 78

Gln Val Gln Leu Gln Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Arg Ser Glu Asp Ser Ala Val Tyr Ser Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 79
<211> LENGTH: 112
<212> TYPE: PRT
<213> ORGANISM: Artificial Sequence
<220> FEATURE:
<223> OTHER INFORMATION: Synethetic Construct

<400> SEQUENCE: 79

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50 55 60

Arg Phe Ser Gly Ser Gly Ser Gly Thr Asp Phe Thr Leu Asn Ile His
65 70 75 80

Pro Val Glu Lys Val Asp Ala Ala Thr Tyr His Cys Gln Gln Ser Thr
85 90 95

Glu Asp Pro Trp Thr Phe Gly Gly Gly Thr Lys Leu Glu Ile Lys Arg
100 105 110

<210> SEQ ID NO 80
<211> LENGTH: 223
<212> TYPE: PRT
<213> ORGANISM: Artificial Sequence
<220> FEATURE:
<223> OTHER INFORMATION: Synethetic Construct

<400> SEQUENCE: 80

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys
210 215 220

<210> SEQ ID NO 81
<211> LENGTH: 220
<212> TYPE: PRT
<213> ORGANISM: Artificial Sequence
<220> FEATURE:
<223> OTHER INFORMATION: Synethetic Construct

<400> SEQUENCE: 81

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Gly Gly Gly Ser Asn Tyr His
165 170 175

Leu Glu Asn Glu Val Ala Arg Leu Lys Lys Leu Gly Gly Gly Gly Ser
180 185 190

Asp Ser Thr Tyr Ser Leu Ser Ser Thr Leu Thr Leu Ser Lys Ala Asp
195 200 205

Tyr Glu Lys His Lys Val Tyr Ala Cys Glu Val Thr
210 215 220

<210> SEQ ID NO 82
<211> LENGTH: 223
<212> TYPE: PRT
<213> ORGANISM: Artificial Sequence
<220> FEATURE:
<223> OTHER INFORMATION: Synethetic Construct

<400> SEQUENCE: 82

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220


<210> SEQ ID NO 83
<211> LENGTH: 124
<212> TYPE: PRT
<213> ORGANISM: Artificial Sequence
<220> FEATURE:
<223> OTHER INFORMATION: Synethetic Construct

<400> SEQUENCE: 83

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120


<210> SEQ ID NO 84
<211> LENGTH: 111
<212> TYPE: PRT
<213> ORGANISM: Artificial Sequence
<220> FEATURE:
<223> OTHER INFORMATION: Synethetic Construct

<400> SEQUENCE: 84

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110


<210> SEQ ID NO 85
<211> LENGTH: 464
<212> TYPE: PRT
```

<213> ORGANISM: Artificial Sequence
<220> FEATURE:
<223> OTHER INFORMATION: Synethetic Construct

<400> SEQUENCE: 85

```
Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Ile Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Gly Thr Tyr Tyr Tyr Gly Ser Arg Val Phe Asp
        115                 120                 125

Tyr Trp Gly Gln Gly Thr Thr Leu Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380
```

Met Ile Thr Asp Phe Phe Pro Glu Asp Ile Thr Val Glu Trp Gln Trp
385 390 395 400

Asn Gly Gln Pro Ala Glu Asn Tyr Lys Asn Thr Gln Pro Ile Met Asp
405 410 415

Thr Asp Gly Ser Tyr Phe Val Tyr Ser Lys Leu Asn Val Gln Lys Ser
420 425 430

Asn Trp Glu Ala Gly Asn Thr Phe Thr Cys Ser Val Leu His Glu Gly
435 440 445

Leu His Asn His His Thr Glu Lys Ser Leu Ser His Ser Pro Gly Lys
450 455 460

<210> SEQ ID NO 86
<211> LENGTH: 121
<212> TYPE: PRT
<213> ORGANISM: Artificial Sequence
<220> FEATURE:
<223> OTHER INFORMATION: Synethetic Construct

<400> SEQUENCE: 86

Glu Val Gln Leu Gln Gln Ser Gly Pro Glu Leu Ile Lys Pro Gly Ala
1 5 10 15

Ser Val Lys Met Ser Cys Lys Ala Ser Gly Tyr Thr Phe Thr Ser Tyr
20 25 30

Val Met His Trp Val Lys Gln Lys Pro Gly Gln Gly Leu Glu Trp Ile
35 40 45

Gly Tyr Ile Asn Pro Tyr Asn Asp Gly Thr Lys Tyr Asn Glu Lys Phe
50 55 60

Lys Gly Lys Ala Thr Leu Thr Ser Asp Lys Ser Ser Ser Thr Ala Tyr
65 70 75 80

Met Glu Leu Ser Ser Leu Thr Ser Glu Asp Ser Ala Val Tyr Tyr Cys
85 90 95

Ala Arg Gly Thr Tyr Tyr Tyr Gly Ser Arg Val Phe Asp Tyr Trp Gly
100 105 110

Gln Gly Thr Thr Leu Thr Val Ser Ser
115 120

<210> SEQ ID NO 87
<211> LENGTH: 239
<212> TYPE: PRT
<213> ORGANISM: Artificial Sequence
<220> FEATURE:
<223> OTHER INFORMATION: Synethetic Construct

<400> SEQUENCE: 87

Met Arg Cys Leu Ala Glu Phe Leu Gly Leu Leu Val Leu Trp Ile Pro
1 5 10 15

Gly Ala Ile Gly Asp Ile Val Met Thr Gln Ala Ala Pro Ser Ile Pro
20 25 30

Val Thr Pro Gly Glu Ser Val Ser Ile Ser Cys Arg Ser Ser Lys Ser
35 40 45

Leu Leu Asn Ser Asn Gly Asn Thr Tyr Leu Tyr Trp Phe Leu Gln Arg
50 55 60

Pro Gly Gln Ser Pro Gln Leu Leu Ile Tyr Arg Met Ser Asn Leu Ala
65 70 75 80

Ser Gly Val Pro Asp Arg Phe Ser Gly Ser Gly Ser Gly Thr Ala Phe
85 90 95

```
Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Ala Gly Thr Lys
        115                 120                 125

Leu Glu Leu Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235


<210> SEQ ID NO 88
<211> LENGTH: 115
<212> TYPE: PRT
<213> ORGANISM: Artificial Sequence
<220> FEATURE:
<223> OTHER INFORMATION: Synethetic Construct

<400> SEQUENCE: 88

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ala Asp
        115


<210> SEQ ID NO 89
<211> LENGTH: 116
<212> TYPE: PRT
<213> ORGANISM: Artificial Sequence
<220> FEATURE:
<223> OTHER INFORMATION: Synethetic Construct

<400> SEQUENCE: 89

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
            20                  25                  30
```

```
Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ser Asp Pro
        115


<210> SEQ ID NO 90
<211> LENGTH: 847
<212> TYPE: PRT
<213> ORGANISM: Artificial Sequence
<220> FEATURE:
<223> OTHER INFORMATION: Synethetic Construct

<400> SEQUENCE: 90

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270
```

```
Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Val Lys Phe
                325                 330                 335

Ser Arg Ser Ala Asp Ala Pro Ala Tyr Gln Gln Gly Gln Asn Gln Leu
            340                 345                 350

Tyr Asn Glu Leu Asn Leu Gly Arg Arg Glu Glu Tyr Asp Val Leu Asp
        355                 360                 365

Lys Arg Arg Gly Arg Asp Pro Glu Met Gly Gly Lys Pro Gln Arg Arg
    370                 375                 380

Lys Asn Pro Gln Glu Gly Leu Tyr Asn Glu Leu Gln Lys Asp Lys Met
385                 390                 395                 400

Ala Glu Ala Tyr Ser Glu Ile Gly Met Lys Gly Glu Arg Arg Arg Gly
                405                 410                 415

Lys Gly His Asp Gly Leu Tyr Gln Gly Leu Ser Thr Ala Thr Lys Asp
            420                 425                 430

Thr Tyr Asp Ala Leu His Met Gln Ala Leu Pro Pro Arg Gly Ser Gly
        435                 440                 445

Ala Thr Asn Phe Ser Leu Leu Lys Gln Ala Gly Asp Val Glu Glu Asn
    450                 455                 460

Pro Gly Pro Met Ala Leu Pro Val Thr Ala Leu Leu Leu Pro Leu Ala
465                 470                 475                 480

Leu Leu Leu His Ala Ala Arg Pro Gln Val Gln Leu Lys Glu Ser Gly
                485                 490                 495

Pro Gly Leu Val Lys Pro Ser Gln Ser Leu Ser Leu Thr Cys Ser Val
            500                 505                 510

Thr Gly Phe Ser Ile Thr Thr Gly Gly Tyr Trp Trp Thr Trp Ile Arg
        515                 520                 525

Gln Phe Pro Gly Gln Lys Leu Glu Trp Met Gly Tyr Ile Phe Ser Ser
    530                 535                 540

Gly Asn Thr Asn Tyr Asn Pro Ser Ile Lys Ser Arg Ile Ser Ile Thr
545                 550                 555                 560

Arg Asp Thr Ser Lys Asn Gln Phe Phe Leu Gln Leu Asn Ser Val Thr
                565                 570                 575

Thr Glu Gly Asp Thr Ala Arg Tyr Tyr Cys Ala Arg Ala Tyr Gly Lys
            580                 585                 590

Leu Gly Phe Asp Tyr Trp Gly Gln Gly Thr Leu Val Thr Val Ser Ser
        595                 600                 605

Gly Gly Gly Gly Ser Gly Gly Gly Gly Ser Gly Gly Gly Gly Ser Gln
    610                 615                 620

Pro Val Leu Thr Gln Ser Pro Ser Ala Ser Ala Ser Leu Gly Asn Ser
625                 630                 635                 640

Val Lys Ile Thr Cys Thr Leu Ser Ser Gln His Ser Thr Tyr Thr Ile
                645                 650                 655

Gly Trp Tyr Gln Gln His Pro Asp Lys Ala Pro Lys Tyr Val Met Tyr
            660                 665                 670

Val Asn Ser Asp Gly Ser His Ser Lys Gly Asp Gly Ile Pro Asp Arg
        675                 680                 685
```

```
Phe Ser Gly Ser Ser Ser Gly Ala His Arg Tyr Leu Ser Ile Ser Asn
    690                 695                 700

Ile Gln Pro Glu Asp Glu Ala Asp Tyr Phe Cys Gly Ser Ser Asp Ser
705                 710                 715                 720

Ser Gly Tyr Val Phe Gly Ser Gly Thr Gln Leu Thr Val Leu Arg Ala
                725                 730                 735

Thr Thr Thr Pro Ala Pro Arg Pro Pro Thr Pro Ala Pro Thr Ile Ala
            740                 745                 750

Ser Gln Pro Leu Ser Leu Arg Pro Glu Ala Cys Arg Pro Ala Ala Gly
        755                 760                 765

Gly Ala Val His Thr Arg Gly Leu Asp Phe Ala Cys Asp Ile Tyr Ile
    770                 775                 780

Trp Ala Pro Leu Ala Gly Thr Cys Gly Val Leu Leu Leu Ser Leu Val
785                 790                 795                 800

Ile Thr Leu Tyr Cys Lys Arg Gly Arg Lys Lys Leu Leu Tyr Ile Phe
                805                 810                 815

Lys Gln Pro Phe Met Arg Pro Val Gln Thr Thr Gln Glu Glu Asp Gly
            820                 825                 830

Cys Ser Cys Arg Phe Pro Glu Glu Glu Glu Gly Gly Cys Glu Leu
        835                 840                 845
```

```
<210> SEQ ID NO 91
<211> LENGTH: 2558
<212> TYPE: DNA
<213> ORGANISM: Artificial Sequence
<220> FEATURE:
<223> OTHER INFORMATION: Synethetic Construct

<400> SEQUENCE: 91

ccatggccct cccggtaacg gctctgctgc ttccactcgc actgctcttg catgctgcca     60

gaccagacat ccagatgaca cagacaacca gcagcctgtc cgcttccctc ggagacaggg    120

tgacaatttc ctgcagggcc agccaggaca tcagcaagta cctgaactgg taccagcaga    180

aacccgacgg caccgtcaag ctcctgatct accacaccag cagactgcac agcggagtgc    240

cttccaggtt cagcggcagc ggctccggca ccgattactc cctgaccatt agcaacttag    300

aacaggagga cattgccacc tacttttgtc agcagggcaa caccctcccc tacacctttg    360

gaggcggaac caagttagaa atcaccggcg gcggcggcag cggaggagga ggcagcggag    420

gcggaggctc cgaggtgaaa ctgcaggaga gcggccccgg actggtcgcc cctagccaat    480

ccctctccgt cacctgcacc gtgagcggag tgagcctgcc tgactacgga gtgagctgga    540

tcagacagcc ccctaggaaa ggactggaat ggctgggcgt gatttggggc agcgagacca    600

cctattacaa cagcgccctg aagtccagac tgacaatcat caaggacaat agcaaaagcc    660

aagtgtttct gaagatgaac agcctgcaga ccgatgacac cgccatctat tattgcgcca    720

agcactacta ctacggagga agctacgcta tggattattg gggccaaggc acaagcgtga    780

ccgtcagcag cacaacaaca cccgccccta gacccccctac ccctgccccc acaattgctt    840

cccagcctct gtccctgaga cccgaggctt gcagacctgc tgccggagga gctgtgcaca    900

ccagaggcct ggacttcgcc tgtgatatct atatctgggc ccccctcgcc ggaacatgcg    960

gagtgctgct gctgagcctg gtgatcacac tctactgccg ggtgaagttc agccggagcg   1020

ccgacgcccc cgcctaccag cagggccaga accagctgta caacgagctg aacctgggcc   1080

ggcgggagga gtacgacgtg ctggacaagc ggcggggccg ggaccccgag atgggcggca   1140

agccccagcg gcggaagaac ccccaggagg gcctgtacaa cgagctgcag aaggacaaga   1200
```

tggccgaggc ctacagcgag atcggcatga agggcgagcg gcggcggggc aagggccacg 1260
acggcctgta ccagggcctg agcaccgcca ccaaggacac ctacgacgcc ctgcacatgc 1320
aggccctgcc cccccggggc agcggcgcca ccaacttcag cctgctgaag caggccggcg 1380
acgtggagga gaaccccggc cccatggccc tcccggtaac ggctctgctg cttccactcg 1440
cactgctctt gcatgctgcc agaccacaag tccagctgaa agagtccggc cccggactgg 1500
tgaagcctag ccagtctctg tctctgacat gcagcgtgac cggcttcagc atcacaaccg 1560
gaggatattg gtggacatgg atcagacagt ttcccggcca gaaactggag tggatgggct 1620
acatcttcag cagcggcaac accaactaca accccagcat caagtctaga atcagcatca 1680
caagagacac cagcaagaac cagttctttc tgcagctgaa ctccgtcaca accgagggcg 1740
ataccgctag atattactgt gctagagcct acggcaagct gggctttgat tactggggcc 1800
aaggcacact ggtgacagtg agctccggag gaggaggaag cggaggcgga ggatccggag 1860
gaggcggaag ccaacccgtg ctgacccaga gccctagcgc tagcgcttct ctgggcaaca 1920
gcgtgaaaat cacatgcaca ctgagcagcc aacacagcac ctataccatc ggctggtatc 1980
agcagcaccc cgacaaggct cccaagtacg tgatgtacgt gaactccgac ggctcccact 2040
ccaaaggcga cggaatcccc gataggttca gcggcagcag ctccggagcc cacagatatc 2100
tgtccatcag caacatccag cccgaagacg aggctgacta cttttgcggc agctccgact 2160
cctccggcta cgtgttcggc agcggcacac aactgacagt gctgagagcg acaacaacac 2220
ccgcccctag accccctacc cctgccccca caattgcttc ccagcctctg tccctgagac 2280
ccgaggcttg cagacctgct gccggaggag ctgtgcacac cagaggcctg gacttcgcct 2340
gtgatatcta tatctgggcc cccctcgccg gaacatgcgg agtgctgctg ctgagcctgg 2400
tgatcacact ctactgcaag cggggccgga agaagctgct gtacatcttc aagcagccct 2460
tcatgcggcc cgtgcagacc acccaggagg aggacggctg cagctgccgg ttccccgagg 2520
aggaggaggg cggctgcgag ctgtaacagc cactcgag 2558

<210> SEQ ID NO 92
<211> LENGTH: 847
<212> TYPE: PRT
<213> ORGANISM: Artificial Sequence
<220> FEATURE:
<223> OTHER INFORMATION: Synethetic Construct

<400> SEQUENCE: 92

Met Ala Leu Pro Val Thr Ala Leu Leu Leu Pro Leu Ala Leu Leu Leu
1               5                   10                  15

His Ala Ala Arg Pro Gln Val Gln Leu Lys Glu Ser Gly Pro Gly Leu
            20                  25                  30

Val Lys Pro Ser Gln Ser Leu Ser Leu Thr Cys Ser Val Thr Gly Phe
        35                  40                  45

Ser Ile Thr Thr Gly Gly Tyr Trp Trp Thr Trp Ile Arg Gln Phe Pro
    50                  55                  60

Gly Gln Lys Leu Glu Trp Met Gly Tyr Ile Phe Ser Ser Gly Asn Thr
65                  70                  75                  80

Asn Tyr Asn Pro Ser Ile Lys Ser Arg Ile Ser Ile Thr Arg Asp Thr
                85                  90                  95

Ser Lys Asn Gln Phe Phe Leu Gln Leu Asn Ser Val Thr Thr Glu Gly
            100                 105                 110

```
Asp Thr Ala Arg Tyr Tyr Cys Ala Arg Ala Tyr Gly Lys Leu Gly Phe
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gln Pro Val Leu
145                 150                 155                 160

Thr Gln Ser Pro Ser Ala Ser Ala Ser Leu Gly Asn Ser Val Lys Ile
                165                 170                 175

Thr Cys Thr Leu Ser Ser Gln His Ser Thr Tyr Thr Ile Gly Trp Tyr
            180                 185                 190

Gln Gln His Pro Asp Lys Ala Pro Lys Tyr Val Met Tyr Val Asn Ser
        195                 200                 205

Asp Gly Ser His Ser Lys Gly Asp Gly Ile Pro Asp Arg Phe Ser Gly
    210                 215                 220

Ser Ser Ser Gly Ala His Arg Tyr Leu Ser Ile Ser Asn Ile Gln Pro
225                 230                 235                 240

Glu Asp Glu Ala Asp Tyr Phe Cys Gly Ser Ser Asp Ser Ser Gly Tyr
                245                 250                 255

Val Phe Gly Ser Gly Thr Gln Leu Thr Val Leu Arg Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Arg Val Lys Phe Ser Arg Ser Ala Asp Ala Pro Ala Tyr Gln
            340                 345                 350

Gln Gly Gln Asn Gln Leu Tyr Asn Glu Leu Asn Leu Gly Arg Arg Glu
        355                 360                 365

Glu Tyr Asp Val Leu Asp Lys Arg Arg Gly Arg Asp Pro Glu Met Gly
    370                 375                 380

Gly Lys Pro Gln Arg Arg Lys Asn Pro Gln Glu Gly Leu Tyr Asn Glu
385                 390                 395                 400

Leu Gln Lys Asp Lys Met Ala Glu Ala Tyr Ser Glu Ile Gly Met Lys
                405                 410                 415

Gly Glu Arg Arg Arg Gly Lys Gly His Asp Gly Leu Tyr Gln Gly Leu
            420                 425                 430

Ser Thr Ala Thr Lys Asp Thr Tyr Asp Ala Leu His Met Gln Ala Leu
        435                 440                 445

Pro Pro Arg Gly Ser Gly Ala Thr Asn Phe Ser Leu Leu Lys Gln Ala
    450                 455                 460

Gly Asp Val Glu Glu Asn Pro Gly Pro Met Ala Leu Pro Val Thr Ala
465                 470                 475                 480

Leu Leu Leu Pro Leu Ala Leu Leu Leu His Ala Ala Arg Pro Asp Ile
                485                 490                 495

Gln Met Thr Gln Thr Thr Ser Ser Leu Ser Ala Ser Leu Gly Asp Arg
            500                 505                 510

Val Thr Ile Ser Cys Arg Ala Ser Gln Asp Ile Ser Lys Tyr Leu Asn
        515                 520                 525
```

Trp Tyr Gln Gln Lys Pro Asp Gly Thr Val Lys Leu Leu Ile Tyr His
530 535 540

Thr Ser Arg Leu His Ser Gly Val Pro Ser Arg Phe Ser Gly Ser Gly
545 550 555 560

Ser Gly Thr Asp Tyr Ser Leu Thr Ile Ser Asn Leu Glu Gln Glu Asp
565 570 575

Ile Ala Thr Tyr Phe Cys Gln Gln Gly Asn Thr Leu Pro Tyr Thr Phe
580 585 590

Gly Gly Gly Thr Lys Leu Glu Ile Thr Gly Gly Gly Gly Ser Gly Gly
595 600 605

Gly Gly Ser Gly Gly Gly Gly Ser Glu Val Lys Leu Gln Glu Ser Gly
610 615 620

Pro Gly Leu Val Ala Pro Ser Gln Ser Leu Ser Val Thr Cys Thr Val
625 630 635 640

Ser Gly Val Ser Leu Pro Asp Tyr Gly Val Ser Trp Ile Arg Gln Pro
645 650 655

Pro Arg Lys Gly Leu Glu Trp Leu Gly Val Ile Trp Gly Ser Glu Thr
660 665 670

Thr Tyr Tyr Asn Ser Ala Leu Lys Ser Arg Leu Thr Ile Ile Lys Asp
675 680 685

Asn Ser Lys Ser Gln Val Phe Leu Lys Met Asn Ser Leu Gln Thr Asp
690 695 700

Asp Thr Ala Ile Tyr Tyr Cys Ala Lys His Tyr Tyr Tyr Gly Gly Ser
705 710 715 720

Tyr Ala Met Asp Tyr Trp Gly Gln Gly Thr Ser Val Thr Val Ser Ser
725 730 735

Thr Thr Thr Pro Ala Pro Arg Pro Pro Thr Pro Ala Pro Thr Ile Ala
740 745 750

Ser Gln Pro Leu Ser Leu Arg Pro Glu Ala Cys Arg Pro Ala Ala Gly
755 760 765

Gly Ala Val His Thr Arg Gly Leu Asp Phe Ala Cys Asp Ile Tyr Ile
770 775 780

Trp Ala Pro Leu Ala Gly Thr Cys Gly Val Leu Leu Leu Ser Leu Val
785 790 795 800

Ile Thr Leu Tyr Cys Lys Arg Gly Arg Lys Lys Leu Leu Tyr Ile Phe
805 810 815

Lys Gln Pro Phe Met Arg Pro Val Gln Thr Thr Gln Glu Glu Asp Gly
820 825 830

Cys Ser Cys Arg Phe Pro Glu Glu Glu Glu Gly Gly Cys Glu Leu
835 840 845

<210> SEQ ID NO 93
<211> LENGTH: 2558
<212> TYPE: DNA
<213> ORGANISM: Artificial Sequence
<220> FEATURE:
<223> OTHER INFORMATION: Synethetic Construct

<400> SEQUENCE: 93
ccatggccct cccggtaacg gctctgctgc ttccactcgc actgctcttg catgctgcca 60
gaccacaagt ccagctgaaa gagtccggcc ccggactggt gaagcctagc cagtctctgt 120
ctctgacatg cagcgtgacc ggcttcagca tcacaaccgg aggatattgg tggacatgga 180
tcagacagtt tcccggccag aaactggagt ggatgggcta catcttcagc agcggcaaca 240
ccaactacaa ccccagcatc aagtctagaa tcagcatcac aagagacacc agcaagaacc 300

```
agttctttct gcagctgaac tccgtcacaa ccgagggcga taccgctaga tattactgtg    360
ctagagccta cggcaagctg ggctttgatt actggggcca aggcacactg gtgacagtga    420
gctccggagg aggaggaagc ggaggcggag gatccggagg aggcggaagc caacccgtgc    480
tgacccagag ccctagcgct agcgcttctc tgggcaacag cgtgaaaatc acatgcacac    540
tgagcagcca acacagcacc tataccatcg gctggtatca gcagcacccc gacaaggctc    600
ccaagtacgt gatgtacgtg aactccgacg gctcccactc caaaggcgac ggaatccccg    660
ataggttcag cggcagcagc tccggagccc acagatatct gtccatcagc aacatccagc    720
ccgaagacga ggctgactac ttttgcggca gctccgactc ctccggctac gtgttcggca    780
gcggcacaca actgacagtg ctgagagcga caacaacacc cgcccctaga ccccctaccc    840
ctgcccccac aattgcttcc cagcctctgt ccctgagacc cgaggcttgc agacctgctg    900
ccggaggagc tgtgcacacc agaggcctgg acttcgcctg tgatatctat atctgggccc    960
ccctcgccgg aacatgcgga gtgctgctgc tgagcctggt gatcacactc tactgccggg   1020
tgaagttcag ccggagcgcc gacgcccccg cctaccagca gggccagaac cagctgtaca   1080
acgagctgaa cctgggccgg cgggaggagt acgacgtgct ggacaagcgg cggggccggg   1140
accccgagat gggcggcaag ccccagcggc ggaagaaccc ccaggagggc ctgtacaacg   1200
agctgcagaa ggacaagatg gccgaggcct acagcgagat cggcatgaag ggcgagcggc   1260
ggcggggcaa gggccacgac ggcctgtacc agggcctgag caccgccacc aaggacacct   1320
acgacgccct gcacatgcag gccctgcccc cccggggcag cggcgccacc aacttcagcc   1380
tgctgaagca ggccggcgac gtggaggaga accccggccc catggccctc ccggtaacgg   1440
ctctgctgct tccactcgca ctgctcttgc atgctgccag accagacatc cagatgacac   1500
agacaaccag cagcctgtcc gcttccctcg gagacagggt gacaatttcc tgcagggcca   1560
gccaggacat cagcaagtac ctgaactggt accagcagaa acccgacggc accgtcaagc   1620
tcctgatcta ccacaccagc agactgcaca gcggagtgcc ttccaggttc agcggcagcg   1680
gctccggcac cgattactcc ctgaccatta gcaacttaga acaggaggac attgccacct   1740
acttttgtca gcagggcaac accctcccct acacctttgg aggcggaacc aagttagaaa   1800
tcaccggcgg cggcggcagc ggaggaggag gcagcggagg cggaggctcc gaggtgaaac   1860
tgcaggagag cggccccgga ctggtcgccc ctagccaatc cctctccgtc acctgcaccg   1920
tgagcggagt gagcctgcct gactacggag tgagctggat cagacagccc cctaggaaag   1980
gactggaatg gctgggcgtg atttggggca gcgagaccac ctattacaac agcgccctga   2040
agtccagact gacaatcatc aaggacaata gcaaaagcca agtgtttctg aagatgaaca   2100
gcctgcagac cgatgacacc gccatctatt attgcgccaa gcactactac tacggaggaa   2160
gctacgctat ggattattgg ggccaaggca caagcgtgac cgtcagcagc acaacaacac   2220
ccgcccctag accccctacc cctgccccca caattgcttc ccagcctctg tccctgagac   2280
ccgaggcttg cagacctgct gccggaggag ctgtgcacac cagaggcctg gacttcgcct   2340
gtgatatcta tatctgggcc cccctcgccg gaacatgcgg agtgctgctg ctgagcctgg   2400
tgatcacact ctactgcaag cggggccgga agaagctgct gtacatcttc aagcagccct   2460
tcatgcggcc cgtgcagacc acccaggagg aggacggctg cagctgccgg ttccccgagg   2520
aggaggaggg cggctgcgag ctgtaacagc cactcgag                           2558
```

METHODS FOR TREATING CD83-EXPRESSING CANCER

CROSS-REFERENCE TO RELATED APPLICATIONS

This application is a U.S. National Stage patent application claiming priority to PCT/US2022/070539 fled Feb. 4, 2022, which claims benefit of U.S. Provisional Application No. 63/153,481, filed Feb. 25, 2021, and of U.S. Provisional Application No. 63/234,366, filed Aug. 18, 2021, which are hereby incorporated herein by reference in their entireties.

SEQUENCE LISTING

This application contains a sequence listing filed in electronic form as an ASCII.txt file entitled "320803-2600 Sequence Listing_ST25" created on Feb. 4, 2022, and having 148,998 bytes. The content of the sequence listing is incorporated herein in its entirety.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

SUMMARY

Chimeric antigen receptor (CAR) polypeptides are disclosed that can be used with adoptive cell transfer to target and kill CD83-expressing cancers. The disclosed CAR polypeptides contain in an ectodomain an anti-CD83 binding agent that can bind CD83-expressing cancer cells.

Also disclosed herein are dual-CAR systems to increase safety and/or efficacy of the CAR-T cells. In some embodiments, a second CAR polypeptide selectively binds a second antigen on the CD83-expressing cancer cells. For example, the first CAR polypeptide can contain in an ectodomain an antigen binding domain that can bind CD83 on cells (anti-CD83 agent). The second CAR polypeptide can contain in an ectodomain an antigen binding domain that can bind CD19 receptor on B cells (anti-CD19 agent).

Also disclosed herein are bicistornic CAR polypeptides having both a CD83 binding domain and a CD19 binding domain to increase safety and/or efficacy of the CAR-T cells.

In some embodiments, a dual CAR T cell disclosed herein can have incomplete endodomains and only function when both CARs bind their target. For example, one CAR can include only the CD3ζ domain, and the other CAR can include only the co-stimulatory domain(s). In these embodiments, dual CAR T cell activation requires co-expression and activation by binding to both targets. This is referred to herein as "and-gating." In other embodiments, the dual CAR T cell disclosed herein can be activated by binding either CD83 or CD19. This is referred to herein as "or-gating."

Also disclosed is an immune effector cell genetically modified to express the disclosed CAR polypeptide(s). In some embodiments, the immune effector cell can be selected from the group consisting of alpha-beta T cells, gamma-delta T cells, Natural Killer (NK) cells, Natural Killer T (NKT) cells, B cells, innate lymphoid cells (ILCs), cytokine induced killer (CIK) cells, cytotoxic T lymphocytes (CTLs), lymphokine activated killer (LAK) cells, and regulatory T cells (Tregs).

The anti-CD83 binding agent or anti-CD19 binding agent is in some embodiments an antibody fragment that specifically binds CD83 or CD19, respectively. For example, the antigen binding domain can be a Fab or a single-chain variable fragment (scFv) of an antibody that specifically binds CD83 or CD19. The binding agent is in some embodiments an aptamer that specifically binds CD83 or CD19. For example, the binding agent can be a peptide aptamer selected from a random sequence pool based on its ability to bind CD83 or CD19. The binding agent can also be a natural ligand of CD83 or CD19, or a variant and/or fragment thereof capable of binding CD83 or CD19.

As with other CARs, the disclosed polypeptides can also contain a transmembrane domain and an endodomain capable of activating an immune effector cell. For example, the endodomain can contain a signaling domain and one or more co-stimulatory signaling regions.

In some embodiments, the intracellular signaling domain is a CD3 zeta (CD3) signaling domain. In some embodiments, the costimulatory signaling region comprises the cytoplasmic domain of CD28, 4-1 BB, or a combination thereof. In some cases, the costimulatory signaling region contains 1, 2, 3, or 4 cytoplasmic domains of one or more intracellular signaling and/or costimulatory molecules. In some embodiments, the co-stimulatory signaling region contains one or more mutations in the cytoplasmic domains of CD28 and/or 4-1 BB that enhance signaling.

In some embodiments, the CAR polypeptide contains an incomplete endodomain. For example, the CAR polypeptide can contain only an intracellular signaling domain or a co-stimulatory domain, but not both. In these embodiments, the immune effector cell is not activated unless it and a second CAR polypeptide (or endogenous T-cell receptor) that contains the missing domain both bind their respective antigens. Therefore, in some embodiments, the CAR polypeptide contains a CD3 zeta (CD3) signaling domain but does not contain a costimulatory signaling region (CSR). In other embodiments, the CAR polypeptide contains the cytoplasmic domain of CD28, 4-1 BB, or a combination thereof, but does not contain a CD3 zeta (CD3ζ) signaling domain (SD).

Also disclosed are isolated nucleic acid sequences encoding the disclosed CAR polypeptides, vectors comprising these isolated nucleic acids, and immune effector cells containing these vectors. In some embodiments, the cell suppresses alloreactive and/or autoreactive donor cells, such as B cells, when the antigen binding domain of the CAR binds to CD83.

Also disclosed is a method of providing an anti-tumor immunity in a subject with a CD83-expressing cancer that involves administering to the subject an effective amount of an immune effector cell genetically modified with a disclosed CD83-specific CAR. In some cases, the cancer can be any CD83-expressing malignancy. In some cases, the cancer comprises a B and/or T cell acute lymphoblastic leukemia (ALL), Diffuse Large B cell Lymphoma (DLBCL), Follicular Lymphoma (FL), Marginal Zone Lymphoma (MZL), Chronic lymphocytic leukemia/Small lymphocytic lymphoma (CLL/SLL), Multiple myeloma (MM), Peripheral T cell lymphoma (PTCL), Cutaneous T cell lymphoma (CTCL), Burkitt Lymphoma, T cell lymphoma, or Multiple Myeloma.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a graph showing the frequency of CD19\CD83+ peripheral B cells from healthy donors versus marrow blasts from patients with B cell ALL (n=3). FIG. 1B shows representative contour plots. FIGS. 1C and 1D are histograms showing CD83 expression among human B lymphoblast cell lines Daudi (FIG. 1C) and Raji (FIG. 1D). *P<0.05.

FIG. 2A also demonstrates very low expression of CD83 among healthy circulating B cells.

FIG. 7D shows CD34+ cells isolated from normal human bone marrow co-incubated with CAR T cells, mock T cells, or media at a 10:1 effector-to-target ratio for 4 hours. Cells were plated in Methocult medium in duplicates and cultured for 14 days, followed by colony counts. Graphs show the number of total colonies from two independent donors. *P<0.05, P=0.001-0.01, *P=0.0001-0.001 and ****P<0.0001. NS=not significant.

FIGS. 8C and 8D are results of xCELLigence cytotoxicity assays showing CD83 CAR T significantly kill Nalm6 and Raji target cells. *P<0.05, P=0.001-0.01, *P=0.0001-0.001, and ****P<0.0001. NS=not significant.

FIG. 9A shows 'AND/OR' CD19/CD83 CAR T cell activation. *Potential synergy achieved with CD19+/CD83+ targets activating 'OR' gated CD19/CD83 CAR T. FIG. 9B contains contour plots showing the day 8 transduction efficiency of CD19, CD83, and 'OR' gated CD19/CD83 CAR T. FIG. 9**C shows CD19 versus CD83 expression on target Raji cells after overnight co-culture with CAR T cells (1:1).

FIGS. 10A and 10B contain xCELLigence cytotoxicity assays showing CD19/CD83 CAR T cytolytic potency against CD19 high and CD19 deficient Raji cell lines. FIGS. 10C to 10H care bar graphs (triplicate means±SD) showing cytokine production by untransduced (UT), CD19, CD83, or bispecific CAR T in response to (FIGS. 10C-10E) CD19 high or (FIG. 10F-10H) CD19 deficient Raji cells (Effector to target ratio 3:1). UT produced negligible cytokine. ****P<0.0001.

DETAILED DESCRIPTION

Figure 1B:
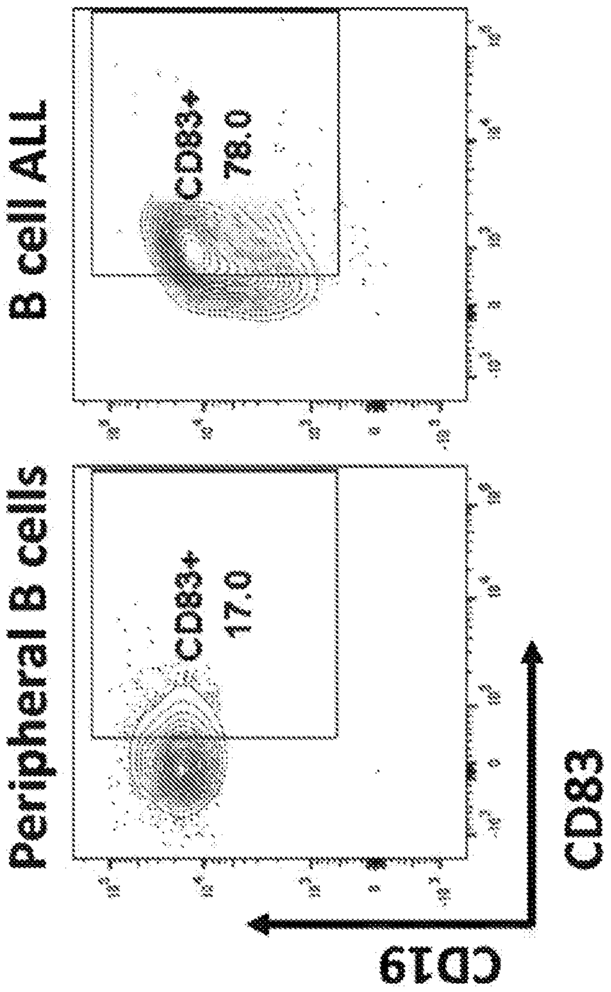
FIGS. 1A to 1D show CD83 is differentially expressed on B cell Acute Lymphoblastic Leukemia compared to healthy B cells.
Figure 1A:
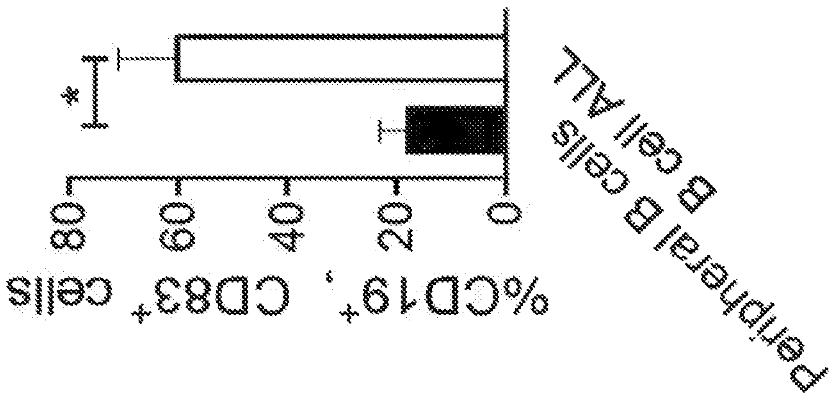
Figure 1C:
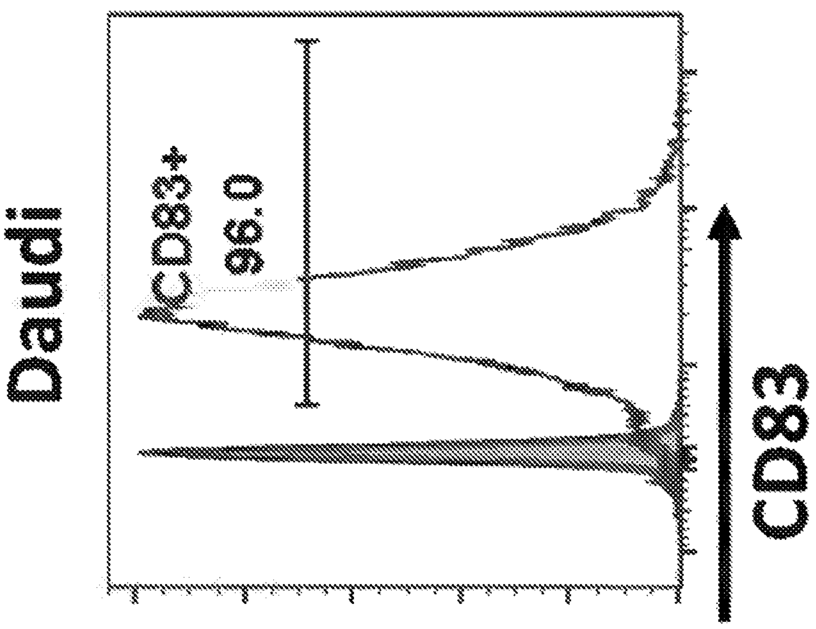
Figure 1D:
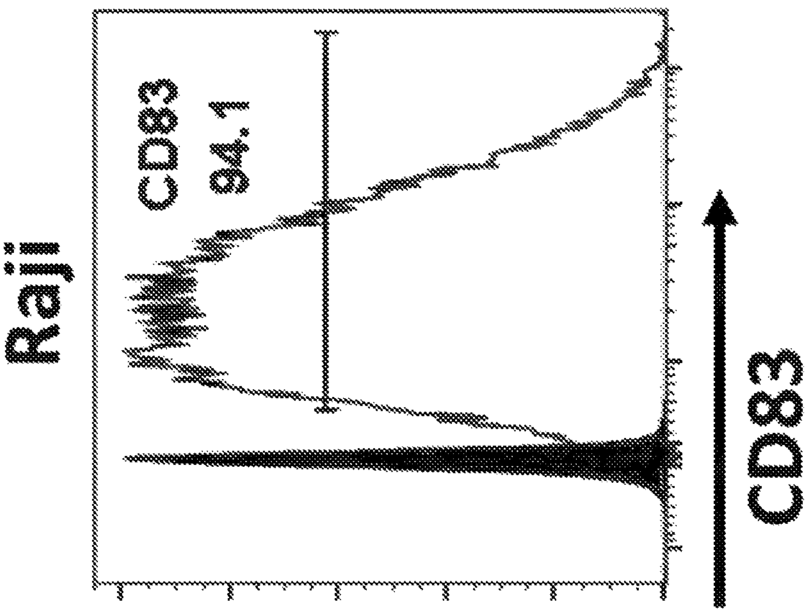

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "protein domain" refers to a portion of a protein, portions of a protein, or an entire protein showing structural integrity; this determination may be based on amino acid composition of a portion of a protein, portions of a protein, or the entire protein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

Chimeric Antigen Receptors (CARs)

CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). Disclosed herein is a CD83-specific chimeric antigen receptor (CAR) that can be that can be expressed in immune effector cells to suppress alloreactive donor cells.

The disclosed CAR is generally made up of three domains: an ectodomain, a transmembrane domain, and an endodomain. The ectodomain comprises the CD83-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and optionally a co-stimulatory signaling region (CSR).

A "signaling domain (SD)" generally contains immunoreceptor tyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a T-cell receptor) containing the missing domain also binds its respective antigen.

In some embodiments, the disclosed CAR is defined by the formula:

SP-CD83-HG-TM-CSR-SD; or

SP-CD83-HG-TM-SD-CSR;

wherein “SP” represents an optional signal peptide,
wherein “CD83” represents a CD83-binding region,
wherein “HG” represents an optional hinge domain,
wherein “TM” represents a transmembrane domain,
wherein “CSR” represents one or more co-stimulatory signaling regions,
wherein “SD” represents a signaling domain, and
wherein “-” represents a peptide bond or linker.

The anti-CD83 binding agent is in some embodiments an antibody fragment that specifically binds CD83. For example, the antigen binding domain can be a Fab or a single-chain variable fragment (scFv) of an antibody that specifically binds CD83. The anti-CD83 binding agent is in some embodiments an aptamer that specifically binds CD83. For example, the anti-CD83 binding agent can be a peptide aptamer selected from a random sequence pool based on its ability to bind CD83. The anti-CD83 binding agent can also be a natural ligand of CD83, or a variant and/or fragment thereof capable of binding CD83.

In some embodiments, the anti-CD83 scFv can comprise a variable heavy ($V_H$) domain having CDR1, CDR2 and CDR3 sequences and a variable light ($V_L$) domain having CDR1, CDR2 and CDR3 sequences.

For example, in some embodiments, the CDR1 sequence of the $V_H$ domain comprises the amino acid sequence GFSITTGGYWWT (SEQ ID NO:1), SDGIS (SEQ ID NO:7), or SNAMI (SEQ ID NO:13); CDR2 sequence of the $V_H$ domain comprises the amino acid sequence GYIFSSGNTNYNPSIKS (SEQ ID NO:2), IISSGGNTYYASWAKG (SEQ ID NO:8), or AMDSNSRTYYATWAKG (SEQ ID NO:14); CDR3 sequence of the $V_H$ domain comprises the amino acid sequence CARAYGKLGFDY (SEQ ID NO:3), VVGGTYSI (SEQ ID NO:9), or GDGGSSDYTEM (SEQ ID NO:15); CDR1 sequence of the $V_L$ comprises the amino acid sequence TLSSQHSTYTIG (SEQ ID NO:4), QSSQSVYNNDFLS (SEQ ID NO:10), or QSSQSVYGNNELS (SEQ ID NO:16); CDR2 sequence of the $V_L$ domain comprises the amino acid sequence VNSDGSHSKGD (SEQ ID NO:5), YASTLAS (SEQ ID NO:11), or QASSLAS (SEQ ID NO:17); and CDR3 sequence of the $V_L$ domain comprises the amino acid sequence GSSDSSGYV (SEQ ID NO:6), TGTYGNSAWYEDA (SEQ ID NO:12), or LGEYSISADNH (SEQ ID NO:18).

For example, in some embodiments, the CDR1 sequence of the $V_H$ domain comprises the amino acid sequence GFSITTGGYWWT (SEQ ID NO:1), CDR2 sequence of the $V_H$ domain comprises the amino acid sequence GYIFSSGNTNYNPSIKS (SEQ ID NO:2), CDR3 sequence of the $V_H$ domain comprises the amino acid sequence CARAYGKLGFDY (SEQ ID NO:3), CDR1 sequence of the $V_L$ comprises the amino acid sequence TLSSQHSTYTIG (SEQ ID NO:4), CDR2 sequence of the $V_L$ domain comprises the amino acid sequence VNSDGSHSKGD (SEQ ID NO:5), and CDR3 sequence of the $V_L$ domain comprises the amino acid sequence GSSDSSGYV (SEQ ID NO:6).

For example, in some embodiments, the CDR1 sequence of the $V_H$ domain comprises the amino acid sequence SDGIS (SEQ ID NO:7), CDR2 sequence of the $V_H$ domain comprises the amino acid sequence IISSGGNTYYASWAKG (SEQ ID NO:8), CDR3 sequence of the $V_H$ domain comprises the amino acid sequence VVGGTYSI (SEQ ID NO:9), CDR1 sequence of the $V_L$ comprises the amino acid sequence QSSQSVYNNDFLS (SEQ ID NO:10), CDR2 sequence of the $V_L$ domain comprises the amino acid sequence YASTLAS (SEQ ID NO:11), and CDR3 sequence of the $V_L$ domain comprises the amino acid sequence TGTYGNSAWYEDA (SEQ ID NO:12).

For example, in some embodiments, the CDR1 sequence of the $V_H$ domain comprises the amino acid sequence SNAMI (SEQ ID NO:13), CDR2 sequence of the $V_H$ domain comprises the amino acid sequence AMDSNSRTYYATWAKG (SEQ ID NO:14), CDR3 sequence of the $V_H$ domain comprises the amino acid sequence GDGGSSDYTEM (SEQ ID NO:15), CDR1 sequence of the $V_L$ comprises the amino acid sequence QSSQSVYGNNELS (SEQ ID NO:16), CDR2 sequence of the $V_L$ domain comprises the amino acid sequence QASSLAS (SEQ ID NO:17), and CDR3 sequence of the $V_L$ domain comprises the amino acid sequence LGEYSISADNH (SEQ ID NO:18).

In some embodiments, the anti-CD83 scFv $V_H$ domain comprises the amino acid sequence:

(SEQ ID NO: 19, VH-GBM00)

QVQLKESGPGLVKPSQSLSLTCSVTGFSITTGGYWWTWIRQFPGQKLEW

MGYIFSSGNTNYNPSIKSRISITRDTSKNQFFLQLNSVTTEGDTARYYC

ARAYGKLGFDYWGQGTLVTVSS.

In some embodiments, the anti-CD83 scFv $V_L$ domain comprises the amino acid sequence:

(SEQ ID NO: 20, VL-GBM00)

QPVLTQSPSASASLGNSVKITCTLSSQHSTYTIGWYQQHPDKAPKYVMY

VNSDGSHSKGDGIPDRFSGSSSGAHRYLSISNIQPEDEADYFCGSSDSS

GYVFGSGTQLTVL.

In some embodiments, the anti-CD83 scFv $V_H$ domain comprises the amino acid sequence:

(SEQ ID NO: 21, 20D04)

METGLRWLLLVAVLKGVQCQSVEESGGRLVTPGTPLTLTCTVSGFSLSN

NAINWVRQAPGKGLEWIGYIWSGGLTYYANWAEGRFTISKTSTTVDLKM

TSPTIEDTATYFCARGINNSALWGPGTLVTVSSGQPKAPSVFPLAPCCG

DTPSSTVTLGCLVKGYLPEPVTVTWNSGTLTNGVRTFPSVRQSSGLYSL

SSVVSVTSSSQPVTCNVAHPATNTKVDKTVAPSTCSKPTCPPPELLGGP

SVFIFPPKPKDTLMISRTPEVTCVVVDVSQDDPEVQFTWYINNEQVRTA

RPPLREQQFNSTIRVVSTLPIAHQDWLRGKEFKCKVHNKALPAPIEKTI

SKARGQPLEPKVYTMGPPREELSSRSVSLTCMINGFYPSDISVEWEKNG

KAEDNYKTTPAVLDSDGSYFLYNKLSVPTSEWQRGDVFTCSVMHEALHN

HYTQKSISRSPGK.

In some embodiments, the anti-CD83 scFv $V_L$ domain comprises the amino acid sequence:

(SEQ ID NO: 22, 20D04)
MDMRAPTQLLGLLLLWLPGARCADVVMTQTPASVSAAVGGTVTINCQAS
ESISNYLSWYQQKPGQPPKLLIYRTSTLASGVSSRFKGSGSGTEYTLTI
SGVQCDDVATYYCQCTSGGKFISDGAAFGGGTEVVVKGDPVAPTVLLFP
PSSDEVATGTVTIVCVANKYFPDVTVTWEVDGTTQTTGIENSKTPQNSA
DCTYNLSSTLTLTSTQYNSHKEYTCKVTQGTTSVVQSFSRKNC.

In some embodiments, the anti-CD83 scFv $V_H$ domain comprises the amino acid sequence:

(SEQ ID NO: 23, 11G05)
METGLRWLLLVAVLKGVQCQSVEESGGRLVTPGTPLTLTCTVSGFTISD
YDLSWVRQAPGEGLKYIGFIAIDGNPYYATWAKGRFTISKTSTTVDLKI
TAPTTEDTATYFCARGAGDLWGPGTLVTVSSGQPKAPSVFPLAPCCGDT
PSSTVTLGCLVKGYLPEPVTVTWNSGTLTNGVRTFPSVRQSSGLYSLSS
VVSVTSSSQPVTCNVAHPATNTKVDKTVAPSTCSKPTCPPPELLGGPSV
FIFPPKPKDTLMISRTPEVTCVVVDVSQDDPEVQFTWYINNEQVRTARP
PLREQQFNSTIRVVSTLPIAHQDWLRGKEFKCKVHNKALPAPIEKTISK
ARGQPLEPKVYTMGPPREELSSRSVSLTCMINGFYPSDISVEWEKNGKA
EDNYKTTPAVLDSDGSYFLYNKLSVPTSEWQRGDVFTCSVMHEALHNHY
TQKSISRSPGK.

In some embodiments, the anti-CD83 scFv $V_L$ domain comprises the amino acid sequence:

(SEQ ID NO: 24, 11G05)
MDTREPTQLLGLLLLWLPGARCADVVMTQTPASVSAAVGGTVTINCQSS
KNVYNNNWLSWFQQKPGQPPKLLIYYASTLASGVPSRFRGSGSGTQFTL
TISDVQCDDAATYYCAGDYSSSSDNGFGGGTEVVVKGDPVAPTVLLFPP
SSDEVATGTVTIVCVANKYFPDVTVTWEVDGTTQTTGIENSKTPQNSAD
CTYNLSSTLTLTSTQYNSHKEYTCKVTQGTTSVVQSFSRKNC.

In some embodiments, the anti-CD83 scFv $V_H$ domain comprises the amino acid sequence:

(SEQ ID NO: 25, 14C12)
METGLRWLLLVAVLKGVHCQSVEESGGRLVTPGTPLTLTCTASGFSRSS
YDMSWVRQAPGKGLEWVGVISTAYNSHYASWAKGRFTISRTSTTVDLKM
TSLTTEDTATYFCARGGSWLDLWGQGTLVTVSSGQPKAPSVFPLAPCCG
DTPSSTVTLGCLVKGYLPEPVTVTWNSGTLTNGVRTFPSVRQSSGLYSL
SSVVSVTSSSQPVTCNVAHPATNTKVDKTVAPSTCSKPTCPPPELLGGP
SVFIFPPKPKDTLMISRTPEVTCVVVDVSQDDPEVQFTWYINNEQVRTA
RPPLREQQFNSTIRVVSTLPIAHQDWLRGKEFKCKVHNKALPAPIEKTI
SKARGQPLEPKVYTMGPPREELSSRSVSLTCMINGFYPSDISVEWEKNG
KAEDNYKTTPAVLDSDGSYFLYNKLSVPTSEWQRGDVFTCSVMHEALHN
HYTQKSISRSPGK.

In some embodiments, the anti-CD83 scFv $V_L$ domain comprises the amino acid sequence:

(SEQ ID NO: 26, 14C12)
MDXRAPTQLLGLLLLWLPGARCALVMTQTPASVSAAVGGTVTINCQSSQ
SVYDNDELSWYQQKPGQPPKLLIYALASKLASGVPSRFKGSGSGTQFAL
TISGVQCDDAATYYCQATHYSSDWYLTFGGGTEVVVKGFPVAPTVLLFP
PSSDEVATGTVTIVCVANKYFPDVTVTWEVDGTTQTTGTENSKTPQNSA
DCTYNLSSTLTLTSTQYNSHKEYTCKVTQGTTSVVQSFSRKNC.

In some embodiments, the anti-CD83 scFv $V_H$ domain comprises the amino acid sequence:

(SEQ ID NO: 27, 020B08)
METGLRWLLLVAVLKGVQCQSVEESGGRLVTPGTPLTLTCTVSGFSLSS
YDMTWVRQAPGKGLEWIGIIYASGTTYYANWAKGRFTISKTSTTVDLKV
TSPTIGDTATYFCAREGAGVSMTLWGPGTLVTVSSGQPKAPSVFPLAPC
CGDTPSSTVTLGCLVKGYLPEPVTVTWNSGTLTNGVRTFPSVRQSSGLY
SLSSVVSVTSSSQPVTCNVAHPATNTKVDKTVAPSTCSKPTCPPPELLG
GPSVFIFPPKPKDTLMISRTPEVTCVVVDVSQDDPEVQFTWYINNEQVR
TARPPLREQQFNSTIRVVSTLPIAHQDWLRGKEFKCKVHNKALPAPIEK
TISKARGQPLEPKVYTMGPPREELSSRSVSLTCMINGFYPSDISVEWEK
NGKAEDNYKTTPAVLDSDGSYFLYNKLSVPTSEWQRGDVFTCSVMHEAL
HNHYTQKSISRSPGK.

In some embodiments, the anti-CD83 scFv $V_L$ domain comprises the amino acid sequence:

(SEQ ID NO: 28, 020B08)
MDMRAPTQLLGLLLLWLPGARCAYDMTQTPASVEVAVGGTVTIKCQASQ
SISTYLDWYQQKPGQPPKLLIYDASDLASGVPSRFKGSGSGTQFTLTIS
DLECADAATYYCQQGYTHSNVDNVFGGGTEVVVKGDPVAPTVLLFPPSS
DEVATGTVTIVCVANKYFPDVTVTWEVDGTTQTTGIENSKTPQNSADCT
YNLSSTLTLTSTQYNSHKEYTCKVTQGTTSVVQSFSRKNC

In some embodiments, the anti-CD83 scFv $V_H$ domain comprises the amino acid sequence:

(SEQ ID NO: 29, 006G05)
METGLRWLLLVAVLKGVQCQSVEESGGRLVSPGTPLTLTCTASGFSLSS
YDMSWVRQAPGKGLEYIGIISSSGSTYYASWAKGRFTISKTSTTVDLEV
TSLTTEDTATYFCSREHAGYSGDTGHLWGPGTLVTVSSGQPKAPSVFPL
APCCGDTPSSTVTLGCLVKGYLPEPVTVTWNSGTLTNGVRTFPSVRQSS
GLYSLSSVVSVTSSSQPVTCNVAHPATNTKVDKTVAPSTCSKPTCPPPE
LLGGPSVGIGPPKPKDTLMISRTPEVTCVVVDVSQDDPEVQFTWYINNE
QVRTARPPLREQQFNSTIRVVSTLPIAHQDWLRGKEFKCKVHNKALPAP
IEKTISKARGQPLEPKVYTMGPPREELSSRSVSLTCMINGFYPSDISVE
WEKNGKAEDNYKTTPAVLDSDGSYFLYNKLSVPTSEWQRGDVFTCSVMH
EALHNHYTQKSISRSPGK.

In some embodiments, the anti-CD83 scFv $V_L$ domain comprises the amino acid sequence:

(SEQ ID NO: 30, 006G05)

MDMRAPTQLLGLLLLWLPGARCAYDMTQTPASVEVAVGGTVAIKCQASQ

SVSSYLAWYQQKPGQPPKPLIYEASMLAAGVSSRFKGSGSGTDFTLTIS

DLECDDAATYYCQQGYSISDIDNAFGGGTEVVVKGDPVAPTVLLFPPSS

DEVATGTVTIVCVANKYFPDVTVTWEVDGTTQTTGIENSKTPQNSADCT

YNLSSTLTLTSTQYNSHKEYTCKVTQGTTSVVQSFSRKNC

In some embodiments, the anti-CD83 scFv $V_H$ domain comprises the amino acid sequence:

(SEQ ID NO: 31, 96G08)

METGLRWLLLVAVLKGVQCQSVEESGGRLVTPGTPLTLTCTVSGIDLSS

DGISWVRQAPGKGLEWIGIISSGGNTYYASWAKGRFTISRTSTTVDLKM

TSLTTEDTATYFCARVVGGTYSIWGQGTLVTVSSASTKGPSVYPLAPGS

AAQTNSMVTLGCLVKGYFPEPVTVTWNSGSLSSGVHTFPAVLQSDLYTL

SSSVTVPSSTWPSETVTCNVAHPASSTKVDKKIVPRDCGCKPCICTVPE

VSSVFIFPPKPDVLTITLTPKVTCVVVDISKDDPEVQFSWFVDDVEVHT

AQTQPREEQFNSTFRSVSELPIMHQDWLNGKEFKCRVNSAAFPAPIEKT

ISKTKGRPKAPQVYTIPPPKEQMAKDKVSLTCMITDFFPEDITVEWQWN

GQPAENYKNTQPIMDTDGSYFVYSKLNVQKSNWEAGNTFTCSVLHEGLH

NHHTEKSLSHSPGK.

In some embodiments, the anti-CD83 scFv $V_L$ domain comprises the amino acid sequence:

(SEQ ID NO: 32, 96G08)

MDTRAPTQLLGLLLLWLPGATFAQVLTQTASPVSAPVGGTVTINCQSSQ

SVYNNDFLSWYQQKPGQPPKLLIYYASTLASGVPSRFKGSGSGTQFTLT

ISDLECDDAATYYCTGTYGNSAWYEDAFGGGTEVVVKRTPVAPTVLLFP

PSSAELATGTATIVCVANKYFPDGTVTWKVDGITQSSGINNSRTPQNSA

DCTYNLSSTLTLSSDEYNSHDEYTCQVAQDSGSPVVQSFSRKSC

In some embodiments, the anti-CD83 scFv $V_H$ domain comprises the amino acid sequence:

(SEQ ID NO: 33, 95F04)

METGLRWLLLVAVLKGVQCQSVEESGGRLVTPGTPLTLTCTVSGIDLSS

NAMIWVRQAPREGLEWIGAMDSNSRTYYATWAKGRFTISRTSSITVDLK

ITSPTTEDTATYFCARGDGGSSDYTEMWGPGTLVTVSSASTKGPSVYPL

APGSAAQTNSMVTLGCLVKGYFPEPVTVTWNSGSLSSGVHTFPAVLQSD

LYTLSSSVTVPSSTWPSETVTCNVAHPASSTKVDKKIVPRDCGCKPCIC

TVPEVSSVFIFPPKPKDVLTITLTPKVTCVVVDISKDDPEVQFSWFVDD

VEVHTAQTQPREEQFNSTFRSVSELPIMHQDWLNGKEFKCRVNSAAFPA

PIEKTISKTKGRPKAPQVYTIPPPKEQMAKDKVSLTCMITDFFPEDITV

EWQWNGQPAENYKNTQPIMDTDGSYFVYSKLNVQKSNWEAGNTFTCSVL

HEGLHNHHTEKSLSHSPGK.

In some embodiments, the anti-CD83 scFv $V_L$ domain comprises the amino acid sequence:

(SEQ ID NO: 34, 95F04)

MDTRAPTQLLGLLLLWLPGATFAQAVVTQTTSPVSAPVGGTVTINCQSSQ

SVYGNNELSWYQQKPGQPPKLLIYQASSLASGVPSRFKGSGSGTQFTLTI

SDLECDDAATYYCLGEYSISADNHFGGGTEVVVKRTPVAPTVLLFPPSSA

ELATGTATIVCVANKYFPDGTVTWKVDGITQSSGINNSRTPQNSADCTYN

LSSTLTLSSDEYNSHDEYTCQVAQDSGSPVVQSFSRKSC

In some embodiments, the anti-CD83 scFv $V_H$ domain comprises the amino acid sequence:

(SEQ ID NO: 35)

QVQLVQSGGAVVQPGRSLRLSCAASGFTFSTYGMHWVRQAPGKGLEWVAA

VSYDGSNKYYADFVKGRFTISRDNPKNTLYLQMNSLRADDTAVYYCARRG

GLDIWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCAAA.

In some embodiments, the anti-CD83 scFv $V_L$ domain comprises the amino acid sequence:

(SEQ ID NO: 36)

LTQPPPASGTPGQQRVTISCSGSSSNIGSNTVNWYQQLPGTAPKLLIYYG

NDQRPSGVPDRFSASKSGTSASLAISGLQSEDEAHYYCAAWDGSLNGGVI

FGGGTKVTLG.

In some embodiments, the anti-CD83 scFv $V_L$ domain comprises the amino acid sequence:

(SEQ ID NO: 37)

VTQPPSASGTPGQRVTISCSGSSSNIGTNPVNWYQQLPGTAPKLLIYTTD

QRPSGVPDRFSGSKSGTSASLAISGLQSEDEADYYCAAWDDSLSGLYVFG

TGTKVTVLG.

In some embodiments, the anti-CD83 scFv $V_L$ domain comprises the amino acid sequence:

(SEQ ID NO: 38)

MTHTPLSLSVTPGQPASISCKSSQSLLHSDGKTYLYWYLQRPGQSPQPLI

YEVSNRFSGVPDRFSGSGSGTDFTLKISRVQAEDVGVYYCMQSLQLWTFG

QGTKVEIKR.

In some embodiments, the anti-CD83 scFv $V_L$ domain comprises the amino acid sequence:

(SEQ ID NO: 39)

MTQSPLSLPVTLGQPASISCRSSQSLIHSDGNTYLDWFQQRPGQSPRRLI

YKVSNRDSGVPDRFSGSGSGTDFTLRISRVEAEDIGVYYCMQATHWPRTF

GQGTKVEIKR.

In some embodiments, the anti-CD83 scFv $V_L$ domain comprises the amino acid sequence:

(SEQ ID NO: 40)
MTQSPLSLPVTLGQPASISCRSSQSLVDSAGNTFLHWFHQRPGQSPRRLI
YKVSNRDSGVPDRFSGSGSGTDFTLKISRVEAEDVGVYYCMQGTHWPRTF
GQGTKVEIKR.

In some embodiments, the anti-CD83 scFv $V_L$ domain comprises the amino acid sequence:

(SEQ ID NO: 41)
LTQSPLSLPVTLGQPASISCKSSQSLVDSDGNTYLNWFQQRPGQSPRRLI
YKVSNRDSGVPDRFSGSGSGTDFTLKISRVEAEDVGVYYCMQGTHWPRTF
GQGTKVEIKR.

In some embodiments, the anti-CD83 scFv $V_L$ domain comprises the amino acid sequence:

(SEQ ID NO: 42)
MTQSPLSLPVTLGQPASISCRSSQSLVHSDGNMYLNWFQQRPGQSPRRLI
YKVSNRDSGVPDRFSGSGSGTDFTLKISRVEAEDVGVYYCMQATQPTWTF
GQGTKLEIKR.

In some embodiments, the anti-CD83 scFv $V_L$ domain comprises the amino acid sequence:

(SEQ ID NO: 43)
MTQSPSSLSASVGDRVTITCQASQDISNYLNWYQQKPGKAPKLLIYDASN
LETGVPSRFSGSGSGTDFTFTISSATYYCQQTYQGTKLEIKR.

In some embodiments, the anti-CD83 scFv $V_L$ domain comprises the amino acid sequence:

(SEQ ID NO: 44)
MTQSPSSLSASVGHPVTITCRASQSLISYLNWYHQKPGKAPKLLIYAASI
LQSGVPSRFSGSGSGTDFTLTISSLQPENFASYYCQHTDSFPRTFGHGTK
VEIKR.

In some embodiments, the anti-CD83 scFv $V_L$ domain comprises the amino acid sequence:

(SEQ ID NO: 45)
LTQPPSASGTPGQGVTISCRGSTSNIGNNVVNWYQHVPGSAPKLLIWSNI
QRPSGIPDRFSGSKSGTSASLAISGLQSEDQAVYYCAVWDDGLAGWVFGG
GTTVTVLS.

In some embodiments, the anti-CD83 scFv $V_L$ domain comprises the amino acid sequence:

(SEQ ID NO: 46)
MTQAPVVSVALEQTVRITCQGDSLAIYYDFWYQHKPGQAPVLVIYGKNNR
PSGIPHRFSGSSSNTDSLTITGAQAEDEADYYCNSRDSSGNHWVFGGGTN
LTVLG.

In some embodiments, the anti-CD83 scFv $V_L$ domain comprises the amino acid sequence:

(SEQ ID NO: 47)
LTQSPLSLPVTLGQPASISCKSNQSLVHSDGNTYLNWFQQRPGQSPRRLI
YKVSNRDSGVPDRFSGSGSGTDFTLKINRVEAEDVGVYYCMQGTQWPRTF
GGQGTKLDIKR.

In some embodiments, the anti-CD83 scFv $V_H$ domain has been humanized and comprises the amino acid sequence:

(SEQ ID NO: 48, VH-GBM01)
QVQLQESGPGLVKPSETLSLTCTVSGFSITTGGYWWTWIRQPPGKGLEWI
GYIFSSGNTNYNPSIKSRVTISVDTSKNQFSLKLSSVTAADTAVYYCARA
YGKLGFDYWGQGTLVTVSS.

In some embodiments, the anti-CD83 scFv $V_H$ domain has been humanized and comprises the amino acid sequence:

(SEQ ID NO: 49, VH-GBM02)
QVQLQESGPGLVKPSQTLSLTCTVSGFSITTGGYWWTWIRQHPGKGLEW
IGYIFSSGNTNYNPSIKSLVTISVDTSKNQFSLKLSSVTAADTAVYYCA
RAYGKLGFDYWGQGTLVTVSS.

In some embodiments, the anti-CD83 scFv $V_H$ domain has been humanized and comprises the amino acid sequence:

(SEQ ID NO: 50, VH-GBM03)
QVQLQESGPGLVKPSQTLSLTCTVSGFSITTGGYWWTWIRQPPGKGLEW
IGYIFSSGNTNYNPSIKSRVTISVDTSKNQFSLKLSSVTAADTAVYYCA
RAYGKLGFDYWGQGTLVTVSS.

In some embodiments, the anti-CD83 scFv $V_H$ domain has been humanized and comprises the amino acid sequence:

(SEQ ID NO: 51, VH-GBM04)
QVQLQESGPGLVKPSETLSLTCTVSGFSITTGGYWWTWIRQPPGKGLEW
IGYIFSSGNTNYNPSIKSRVTISRDTSKNQFSLKLSSVTAADTAVYYCA
RAYGKLGFDYWGQGTLVTVSS.

In some embodiments, the anti-CD83 scFv $V_H$ domain has been humanized and comprises the amino acid sequence:

(SEQ ID NO: 52, VH-GBM05)
QVQLQESGPGLVKPSETLSLTCTVSGFSITTGGYWWTWIRQPPGKGLEW
IGYIFSSGNTNYNPSIKSRVTISVDTSKNQFSLKLSSVTAADTARYYCA
RAYGKLGFDYWGQGTLVTVSS.

In some embodiments, the anti-CD83 scFv $V_H$ domain has been humanized and comprises the amino acid sequence:

```
(SEQ ID NO: 53, VH-GBM06)
QVQLQESGPGLVKPSETLSLTCTVSGFSITTGGYWWTWIRQPPGKGLEW
IGYIFSSGNTNYNPSIKSRISITRDTSKNQFFLQLNSVTTEGDTARYYC
ARAYGKLGFDYWGQGTLVTVSS.
```

In some embodiments, the anti-CD83 scFv $V_L$ domain has been humanized and comprises the amino acid sequence:

```
(SEQ ID NO: 54, VL-GBM01)
QLVLTQSPSASASLGASVKLTCTLSSQHSTYTIGWHQQQPEKGPRYLMK
VNSDGSHSKGDGIPDRFSGSSSGAERYLTISSLQSEDEADYYCGSSDSS
GYVFGSGTKVTVL.
```

In some embodiments, the anti-CD83 scFv $V_L$ domain has been humanized and comprises the amino acid sequence:

```
(SEQ ID NO: 55, VL-GBM02)
LPVLTQPPSASALLGASIKLTCTLSSQHSTYTIGWYQQRPGRSPQYIMK
VNSDGSHSKGDGIPDRFMGSSSGADRYLTFSNLQSDDEAEYHCGSSDSS
GYVFGSGTKVTVL.
```

The heavy and light chains are preferably separated by a linker. Suitable linkers for scFv antibodies are known in the art. In some embodiments, the linker comprises the amino acid sequence GGGGSGGGGSGGGGS (SEQ ID NO:56).

In some embodiments, the anti-CD83 scFv comprises an amino acid sequence:

```
(SEQ ID NO: 57)
QPVLTQSPSASASLGNSVKITCTLSSQHSTYTIGWYQQHPDKAPKYVMY
VNSDGSHSKGDGIPDRFSGSSSGAHRYLSISNIQPEDEADYFCGSSDSS
GYVFGSGTQLTVLRAAASSGGGGSGGGGSGGGGSQPVLTQSPSASASLG
NSVKITCTLSSQHSTYTIGWYQQHPDKAPKYVMYVNSDGSHSKGDGIPD
RFSGSSSGAHRYLSISNIQPEDEADYFCGSSDSSGYVFGSGTQLTVLRA
AA.
```

In some embodiments, the anti-CD83 scFv comprises an amino acid sequence:

```
(SEQ ID NO: 58)
QVQLKESGPGLVKPSQSLSLTCSVTGFSITTGGYWWTWIRQFPGQKLEW
MGYIFSSGNTNYNPSIKSRISITRDTSKNQFFLQLNSVTTEGDTARYYC
ARAYGKLGFDYWGQGTLVTVSSGGGGSGGGGSGGGGSQVQLKESGPGLV
KPSQSLSLTCSVTGFSITTGGYWWTWIRQFPGQKLEWMGYIFSSGNTNY
NPSIKSRISITRDTSKNQFFLQLNSVTTEGDTARYYCARAYGKLGFDYW
GQGTLVTV.
```

In some embodiments, the anti-CD83 scFv comprises an amino acid sequence:

```
(SEQ ID NO: 59)
QVQLQESGPGLVKPSETLSLTCTVSGFSITTGGYWWTWIRQPPGKGLEW
IGYIFSSGNTNYNPSIKSRVTISVDTSKNQFSLKLSSVTAADTAVYYCA
RAYGKLGFDYWGQGTLVTVSSGGGGSGGGGSGGGGSQLVLTQSPSASAS
LGASVKLTCTLSSQHSTYTIGWHQQQPEKGPRYLMKVNSDGSHSKGDGI
PDRFSGSSSGAERYLTISSLQSEDEADYYCGSSDSSGYVFGSGTKVTV
L.
```

In some embodiments, the anti-CD83 scFv comprises an amino acid sequence:

```
(SEQ ID NO: 60)
QVQLQESGPGLVKPSQTLSLTCTVSGFSITTGGYWWTWIRQHPGKGLEW
IGYIFSSGNTNYNPSIKSLVTISVDTSKNQFSLKLSSVTAADTAVYYCA
RAYGKLGFDYWGQGTLVTVSSGGGGSGGGGSGGGGSQLVLTQSPSASAS
LGASVKLTCTLSSQHSTYTIGWHQQQPEKGPRYLMKVNSDGSHSKGDGI
PDRFSGSSSGAERYLTISSLQSEDEADYYCGSSDSSGYVFGSGTKVTV
L.
```

In some embodiments, the anti-CD83 scFv comprises an amino acid sequence:

```
(SEQ ID NO: 61)
QVQLQESGPGLVKPSQTLSLTCTVSGFSITTGGYWWTWIRQPPGKGLEW
IGYIFSSGNTNYNPSIKSRVTISVDTSKNQFSLKLSSVTAADTAVYYCA
RAYGKLGFDYWGQGTLVTVSSGGGGSGGGGSGGGGSQLVLTQSPSASAS
LGASVKLTCTLSSQHSTYTIGWHQQQPEKGPRYLMKVNSDGSHSKGDGI
PDRFSGSSSGAERYLTISSLQSEDEADYYCGSSDSSGYVFGSGTKVTV
L.
```

In some embodiments, the anti-CD83 scFv comprises an amino acid sequence:

```
(SEQ ID NO: 62)
QVQLQESGPGLVKPSETLSLTCTVSGFSITTGGYWWTWIRQPPGKGLEW
IGYIFSSGNTNYNPSIKSRVTISRDTSKNQFSLKLSSVTAADTAVYYCA
RAYGKLGFDYWGQGTLVTVSSGGGGSGGGGSGGGGSQLVLTQSPSASAS
LGASVKLTCTLSSQHSTYTIGWHQQQPEKGPRYLMKVNSDGSHSKGDGI
PDRFSGSSSGAERYLTISSLQSEDEADYYCGSSDSSGYVFGSGTKVTV
L.
```

In some embodiments, the anti-CD83 scFv comprises an amino acid sequence:

```
(SEQ ID NO: 63)
QVQLQESGPGLVKPSETLSLTCTVSGFSITTGGYWWTWIRQPPGKGLEW
IGYIFSSGNTNYNPSIKSRVTISVDTSKNQFSLKLSSVTAADTARYYCA
RAYGKLGFDYWGQGTLVTVSSGGGGSGGGGSGGGGSQLVLTQSPSASAS
```

-continued

LGASVKLTCTLSSQHSTYTIGWHQQQPEKGPRYLMKVNSDGSHSKGDGI
PDRFSGSSSGAERYLTISSLQSEDEADYYCGSSDSSGYVFGSGTKVTV
L.

In some embodiments, the anti-CD83 scFv comprises an amino acid sequence:

(SEQ ID NO: 64)
QVQLQESGPGLVKPSETLSLTCTVSGFSITTGGYWWTWIRQPPGKGLEW
IGYIFSSGNTNYNPSIKSRISITRDTSKNQFFLQLNSVTTEGDTARYYC
ARAYGKLGFDYWGQGTLVTVSSGGGGSGGGGSGGGGSQLVLTQSPSASA
SLGASVKLTCTLSSQHSTYTIGWHQQQPEKGPRYLMKVNSDGSHSKGDG
IPDRFSGSSSGAERYLTISSLQSEDEADYYCGSSDSSGYVFGSGTKVTV
L.

In some embodiments, the anti-CD83 scFv comprises an amino acid sequence:

(SEQ ID NO: 65)
QVQLQESGPGLVKPSETLSLTCTVSGFSITTGGYWWTWIRQPPGKGLEW
IGYIFSSGNTNYNPSIKSRVTISVDTSKNQFSLKLSSVTAADTAVYYCA
RAYGKLGFDYWGQGTLVTVSSGGGGSGGGGSGGGGSLPVLTQPPSASAL
LGASIKLTCTLSSQHSTYTIGWYQQRPGRSPQYIMKVNSDGSHSKGDGI
PDRFMGSSSGADRYLTFSNLQSDDEAEYHCGSSDSSGYVFGSGTKVTV
L.

In some embodiments, the anti-CD83 scFv comprises an amino acid sequence:

(SEQ ID NO: 66)
QVQLQESGPGLVKPSQTLSLTCTVSGFSITTGGYWWTWIRQHPGKGLEW
IGYIFSSGNTNYNPSIKSLVTISVDTSKNQFSLKLSSVTAADTAVYYCA
RAYGKLGFDYWGQGTLVTVSSGGGGSGGGGSGGGGSLPVLTQPPSASAL
LGASIKLTCTLSSQHSTYTIGWYQQRPGRSPQYIMKVNSDGSHSKGDGI
PDRFMGSSSGADRYLTFSNLQSDDEAEYHCGSSDSSGYVFGSGTKVTV
L.

In some embodiments, the anti-CD83 scFv comprises an amino acid sequence:

(SEQ ID NO: 67)
QVQLQESGPGLVKPSQTLSLTCTVSGFSITTGGYWWTWIRQPPGKGLEW
IGYIFSSGNTNYNPSIKSRVTISVDTSKNQFSLKLSSVTAADTAVYYCA
RAYGKLGFDYWGQGTLVTVSSGGGGSGGGGSGGGGSLPVLTQPPSASAL
LGASIKLTCTLSSQHSTYTIGWYQQRPGRSPQYIMKVNSDGSHSKGDGI
PDRFMGSSSGADRYLTFSNLQSDDEAEYHCGSSDSSGYVFGSGTKVTV
L.

In some embodiments, the anti-CD83 scFv comprises an amino acid sequence:

(SEQ ID NO: 68)
QVQLQESGPGLVKPSETLSLTCTVSGFSITTGGYWWTWIRQPPGKGLEW
IGYIFSSGNTNYNPSIKSRVTISRDTSKNQFSLKLSSVTAADTAVYYCA
RAYGKLGFDYWGQGTLVTVSSGGGGSGGGGSGGGGSLPVLTQPPSASAL
LGASIKLTCTLSSQHSTYTIGWYQQRPGRSPQYIMKVNSDGSHSKGDGI
PDRFMGSSSGADRYLTFSNLQSDDEAEYHCGSSDSSGYVFGSGTKVTV
L.

In some embodiments, the anti-CD83 scFv comprises an amino acid sequence:

(SEQ ID NO: 69)
QVQLQESGPGLVKPSETLSLTCTVSGFSITTGGYWWTWIRQPPGKGLEW
IGYIFSSGNTNYNPSIKSRVTISVDTSKNQFSLKLSSVTAADTARYYCA
RAYGKLGFDYWGQGTLVTVSSGGGGSGGGGSGGGGSLPVLTQPPSASAL
LGASIKLTCTLSSQHSTYTIGWYQQRPGRSPQYIMKVNSDGSHSKGDGI
PDRFMGSSSGADRYLTFSNLQSDDEAEYHCGSSDSSGYVFGSGTKVTV
L.

In some embodiments, the anti-CD83 scFv comprises an amino acid sequence:

(SEQ ID NO: 70)
QVQLQESGPGLVKPSETLSLTCTVSGFSITTGGYWWTWIRQPPGKGLEW
IGYIFSSGNTNYNPSIKSRISITRDTSKNQFFLQLNSVTTEGDTARYYC
ARAYGKLGFDYWGQGTLVTVSSGGGGSGGGGSGGGGSLPVLTQPPSASA
LLGASIKLTCTLSSQHSTYTIGWYQQRPGRSPQYIMKVNSDGSHSKGDG
IPDRFMGSSSGADRYLTFSNLQSDDEAEYHCGSSDSSGYVFGSGTKVTV
L.

In some embodiments, the anti-CD83 scFv comprises an amino acid sequence:

(SEQ ID NO: 71)
QVQLKESGPGLVKPSQSLSLTCSVTGFSITTGGYWWTWIRQFPGQKLEW
MGYIFSSGNTNYNPSIKSRISITRDTSKNQFFLQLNSVTTEGDTARYYC
ARAYGKLGFDYWGQGTLVTVSSGGGGGGGGSGGGGSQPVLTQSPSASAS
LGNSVKITCTLSSQHSTYTIGWYQQHPDKAPKYVMYVNSDGSHSKGDGI
PDRFSGSSSGAHRYLSISNIQPEDEADYFCGSSDSSGYVFGSGTQLTV
L.

Also disclosed herein are dual-CAR systems to increase safety and/or efficacy of the CAR-T cells. In some embodiments, a second CAR polypeptide selectively binds a second antigen on the CD83-expressing cancer cells. For example, the first CAR polypeptide can contain in an ectodomain an antigen binding domain that can bind CD83 on cells (anti-CD83 agent). In the case of B cell cancers, the second CAR polypeptide can contain in an ectodomain an antigen binding domain that can bind CD19 receptor on B cells (anti-CD19 agent).

Therefore, also disclosed herein is a CD19-specific CAR that can be that can be expressed in the disclosed CD83 CAR immune effector cells to target CD83-expressing cancer cells. For example, in some embodiments, the disclosed anti-CD19 CAR is defined by the formula:

SP-CD19-HG-TM-CSR-SD; or

SP-CD19-HG-TM-SD-CSR;

wherein "SP" represents an optional signal peptide,
wherein "CD19" represents a CD19-binding region,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

In some embodiments, a dual CAR T cell disclosed herein can have incomplete endodomains and only function when both CARs bind their target. For example, one CAR can include only the CD3ζ domain, and the other CAR can include only the co-stimulatory domain(s). In these embodiments, dual CAR T cell activation requires co-expression and activation by binding to both targets. This is referred to herein as "AND-gating." In other embodiments, the dual CAR T cell disclosed herein can be activated by binding either CD83 or CD19. This is referred to herein as "OR-gating."

The OR-gated CD19/CD83 bispecific CAR T is designed to eliminate B cell malignancies even after CD19 antigen loss occurs. The OR-gated CD19/CD83 CAR T could also provide synergistic potency against B cell lymphoma when both CD19 and CD83 are expressed concurrently. The AND-gated CD19/CD83 CAR T are designed to fully eliminate on-target/off-tumor toxicity, such as B cell aplasia Therefore, in some embodiments, the endodomain of each CAR contains an SD or a CSR, but not both. In these embodiments, an immune effector cell containing the disclosed CARs is only activated if both the anti-CD19 and anti-CD83 CARs bind their respective antigens. For example, in some embodiments, the disclosed anti-CD83 and anti-CD19 CARs are defined by the formulas:

SP-CD83-HG-TM-SD and SP-CD19-HG-TM-CSR;
or

SP-CD83-HG-TM-CSR and SP-CD19-HG-TM-SD;

wherein "SP" represents an optional signal peptide,
wherein "CD83" represents a CD83-binding region,
wherein "CD19" represents a CD19-binding region,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

In some embodiments, the anti-CD19 scFv can comprise a variable heavy ($V_H$) domain having CDR1, CDR2 and CDR3 sequences and a variable light ($V_L$) domain having CDR1, CDR2 and CDR3 sequences.

In some embodiments, the anti-CD19 scFv comprises an scFv described in US20160145337, which is incorporated by reference for the teaching of this antibody. For example, in some embodiments, the CDR1 sequence of the VH domain comprises the amino acid sequence SYWMN (SEQ ID NO:72), CDR2 sequence of the VH domain comprises the amino acid sequence QIWPGDGDTNYNGKFKG (SEQ ID NO:73), CDR3 sequence of the VH domain comprises the amino acid sequence RETTTVGRYYYAMDY (SEQ ID NO:74), CDR1 sequence of the VL comprises the amino acid sequence KASQSVDYDGDSYLN (SEQ ID NO:75), CDR2 sequence of the VL domain comprises the amino acid sequence DASNLVS (SEQ ID NO:76), and CDR3 sequence of the VL domain comprises the amino acid sequence QQSTEDPWT (SEQ ID NO:77). In some embodiments, the anti-CD19 scFv $V_H$ domain has been humanized and comprises the amino acid sequence: QVQLQESGAELVRPGSSVKISCKASGYAFSSYWMNWVKQRPGQGLEWIGQIWPG DGDTNYNGKFKGKATLTADESSSTAYMQLSSLRSEDSAVYSCARRETTTVGRYYY AMDYWGQGTTVTVSS (SEQ ID NO:78). In some embodiments, the anti-CD19 scFv $V_L$ domain has been humanized and comprises the amino acid sequence:

```
                                        (SEQ ID NO: 79)
DIQLTQSPASLAVSLGQRATISCKASQSVDYDGDSYLNWYQQIPGQPPK

LLIYDASNLVSGIPPRFSGSGSGTDFTLNIHPVEKVDAATYHCQQSTED

PWTFGGGTKLEIKR.
```

In some embodiments, the anti-CD19 scFv comprises an scFv described in WO2016168773, which is incorporated by reference for the teaching of this antibody. In some embodiments, the anti-CD19 scFv $V_H$ domain has been humanized and comprises the amino acid sequence: EVKLQESGPGLVAPSQSLSVTCTVSGVSLPDYGVSWIRQPPRKGLEWLGVIWGSE TTYYNSALKSRLTIIKDNSKSQVFLKMNSLQTDDTAIYYCAKHYYYGGSYAMDYWG QGTSVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSC (SEQ ID NO:80). In some embodiments, the anti-CD19 scFv $V_L$ domain has been humanized and comprises the amino acid sequence: DIQMTQTTSSLSASLGDRVTISCRASQDISKYLNWYQQKPDGTVKLLIYHTSRLHSG VPSRFSGSGSGTDYSLTISNLEQEDIATYFCQQGNTLPYTFGGGTKLEIKRTVAAPS VFIFPPSDEQLKSGTASVVCLLNNFYPREAKVQWKVDNALQSGNSQESVTEQDSG GGGSNYHLENEVARLKKLGGGGSDSTYSLSSTLTLSKADYEKHKVYACEVT (SEQ ID NO:81). In some embodiments, the anti-CD19 scFv $V_L$ domain has been humanized and comprises the amino acid sequence:

```
                                        (SEQ ID NO: 82)
EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSC.
```

In some embodiments, the anti-CD19 scFv comprises an scFv described in US20160039942, which is incorporated by reference for the teaching of this antibody. In some embodiments, the anti-CD19 scFv $V_H$ domain has been humanized and comprises the amino acid sequence: QVQLQQSGAELVRPGSSVKISCKASGYAFSSYWMNWVKQRPGQGLEWIGQIWPG DGDTNYNGKFKGKATLTADESSSTAYMQLSSLASED-SAVYFCARRETTTVGRYYY AMDYWGQGTTVTVSS (SEQ ID NO:83). In some embodiments, the anti-CD19 scFv $V_L$ domain has been humanized and comprises the amino acid sequence:

```
                                    (SEQ ID NO: 84)
DIQLTQSPASLAVSLGQRATISCKASQSVDYDGDSYLNWYQQIPGQPPK

LLIYDASNLVSGIPPRFSGSGSGTDFTLNIHPVEKVDAATYHCQQSTED

PWTFGGGTKLEIK.
```

In some embodiments, the anti-CD19 scFv comprises an scFv described in WO2014184143, which is incorporated by reference for the teaching of this antibody. In some embodiments, the anti-CD19 scFv $V_H$ domain has been humanized and comprises the amino acid sequence: MEWSWI-FLFLLSGTAGVHSEVQLQQSGPELIKPGASVKMSCK-ASGYTFTSYVMHW VKQKPGQGLEWIGY-INPYNDGTKYNEKFKGKATLTSDKSSSTAYMELSSL-TSEDSA VYYCARGTYYYGSRVFDYWGQGTTLTVS-SAKTTPPSVYPLAPGSAAQTNSMVTLG CLVKGYF-PEPVTVTWNSGSLSSGVHTFPAVLQSD-LYTLSSSVTVPSSTWPSETVTC NVAHPASSTKVDKKIVPRDCGCKPCICTVPE-VSSVFIFPPKPKDVLTITLTPKVTCVV VDISKDDPE-VQFSWFVDDVEVHTAQTQPREEQFN-STFRSVSELPIMHQDWLNGKE FKCRVNSAAFPAPIEKTISKTKGRPKAPQVY-TIPPPKEQMAKDKVSLTCMITDFFPED ITVEWQWNGQPAENYKNTQPIMDTDGSYFVYSK-LNVQKSNWEAGNTFTCSVLHEG LHNHHTEKSLSHSPGK (SEQ ID NO:85). In some embodiments, the anti-CD19 scFv $V_H$ domain has been humanized and comprises the amino acid sequence: EVQLQQSGPELIKPGASVKMSCKASGYTFT-SYVMHWVKQKPGQGLEWIGYINPYN DGT-KYNEKFKGKATLTSDKSSSTAYMELSSLTSEDSAVYY-CARGTYYYGSRVFDY WGQGTTLTVSS (SEQ ID NO:86). In some embodiments, the anti-CD19 scFv $V_L$ domain has been humanized and comprises the amino acid sequence: MRCLAEFLGLLVLWIPGAIGDIVMTQAAP-SIPVTPGESVSISCRSSKSLLNSNGNTYL YWFLQRPGQSPQLLIYRMSN-LASGVPDRFSGSGSGTAFTLRISRVEAEDVGVYYC MQHLEYPFTFGAGTKLELKRADAAPTVSIFPPSSE-QLTSGGASVVCFLNNFYPKDIN VKWKIDGSER-QNGVLNSWTDQDSKDSTYSMSSTLTLTKDEYERHN-SYTCEATHKT STSPIVKSFNRNEC (SEQ ID NO:87). In some embodiments, the anti-CD19 scFv $V_L$ domain has been humanized and comprises the amino acid sequence: DIVMTQAAPSIPVTPGESVSISCRSSKSLLNSNGNTY-LYWFLQRPGQSPQLLIYRMS NLASGVPDRFSGSGSGTAFTLRISRVEAE-DVGVYYCMQHLEYPFTFGAGTKLELKR AD (SEQ ID NO:88). In some embodiments, the anti-CD19 scFv $V_L$ domain has been humanized and comprises the amino acid sequence:

```
                                    (SEQ ID NO: 89)
DIVMTQAAPSIPVTPGESVSISCRSSKSLLNSNGNTYLYWFLQRPGQSP

QLLIYRMSNLASGVPDRFSGSGSGTAFTLRISRVEAEDVGVYYCMQHLE

YPFTFGAGTKLELKRSDP.
```

In some embodiments, the anti-CD19 scFv comprises an antigen binding domain of clone FMC63, described in Hohmann, A. W. Mol. Immunol. 34(16-17):1157-1165, which is incorporated by reference for the teaching of this antibody.

In some embodiments, the CAR is a CAR described in Nicholson et al., Molecular Immunology, 34(16-17): 1157-1165 (1997), which is incorporated by reference for the teaching of CARs containing FMC63 anti-CD19 scFvs.

In some embodiments, the CD19 scFv may comprise an amino acid sequence selected from the group consisting of any of SEQ ID NOs: 123-267 and 624.

In some embodiments, the anti-CD19 scFv comprises the FVS191 or FVS192 scFv describe in Bejcek B E, et al. Cancer Res. 1995 55(11):2346-51, which is incorporated by reference for the teaching of this antibody.

In some embodiments, the anti-CD19 scFv comprises an antigen binding domain of clone SJ25C1, B43, B4, AB1, BU12, F974A2, HD37, SJ25-C1, HIB19, or 4G7.

Also disclosed is a CAR polypeptide having a CD83 antigen binding domain, a CD19 antigen binding domain, a transmembrane domain, an intracellular signaling domain, and a co-stimulatory signaling region. In some embodiments, the CAR polypeptide has a loop configuration defined by the formula:

SP-CD19$V_L$-CD83$V_H$-CD83$V_L$-CD19$V_H$-HG-TM-SD,

SP-CD19$V_L$-CD83$V_L$-CD83$V_H$-CD19$V_H$-HG-TM-SD,

SP-CD19$V_H$-CD83$V_H$-CD83$V_L$-CD19$V_L$-HG-TM-SD,

SP-CD19$V_H$-CD83$V_L$-CD83$V_H$-CD19$V_L$-HG-TM-SD,

SP-CD83$V_L$-CD19$V_H$-CD19$V_L$-CD839$V_H$-HG-TM-SD,

SP-CD83$V_L$-CD19$V_L$-CD19$V_H$-CD83$V_H$-HG-TM-SD,

SP-CD83$V_H$-CD19$V_H$-CD19$V_L$-CD83$V_L$-HG-TM-SD,

SP-CD83$V_H$-CD19$V_L$-CD19$V_H$-CD83$V_L$-HG-TM-SD, wherein "SP" represents an optional signal peptide,
wherein "CD83$V_H$" represents a CD83$V_H$ domain,
wherein "CD83$V_L$" represents a CD83$V_L$ domain,
wherein "CD19$V_H$" represents a CD83$V_H$ domain,
wherein "CD19$V_L$" represents a CD83$V_L$ domain,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

In some embodiments, the CAR polypeptide has a tandem configuration defined by the formula:

SP-CD19$V_H$-CD19$V_L$-CD83$V_L$-CD83$V_H$-HG-TM-SD,

SP-CD19$V_H$-CD19$V_L$-CD83$V_H$-CD83$V_L$-HG-TM-SD,

SP-CD19$V_L$-CD19$V_H$-CD83$V_L$-CD83$V_H$-HG-TM-SD,

SP-CD19$V_L$-CD19$V_H$-CD83$V_H$-CD83$V_L$-HG-TM-SD,

SP-CD83$V_H$-CD83$V_L$-CD19$V_L$-CD19$V_H$-HG-TM-SD,

SP-CD83$V_H$-CD83$V_L$-CD19$V_H$-CD19$V_L$-HG-TM-SD,

SP-CD83$V_L$-CD83$V_H$-CD19$V_L$-CD19$V_H$-HG-TM-SD,

SP-CD83$V_L$-CD83$V_H$-CD19$V_H$-CD19$V_L$-HG-TM-SD, wherein "SP" represents an optional signal peptide, wherein "CD83$V_H$" represents a CD83$V_H$ domain, wherein "CD83$V_L$" represents a CD83$V_L$ domain, wherein "CD19$V_H$" represents a CD83$V_H$ domain, wherein "CD19$V_L$" represents a CD83$V_L$ domain, wherein "HG" represents an optional hinge domain, wherein "TM" represents a transmembrane domain, wherein "CSR" represents one or more co-stimulatory signaling regions, wherein "SD" represents a signaling domain, and wherein "-" represents a peptide bond or linker.

In some embodiments, the CAR polypeptide has the amino acid sequence:

malpvtalllplalllhaarpDIQMTQTTSSLSASLGDRVTISCRASQD
ISKYLNWYQQKPDGTVKLLIYHTSRLHSGVPSRFSGSGSGTDYSLTISN
LEQEDIATYFCQQGNTLPYTFGGGTKLEITGGGGSGGGGSGGGGSEVKL
QESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYG
GSYAMDYWGQGTSVTVSStttpaprpptpaptiasqplslrpeacrpaa
ggavhtrgldfacdiyiwaplagtcgvlllslvitlycRVKFSRSADAP
AYQQGQNQLYNELNLGRREEYDVLDKRRGRDPEMGGKPQRRKNPQEGLY
NELQKDKMAEAYSEIGMKGERRRGKGHDGLYQGLSTATKDTYDALHMQA
LPPRgsgatnfsllkqagdveenpgpMALPVTALLLPLALLLHAARPQV
QLKESGPGLVKPSQSLSLTCSVTGFSITTGGYWWTWIRQFPGQKLEWMG
YIFSSGNTNYNPSIKSRISITRDTSKNQFFLQLNSVTTEGDTARYYCAR
AYGKLGFDYWGQGTLVTVSSGGGGSGGGGSGGGGSQPVLTQSPSASASL
GNSVKITCTLSSQHSTYTIGWYQQHPDKAPKYVMYVNSDGSHSKGDGIP
DRFSGSSSGAHRYLSISNIQPEDEADYFCGSSDSSGYVFGSGTQLTVLR
Atttpaprpptpaptiasqplslrpeacrpaaggavhtrgldfacdiyi
waplagtcgvlllslvitlycKRGRKKLLYIFKQPFMRPVQTTQEEDGC
SCRFPEEEEGGCEL (SEQ ID NO: 90, hCD19CD3z-hCD83BB,
labeled as follows: cd8sp-HCD19SCFV-cd8tm&hinge-
CD3Z-p2a-CD8SP-HCD83SCFV-cd8tm&hinge-H41BB).

Therefore, in some embodiments, the CAR polypeptide is encoded by the nucleic acid sequence:

(SEQ ID NO: 91, hCD19CD3z-hCD83BB)
CCATGGCCCTCCCGGTAACGGCTCTGCTGCTTCCACTCGCACTGCTCTT
GCATGCTGCCAGACCAGACATCCAGATGACACAGACAACCAGCAGCCTG
TCCGCTTCCCTCGGAGACAGGGTGACAATTTCCTGCAGGGCCAGCCAGG
ACATCAGCAAGTACCTGAACTGGTACCAGCAGAAACCCGACGGCACCGT
CAAGCTCCTGATCTACCACACCAGCAGACTGCACAGCGGAGTGCCTTCC
AGGTTCAGCGGCAGCGGCTCCGGCACCGATTACTCCCTGACCATTAGCA
ACTTAGAACAGGAGGACATTGCCACCTACTTTTGTCAGCAGGGCAACAC
CCTCCCCTACACCTTTGGAGGCGGAACCAAGTTAGAAATCACCGGCGGC
GGCGGCAGCGGAGGAGGAGGCAGCGGAGGCGGAGGCTCCGAGGTGAAAC
TGCAGGAGAGCGGCCCCGGACTGGTCGCCCCTAGCCAATCCCTCTCCGT
CACCTGCACCGTGAGCGGAGTGAGCCTGCCTGACTACGGAGTGAGCTGG
ATCAGACAGCCCCCTAGGAAAGGACTGGAATGGCTGGGCGTGATTTGGG
GCAGCGAGACCACCTATTACAACAGCGCCCTGAAGTCCAGACTGACAAT
CATCAAGGACAATAGCAAAAGCCAAGTGTTTCTGAAGATGAACAGCCTG
CAGACCGATGACACCGCCATCTATTATTGCGCCAAGCACTACTACTACG
GAGGAAGCTACGCTATGGATTATTGGGGCCAAGGCACAAGCGTGACCGT
CAGCAGCACAACAACACCCGCCCCTAGACCCCCTACCCCTGCCCCCACA
ATTGCTTCCCAGCCTCTGTCCCTGAGACCCGAGGCTTGCAGACCTGCTG
CCGGAGGAGCTGTGCACACCAGAGGCCTGGACTTCGCCTGTGATATCTA
TATCTGGGCCCCCCTCGCCGGAACATGCGGAGTGCTGCTGCTGAGCCTG
GTGATCACACTCTACTGCCGGGTGAAGTTCAGCCGGAGCGCCGACGCCC
CCGCCTACCAGCAGGGCCAGAACCAGCTGTACAACGAGCTGAACCTGGG
CCGGCGGGAGGAGTACGACGTGCTGGACAAGCGGCGGGGCCGGGACCCC
GAGATGGGCGGCAAGCCCCAGCGGCGGAAGAACCCCCAGGAGGGCCTGT
ACAACGAGCTGCAGAAGGACAAGATGGCCGAGGCCTACAGCGAGATCGG
CATGAAGGGCGAGCGGCGGCGGGGCAAGGGCCACGACGGCCTGTACCAG
GGCCTGAGCACCGCCACCAAGGACACCTACGACGCCCTGCACATGCAGG
CCCTGCCCCCCCGGGGCAGCGGCGCCACCAACTTCAGCCTGCTGAAGCA
GGCCGGCGACGTGGAGGAGAACCCCGGCCCCATGGCCCTCCCGGTAACG
GCTCTGCTGCTTCCACTCGCACTGCTCTTGCATGCTGCCAGACCACAAG
TCCAGCTGAAAGAGTCCGGCCCCGGACTGGTGAAGCCTAGCCAGTCTCT
GTCTCTGACATGCAGCGTGACCGGCTTCAGCATCACAACCGGAGGATAT
TGGTGGACATGGATCAGACAGTTTCCCGGCCAGAAACTGGAGTGGATGG
GCTACATCTTCAGCAGCGGCAACACCAACTACAACCCCAGCATCAAGTC
TAGAATCAGCATCACAAGAGACACCAGCAAGAACCAGTTCTTTCTGCAG
CTGAACTCCGTCACAACCGAGGGCGATACCGCTAGATATTACTGTGCTA
GAGCCTACGGCAAGCTGGGCTTTGATTACTGGGGCCAAGGCACACTGGT
GACAGTGAGCTCCGGAGGAGGAGGAAGCGGAGGCGGAGGATCCGGAGGA

-continued

GGCGGAAGCCAACCCGTGCTGACCCAGAGCCCTAGCGCTAGCGCTTCTC
TGGGCAACAGCGTGAAAATCACATGCACACTGAGCAGCCAACACAGCAC
CTATACCATCGGCTGGTATCAGCAGCACCCCGACAAGGCTCCCAAGTAC
GTGATGTACGTGAACTCCGACGGCTCCCACTCCAAAGGCGACGGAATCC
CCGATAGGTTCAGCGGCAGCAGCTCCGGAGCCCACAGATATCTGTCCAT
CAGCAACATCCAGCCCGAAGACGAGGCTGACTACTTTTGCGGCAGCTCC
GACTCCTCCGGCTACGTGTTCGGCAGCGGCACACAACTGACAGTGCTGA
GAGCGACAACAACACCCGCCCCTAGACCCCCTACCCCTGCCCCCACAAT
TGCTTCCCAGCCTCTGTCCCTGAGACCCGAGGCTTGCAGACCTGCTGCC
GGAGGAGCTGTGCACACCAGAGGCCTGGACTTCGCCTGTGATATCTATA
TCTGGGCCCCCCTCGCCGGAACATGCGGAGTGCTGCTGCTGAGCCTGGT
GATCACACTCTACTGCAAGCGGGGCCGGAAGAAGCTGCTGTACATCTTC
AAGCAGCCCTTCATGCGGCCCGTGCAGACCACCCAGGAGGAGGACGGCT
GCAGCTGCCGGTTCCCCGAGGAGGAGGAGGGCGGCTGCGAGCTGTAACA
GCCACTCGAG.

In some embodiments, the CAR polypeptide has the amino acid sequence:

malpvtalllplalllhaarp**QVQLKESGPGLVKPSQSLSLTCSVTGFS
ITTGGYWWTWIRQFPGQKLEWMGYIFSSGNTNYNPSIKSRISITRDTSK
NQFFLQLNSVTTEGDTARYYCARAYGKLGFDYWGQGTLVTVSSGGGGSG
GGGSGGGGSQPVLTQSPSASASLGNSVKITCTLSSQHSTYTIGWYQQHP
DKAPKYVMYVNSDGSHSKGDGIPDRFSGSSSGAHRYLSISNIQPEDEAD
YFCGSSDSSGYVFGSGTQLTVLRA**tttpaprpptpaptiasqplslrpe
acrpaaggavhtrgldfacdiyiwaplagtcgvlllslvitlycRVKFS
RSADAPAYQQGQNQLYNELNLGRREEYDVLDKRRGRDPEMGGKPQRRKN
PQEGLYNELQKDKMAEAYSEIGMKGERRRGKGHDGLYQGLSTATKDTYD
ALHMQALPPRgsgatnfsllkqagdveenpgpMALPVTALLLPLALLLH
AARP**DIQMTQTTSSLSASLGDRVTISCRASQDISKYLNWYQQKPDGTVK
LLIYHTSRLHSGVPSRFSGSGSGTDYSLTISNLEQEDIATYFCQQGNTL
PYTFGGGTKLEITGGGGSGGGGSGGGGSEVKLQESGPGLVAPSQSLSVT
CTVSGVSLPDYGVSWIRQPPRKGLEWLGVIWGSETTYYNSALKSRLTII
KDNSKSQVFLKMNSLQTDDTAIYYCAKHYYYGGSYAMDYWGQGTSVTVS
S**tttpaprpptpaptiasqplslrpeacrpaaggavhtrgldfacdiyi
waplagtcgvlllslvitlycKRGRKKLLYIFKQPFMRPVQTTQEEDGC
SCRFPEEEEGGCEL (SEQ ID NO: 92, hCD83CD3z-hCD19BB, labeled as follows: cd8sp-HCD83SCFV-cd8tm&hinge-CD3Z-p2a-CD8SP-HCD19SCFV-cd8tm&hinge-H41BB).

Therefore, in some embodiments, the CAR polypeptide is encoded by the nucleic acid sequence:

(SEQ ID NO: 93, hCD83CD3z-hCD19BB)

CCATGGCCCTCCCGGTAACGGCTCTGCTGCTTCCACTCGCACTGCTCTT
GCATGCTGCCAGACCACAAGTCCAGCTGAAAGAGTCCGGCCCCGGACTG
GTGAAGCCTAGCCAGTCTCTGTCTCTGACATGCAGCGTGACCGGCTTCA
GCATCACAACCGGAGGATATTGGTGGACATGGATCAGACAGTTTCCCGG
CCAGAAACTGGAGTGGATGGGCTACATCTTCAGCAGCGGCAACACCAAC
TACAACCCCAGCATCAAGTCTAGAATCAGCATCACAAGAGACACCAGCA
AGAACCAGTTCTTTCTGCAGCTGAACTCCGTCACAACCGAGGGCGATAC
CGCTAGATATTACTGTGCTAGAGCCTACGGCAAGCTGGGCTTTGATTAC
TGGGGCCAAGGCACACTGGTGACAGTGAGCTCCGGAGGAGGAGGAAGCG
GAGGCGGAGGATCCGGAGGAGGCGGAAGCCAACCCGTGCTGACCCAGAG
CCCTAGCGCTAGCGCTTCTCTGGGCAACAGCGTGAAAATCACATGCACA
CTGAGCAGCCAACACAGCACCTATACCATCGGCTGGTATCAGCAGCACC
CCGACAAGGCTCCCAAGTACGTGATGTACGTGAACTCCGACGGCTCCCA
CTCCAAAGGCGACGGAATCCCCGATAGGTTCAGCGGCAGCAGCTCCGGA
GCCCACAGATATCTGTCCATCAGCAACATCCAGCCCGAAGACGAGGCTG
ACTACTTTTGCGGCAGCTCCGACTCCTCCGGCTACGTGTTCGGCAGCGG
CACACAACTGACAGTGCTGAGAGCGACAACAACACCCGCCCCTAGACCC
CCTACCCCTGCCCCCACAATTGCTTCCCAGCCTCTGTCCCTGAGACCCG
AGGCTTGCAGACCTGCTGCCGGAGGAGCTGTGCACACCAGAGGCCTGGA
CTTCGCCTGTGATATCTATATCTGGGCCCCCCTCGCCGGAACATGCGGA
GTGCTGCTGCTGAGCCTGGTGATCACACTCTACTGCCGGGTGAAGTTCA
GCCGGAGCGCCGACGCCCCCGCCTACCAGCAGGGCCAGAACCAGCTGTA
CAACGAGCTGAACCTGGGCCGGGGGGAGGAGTACGACGTGCTGGACAAG
CGGCGGGGCCGGGACCCCGAGATGGGCGGCAAGCCCCAGCGGCGGAAGA
ACCCCCAGGAGGGCCTGTACAACGAGCTGCAGAAGGACAAGATGGCCGA
GGCCTACAGCGAGATCGGCATGAAGGGCGAGCGGCGGCGGGGCAAGGGC
CACGACGGCCTGTACCAGGGCCTGAGCACCGCCACCAAGGACACCTACG
ACGCCCTGCACATGCAGGCCCTGCCCCCCCGGGGCAGCGGCGCCACCAA
CTTCAGCCTGCTGAAGCAGGCCGGCGACGTGGAGGAGAACCCCGGCCCC
ATGGCCCTCCCGGTAACGGCTCTGCTGCTTCCACTCGCACTGCTCTTGC
ATGCTGCCAGACCAGACATCCAGATGACACAGACAACCAGCAGCCTGTC
CGCTTCCCTCGGAGACAGGGTGACAATTTCCTGCAGGGCCAGCCAGGAC
ATCAGCAAGTACCTGAACTGGTACCAGCAGAAACCCGACGGCACCGTCA
AGCTCCTGATCTACCACACCAGCAGACTGCACAGCGGAGTGCCTTCCAG
GTTCAGCGGCAGCGGCTCCGGCACCGATTACTCCCTGACCATTAGCAAC
TTAGAACAGGAGGACATTGCCACCTACTTTTGTCAGCAGGGCAACACCC
TCCCCTACACCTTTGGAGGCGGAACCAAGTTAGAAATCACCGGCGGCGG
CGGCAGCGGAGGAGGAGGCAGCGGAGGCGGAGGCTCCGAGGTGAAACTG

-continued

```
CAGGAGAGCGGCCCCGGACTGGTCGCCCCTAGCCAATCCCTCTCCGTCA

CCTGCACCGTGAGCGGAGTGAGCCTGCCTGACTACGGAGTGAGCTGGAT

CAGACAGCCCCCTAGGAAAGGACTGGAATGGCTGGGCGTGATTTGGGGC

AGCGAGACCACCTATTACAACAGCGCCCTGAAGTCCAGACTGACAATCA

TCAAGGACAATAGCAAAAGCCAAGTGTTTCTGAAGATGAACAGCCTGCA

GACCGATGACACCGCCATCTATTATTGCGCCAAGCACTACTACTACGGA

GGAAGCTACGCTATGGATTATTGGGGCCAAGGCACAAGCGTGACCGTCA

GCAGCACAACAACACCCGCCCCTAGACCCCCTACCCCTGCCCCCACAAT

TGCTTCCCAGCCTCTGTCCCTGAGACCCGAGGCTTGCAGACCTGCTGCC

GGAGGAGCTGTGCACACCAGAGGCCTGGACTTCGCCTGTGATATCTATA

TCTGGGCCCCCCTCGCCGGAACATGCGGAGTGCTGCTGCTGAGCCTGGT

GATCACACTCTACTGCAAGCGGGGCCGGAAGAAGCTGCTGTACATCTTC

AAGCAGCCCTTCATGCGGCCCGTGCAGACCACCCAGGAGGAGGACGGCT

GCAGCTGCCGGTTCCCCGAGGAGGAGGAGGGCGGCTGCGAGCTGTAACA

GCCACTCGAG.
```

As with other CARs, the disclosed polypeptides can also contain a transmembrane domain and an endodomain capable of activating an immune effector cell. For example, the endodomain can contain a signaling domain and one or more co-stimulatory signaling regions.

In some embodiments, the intracellular signaling domain is a CD3 zeta (CD3ζ) signaling domain. In some embodiments, the costimulatory signaling region comprises the cytoplasmic domain of CD28, 4-1 BB, or a combination thereof. In some cases, the costimulatory signaling region contains 1, 2, 3, or 4 cytoplasmic domains of one or more intracellular signaling and/or costimulatory molecules. In some embodiments, the co-stimulatory signaling region contains one or more mutations in the cytoplasmic domains of CD28 and/or 4-1 BB that enhance signaling.

In some embodiments, the CAR polypeptide contains an incomplete endodomain. For example, the CAR polypeptide can contain only an intracellular signaling domain or a co-stimulatory domain, but not both. In these embodiments, the immune effector cell is not activated unless it and a second CAR polypeptide (or endogenous T-cell receptor) that contains the missing domain both bind their respective antigens. Therefore, in some embodiments, the CAR polypeptide contains a CD3 zeta (CD3ζ) signaling domain but does not contain a costimulatory signaling region (CSR). In other embodiments, the CAR polypeptide contains the cytoplasmic domain of CD28, 4-1 BB, or a combination thereof, but does not contain a CD3 zeta (CD3ζ) signaling domain (SD).

Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell suppresses alloreactive donor cells, such as T cells, when the antigen binding domain of the CAR binds to CD83.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD123, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-CD83 scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1, 2, and 3 below provide some example combinations of CD83-binding region, co-stimulatory signaling regions, and intracellular signaling domain that can occur in the disclosed CARs.

TABLE 1

| First Generation CARs | |
|---|---|
| ScFv | Signal Domain |
| CD83 | CD8 |
| CD83 | CD3ζ |
| CD83 | CD3δ |
| CD83 | CD3γ |
| CD83 | CD3ε |
| CD83 | FcγRI-γ |
| CD83 | FcγRIII-γ |
| CD83 | FcεRIβ |
| CD83 | FcεRIγ |
| CD83 | DAP10 |
| CD83 | DAP12 |
| CD83 | CD32 |
| CD83 | CD79a |

TABLE 2

| Second Generation CARs | | |
|---|---|---|
| ScFv | Co-stimulatory Signal | Signal Domain |
| CD83 | CD28 | CD8 |
| CD83 | CD28 | CD3ζ |
| CD83 | CD28 | CD3δ |
| CD83 | CD28 | CD3γ |
| CD83 | CD28 | CD3ε |
| CD83 | CD28 | FcγRI-γ |
| CD83 | CD28 | FcγRIII-γ |
| CD83 | CD28 | FcεRIβ |
| CD83 | CD28 | FcεRIγ |
| CD83 | CD28 | DAP10 |
| CD83 | CD28 | DAP12 |
| CD83 | CD28 | CD32 |
| CD83 | CD28 | CD79a |
| CD83 | CD28 | CD79b |
| CD83 | CD8 | CD8 |
| CD83 | CD8 | CD3ζ |
| CD83 | CD8 | CD3δ |
| CD83 | CD8 | CD3γ |
| CD83 | CD8 | CD3ε |
| CD83 | CD8 | FcγRI-γ |
| CD83 | CD8 | FcγRIII-γ |
| CD83 | CD8 | FcεRIβ |
| CD83 | CD8 | FcεRIγ |
| CD83 | CD8 | DAP10 |
| CD83 | CD8 | DAP12 |
| CD83 | CD8 | CD32 |
| CD83 | CD8 | CD79a |
| CD83 | CD8 | CD79b |
| CD83 | CD4 | CD8 |
| CD83 | CD4 | CD3ζ |
| CD83 | CD4 | CD3δ |
| CD83 | CD4 | CD3γ |
| CD83 | CD4 | CD3ε |
| CD83 | CD4 | FcγRI-γ |
| CD83 | CD4 | FcγRIII-γ |
| CD83 | CD4 | FcεRIβ |
| CD83 | CD4 | FcεRIγ |
| CD83 | CD4 | DAP10 |
| CD83 | CD4 | DAP12 |
| CD83 | CD4 | CD32 |
| CD83 | CD4 | CD79a |
| CD83 | CD4 | CD79b |
| CD83 | b2c | CD8 |
| CD83 | b2c | CD3ζ |
| CD83 | b2c | CD3δ |
| CD83 | b2c | CD3γ |
| CD83 | b2c | CD3ε |
| CD83 | b2c | FcγRI-γ |
| CD83 | b2c | FcγRIII-γ |
| CD83 | b2c | FcεRIβ |
| CD83 | b2c | FcεRIγ |
| CD83 | b2c | DAP10 |
| CD83 | b2c | DAP12 |
| CD83 | b2c | CD32 |
| CD83 | b2c | CD79a |
| CD83 | b2c | CD79b |
| CD83 | CD137/41BB | CD8 |
| CD83 | CD137/41BB | CD3ζ |
| CD83 | CD137/41BB | CD3δ |
| CD83 | CD137/41BB | CD3γ |
| CD83 | CD137/41BB | CD3ε |
| CD83 | CD137/41BB | FcγRI-γ |
| CD83 | CD137/41BB | FcγRIII-γ |
| CD83 | CD137/41BB | FcεRIβ |
| CD83 | CD137/41BB | FcεRIγ |
| CD83 | CD137/41BB | DAP10 |
| CD83 | CD137/41BB | DAP12 |
| CD83 | CD137/41BB | CD32 |
| CD83 | CD137/41BB | CD79a |
| CD83 | CD137/41BB | CD79b |
| CD83 | ICOS | CD8 |
| CD83 | ICOS | CD3ζ |
| CD83 | ICOS | CD3δ |
| CD83 | ICOS | CD3γ |
| CD83 | ICOS | CD3ε |

TABLE 2-continued

| Second Generation CARs | | |
|---|---|---|
| ScFv | Co-stimulatory Signal | Signal Domain |
| CD83 | ICOS | FcγRI-γ |
| CD83 | ICOS | FcγRIII-γ |
| CD83 | ICOS | FcεRIβ |
| CD83 | ICOS | FcεRIγ |
| CD83 | ICOS | DAP10 |
| CD83 | ICOS | DAP12 |
| CD83 | ICOS | CD32 |
| CD83 | ICOS | CD79a |
| CD83 | ICOS | CD79b |
| CD83 | CD27 | CD8 |
| CD83 | CD27 | CD3ζ |
| CD83 | CD27 | CD3δ |
| CD83 | CD27 | CD3γ |
| CD83 | CD27 | CD3ε |
| CD83 | CD27 | FcγRI-γ |
| CD83 | CD27 | FcγRIII-γ |
| CD83 | CD27 | FcεRIβ |
| CD83 | CD27 | FcεRIγ |
| CD83 | CD27 | DAP10 |
| CD83 | CD27 | DAP12 |
| CD83 | CD27 | CD32 |
| CD83 | CD27 | CD79a |
| CD83 | CD27 | CD79b |
| CD83 | CD28δ | CD8 |
| CD83 | CD28δ | CD3ζ |
| CD83 | CD28δ | CD3δ |
| CD83 | CD28δ | CD3γ |
| CD83 | CD28δ | CD3ε |
| CD83 | CD28δ | FcγRI-γ |
| CD83 | CD28δ | FcγRIII-γ |
| CD83 | CD28δ | FcεRIβ |
| CD83 | CD28δ | FcεRIγ |
| CD83 | CD28δ | DAP10 |
| CD83 | CD28δ | DAP12 |
| CD83 | CD28δ | CD32 |
| CD83 | CD28δ | CD79a |
| CD83 | CD28δ | CD79b |
| CD83 | CD80 | CD8 |
| CD83 | CD80 | CD3ζ |
| CD83 | CD80 | CD3δ |
| CD83 | CD80 | CD3γ |
| CD83 | CD80 | CD3ε |
| CD83 | CD80 | FcγRI-γ |
| CD83 | CD80 | FcγRIII-γ |
| CD83 | CD80 | FcεRIβ |
| CD83 | CD80 | FcεRIγ |
| CD83 | CD80 | DAP10 |
| CD83 | CD80 | DAP12 |
| CD83 | CD80 | CD32 |
| CD83 | CD80 | CD79a |
| CD83 | CD80 | CD79b |
| CD83 | CD86 | CD8 |
| CD83 | CD86 | CD3ζ |
| CD83 | CD86 | CD3δ |
| CD83 | CD86 | CD3γ |
| CD83 | CD86 | CD3ε |
| CD83 | CD86 | FcγRI-γ |
| CD83 | CD86 | FcγRIII-γ |
| CD83 | CD86 | FcεRIβ |
| CD83 | CD86 | FcεRIγ |
| CD83 | CD86 | DAP10 |
| CD83 | CD86 | DAP12 |
| CD83 | CD86 | CD32 |
| CD83 | CD86 | CD79a |
| CD83 | CD86 | CD79b |
| CD83 | OX40 | CD8 |
| CD83 | OX40 | CD3ζ |
| CD83 | OX40 | CD3δ |
| CD83 | OX40 | CD3γ |
| CD83 | OX40 | CD3ε |
| CD83 | OX40 | FcγRI-γ |
| CD83 | OX40 | FcγRIII-γ |
| CD83 | OX40 | FcεRIβ |
| CD83 | OX40 | FcεRIγ |
| CD83 | OX40 | DAP10 |

TABLE 2-continued

| Second Generation CARs | | |
|---|---|---|
| ScFv | Co-stimulatory Signal | Signal Domain |
| CD83 | OX40 | DAP12 |
| CD83 | OX40 | CD32 |
| CD83 | OX40 | CD79a |
| CD83 | OX40 | CD79b |
| CD83 | DAP10 | CD8 |
| CD83 | DAP10 | CD3ζ |
| CD83 | DAP10 | CD3δ |
| CD83 | DAP10 | CD3γ |
| CD83 | DAP10 | CD3ε |
| CD83 | DAP10 | FcγRI-γ |
| CD83 | DAP10 | FcγRIII-γ |
| CD83 | DAP10 | FcεRIβ |
| CD83 | DAP10 | FcεRIγ |
| CD83 | DAP10 | DAP10 |
| CD83 | DAP10 | DAP12 |
| CD83 | DAP10 | CD32 |
| CD83 | DAP10 | CD79a |
| CD83 | DAP10 | CD79b |
| CD83 | DAP12 | CD8 |
| CD83 | DAP12 | CD3ζ |
| CD83 | DAP12 | CD3δ |
| CD83 | DAP12 | CD3γ |
| CD83 | DAP12 | CD3ε |
| CD83 | DAP12 | FcγRI-γ |
| CD83 | DAP12 | FcγRIII-γ |
| CD83 | DAP12 | FcεRIβ |
| CD83 | DAP12 | FcεRIγ |
| CD83 | DAP12 | DAP10 |
| CD83 | DAP12 | DAP12 |
| CD83 | DAP12 | CD32 |
| CD83 | DAP12 | CD79a |
| CD83 | DAP12 | CD79b |
| CD83 | MyD88 | CD8 |
| CD83 | MyD88 | CD3ζ |
| CD83 | MyD88 | CD3δ |
| CD83 | MyD88 | CD3γ |
| CD83 | MyD88 | CD3ε |
| CD83 | MyD88 | FcγRI-γ |
| CD83 | MyD88 | FcγRIII-γ |
| CD83 | MyD88 | FcεRIβ |
| CD83 | MyD88 | FcεRIγ |
| CD83 | MyD88 | DAP10 |
| CD83 | MyD88 | DAP12 |
| CD83 | MyD88 | CD32 |
| CD83 | MyD88 | CD79a |
| CD83 | MyD88 | CD79b |
| CD83 | CD7 | CD8 |
| CD83 | CD7 | CD3ζ |
| CD83 | CD7 | CD3δ |
| CD83 | CD7 | CD3γ |
| CD83 | CD7 | CD3ε |
| CD83 | CD7 | FcγRI-γ |
| CD83 | CD7 | FcγRIII-γ |
| CD83 | CD7 | FcεRIβ |
| CD83 | CD7 | FcεRIγ |
| CD83 | CD7 | DAP10 |
| CD83 | CD7 | DAP12 |
| CD83 | CD7 | CD32 |
| CD83 | CD7 | CD79a |
| CD83 | CD7 | CD79b |
| CD83 | BTNL3 | CD8 |
| CD83 | BTNL3 | CD3ζ |
| CD83 | BTNL3 | CD3δ |
| CD83 | BTNL3 | CD3γ |
| CD83 | BTNL3 | CD3ε |
| CD83 | BTNL3 | FcγRI-γ |
| CD83 | BTNL3 | FcγRIII-γ |
| CD83 | BTNL3 | FcεRIβ |
| CD83 | BTNL3 | FcεRIγ |
| CD83 | BTNL3 | DAP10 |
| CD83 | BTNL3 | DAP12 |
| CD83 | BTNL3 | CD32 |
| CD83 | BTNL3 | CD79a |
| CD83 | BTNL3 | CD79b |
| CD83 | NKG2D | CD8 |

TABLE 2-continued

| Second Generation CARs | | |
|---|---|---|
| ScFv | Co-stimulatory Signal | Signal Domain |
| CD83 | NKG2D | CD3ζ |
| CD83 | NKG2D | CD3δ |
| CD83 | NKG2D | CD3γ |
| CD83 | NKG2D | CD3ε |
| CD83 | NKG2D | FcγRI-γ |
| CD83 | NKG2D | FcγRIII-γ |
| CD83 | NKG2D | FcεRIβ |
| CD83 | NKG2D | FcεRIγ |
| CD83 | NKG2D | DAP10 |
| CD83 | NKG2D | DAP12 |
| CD83 | NKG2D | CD32 |
| CD83 | NKG2D | CD79a |
| CD83 | NKG2D | CD79b |

TABLE 3

| Third Generation CARs | | | |
|---|---|---|---|
| ScFv | Co-stimulatory Signal | Co-stimulatory Signal | Signal Domain |
| CD83 | CD28 | CD28 | CD8 |
| CD83 | CD28 | CD28 | CD3ζ |
| CD83 | CD28 | CD28 | CD3δ |
| CD83 | CD28 | CD28 | CD3γ |
| CD83 | CD28 | CD28 | CD3ε |
| CD83 | CD28 | CD28 | FcγRI-γ |
| CD83 | CD28 | CD28 | FcγRIII-γ |
| CD83 | CD28 | CD28 | FcεRIβ |
| CD83 | CD28 | CD28 | FcεRIγ |
| CD83 | CD28 | CD28 | DAP10 |
| CD83 | CD28 | CD28 | DAP12 |
| CD83 | CD28 | CD28 | CD32 |
| CD83 | CD28 | CD28 | CD79a |
| CD83 | CD28 | CD28 | CD79b |
| CD83 | CD28 | CD8 | CD8 |
| CD83 | CD28 | CD8 | CD3ζ |
| CD83 | CD28 | CD8 | CD3δ |
| CD83 | CD28 | CD8 | CD3γ |
| CD83 | CD28 | CD8 | CD3ε |
| CD83 | CD28 | CD8 | FcγRI-γ |
| CD83 | CD28 | CD8 | FcγRIII-γ |
| CD83 | CD28 | CD8 | FcεRIβ |
| CD83 | CD28 | CD8 | FcεRIγ |
| CD83 | CD28 | CD8 | DAP10 |
| CD83 | CD28 | CD8 | DAP12 |
| CD83 | CD28 | CD8 | CD32 |
| CD83 | CD28 | CD8 | CD79a |
| CD83 | CD28 | CD8 | CD79b |
| CD83 | CD28 | CD4 | CD8 |
| CD83 | CD28 | CD4 | CD3ζ |
| CD83 | CD28 | CD4 | CD3δ |
| CD83 | CD28 | CD4 | CD3γ |
| CD83 | CD28 | CD4 | CD3ε |
| CD83 | CD28 | CD4 | FcγRI-γ |
| CD83 | CD28 | CD4 | FcγRIII-γ |
| CD83 | CD28 | CD4 | FcεRIβ |
| CD83 | CD28 | CD4 | FcεRIγ |
| CD83 | CD28 | CD4 | DAP10 |
| CD83 | CD28 | CD4 | DAP12 |
| CD83 | CD28 | CD4 | CD32 |
| CD83 | CD28 | CD4 | CD79a |
| CD83 | CD28 | CD4 | CD79b |
| CD83 | CD28 | b2c | CD8 |
| CD83 | CD28 | b2c | CD3ζ |
| CD83 | CD28 | b2c | CD3δ |
| CD83 | CD28 | b2c | CD3γ |
| CD83 | CD28 | b2c | CD3ε |
| CD83 | CD28 | b2c | FcγRI-γ |
| CD83 | CD28 | b2c | FcγRIII-γ |
| CD83 | CD28 | b2c | FcεRIβ |
| CD83 | CD28 | b2c | FcεRIγ |

TABLE 3-continued

Third Generation CARs

| ScFv | Co-stimulatory Signal | Co-stimulatory Signal | Signal Domain |
|---|---|---|---|
| CD83 | CD28 | b2c | DAP10 |
| CD83 | CD28 | b2c | DAP12 |
| CD83 | CD28 | b2c | CD32 |
| CD83 | CD28 | b2c | CD79a |
| CD83 | CD28 | b2c | CD79b |
| CD83 | CD28 | CD137/41BB | CD8 |
| CD83 | CD28 | CD137/41BB | CD3ζ |
| CD83 | CD28 | CD137/41BB | CD3δ |
| CD83 | CD28 | CD137/41BB | CD3γ |
| CD83 | CD28 | CD137/41BB | CD3ε |
| CD83 | CD28 | CD137/41BB | FcγRI-γ |
| CD83 | CD28 | CD137/41BB | FcγRIII-γ |
| CD83 | CD28 | CD137/41BB | FcεRIβ |
| CD83 | CD28 | CD137/41BB | FcεRIγ |
| CD83 | CD28 | CD137/41BB | DAP10 |
| CD83 | CD28 | CD137/41BB | DAP12 |
| CD83 | CD28 | CD137/41BB | CD32 |
| CD83 | CD28 | CD137/41BB | CD79a |
| CD83 | CD28 | CD137/41BB | CD79b |
| CD83 | CD28 | ICOS | CD8 |
| CD83 | CD28 | ICOS | CD3ζ |
| CD83 | CD28 | ICOS | CD3δ |
| CD83 | CD28 | ICOS | CD3γ |
| CD83 | CD28 | ICOS | CD3ε |
| CD83 | CD28 | ICOS | FcγRI-γ |
| CD83 | CD28 | ICOS | FcγRIII-γ |
| CD83 | CD28 | ICOS | FcεRIβ |
| CD83 | CD28 | ICOS | FcεRIγ |
| CD83 | CD28 | ICOS | DAP10 |
| CD83 | CD28 | ICOS | DAP12 |
| CD83 | CD28 | ICOS | CD32 |
| CD83 | CD28 | ICOS | CD79a |
| CD83 | CD28 | ICOS | CD79b |
| CD83 | CD28 | CD27 | CD8 |
| CD83 | CD28 | CD27 | CD3ζ |
| CD83 | CD28 | CD27 | CD3δ |
| CD83 | CD28 | CD27 | CD3γ |
| CD83 | CD28 | CD27 | CD3ε |
| CD83 | CD28 | CD27 | FcγRI-γ |
| CD83 | CD28 | CD27 | FcγRIII-γ |
| CD83 | CD28 | CD27 | FcεRIβ |
| CD83 | CD28 | CD27 | FcεRIγ |
| CD83 | CD28 | CD27 | DAP10 |
| CD83 | CD28 | CD27 | DAP12 |
| CD83 | CD28 | CD27 | CD32 |
| CD83 | CD28 | CD27 | CD79a |
| CD83 | CD28 | CD27 | CD79b |
| CD83 | CD28 | CD28δ | CD8 |
| CD83 | CD28 | CD28δ | CD3ζ |
| CD83 | CD28 | CD28δ | CD3δ |
| CD83 | CD28 | CD28δ | CD3γ |
| CD83 | CD28 | CD28δ | CD3ε |
| CD83 | CD28 | CD28δ | FcγRI-γ |
| CD83 | CD28 | CD28δ | FcγRIII-γ |
| CD83 | CD28 | CD28δ | FcεRIβ |
| CD83 | CD28 | CD28δ | FcεRIγ |
| CD83 | CD28 | CD28δ | DAP10 |
| CD83 | CD28 | CD28δ | DAP12 |
| CD83 | CD28 | CD28δ | CD32 |
| CD83 | CD28 | CD28δ | CD79a |
| CD83 | CD28 | CD28δ | CD79b |
| CD83 | CD28 | CD80 | CD8 |
| CD83 | CD28 | CD80 | CD3ζ |
| CD83 | CD28 | CD80 | CD3δ |
| CD83 | CD28 | CD80 | CD3γ |
| CD83 | CD28 | CD80 | CD3ε |
| CD83 | CD28 | CD80 | FcγRI-γ |
| CD83 | CD28 | CD80 | FcγRIII-γ |
| CD83 | CD28 | CD80 | FcεRIβ |
| CD83 | CD28 | CD80 | FcεRIγ |
| CD83 | CD28 | CD80 | DAP10 |
| CD83 | CD28 | CD80 | DAP12 |
| CD83 | CD28 | CD80 | CD32 |
| CD83 | CD28 | CD80 | CD79a |
| CD83 | CD28 | CD80 | CD79b |

TABLE 3-continued

Third Generation CARs

| ScFv | Co-stimulatory Signal | Co-stimulatory Signal | Signal Domain |
|---|---|---|---|
| CD83 | CD28 | CD86 | CD8 |
| CD83 | CD28 | CD86 | CD3ζ |
| CD83 | CD28 | CD86 | CD3δ |
| CD83 | CD28 | CD86 | CD3γ |
| CD83 | CD28 | CD86 | CD3ε |
| CD83 | CD28 | CD86 | FcγRI-γ |
| CD83 | CD28 | CD86 | FcγRIII-γ |
| CD83 | CD28 | CD86 | FcεRIβ |
| CD83 | CD28 | CD86 | FcεRIγ |
| CD83 | CD28 | CD86 | DAP10 |
| CD83 | CD28 | CD86 | DAP12 |
| CD83 | CD28 | CD86 | CD32 |
| CD83 | CD28 | CD86 | CD79a |
| CD83 | CD28 | CD86 | CD79b |
| CD83 | CD28 | OX40 | CD8 |
| CD83 | CD28 | OX40 | CD3ζ |
| CD83 | CD28 | OX40 | CD3δ |
| CD83 | CD28 | OX40 | CD3γ |
| CD83 | CD28 | OX40 | CD3ε |
| CD83 | CD28 | OX40 | FcγRI-γ |
| CD83 | CD28 | OX40 | FcγRIII-γ |
| CD83 | CD28 | OX40 | FcεRIβ |
| CD83 | CD28 | OX40 | FcεRIγ |
| CD83 | CD28 | OX40 | DAP10 |
| CD83 | CD28 | OX40 | DAP12 |
| CD83 | CD28 | OX40 | CD32 |
| CD83 | CD28 | OX40 | CD79a |
| CD83 | CD28 | OX40 | CD79b |
| CD83 | CD28 | DAP10 | CD8 |
| CD83 | CD28 | DAP10 | CD3ζ |
| CD83 | CD28 | DAP10 | CD3δ |
| CD83 | CD28 | DAP10 | CD3γ |
| CD83 | CD28 | DAP10 | CD3ε |
| CD83 | CD28 | DAP10 | FcγRI-γ |
| CD83 | CD28 | DAP10 | FcγRIII-γ |
| CD83 | CD28 | DAP10 | FcεRIβ |
| CD83 | CD28 | DAP10 | FcεRIγ |
| CD83 | CD28 | DAP10 | DAP10 |
| CD83 | CD28 | DAP10 | DAP12 |
| CD83 | CD28 | DAP10 | CD32 |
| CD83 | CD28 | DAP10 | CD79a |
| CD83 | CD28 | DAP10 | CD79b |
| CD83 | CD28 | DAP12 | CD8 |
| CD83 | CD28 | DAP12 | CD3ζ |
| CD83 | CD28 | DAP12 | CD3δ |
| CD83 | CD28 | DAP12 | CD3γ |
| CD83 | CD28 | DAP12 | CD3ε |
| CD83 | CD28 | DAP12 | FcγRI-γ |
| CD83 | CD28 | DAP12 | FcγRIII-γ |
| CD83 | CD28 | DAP12 | FcεRIβ |
| CD83 | CD28 | DAP12 | FcεRIγ |
| CD83 | CD28 | DAP12 | DAP10 |
| CD83 | CD28 | DAP12 | DAP12 |
| CD83 | CD28 | DAP12 | CD32 |
| CD83 | CD28 | DAP12 | CD79a |
| CD83 | CD28 | DAP12 | CD79b |
| CD83 | CD28 | MyD88 | CD8 |
| CD83 | CD28 | MyD88 | CD3ζ |
| CD83 | CD28 | MyD88 | CD3δ |
| CD83 | CD28 | MyD88 | CD3γ |
| CD83 | CD28 | MyD88 | CD3ε |
| CD83 | CD28 | MyD88 | FcγRI-γ |
| CD83 | CD28 | MyD88 | FcγRIII-γ |
| CD83 | CD28 | MyD88 | FcεRIβ |
| CD83 | CD28 | MyD88 | FcεRIγ |
| CD83 | CD28 | MyD88 | DAP10 |
| CD83 | CD28 | MyD88 | DAP12 |
| CD83 | CD28 | MyD88 | CD32 |
| CD83 | CD28 | MyD88 | CD79a |
| CD83 | CD28 | MyD88 | CD79b |
| CD83 | CD28 | CD7 | CD8 |
| CD83 | CD28 | CD7 | CD3ζ |
| CD83 | CD28 | CD7 | CD3δ |
| CD83 | CD28 | CD7 | CD3γ |
| CD83 | CD28 | CD7 | CD3ε |

TABLE 3-continued

Third Generation CARs

| ScFv | Co-stimulatory Signal | Co-stimulatory Signal | Signal Domain |
|---|---|---|---|
| CD83 | CD28 | CD7 | FcγRI-γ |
| CD83 | CD28 | CD7 | FcγRIII-γ |
| CD83 | CD28 | CD7 | FcεRIβ |
| CD83 | CD28 | CD7 | FcεRIγ |
| CD83 | CD28 | CD7 | DAP10 |
| CD83 | CD28 | CD7 | DAP12 |
| CD83 | CD28 | CD7 | CD32 |
| CD83 | CD28 | CD7 | CD79a |
| CD83 | CD28 | CD7 | CD79b |
| CD83 | CD28 | BTNL3 | CD8 |
| CD83 | CD28 | BTNL3 | CD3ζ |
| CD83 | CD28 | BTNL3 | CD3δ |
| CD83 | CD28 | BTNL3 | CD3γ |
| CD83 | CD28 | BTNL3 | CD3ε |
| CD83 | CD28 | BTNL3 | FcγRI-γ |
| CD83 | CD28 | BTNL3 | FcγRIII-γ |
| CD83 | CD28 | BTNL3 | FcεRIβ |
| CD83 | CD28 | BTNL3 | FcεRIγ |
| CD83 | CD28 | BTNL3 | DAP10 |
| CD83 | CD28 | BTNL3 | DAP12 |
| CD83 | CD28 | BTNL3 | CD32 |
| CD83 | CD28 | BTNL3 | CD79a |
| CD83 | CD28 | BTNL3 | CD79b |
| CD83 | CD28 | NKG2D | CD8 |
| CD83 | CD28 | NKG2D | CD3ζ |
| CD83 | CD28 | NKG2D | CD3δ |
| CD83 | CD28 | NKG2D | CD3γ |
| CD83 | CD28 | NKG2D | CD3ε |
| CD83 | CD28 | NKG2D | FcγRI-γ |
| CD83 | CD28 | NKG2D | FcγRIII-γ |
| CD83 | CD28 | NKG2D | FcεRIβ |
| CD83 | CD28 | NKG2D | FcεRIγ |
| CD83 | CD28 | NKG2D | DAP10 |
| CD83 | CD28 | NKG2D | DAP12 |
| CD83 | CD28 | NKG2D | CD32 |
| CD83 | CD28 | NKG2D | CD79a |
| CD83 | CD28 | NKG2D | CD79b |
| CD83 | CD8 | CD28 | CD8 |
| CD83 | CD8 | CD28 | CD3ζ |
| CD83 | CD8 | CD28 | CD3δ |
| CD83 | CD8 | CD28 | CD3γ |
| CD83 | CD8 | CD28 | CD3ε |
| CD83 | CD8 | CD28 | FcγRI-γ |
| CD83 | CD8 | CD28 | FcγRIII-γ |
| CD83 | CD8 | CD28 | FcεRIβ |
| CD83 | CD8 | CD28 | FcεRIγ |
| CD83 | CD8 | CD28 | DAP10 |
| CD83 | CD8 | CD28 | DAP12 |
| CD83 | CD8 | CD28 | CD32 |
| CD83 | CD8 | CD28 | CD79a |
| CD83 | CD8 | CD28 | CD79b |
| CD83 | CD8 | CD8 | CD8 |
| CD83 | CD8 | CD8 | CD3ζ |
| CD83 | CD8 | CD8 | CD3δ |
| CD83 | CD8 | CD8 | CD3γ |
| CD83 | CD8 | CD8 | CD3ε |
| CD83 | CD8 | CD8 | FcγRI-γ |
| CD83 | CD8 | CD8 | FcγRIII-γ |
| CD83 | CD8 | CD8 | FcεRIβ |
| CD83 | CD8 | CD8 | FcεRIγ |
| CD83 | CD8 | CD8 | DAP10 |
| CD83 | CD8 | CD8 | DAP12 |
| CD83 | CD8 | CD8 | CD32 |
| CD83 | CD8 | CD8 | CD79a |
| CD83 | CD8 | CD8 | CD79b |
| CD83 | CD8 | CD4 | CD8 |
| CD83 | CD8 | CD4 | CD3ζ |
| CD83 | CD8 | CD4 | CD3δ |
| CD83 | CD8 | CD4 | CD3γ |
| CD83 | CD8 | CD4 | CD3ε |
| CD83 | CD8 | CD4 | FcγRI-γ |
| CD83 | CD8 | CD4 | FcγRIII-γ |
| CD83 | CD8 | CD4 | FcεRIβ |
| CD83 | CD8 | CD4 | FcεRIγ |
| CD83 | CD8 | CD4 | DAP10 |

TABLE 3-continued

Third Generation CARs

| ScFv | Co-stimulatory Signal | Co-stimulatory Signal | Signal Domain |
|---|---|---|---|
| CD83 | CD8 | CD4 | DAP12 |
| CD83 | CD8 | CD4 | CD32 |
| CD83 | CD8 | CD4 | CD79a |
| CD83 | CD8 | CD4 | CD79b |
| CD83 | CD8 | b2c | CD8 |
| CD83 | CD8 | b2c | CD3ζ |
| CD83 | CD8 | b2c | CD3δ |
| CD83 | CD8 | b2c | CD3γ |
| CD83 | CD8 | b2c | CD3ε |
| CD83 | CD8 | b2c | FcγRI-γ |
| CD83 | CD8 | b2c | FcγRIII-γ |
| CD83 | CD8 | b2c | FcεRIβ |
| CD83 | CD8 | b2c | FcεRIγ |
| CD83 | CD8 | b2c | DAP10 |
| CD83 | CD8 | b2c | DAP12 |
| CD83 | CD8 | b2c | CD32 |
| CD83 | CD8 | b2c | CD79a |
| CD83 | CD8 | b2c | CD79b |
| CD83 | CD8 | CD137/41BB | CD8 |
| CD83 | CD8 | CD137/41BB | CD3ζ |
| CD83 | CD8 | CD137/41BB | CD3δ |
| CD83 | CD8 | CD137/41BB | CD3γ |
| CD83 | CD8 | CD137/41BB | CD3ε |
| CD83 | CD8 | CD137/41BB | FcγRI-γ |
| CD83 | CD8 | CD137/41BB | FcγRIII-γ |
| CD83 | CD8 | CD137/41BB | FcεRIβ |
| CD83 | CD8 | CD137/41BB | FcεRIγ |
| CD83 | CD8 | CD137/41BB | DAP10 |
| CD83 | CD8 | CD137/41BB | DAP12 |
| CD83 | CD8 | CD137/41BB | CD32 |
| CD83 | CD8 | CD137/41BB | CD79a |
| CD83 | CD8 | CD137/41BB | CD79b |
| CD83 | CD8 | ICOS | CD8 |
| CD83 | CD8 | ICOS | CD3ζ |
| CD83 | CD8 | ICOS | CD3δ |
| CD83 | CD8 | ICOS | CD3γ |
| CD83 | CD8 | ICOS | CD3ε |
| CD83 | CD8 | ICOS | FcγRI-γ |
| CD83 | CD8 | ICOS | FcγRIII-γ |
| CD83 | CD8 | ICOS | FcεRIβ |
| CD83 | CD8 | ICOS | FcεRIγ |
| CD83 | CD8 | ICOS | DAP10 |
| CD83 | CD8 | ICOS | DAP12 |
| CD83 | CD8 | ICOS | CD32 |
| CD83 | CD8 | ICOS | CD79a |
| CD83 | CD8 | ICOS | CD79b |
| CD83 | CD8 | CD27 | CD8 |
| CD83 | CD8 | CD27 | CD3ζ |
| CD83 | CD8 | CD27 | CD3δ |
| CD83 | CD8 | CD27 | CD3γ |
| CD83 | CD8 | CD27 | CD3ε |
| CD83 | CD8 | CD27 | FcγRI-γ |
| CD83 | CD8 | CD27 | FcγRIII-γ |
| CD83 | CD8 | CD27 | FcεRIβ |
| CD83 | CD8 | CD27 | FcεRIγ |
| CD83 | CD8 | CD27 | DAP10 |
| CD83 | CD8 | CD27 | DAP12 |
| CD83 | CD8 | CD27 | CD32 |
| CD83 | CD8 | CD27 | CD79a |
| CD83 | CD8 | CD27 | CD79b |
| CD83 | CD8 | CD28δ | CD8 |
| CD83 | CD8 | CD28δ | CD3ζ |
| CD83 | CD8 | CD28δ | CD3δ |
| CD83 | CD8 | CD28δ | CD3γ |
| CD83 | CD8 | CD28δ | CD3ε |
| CD83 | CD8 | CD28δ | FcγRI-γ |
| CD83 | CD8 | CD28δ | FcγRIII-γ |
| CD83 | CD8 | CD28δ | FcεRIβ |
| CD83 | CD8 | CD28δ | FcεRIγ |
| CD83 | CD8 | CD28δ | DAP10 |
| CD83 | CD8 | CD28δ | DAP12 |
| CD83 | CD8 | CD28δ | CD32 |
| CD83 | CD8 | CD28δ | CD79a |
| CD83 | CD8 | CD28δ | CD79b |
| CD83 | CD8 | CD80 | CD8 |

TABLE 3-continued

| Third Generation CARs | | | |
|---|---|---|---|
| ScFv | Co-stimulatory Signal | Co-stimulatory Signal | Signal Domain |
| CD83 | CD8 | CD80 | CD3ζ |
| CD83 | CD8 | CD80 | CD3δ |
| CD83 | CD8 | CD80 | CD3γ |
| CD83 | CD8 | CD80 | CD3ε |
| CD83 | CD8 | CD80 | FcγRI-γ |
| CD83 | CD8 | CD80 | FcγRIII-γ |
| CD83 | CD8 | CD80 | FcεRIβ |
| CD83 | CD8 | CD80 | FcεRIγ |
| CD83 | CD8 | CD80 | DAP10 |
| CD83 | CD8 | CD80 | DAP12 |
| CD83 | CD8 | CD80 | CD32 |
| CD83 | CD8 | CD80 | CD79a |
| CD83 | CD8 | CD80 | CD79b |
| CD83 | CD8 | CD86 | CD8 |
| CD83 | CD8 | CD86 | CD3ζ |
| CD83 | CD8 | CD86 | CD3δ |
| CD83 | CD8 | CD86 | CD3γ |
| CD83 | CD8 | CD86 | CD3ε |
| CD83 | CD8 | CD86 | FcγRI-γ |
| CD83 | CD8 | CD86 | FcγRIII-γ |
| CD83 | CD8 | CD86 | FcεRIβ |
| CD83 | CD8 | CD86 | FcεRIγ |
| CD83 | CD8 | CD86 | DAP10 |
| CD83 | CD8 | CD86 | DAP12 |
| CD83 | CD8 | CD86 | CD32 |
| CD83 | CD8 | CD86 | CD79a |
| CD83 | CD8 | CD86 | CD79b |
| CD83 | CD8 | OX40 | CD8 |
| CD83 | CD8 | OX40 | CD3ζ |
| CD83 | CD8 | OX40 | CD3δ |
| CD83 | CD8 | OX40 | CD3γ |
| CD83 | CD8 | OX40 | CD3ε |
| CD83 | CD8 | OX40 | FcγRI-γ |
| CD83 | CD8 | OX40 | FcγRIII-γ |
| CD83 | CD8 | OX40 | FcεRIβ |
| CD83 | CD8 | OX40 | FcεRIγ |
| CD83 | CD8 | OX40 | DAP10 |
| CD83 | CD8 | OX40 | DAP12 |
| CD83 | CD8 | OX40 | CD32 |
| CD83 | CD8 | OX40 | CD79a |
| CD83 | CD8 | OX40 | CD79b |
| CD83 | CD8 | DAP10 | CD8 |
| CD83 | CD8 | DAP10 | CD3ζ |
| CD83 | CD8 | DAP10 | CD3δ |
| CD83 | CD8 | DAP10 | CD3γ |
| CD83 | CD8 | DAP10 | CD3ε |
| CD83 | CD8 | DAP10 | FcγRI-γ |
| CD83 | CD8 | DAP10 | FcγRIII-γ |
| CD83 | CD8 | DAP10 | FcεRIβ |
| CD83 | CD8 | DAP10 | FcεRIγ |
| CD83 | CD8 | DAP10 | DAP10 |
| CD83 | CD8 | DAP10 | DAP12 |
| CD83 | CD8 | DAP10 | CD32 |
| CD83 | CD8 | DAP10 | CD79a |
| CD83 | CD8 | DAP10 | CD79b |
| CD83 | CD8 | DAP12 | CD8 |
| CD83 | CD8 | DAP12 | CD3ζ |
| CD83 | CD8 | DAP12 | CD3δ |
| CD83 | CD8 | DAP12 | CD3γ |
| CD83 | CD8 | DAP12 | CD3ε |
| CD83 | CD8 | DAP12 | FcγRI-γ |
| CD83 | CD8 | DAP12 | FcγRIII-γ |
| CD83 | CD8 | DAP12 | FcεRIβ |
| CD83 | CD8 | DAP12 | FcεRIγ |
| CD83 | CD8 | DAP12 | DAP10 |
| CD83 | CD8 | DAP12 | DAP12 |
| CD83 | CD8 | DAP12 | CD32 |
| CD83 | CD8 | DAP12 | CD79a |
| CD83 | CD8 | DAP12 | CD79b |
| CD83 | CD8 | MyD88 | CD8 |
| CD83 | CD8 | MyD88 | CD3ζ |
| CD83 | CD8 | MyD88 | CD3δ |
| CD83 | CD8 | MyD88 | CD3γ |
| CD83 | CD8 | MyD88 | CD3ε |
| CD83 | CD8 | MyD88 | FcγRI-γ |

TABLE 3-continued

| Third Generation CARs | | | |
|---|---|---|---|
| ScFv | Co-stimulatory Signal | Co-stimulatory Signal | Signal Domain |
| CD83 | CD8 | MyD88 | FcγRIII-γ |
| CD83 | CD8 | MyD88 | FcεRIβ |
| CD83 | CD8 | MyD88 | FcεRIγ |
| CD83 | CD8 | MyD88 | DAP10 |
| CD83 | CD8 | MyD88 | DAP12 |
| CD83 | CD8 | MyD88 | CD32 |
| CD83 | CD8 | MyD88 | CD79a |
| CD83 | CD8 | MyD88 | CD79b |
| CD83 | CD8 | CD7 | CD8 |
| CD83 | CD8 | CD7 | CD3ζ |
| CD83 | CD8 | CD7 | CD3δ |
| CD83 | CD8 | CD7 | CD3γ |
| CD83 | CD8 | CD7 | CD3ε |
| CD83 | CD8 | CD7 | FcγRI-γ |
| CD83 | CD8 | CD7 | FcγRIII-γ |
| CD83 | CD8 | CD7 | FcεRIβ |
| CD83 | CD8 | CD7 | FcεRIγ |
| CD83 | CD8 | CD7 | DAP10 |
| CD83 | CD8 | CD7 | DAP12 |
| CD83 | CD8 | CD7 | CD32 |
| CD83 | CD8 | CD7 | CD79a |
| CD83 | CD8 | CD7 | CD79b |
| CD83 | CD8 | BTNL3 | CD8 |
| CD83 | CD8 | BTNL3 | CD3ζ |
| CD83 | CD8 | BTNL3 | CD3δ |
| CD83 | CD8 | BTNL3 | CD3γ |
| CD83 | CD8 | BTNL3 | CD3ε |
| CD83 | CD8 | BTNL3 | FcγRI-γ |
| CD83 | CD8 | BTNL3 | FcγRIII-γ |
| CD83 | CD8 | BTNL3 | FcεRIβ |
| CD83 | CD8 | BTNL3 | FcεRIγ |
| CD83 | CD8 | BTNL3 | DAP10 |
| CD83 | CD8 | BTNL3 | DAP12 |
| CD83 | CD8 | BTNL3 | CD32 |
| CD83 | CD8 | BTNL3 | CD79a |
| CD83 | CD8 | BTNL3 | CD79b |
| CD83 | CD8 | NKG2D | CD8 |
| CD83 | CD8 | NKG2D | CD3ζ |
| CD83 | CD8 | NKG2D | CD3δ |
| CD83 | CD8 | NKG2D | CD3γ |
| CD83 | CD8 | NKG2D | CD3ε |
| CD83 | CD8 | NKG2D | FcγRI-γ |
| CD83 | CD8 | NKG2D | FcγRIII-γ |
| CD83 | CD8 | NKG2D | FcεRIβ |
| CD83 | CD8 | NKG2D | FcεRIγ |
| CD83 | CD8 | NKG2D | DAP10 |
| CD83 | CD8 | NKG2D | DAP12 |
| CD83 | CD8 | NKG2D | CD32 |
| CD83 | CD8 | NKG2D | CD79a |
| CD83 | CD8 | NKG2D | CD79b |
| CD83 | CD4 | CD28 | CD8 |
| CD83 | CD4 | CD28 | CD3ζ |
| CD83 | CD4 | CD28 | CD3δ |
| CD83 | CD4 | CD28 | CD3γ |
| CD83 | CD4 | CD28 | CD3ε |
| CD83 | CD4 | CD28 | FcγRI-γ |
| CD83 | CD4 | CD28 | FcγRIII-γ |
| CD83 | CD4 | CD28 | FcεRIβ |
| CD83 | CD4 | CD28 | FcεRIγ |
| CD83 | CD4 | CD28 | DAP10 |
| CD83 | CD4 | CD28 | DAP12 |
| CD83 | CD4 | CD28 | CD32 |
| CD83 | CD4 | CD28 | CD79a |
| CD83 | CD4 | CD28 | CD79b |
| CD83 | CD4 | CD8 | CD8 |
| CD83 | CD4 | CD8 | CD3ζ |
| CD83 | CD4 | CD8 | CD3δ |
| CD83 | CD4 | CD8 | CD3γ |
| CD83 | CD4 | CD8 | CD3ε |
| CD83 | CD4 | CD8 | FcγRI-γ |
| CD83 | CD4 | CD8 | FcγRIII-γ |
| CD83 | CD4 | CD8 | FcεRIβ |
| CD83 | CD4 | CD8 | FcεRIγ |
| CD83 | CD4 | CD8 | DAP10 |
| CD83 | CD4 | CD8 | DAP12 |

TABLE 3-continued

| Third Generation CARs | | | |
|---|---|---|---|
| ScFv | Co-stimulatory Signal | Co-stimulatory Signal | Signal Domain |
| CD83 | CD4 | CD8 | CD32 |
| CD83 | CD4 | CD8 | CD79a |
| CD83 | CD4 | CD8 | CD79b |
| CD83 | CD4 | CD4 | CD8 |
| CD83 | CD4 | CD4 | CD3ζ |
| CD83 | CD4 | CD4 | CD3δ |
| CD83 | CD4 | CD4 | CD3γ |
| CD83 | CD4 | CD4 | CD3ε |
| CD83 | CD4 | CD4 | FcγRI-γ |
| CD83 | CD4 | CD4 | FcγRIII-γ |
| CD83 | CD4 | CD4 | FcεRIβ |
| CD83 | CD4 | CD4 | FcεRIγ |
| CD83 | CD4 | CD4 | DAP10 |
| CD83 | CD4 | CD4 | DAP12 |
| CD83 | CD4 | CD4 | CD32 |
| CD83 | CD4 | CD4 | CD79a |
| CD83 | CD4 | CD4 | CD79b |
| CD83 | CD4 | b2c | CD8 |
| CD83 | CD4 | b2c | CD3ζ |
| CD83 | CD4 | b2c | CD3δ |
| CD83 | CD4 | b2c | CD3γ |
| CD83 | CD4 | b2c | CD3ε |
| CD83 | CD4 | b2c | FcγRI-γ |
| CD83 | CD4 | b2c | FcγRIII-γ |
| CD83 | CD4 | b2c | FcεRIβ |
| CD83 | CD4 | b2c | FcεRIγ |
| CD83 | CD4 | b2c | DAP10 |
| CD83 | CD4 | b2c | DAP12 |
| CD83 | CD4 | b2c | CD32 |
| CD83 | CD4 | b2c | CD79a |
| CD83 | CD4 | b2c | CD79b |
| CD83 | CD4 | CD137/41BB | CD8 |
| CD83 | CD4 | CD137/41BB | CD3ζ |
| CD83 | CD4 | CD137/41BB | CD3δ |
| CD83 | CD4 | CD137/41BB | CD3γ |
| CD83 | CD4 | CD137/41BB | CD3ε |
| CD83 | CD4 | CD137/41BB | FcγRI-γ |
| CD83 | CD4 | CD137/41BB | FcγRIII-γ |
| CD83 | CD4 | CD137/41BB | FcεRIβ |
| CD83 | CD4 | CD137/41BB | FcεRIγ |
| CD83 | CD4 | CD137/41BB | DAP10 |
| CD83 | CD4 | CD137/41BB | DAP12 |
| CD83 | CD4 | CD137/41BB | CD32 |
| CD83 | CD4 | CD137/41BB | CD79a |
| CD83 | CD4 | CD137/41BB | CD79b |
| CD83 | CD4 | ICOS | CD8 |
| CD83 | CD4 | ICOS | CD3ζ |
| CD83 | CD4 | ICOS | CD3δ |
| CD83 | CD4 | ICOS | CD3γ |
| CD83 | CD4 | ICOS | CD3ε |
| CD83 | CD4 | ICOS | FcγRI-γ |
| CD83 | CD4 | ICOS | FcγRIII-γ |
| CD83 | CD4 | ICOS | FcεRIβ |
| CD83 | CD4 | ICOS | FcεRIγ |
| CD83 | CD4 | ICOS | DAP10 |
| CD83 | CD4 | ICOS | DAP12 |
| CD83 | CD4 | ICOS | CD32 |
| CD83 | CD4 | ICOS | CD79a |
| CD83 | CD4 | ICOS | CD79b |
| CD83 | CD4 | CD27 | CD8 |
| CD83 | CD4 | CD27 | CD3ζ |
| CD83 | CD4 | CD27 | CD3δ |
| CD83 | CD4 | CD27 | CD3γ |
| CD83 | CD4 | CD27 | CD3ε |
| CD83 | CD4 | CD27 | FcγRI-γ |
| CD83 | CD4 | CD27 | FcγRIII-γ |
| CD83 | CD4 | CD27 | FcεRIβ |
| CD83 | CD4 | CD27 | FcεRIγ |
| CD83 | CD4 | CD27 | DAP10 |
| CD83 | CD4 | CD27 | DAP12 |
| CD83 | CD4 | CD27 | CD32 |
| CD83 | CD4 | CD27 | CD79a |
| CD83 | CD4 | CD27 | CD79b |
| CD83 | CD4 | CD28δ | CD8 |
| CD83 | CD4 | CD28δ | CD3ζ |

TABLE 3-continued

| Third Generation CARs | | | |
|---|---|---|---|
| ScFv | Co-stimulatory Signal | Co-stimulatory Signal | Signal Domain |
| CD83 | CD4 | CD28δ | CD3δ |
| CD83 | CD4 | CD28δ | CD3γ |
| CD83 | CD4 | CD28δ | CD3ε |
| CD83 | CD4 | CD28δ | FcγRI-γ |
| CD83 | CD4 | CD28δ | FcγRIII-γ |
| CD83 | CD4 | CD28δ | FcεRIβ |
| CD83 | CD4 | CD28δ | FcεRIγ |
| CD83 | CD4 | CD28δ | DAP10 |
| CD83 | CD4 | CD28δ | DAP12 |
| CD83 | CD4 | CD28δ | CD32 |
| CD83 | CD4 | CD28δ | CD79a |
| CD83 | CD4 | CD28δ | CD79b |
| CD83 | CD4 | CD80 | CD8 |
| CD83 | CD4 | CD80 | CD3ζ |
| CD83 | CD4 | CD80 | CD3δ |
| CD83 | CD4 | CD80 | CD3γ |
| CD83 | CD4 | CD80 | CD3ε |
| CD83 | CD4 | CD80 | FcγRI-γ |
| CD83 | CD4 | CD80 | FcγRIII-γ |
| CD83 | CD4 | CD80 | FcεRIβ |
| CD83 | CD4 | CD80 | FcεRIγ |
| CD83 | CD4 | CD80 | DAP10 |
| CD83 | CD4 | CD80 | DAP12 |
| CD83 | CD4 | CD80 | CD32 |
| CD83 | CD4 | CD80 | CD79a |
| CD83 | CD4 | CD80 | CD79b |
| CD83 | CD4 | CD86 | CD8 |
| CD83 | CD4 | CD86 | CD3ζ |
| CD83 | CD4 | CD86 | CD3δ |
| CD83 | CD4 | CD86 | CD3γ |
| CD83 | CD4 | CD86 | CD3ε |
| CD83 | CD4 | CD86 | FcγRI-γ |
| CD83 | CD4 | CD86 | FcγRIII-γ |
| CD83 | CD4 | CD86 | FcεRIβ |
| CD83 | CD4 | CD86 | FcεRIγ |
| CD83 | CD4 | CD86 | DAP10 |
| CD83 | CD4 | CD86 | DAP12 |
| CD83 | CD4 | CD86 | CD32 |
| CD83 | CD4 | CD86 | CD79a |
| CD83 | CD4 | CD86 | CD79b |
| CD83 | CD4 | OX40 | CD8 |
| CD83 | CD4 | OX40 | CD3ζ |
| CD83 | CD4 | OX40 | CD3δ |
| CD83 | CD4 | OX40 | CD3γ |
| CD83 | CD4 | OX40 | CD3ε |
| CD83 | CD4 | OX40 | FcγRI-γ |
| CD83 | CD4 | OX40 | FcγRIII-γ |
| CD83 | CD4 | OX40 | FcεRIβ |
| CD83 | CD4 | OX40 | FcεRIγ |
| CD83 | CD4 | OX40 | DAP10 |
| CD83 | CD4 | OX40 | DAP12 |
| CD83 | CD4 | OX40 | CD32 |
| CD83 | CD4 | OX40 | CD79a |
| CD83 | CD4 | OX40 | CD79b |
| CD83 | CD4 | DAP10 | CD8 |
| CD83 | CD4 | DAP10 | CD3ζ |
| CD83 | CD4 | DAP10 | CD3δ |
| CD83 | CD4 | DAP10 | CD3γ |
| CD83 | CD4 | DAP10 | CD3ε |
| CD83 | CD4 | DAP10 | FcγRI-γ |
| CD83 | CD4 | DAP10 | FcγRIII-γ |
| CD83 | CD4 | DAP10 | FcεRIβ |
| CD83 | CD4 | DAP10 | FcεRIγ |
| CD83 | CD4 | DAP10 | DAP10 |
| CD83 | CD4 | DAP10 | DAP12 |
| CD83 | CD4 | DAP10 | CD32 |
| CD83 | CD4 | DAP10 | CD79a |
| CD83 | CD4 | DAP10 | CD79b |
| CD83 | CD4 | DAP12 | CD8 |
| CD83 | CD4 | DAP12 | CD3ζ |
| CD83 | CD4 | DAP12 | CD3δ |
| CD83 | CD4 | DAP12 | CD3γ |
| CD83 | CD4 | DAP12 | CD3ε |
| CD83 | CD4 | DAP12 | FcγRI-γ |
| CD83 | CD4 | DAP12 | FcγRIII-γ |

TABLE 3-continued

Third Generation CARs

| ScFv | Co-stimulatory Signal | Co-stimulatory Signal | Signal Domain |
|---|---|---|---|
| CD83 | CD4 | DAP12 | FcεRIβ |
| CD83 | CD4 | DAP12 | FcεRIγ |
| CD83 | CD4 | DAP12 | DAP10 |
| CD83 | CD4 | DAP12 | DAP12 |
| CD83 | CD4 | DAP12 | CD32 |
| CD83 | CD4 | DAP12 | CD79a |
| CD83 | CD4 | DAP12 | CD79b |
| CD83 | CD4 | MyD88 | CD8 |
| CD83 | CD4 | MyD88 | CD3ζ |
| CD83 | CD4 | MyD88 | CD3δ |
| CD83 | CD4 | MyD88 | CD3γ |
| CD83 | CD4 | MyD88 | CD3ε |
| CD83 | CD4 | MyD88 | FcγRI-γ |
| CD83 | CD4 | MyD88 | FcγRIII-γ |
| CD83 | CD4 | MyD88 | FcεRIβ |
| CD83 | CD4 | MyD88 | FcεRIγ |
| CD83 | CD4 | MyD88 | DAP10 |
| CD83 | CD4 | MyD88 | DAP12 |
| CD83 | CD4 | MyD88 | CD32 |
| CD83 | CD4 | MyD88 | CD79a |
| CD83 | CD4 | MyD88 | CD79b |
| CD83 | CD4 | CD7 | CD8 |
| CD83 | CD4 | CD7 | CD3ζ |
| CD83 | CD4 | CD7 | CD3δ |
| CD83 | CD4 | CD7 | CD3γ |
| CD83 | CD4 | CD7 | CD3ε |
| CD83 | CD4 | CD7 | FcγRI-γ |
| CD83 | CD4 | CD7 | FcγRIII-γ |
| CD83 | CD4 | CD7 | FcεRIβ |
| CD83 | CD4 | CD7 | FcεRIγ |
| CD83 | CD4 | CD7 | DAP10 |
| CD83 | CD4 | CD7 | DAP12 |
| CD83 | CD4 | CD7 | CD32 |
| CD83 | CD4 | CD7 | CD79a |
| CD83 | CD4 | CD7 | CD79b |
| CD83 | CD4 | BTNL3 | CD8 |
| CD83 | CD4 | BTNL3 | CD3ζ |
| CD83 | CD4 | BTNL3 | CD3δ |
| CD83 | CD4 | BTNL3 | CD3γ |
| CD83 | CD4 | BTNL3 | CD3ε |
| CD83 | CD4 | BTNL3 | FcγRI-γ |
| CD83 | CD4 | BTNL3 | FcγRIII-γ |
| CD83 | CD4 | BTNL3 | FcεRIβ |
| CD83 | CD4 | BTNL3 | FcεRIγ |
| CD83 | CD4 | BTNL3 | DAP10 |
| CD83 | CD4 | BTNL3 | DAP12 |
| CD83 | CD4 | BTNL3 | CD32 |
| CD83 | CD4 | BTNL3 | CD79a |
| CD83 | CD4 | BTNL3 | CD79b |
| CD83 | CD4 | NKG2D | CD8 |
| CD83 | CD4 | NKG2D | CD3ζ |
| CD83 | CD4 | NKG2D | CD3δ |
| CD83 | CD4 | NKG2D | CD3γ |
| CD83 | CD4 | NKG2D | CD3ε |
| CD83 | CD4 | NKG2D | FcγRI-γ |
| CD83 | CD4 | NKG2D | FcγRIII-γ |
| CD83 | CD4 | NKG2D | FcεRIβ |
| CD83 | CD4 | NKG2D | FcεRIγ |
| CD83 | CD4 | NKG2D | DAP10 |
| CD83 | CD4 | NKG2D | DAP12 |
| CD83 | CD4 | NKG2D | CD32 |
| CD83 | CD4 | NKG2D | CD79a |
| CD83 | CD4 | NKG2D | CD79b |
| CD83 | b2c | CD28 | CD8 |
| CD83 | b2c | CD28 | CD3ζ |
| CD83 | b2c | CD28 | CD3δ |
| CD83 | b2c | CD28 | CD3γ |
| CD83 | b2c | CD28 | CD3ε |
| CD83 | b2c | CD28 | FcγRI-γ |
| CD83 | b2c | CD28 | FcγRIII-γ |
| CD83 | b2c | CD28 | FcεRIβ |
| CD83 | b2c | CD28 | FcεRIγ |
| CD83 | b2c | CD28 | DAP10 |
| CD83 | b2c | CD28 | DAP12 |
| CD83 | b2c | CD28 | CD32 |

TABLE 3-continued

Third Generation CARs

| ScFv | Co-stimulatory Signal | Co-stimulatory Signal | Signal Domain |
|---|---|---|---|
| CD83 | b2c | CD28 | CD79a |
| CD83 | b2c | CD28 | CD79b |
| CD83 | b2c | CD8 | CD8 |
| CD83 | b2c | CD8 | CD3ζ |
| CD83 | b2c | CD8 | CD3δ |
| CD83 | b2c | CD8 | CD3γ |
| CD83 | b2c | CD8 | CD3ε |
| CD83 | b2c | CD8 | FcγRI-γ |
| CD83 | b2c | CD8 | FcγRIII-γ |
| CD83 | b2c | CD8 | FcεRIβ |
| CD83 | b2c | CD8 | FcεRIγ |
| CD83 | b2c | CD8 | DAP10 |
| CD83 | b2c | CD8 | DAP12 |
| CD83 | b2c | CD8 | CD32 |
| CD83 | b2c | CD8 | CD79a |
| CD83 | b2c | CD8 | CD79b |
| CD83 | b2c | CD4 | CD8 |
| CD83 | b2c | CD4 | CD3ζ |
| CD83 | b2c | CD4 | CD3δ |
| CD83 | b2c | CD4 | CD3γ |
| CD83 | b2c | CD4 | CD3ε |
| CD83 | b2c | CD4 | FcγRI-γ |
| CD83 | b2c | CD4 | FcγRIII-γ |
| CD83 | b2c | CD4 | FcεRIβ |
| CD83 | b2c | CD4 | FcεRIγ |
| CD83 | b2c | CD4 | DAP10 |
| CD83 | b2c | CD4 | DAP12 |
| CD83 | b2c | CD4 | CD32 |
| CD83 | b2c | CD4 | CD79a |
| CD83 | b2c | CD4 | CD79b |
| CD83 | b2c | b2c | CD8 |
| CD83 | b2c | b2c | CD3ζ |
| CD83 | b2c | b2c | CD3δ |
| CD83 | b2c | b2c | CD3γ |
| CD83 | b2c | b2c | CD3ε |
| CD83 | b2c | b2c | FcγRI-γ |
| CD83 | b2c | b2c | FcγRIII-γ |
| CD83 | b2c | b2c | FcεRIβ |
| CD83 | b2c | b2c | FcεRIγ |
| CD83 | b2c | b2c | DAP10 |
| CD83 | b2c | b2c | DAP12 |
| CD83 | b2c | b2c | CD32 |
| CD83 | b2c | b2c | CD79a |
| CD83 | b2c | b2c | CD79b |
| CD83 | b2c | CD137/41BB | CD8 |
| CD83 | b2c | CD137/41BB | CD3ζ |
| CD83 | b2c | CD137/41BB | CD3δ |
| CD83 | b2c | CD137/41BB | CD3γ |
| CD83 | b2c | CD137/41BB | CD3ε |
| CD83 | b2c | CD137/41BB | FcγRI-γ |
| CD83 | b2c | CD137/41BB | FcγRIII-γ |
| CD83 | b2c | CD137/41BB | FcεRIβ |
| CD83 | b2c | CD137/41BB | FcεRIγ |
| CD83 | b2c | CD137/41BB | DAP10 |
| CD83 | b2c | CD137/41BB | DAP12 |
| CD83 | b2c | CD137/41BB | CD32 |
| CD83 | b2c | CD137/41BB | CD79a |
| CD83 | b2c | CD137/41BB | CD79b |
| CD83 | b2c | ICOS | CD8 |
| CD83 | b2c | ICOS | CD3ζ |
| CD83 | b2c | ICOS | CD3δ |
| CD83 | b2c | ICOS | CD3γ |
| CD83 | b2c | ICOS | CD3ε |
| CD83 | b2c | ICOS | FcγRI-γ |
| CD83 | b2c | ICOS | FcγRIII-γ |
| CD83 | b2c | ICOS | FcεRIβ |
| CD83 | b2c | ICOS | FcεRIγ |
| CD83 | b2c | ICOS | DAP10 |
| CD83 | b2c | ICOS | DAP12 |
| CD83 | b2c | ICOS | CD32 |
| CD83 | b2c | ICOS | CD79a |
| CD83 | b2c | ICOS | CD79b |
| CD83 | b2c | CD27 | CD8 |
| CD83 | b2c | CD27 | CD3ζ |
| CD83 | b2c | CD27 | CD3δ |

TABLE 3-continued

Third Generation CARs

| ScFv | Co-stimulatory Signal | Co-stimulatory Signal | Signal Domain |
|---|---|---|---|
| CD83 | b2c | CD27 | CD3γ |
| CD83 | b2c | CD27 | CD3ε |
| CD83 | b2c | CD27 | FcγRI-γ |
| CD83 | b2c | CD27 | FcγRIII-γ |
| CD83 | b2c | CD27 | FcεRIβ |
| CD83 | b2c | CD27 | FcεRIγ |
| CD83 | b2c | CD27 | DAP10 |
| CD83 | b2c | CD27 | DAP12 |
| CD83 | b2c | CD27 | CD32 |
| CD83 | b2c | CD27 | CD79a |
| CD83 | b2c | CD27 | CD79b |
| CD83 | b2c | CD28δ | CD8 |
| CD83 | b2c | CD28δ | CD3ζ |
| CD83 | b2c | CD28δ | CD3δ |
| CD83 | b2c | CD28δ | CD3γ |
| CD83 | b2c | CD28δ | CD3ε |
| CD83 | b2c | CD28δ | FcγRI-γ |
| CD83 | b2c | CD28δ | FcγRIII-γ |
| CD83 | b2c | CD28δ | FcεRIβ |
| CD83 | b2c | CD28δ | FcεRIγ |
| CD83 | b2c | CD28δ | DAP10 |
| CD83 | b2c | CD28δ | DAP12 |
| CD83 | b2c | CD28δ | CD32 |
| CD83 | b2c | CD28δ | CD79a |
| CD83 | b2c | CD28δ | CD79b |
| CD83 | b2c | CD80 | CD8 |
| CD83 | b2c | CD80 | CD3ζ |
| CD83 | b2c | CD80 | CD3δ |
| CD83 | b2c | CD80 | CD3γ |
| CD83 | b2c | CD80 | CD3ε |
| CD83 | b2c | CD80 | FcγRI-γ |
| CD83 | b2c | CD80 | FcγRIII-γ |
| CD83 | b2c | CD80 | FcεRIβ |
| CD83 | b2c | CD80 | FcεRIγ |
| CD83 | b2c | CD80 | DAP10 |
| CD83 | b2c | CD80 | DAP12 |
| CD83 | b2c | CD80 | CD32 |
| CD83 | b2c | CD80 | CD79a |
| CD83 | b2c | CD80 | CD79b |
| CD83 | b2c | CD86 | CD8 |
| CD83 | b2c | CD86 | CD3ζ |
| CD83 | b2c | CD86 | CD3δ |
| CD83 | b2c | CD86 | CD3γ |
| CD83 | b2c | CD86 | CD3ε |
| CD83 | b2c | CD86 | FcγRI-γ |
| CD83 | b2c | CD86 | FcγRIII-γ |
| CD83 | b2c | CD86 | FcεRIβ |
| CD83 | b2c | CD86 | FcεRIγ |
| CD83 | b2c | CD86 | DAP10 |
| CD83 | b2c | CD86 | DAP12 |
| CD83 | b2c | CD86 | CD32 |
| CD83 | b2c | CD86 | CD79a |
| CD83 | b2c | CD86 | CD79b |
| CD83 | b2c | OX40 | CD8 |
| CD83 | b2c | OX40 | CD3ζ |
| CD83 | b2c | OX40 | CD3δ |
| CD83 | b2c | OX40 | CD3γ |
| CD83 | b2c | OX40 | CD3ε |
| CD83 | b2c | OX40 | FcγRI-γ |
| CD83 | b2c | OX40 | FcγRIII-γ |
| CD83 | b2c | OX40 | FcεRIβ |
| CD83 | b2c | OX40 | FcεRIγ |
| CD83 | b2c | OX40 | DAP10 |
| CD83 | b2c | OX40 | DAP12 |
| CD83 | b2c | OX40 | CD32 |
| CD83 | b2c | OX40 | CD79a |
| CD83 | b2c | OX40 | CD79b |
| CD83 | b2c | DAP10 | CD8 |
| CD83 | b2c | DAP10 | CD3ζ |
| CD83 | b2c | DAP10 | CD3δ |
| CD83 | b2c | DAP10 | CD3γ |
| CD83 | b2c | DAP10 | CD3ε |
| CD83 | b2c | DAP10 | FcγRI-γ |
| CD83 | b2c | DAP10 | FcγRIII-γ |
| CD83 | b2c | DAP10 | FcεRIβ |
| CD83 | b2c | DAP10 | FcεRIγ |
| CD83 | b2c | DAP10 | DAP10 |
| CD83 | b2c | DAP10 | DAP12 |
| CD83 | b2c | DAP10 | CD32 |
| CD83 | b2c | DAP10 | CD79a |
| CD83 | b2c | DAP10 | CD79b |
| CD83 | b2c | DAP12 | CD8 |
| CD83 | b2c | DAP12 | CD3ζ |
| CD83 | b2c | DAP12 | CD3δ |
| CD83 | b2c | DAP12 | CD3γ |
| CD83 | b2c | DAP12 | CD3ε |
| CD83 | b2c | DAP12 | FcγRI-γ |
| CD83 | b2c | DAP12 | FcγRIII-γ |
| CD83 | b2c | DAP12 | FcεRIβ |
| CD83 | b2c | DAP12 | FcεRIγ |
| CD83 | b2c | DAP12 | DAP10 |
| CD83 | b2c | DAP12 | DAP12 |
| CD83 | b2c | DAP12 | CD32 |
| CD83 | b2c | DAP12 | CD79a |
| CD83 | b2c | DAP12 | CD79b |
| CD83 | b2c | MyD88 | CD8 |
| CD83 | b2c | MyD88 | CD3ζ |
| CD83 | b2c | MyD88 | CD3δ |
| CD83 | b2c | MyD88 | CD3γ |
| CD83 | b2c | MyD88 | CD3ε |
| CD83 | b2c | MyD88 | FcγRI-γ |
| CD83 | b2c | MyD88 | FcγRIII-γ |
| CD83 | b2c | MyD88 | FcεRIβ |
| CD83 | b2c | MyD88 | FcεRIγ |
| CD83 | b2c | MyD88 | DAP10 |
| CD83 | b2c | MyD88 | DAP12 |
| CD83 | b2c | MyD88 | CD32 |
| CD83 | b2c | MyD88 | CD79a |
| CD83 | b2c | MyD88 | CD79b |
| CD83 | b2c | CD7 | CD8 |
| CD83 | b2c | CD7 | CD3ζ |
| CD83 | b2c | CD7 | CD3δ |
| CD83 | b2c | CD7 | CD3γ |
| CD83 | b2c | CD7 | CD3ε |
| CD83 | b2c | CD7 | FcγRI-γ |
| CD83 | b2c | CD7 | FcγRIII-γ |
| CD83 | b2c | CD7 | FcεRIβ |
| CD83 | b2c | CD7 | FcεRIγ |
| CD83 | b2c | CD7 | DAP10 |
| CD83 | b2c | CD7 | DAP12 |
| CD83 | b2c | CD7 | CD32 |
| CD83 | b2c | CD7 | CD79a |
| CD83 | b2c | CD7 | CD79b |
| CD83 | b2c | BTNL3 | CD8 |
| CD83 | b2c | BTNL3 | CD3ζ |
| CD83 | b2c | BTNL3 | CD3δ |
| CD83 | b2c | BTNL3 | CD3γ |
| CD83 | b2c | BTNL3 | CD3ε |
| CD83 | b2c | BTNL3 | FcγRI-γ |
| CD83 | b2c | BTNL3 | FcγRIII-γ |
| CD83 | b2c | BTNL3 | FcεRIβ |
| CD83 | b2c | BTNL3 | FcεRIγ |
| CD83 | b2c | BTNL3 | DAP10 |
| CD83 | b2c | BTNL3 | DAP12 |
| CD83 | b2c | BTNL3 | CD32 |
| CD83 | b2c | BTNL3 | CD79a |
| CD83 | b2c | BTNL3 | CD79b |
| CD83 | b2c | NKG2D | CD8 |
| CD83 | b2c | NKG2D | CD3ζ |
| CD83 | b2c | NKG2D | CD3δ |
| CD83 | b2c | NKG2D | CD3γ |
| CD83 | b2c | NKG2D | CD3ε |
| CD83 | b2c | NKG2D | FcγRI-γ |
| CD83 | b2c | NKG2D | FcγRIII-γ |
| CD83 | b2c | NKG2D | FcεRIβ |
| CD83 | b2c | NKG2D | FcεRIγ |
| CD83 | b2c | NKG2D | DAP10 |
| CD83 | b2c | NKG2D | DAP12 |
| CD83 | b2c | NKG2D | CD32 |
| CD83 | b2c | NKG2D | CD79a |

TABLE 3-continued

Third Generation CARs

| ScFv | Co-stimulatory Signal | Co-stimulatory Signal | Signal Domain |
|---|---|---|---|
| CD83 | b2c | NKG2D | CD79b |
| CD83 | CD137/41BB | CD28 | CD8 |
| CD83 | CD137/41BB | CD28 | CD3ζ |
| CD83 | CD137/41BB | CD28 | CD3δ |
| CD83 | CD137/41BB | CD28 | CD3γ |
| CD83 | CD137/41BB | CD28 | CD3ε |
| CD83 | CD137/41BB | CD28 | FcγRI-γ |
| CD83 | CD137/41BB | CD28 | FcγRIII-γ |
| CD83 | CD137/41BB | CD28 | FcεRIβ |
| CD83 | CD137/41BB | CD28 | FcεRIγ |
| CD83 | CD137/41BB | CD28 | DAP10 |
| CD83 | CD137/41BB | CD28 | DAP12 |
| CD83 | CD137/41BB | CD28 | CD32 |
| CD83 | CD137/41BB | CD28 | CD79a |
| CD83 | CD137/41BB | CD28 | CD79b |
| CD83 | CD137/41BB | CD8 | CD8 |
| CD83 | CD137/41BB | CD8 | CD3ζ |
| CD83 | CD137/41BB | CD8 | CD3δ |
| CD83 | CD137/41BB | CD8 | CD3γ |
| CD83 | CD137/41BB | CD8 | CD3ε |
| CD83 | CD137/41BB | CD8 | FcγRI-γ |
| CD83 | CD137/41BB | CD8 | FcγRIII-γ |
| CD83 | CD137/41BB | CD8 | FcεRIβ |
| CD83 | CD137/41BB | CD8 | FcεRIγ |
| CD83 | CD137/41BB | CD8 | DAP10 |
| CD83 | CD137/41BB | CD8 | DAP12 |
| CD83 | CD137/41BB | CD8 | CD32 |
| CD83 | CD137/41BB | CD8 | CD79a |
| CD83 | CD137/41BB | CD8 | CD79b |
| CD83 | CD137/41BB | CD4 | CD8 |
| CD83 | CD137/41BB | CD4 | CD3ζ |
| CD83 | CD137/41BB | CD4 | CD3δ |
| CD83 | CD137/41BB | CD4 | CD3γ |
| CD83 | CD137/41BB | CD4 | CD3ε |
| CD83 | CD137/41BB | CD4 | FcγRI-γ |
| CD83 | CD137/41BB | CD4 | FcγRIII-γ |
| CD83 | CD137/41BB | CD4 | FcεRIβ |
| CD83 | CD137/41BB | CD4 | FcεRIγ |
| CD83 | CD137/41BB | CD4 | DAP10 |
| CD83 | CD137/41BB | CD4 | DAP12 |
| CD83 | CD137/41BB | CD4 | CD32 |
| CD83 | CD137/41BB | CD4 | CD79a |
| CD83 | CD137/41BB | CD4 | CD79b |
| CD83 | CD137/41BB | b2c | CD8 |
| CD83 | CD137/41BB | b2c | CD3ζ |
| CD83 | CD137/41BB | b2c | CD3δ |
| CD83 | CD137/41BB | b2c | CD3γ |
| CD83 | CD137/41BB | b2c | CD3ε |
| CD83 | CD137/41BB | b2c | FcγRI-γ |
| CD83 | CD137/41BB | b2c | FcγRIII-γ |
| CD83 | CD137/41BB | b2c | FcεRIβ |
| CD83 | CD137/41BB | b2c | FcεRIγ |
| CD83 | CD137/41BB | b2c | DAP10 |
| CD83 | CD137/41BB | b2c | DAP12 |
| CD83 | CD137/41BB | b2c | CD32 |
| CD83 | CD137/41BB | b2c | CD79a |
| CD83 | CD137/41BB | b2c | CD79b |
| CD83 | CD137/41BB | CD137/41BB | CD8 |
| CD83 | CD137/41BB | CD137/41BB | CD3ζ |
| CD83 | CD137/41BB | CD137/41BB | CD3δ |
| CD83 | CD137/41BB | CD137/41BB | CD3γ |
| CD83 | CD137/41BB | CD137/41BB | CD3ε |
| CD83 | CD137/41BB | CD137/41BB | FcγRI-γ |
| CD83 | CD137/41BB | CD137/41BB | FcγRIII-γ |
| CD83 | CD137/41BB | CD137/41BB | FcεRIβ |
| CD83 | CD137/41BB | CD137/41BB | FcεRIγ |
| CD83 | CD137/41BB | CD137/41BB | DAP10 |
| CD83 | CD137/41BB | CD137/41BB | DAP12 |
| CD83 | CD137/41BB | CD137/41BB | CD32 |
| CD83 | CD137/41BB | CD137/41BB | CD79a |
| CD83 | CD137/41BB | CD137/41BB | CD79b |
| CD83 | CD137/41BB | ICOS | CD8 |
| CD83 | CD137/41BB | ICOS | CD3ζ |
| CD83 | CD137/41BB | ICOS | CD3δ |
| CD83 | CD137/41BB | ICOS | CD3γ |
| CD83 | CD137/41BB | ICOS | CD3ε |
| CD83 | CD137/41BB | ICOS | FcγRI-γ |
| CD83 | CD137/41BB | ICOS | FcγRIII-γ |
| CD83 | CD137/41BB | ICOS | FcεRIβ |
| CD83 | CD137/41BB | ICOS | FcεRIγ |
| CD83 | CD137/41BB | ICOS | DAP10 |
| CD83 | CD137/41BB | ICOS | DAP12 |
| CD83 | CD137/41BB | ICOS | CD32 |
| CD83 | CD137/41BB | ICOS | CD79a |
| CD83 | CD137/41BB | ICOS | CD79b |
| CD83 | CD137/41BB | CD27 | CD8 |
| CD83 | CD137/41BB | CD27 | CD3ζ |
| CD83 | CD137/41BB | CD27 | CD3δ |
| CD83 | CD137/41BB | CD27 | CD3γ |
| CD83 | CD137/41BB | CD27 | CD3ε |
| CD83 | CD137/41BB | CD27 | FcγRI-γ |
| CD83 | CD137/41BB | CD27 | FcγRIII-γ |
| CD83 | CD137/41BB | CD27 | FcεRIβ |
| CD83 | CD137/41BB | CD27 | FcεRIγ |
| CD83 | CD137/41BB | CD27 | DAP10 |
| CD83 | CD137/41BB | CD27 | DAP12 |
| CD83 | CD137/41BB | CD27 | CD32 |
| CD83 | CD137/41BB | CD27 | CD79a |
| CD83 | CD137/41BB | CD27 | CD79b |
| CD83 | CD137/41BB | CD28δ | CD8 |
| CD83 | CD137/41BB | CD28δ | CD3ζ |
| CD83 | CD137/41BB | CD28δ | CD3δ |
| CD83 | CD137/41BB | CD28δ | CD3γ |
| CD83 | CD137/41BB | CD28δ | CD3ε |
| CD83 | CD137/41BB | CD28δ | FcγRI-γ |
| CD83 | CD137/41BB | CD28δ | FcγRIII-γ |
| CD83 | CD137/41BB | CD28δ | FcεRIβ |
| CD83 | CD137/41BB | CD28δ | FcεRIγ |
| CD83 | CD137/41BB | CD28δ | DAP10 |
| CD83 | CD137/41BB | CD28δ | DAP12 |
| CD83 | CD137/41BB | CD28δ | CD32 |
| CD83 | CD137/41BB | CD28δ | CD79a |
| CD83 | CD137/41BB | CD28δ | CD79b |
| CD83 | CD137/41BB | CD80 | CD8 |
| CD83 | CD137/41BB | CD80 | CD3ζ |
| CD83 | CD137/41BB | CD80 | CD3δ |
| CD83 | CD137/41BB | CD80 | CD3γ |
| CD83 | CD137/41BB | CD80 | CD3ε |
| CD83 | CD137/41BB | CD80 | FcγRI-γ |
| CD83 | CD137/41BB | CD80 | FcγRIII-γ |
| CD83 | CD137/41BB | CD80 | FcεRIβ |
| CD83 | CD137/41BB | CD80 | FcεRIγ |
| CD83 | CD137/41BB | CD80 | DAP10 |
| CD83 | CD137/41BB | CD80 | DAP12 |
| CD83 | CD137/41BB | CD80 | CD32 |
| CD83 | CD137/41BB | CD80 | CD79a |
| CD83 | CD137/41BB | CD80 | CD79b |
| CD83 | CD137/41BB | CD86 | CD8 |
| CD83 | CD137/41BB | CD86 | CD3ζ |
| CD83 | CD137/41BB | CD86 | CD3δ |
| CD83 | CD137/41BB | CD86 | CD3γ |
| CD83 | CD137/41BB | CD86 | CD3ε |
| CD83 | CD137/41BB | CD86 | FcγRI-γ |
| CD83 | CD137/41BB | CD86 | FcγRIII-γ |
| CD83 | CD137/41BB | CD86 | FcεRIβ |
| CD83 | CD137/41BB | CD86 | FcεRIγ |
| CD83 | CD137/41BB | CD86 | DAP10 |
| CD83 | CD137/41BB | CD86 | DAP12 |
| CD83 | CD137/41BB | CD86 | CD32 |
| CD83 | CD137/41BB | CD86 | CD79a |
| CD83 | CD137/41BB | CD86 | CD79b |
| CD83 | CD137/41BB | OX40 | CD8 |
| CD83 | CD137/41BB | OX40 | CD3ζ |
| CD83 | CD137/41BB | OX40 | CD3δ |
| CD83 | CD137/41BB | OX40 | CD3γ |
| CD83 | CD137/41BB | OX40 | CD3ε |
| CD83 | CD137/41BB | OX40 | FcγRI-γ |
| CD83 | CD137/41BB | OX40 | FcγRIII-γ |
| CD83 | CD137/41BB | OX40 | FcεRIβ |
| CD83 | CD137/41BB | OX40 | FcεRIγ |

TABLE 3-continued

| Third Generation CARs | | | |
|---|---|---|---|
| ScFv | Co-stimulatory Signal | Co-stimulatory Signal | Signal Domain |
| CD83 | CD137/41BB | OX40 | DAP10 |
| CD83 | CD137/41BB | OX40 | DAP12 |
| CD83 | CD137/41BB | OX40 | CD32 |
| CD83 | CD137/41BB | OX40 | CD79a |
| CD83 | CD137/41BB | OX40 | CD79b |
| CD83 | CD137/41BB | DAP10 | CD8 |
| CD83 | CD137/41BB | DAP10 | CD3ζ |
| CD83 | CD137/41BB | DAP10 | CD3δ |
| CD83 | CD137/41BB | DAP10 | CD3γ |
| CD83 | CD137/41BB | DAP10 | CD3ε |
| CD83 | CD137/41BB | DAP10 | FcγRI-γ |
| CD83 | CD137/41BB | DAP10 | FcγRIII-γ |
| CD83 | CD137/41BB | DAP10 | FcεRIβ |
| CD83 | CD137/41BB | DAP10 | FcεRIγ |
| CD83 | CD137/41BB | DAP10 | DAP10 |
| CD83 | CD137/41BB | DAP10 | DAP12 |
| CD83 | CD137/41BB | DAP10 | CD32 |
| CD83 | CD137/41BB | DAP10 | CD79a |
| CD83 | CD137/41BB | DAP10 | CD79b |
| CD83 | CD137/41BB | DAP12 | CD8 |
| CD83 | CD137/41BB | DAP12 | CD3ζ |
| CD83 | CD137/41BB | DAP12 | CD3δ |
| CD83 | CD137/41BB | DAP12 | CD3γ |
| CD83 | CD137/41BB | DAP12 | CD3ε |
| CD83 | CD137/41BB | DAP12 | FcγRI-γ |
| CD83 | CD137/41BB | DAP12 | FcγRIII-γ |
| CD83 | CD137/41BB | DAP12 | FcεRIβ |
| CD83 | CD137/41BB | DAP12 | FcεRIγ |
| CD83 | CD137/41BB | DAP12 | DAP10 |
| CD83 | CD137/41BB | DAP12 | DAP12 |
| CD83 | CD137/41BB | DAP12 | CD32 |
| CD83 | CD137/41BB | DAP12 | CD79a |
| CD83 | CD137/41BB | DAP12 | CD79b |
| CD83 | CD137/41BB | MyD88 | CD8 |
| CD83 | CD137/41BB | MyD88 | CD3ζ |
| CD83 | CD137/41BB | MyD88 | CD3δ |
| CD83 | CD137/41BB | MyD88 | CD3γ |
| CD83 | CD137/41BB | MyD88 | CD3ε |
| CD83 | CD137/41BB | MyD88 | FcγRI-γ |
| CD83 | CD137/41BB | MyD88 | FcγRIII-γ |
| CD83 | CD137/41BB | MyD88 | FcεRIβ |
| CD83 | CD137/41BB | MyD88 | FcεRIγ |
| CD83 | CD137/41BB | MyD88 | DAP10 |
| CD83 | CD137/41BB | MyD88 | DAP12 |
| CD83 | CD137/41BB | MyD88 | CD32 |
| CD83 | CD137/41BB | MyD88 | CD79a |
| CD83 | CD137/41BB | MyD88 | CD79b |
| CD83 | CD137/41BB | CD7 | CD8 |
| CD83 | CD137/41BB | CD7 | CD3ζ |
| CD83 | CD137/41BB | CD7 | CD3δ |
| CD83 | CD137/41BB | CD7 | CD3γ |
| CD83 | CD137/41BB | CD7 | CD3ε |
| CD83 | CD137/41BB | CD7 | FcγRI-γ |
| CD83 | CD137/41BB | CD7 | FcγRIII-γ |
| CD83 | CD137/41BB | CD7 | FcεRIβ |
| CD83 | CD137/41BB | CD7 | FcεRIγ |
| CD83 | CD137/41BB | CD7 | DAP10 |
| CD83 | CD137/41BB | CD7 | DAP12 |
| CD83 | CD137/41BB | CD7 | CD32 |
| CD83 | CD137/41BB | CD7 | CD79a |
| CD83 | CD137/41BB | CD7 | CD79b |
| CD83 | CD137/41BB | BTNL3 | CD8 |
| CD83 | CD137/41BB | BTNL3 | CD3ζ |
| CD83 | CD137/41BB | BTNL3 | CD3δ |
| CD83 | CD137/41BB | BTNL3 | CD3γ |
| CD83 | CD137/41BB | BTNL3 | CD3ε |
| CD83 | CD137/41BB | BTNL3 | FcγRI-γ |
| CD83 | CD137/41BB | BTNL3 | FcγRIII-γ |
| CD83 | CD137/41BB | BTNL3 | FcεRIβ |
| CD83 | CD137/41BB | BTNL3 | FcεRIγ |
| CD83 | CD137/41BB | BTNL3 | DAP10 |
| CD83 | CD137/41BB | BTNL3 | DAP12 |
| CD83 | CD137/41BB | BTNL3 | CD32 |
| CD83 | CD137/41BB | BTNL3 | CD79a |
| CD83 | CD137/41BB | BTNL3 | CD79b |

TABLE 3-continued

| Third Generation CARs | | | |
|---|---|---|---|
| ScFv | Co-stimulatory Signal | Co-stimulatory Signal | Signal Domain |
| CD83 | CD137/41BB | NKG2D | CD8 |
| CD83 | CD137/41BB | NKG2D | CD3ζ |
| CD83 | CD137/41BB | NKG2D | CD3δ |
| CD83 | CD137/41BB | NKG2D | CD3γ |
| CD83 | CD137/41BB | NKG2D | CD3ε |
| CD83 | CD137/41BB | NKG2D | FcγRI-γ |
| CD83 | CD137/41BB | NKG2D | FcγRIII-γ |
| CD83 | CD137/41BB | NKG2D | FcεRIβ |
| CD83 | CD137/41BB | NKG2D | FcεRIγ |
| CD83 | CD137/41BB | NKG2D | DAP10 |
| CD83 | CD137/41BB | NKG2D | DAP12 |
| CD83 | CD137/41BB | NKG2D | CD32 |
| CD83 | CD137/41BB | NKG2D | CD79a |
| CD83 | CD137/41BB | NKG2D | CD79b |
| CD83 | ICOS | CD28 | CD8 |
| CD83 | ICOS | CD28 | CD3ζ |
| CD83 | ICOS | CD28 | CD3δ |
| CD83 | ICOS | CD28 | CD3γ |
| CD83 | ICOS | CD28 | CD3ε |
| CD83 | ICOS | CD28 | FcγRI-γ |
| CD83 | ICOS | CD28 | FcγRIII-γ |
| CD83 | ICOS | CD28 | FcεRIβ |
| CD83 | ICOS | CD28 | FcεRIγ |
| CD83 | ICOS | CD28 | DAP10 |
| CD83 | ICOS | CD28 | DAP12 |
| CD83 | ICOS | CD28 | CD32 |
| CD83 | ICOS | CD28 | CD79a |
| CD83 | ICOS | CD28 | CD79b |
| CD83 | ICOS | CD8 | CD8 |
| CD83 | ICOS | CD8 | CD3ζ |
| CD83 | ICOS | CD8 | CD3δ |
| CD83 | ICOS | CD8 | CD3γ |
| CD83 | ICOS | CD8 | CD3ε |
| CD83 | ICOS | CD8 | FcγRI-γ |
| CD83 | ICOS | CD8 | FcγRIII-γ |
| CD83 | ICOS | CD8 | FcεRIβ |
| CD83 | ICOS | CD8 | FcεRIγ |
| CD83 | ICOS | CD8 | DAP10 |
| CD83 | ICOS | CD8 | DAP12 |
| CD83 | ICOS | CD8 | CD32 |
| CD83 | ICOS | CD8 | CD79a |
| CD83 | ICOS | CD8 | CD79b |
| CD83 | ICOS | CD4 | CD8 |
| CD83 | ICOS | CD4 | CD3ζ |
| CD83 | ICOS | CD4 | CD3δ |
| CD83 | ICOS | CD4 | CD3γ |
| CD83 | ICOS | CD4 | CD3ε |
| CD83 | ICOS | CD4 | FcγRI-γ |
| CD83 | ICOS | CD4 | FcγRIII-γ |
| CD83 | ICOS | CD4 | FcεRIβ |
| CD83 | ICOS | CD4 | FcεRIγ |
| CD83 | ICOS | CD4 | DAP10 |
| CD83 | ICOS | CD4 | DAP12 |
| CD83 | ICOS | CD4 | CD32 |
| CD83 | ICOS | CD4 | CD79a |
| CD83 | ICOS | CD4 | CD79b |
| CD83 | ICOS | b2c | CD8 |
| CD83 | ICOS | b2c | CD3ζ |
| CD83 | ICOS | b2c | CD3δ |
| CD83 | ICOS | b2c | CD3γ |
| CD83 | ICOS | b2c | CD3ε |
| CD83 | ICOS | b2c | FcγRI-γ |
| CD83 | ICOS | b2c | FcγRIII-γ |
| CD83 | ICOS | b2c | FcεRIβ |
| CD83 | ICOS | b2c | FcεRIγ |
| CD83 | ICOS | b2c | DAP10 |
| CD83 | ICOS | b2c | DAP12 |
| CD83 | ICOS | b2c | CD32 |
| CD83 | ICOS | b2c | CD79a |
| CD83 | ICOS | b2c | CD79b |
| CD83 | ICOS | CD137/41BB | CD8 |
| CD83 | ICOS | CD137/41BB | CD3ζ |
| CD83 | ICOS | CD137/41BB | CD3δ |
| CD83 | ICOS | CD137/41BB | CD3γ |
| CD83 | ICOS | CD137/41BB | CD3ε |

TABLE 3-continued

| Third Generation CARs | | | |
|---|---|---|---|
| ScFv | Co-stimulatory Signal | Co-stimulatory Signal | Signal Domain |
| CD83 | ICOS | CD137/41BB | FcγRI-γ |
| CD83 | ICOS | CD137/41BB | FcγRIII-γ |
| CD83 | ICOS | CD137/41BB | FcεRIβ |
| CD83 | ICOS | CD137/41BB | FcεRIγ |
| CD83 | ICOS | CD137/41BB | DAP10 |
| CD83 | ICOS | CD137/41BB | DAP12 |
| CD83 | ICOS | CD137/41BB | CD32 |
| CD83 | ICOS | CD137/41BB | CD79a |
| CD83 | ICOS | CD137/41BB | CD79b |
| CD83 | ICOS | ICOS | CD8 |
| CD83 | ICOS | ICOS | CD3ζ |
| CD83 | ICOS | ICOS | CD3δ |
| CD83 | ICOS | ICOS | CD3γ |
| CD83 | ICOS | ICOS | CD3ε |
| CD83 | ICOS | ICOS | FcγRI-γ |
| CD83 | ICOS | ICOS | FcγRIII-γ |
| CD83 | ICOS | ICOS | FcεRIβ |
| CD83 | ICOS | ICOS | FcεRIγ |
| CD83 | ICOS | ICOS | DAP10 |
| CD83 | ICOS | ICOS | DAP12 |
| CD83 | ICOS | ICOS | CD32 |
| CD83 | ICOS | ICOS | CD79a |
| CD83 | ICOS | ICOS | CD79b |
| CD83 | ICOS | CD27 | CD8 |
| CD83 | ICOS | CD27 | CD3ζ |
| CD83 | ICOS | CD27 | CD3δ |
| CD83 | ICOS | CD27 | CD3γ |
| CD83 | ICOS | CD27 | CD3ε |
| CD83 | ICOS | CD27 | FcγRI-γ |
| CD83 | ICOS | CD27 | FcγRIII-γ |
| CD83 | ICOS | CD27 | FcεRIβ |
| CD83 | ICOS | CD27 | FcεRIγ |
| CD83 | ICOS | CD27 | DAP10 |
| CD83 | ICOS | CD27 | DAP12 |
| CD83 | ICOS | CD27 | CD32 |
| CD83 | ICOS | CD27 | CD79a |
| CD83 | ICOS | CD27 | CD79b |
| CD83 | ICOS | CD28δ | CD8 |
| CD83 | ICOS | CD28δ | CD3ζ |
| CD83 | ICOS | CD28δ | CD3δ |
| CD83 | ICOS | CD28δ | CD3γ |
| CD83 | ICOS | CD28δ | CD3ε |
| CD83 | ICOS | CD28δ | FcγRI-γ |
| CD83 | ICOS | CD28δ | FcγRIII-γ |
| CD83 | ICOS | CD28δ | FcεRIβ |
| CD83 | ICOS | CD28δ | FcεRIγ |
| CD83 | ICOS | CD28δ | DAP10 |
| CD83 | ICOS | CD28δ | DAP12 |
| CD83 | ICOS | CD28δ | CD32 |
| CD83 | ICOS | CD28δ | CD79a |
| CD83 | ICOS | CD28δ | CD79b |
| CD83 | ICOS | CD80 | CD8 |
| CD83 | ICOS | CD80 | CD3ζ |
| CD83 | ICOS | CD80 | CD3δ |
| CD83 | ICOS | CD80 | CD3γ |
| CD83 | ICOS | CD80 | CD3ε |
| CD83 | ICOS | CD80 | FcγRI-γ |
| CD83 | ICOS | CD80 | FcγRIII-γ |
| CD83 | ICOS | CD80 | FcεRIβ |
| CD83 | ICOS | CD80 | FcεRIγ |
| CD83 | ICOS | CD80 | DAP10 |
| CD83 | ICOS | CD80 | DAP12 |
| CD83 | ICOS | CD80 | CD32 |
| CD83 | ICOS | CD80 | CD79a |
| CD83 | ICOS | CD80 | CD79b |
| CD83 | ICOS | CD86 | CD8 |
| CD83 | ICOS | CD86 | CD3ζ |
| CD83 | ICOS | CD86 | CD3δ |
| CD83 | ICOS | CD86 | CD3γ |
| CD83 | ICOS | CD86 | CD3ε |
| CD83 | ICOS | CD86 | FcγRI-γ |
| CD83 | ICOS | CD86 | FcγRIII-γ |
| CD83 | ICOS | CD86 | FcεRIβ |
| CD83 | ICOS | CD86 | FcεRIγ |
| CD83 | ICOS | CD86 | DAP10 |

TABLE 3-continued

| Third Generation CARs | | | |
|---|---|---|---|
| ScFv | Co-stimulatory Signal | Co-stimulatory Signal | Signal Domain |
| CD83 | ICOS | CD86 | DAP12 |
| CD83 | ICOS | CD86 | CD32 |
| CD83 | ICOS | CD86 | CD79a |
| CD83 | ICOS | CD86 | CD79b |
| CD83 | ICOS | OX40 | CD8 |
| CD83 | ICOS | OX40 | CD3ζ |
| CD83 | ICOS | OX40 | CD3δ |
| CD83 | ICOS | OX40 | CD3γ |
| CD83 | ICOS | OX40 | CD3ε |
| CD83 | ICOS | OX40 | FcγRI-γ |
| CD83 | ICOS | OX40 | FcγRIII-γ |
| CD83 | ICOS | OX40 | FcεRIβ |
| CD83 | ICOS | OX40 | FcεRIγ |
| CD83 | ICOS | OX40 | DAP10 |
| CD83 | ICOS | OX40 | DAP12 |
| CD83 | ICOS | OX40 | CD32 |
| CD83 | ICOS | OX40 | CD79a |
| CD83 | ICOS | OX40 | CD79b |
| CD83 | ICOS | DAP10 | CD8 |
| CD83 | ICOS | DAP10 | CD3ζ |
| CD83 | ICOS | DAP10 | CD3δ |
| CD83 | ICOS | DAP10 | CD3γ |
| CD83 | ICOS | DAP10 | CD3ε |
| CD83 | ICOS | DAP10 | FcγRI-γ |
| CD83 | ICOS | DAP10 | FcγRIII-γ |
| CD83 | ICOS | DAP10 | FcεRIβ |
| CD83 | ICOS | DAP10 | FcεRIγ |
| CD83 | ICOS | DAP10 | DAP10 |
| CD83 | ICOS | DAP10 | DAP12 |
| CD83 | ICOS | DAP10 | CD32 |
| CD83 | ICOS | DAP10 | CD79a |
| CD83 | ICOS | DAP10 | CD79b |
| CD83 | ICOS | DAP12 | CD8 |
| CD83 | ICOS | DAP12 | CD3ζ |
| CD83 | ICOS | DAP12 | CD3δ |
| CD83 | ICOS | DAP12 | CD3γ |
| CD83 | ICOS | DAP12 | CD3ε |
| CD83 | ICOS | DAP12 | FcγRI-γ |
| CD83 | ICOS | DAP12 | FcγRIII-γ |
| CD83 | ICOS | DAP12 | FcεRIβ |
| CD83 | ICOS | DAP12 | FcεRIγ |
| CD83 | ICOS | DAP12 | DAP10 |
| CD83 | ICOS | DAP12 | DAP12 |
| CD83 | ICOS | DAP12 | CD32 |
| CD83 | ICOS | DAP12 | CD79a |
| CD83 | ICOS | DAP12 | CD79b |
| CD83 | ICOS | MyD88 | CD8 |
| CD83 | ICOS | MyD88 | CD3ζ |
| CD83 | ICOS | MyD88 | CD3δ |
| CD83 | ICOS | MyD88 | CD3γ |
| CD83 | ICOS | MyD88 | CD3ε |
| CD83 | ICOS | MyD88 | FcγRI-γ |
| CD83 | ICOS | MyD88 | FcγRIII-γ |
| CD83 | ICOS | MyD88 | FcεRIβ |
| CD83 | ICOS | MyD88 | FcεRIγ |
| CD83 | ICOS | MyD88 | DAP10 |
| CD83 | ICOS | MyD88 | DAP12 |
| CD83 | ICOS | MyD88 | CD32 |
| CD83 | ICOS | MyD88 | CD79a |
| CD83 | ICOS | MyD88 | CD79b |
| CD83 | ICOS | CD7 | CD8 |
| CD83 | ICOS | CD7 | CD3ζ |
| CD83 | ICOS | CD7 | CD3δ |
| CD83 | ICOS | CD7 | CD3γ |
| CD83 | ICOS | CD7 | CD3ε |
| CD83 | ICOS | CD7 | FcγRI-γ |
| CD83 | ICOS | CD7 | FcγRIII-γ |
| CD83 | ICOS | CD7 | FcεRIβ |
| CD83 | ICOS | CD7 | FcεRIγ |
| CD83 | ICOS | CD7 | DAP10 |
| CD83 | ICOS | CD7 | DAP12 |
| CD83 | ICOS | CD7 | CD32 |
| CD83 | ICOS | CD7 | CD79a |
| CD83 | ICOS | CD7 | CD79b |
| CD83 | ICOS | BTNL3 | CD8 |

TABLE 3-continued

Third Generation CARs

| ScFv | Co-stimulatory Signal | Co-stimulatory Signal | Signal Domain |
|---|---|---|---|
| CD83 | ICOS | BTNL3 | CD3ζ |
| CD83 | ICOS | BTNL3 | CD3δ |
| CD83 | ICOS | BTNL3 | CD3γ |
| CD83 | ICOS | BTNL3 | CD3ε |
| CD83 | ICOS | BTNL3 | FcγRI-γ |
| CD83 | ICOS | BTNL3 | FcγRIII-γ |
| CD83 | ICOS | BTNL3 | FcεRIβ |
| CD83 | ICOS | BTNL3 | FcεRIγ |
| CD83 | ICOS | BTNL3 | DAP10 |
| CD83 | ICOS | BTNL3 | DAP12 |
| CD83 | ICOS | BTNL3 | CD32 |
| CD83 | ICOS | BTNL3 | CD79a |
| CD83 | ICOS | BTNL3 | CD79b |
| CD83 | ICOS | NKG2D | CD8 |
| CD83 | ICOS | NKG2D | CD3ζ |
| CD83 | ICOS | NKG2D | CD3δ |
| CD83 | ICOS | NKG2D | CD3γ |
| CD83 | ICOS | NKG2D | CD3ε |
| CD83 | ICOS | NKG2D | FcγRI-γ |
| CD83 | ICOS | NKG2D | FcγRIII-γ |
| CD83 | ICOS | NKG2D | FcεRIβ |
| CD83 | ICOS | NKG2D | FcεRIγ |
| CD83 | ICOS | NKG2D | DAP10 |
| CD83 | ICOS | NKG2D | DAP12 |
| CD83 | ICOS | NKG2D | CD32 |
| CD83 | ICOS | NKG2D | CD79a |
| CD83 | ICOS | NKG2D | CD79b |
| CD83 | CD27 | CD28 | CD8 |
| CD83 | CD27 | CD28 | CD3ζ |
| CD83 | CD27 | CD28 | CD3δ |
| CD83 | CD27 | CD28 | CD3γ |
| CD83 | CD27 | CD28 | CD3ε |
| CD83 | CD27 | CD28 | FcγRI-γ |
| CD83 | CD27 | CD28 | FcγRIII-γ |
| CD83 | CD27 | CD28 | FcεRIβ |
| CD83 | CD27 | CD28 | FcεRIγ |
| CD83 | CD27 | CD28 | DAP10 |
| CD83 | CD27 | CD28 | DAP12 |
| CD83 | CD27 | CD28 | CD32 |
| CD83 | CD27 | CD28 | CD79a |
| CD83 | CD27 | CD28 | CD79b |
| CD83 | CD27 | CD8 | CD8 |
| CD83 | CD27 | CD8 | CD3ζ |
| CD83 | CD27 | CD8 | CD3δ |
| CD83 | CD27 | CD8 | CD3γ |
| CD83 | CD27 | CD8 | CD3ε |
| CD83 | CD27 | CD8 | FcγRI-γ |
| CD83 | CD27 | CD8 | FcγRIII-γ |
| CD83 | CD27 | CD8 | FcεRIβ |
| CD83 | CD27 | CD8 | FcεRIγ |
| CD83 | CD27 | CD8 | DAP10 |
| CD83 | CD27 | CD8 | DAP12 |
| CD83 | CD27 | CD8 | CD32 |
| CD83 | CD27 | CD8 | CD79a |
| CD83 | CD27 | CD8 | CD79b |
| CD83 | CD27 | CD4 | CD8 |
| CD83 | CD27 | CD4 | CD3ζ |
| CD83 | CD27 | CD4 | CD3δ |
| CD83 | CD27 | CD4 | CD3γ |
| CD83 | CD27 | CD4 | CD3ε |
| CD83 | CD27 | CD4 | FcγRI-γ |
| CD83 | CD27 | CD4 | FcγRIII-γ |
| CD83 | CD27 | CD4 | FcεRIβ |
| CD83 | CD27 | CD4 | FcεRIγ |
| CD83 | CD27 | CD4 | DAP10 |
| CD83 | CD27 | CD4 | DAP12 |
| CD83 | CD27 | CD4 | CD32 |
| CD83 | CD27 | CD4 | CD79a |
| CD83 | CD27 | CD4 | CD79b |
| CD83 | CD27 | b2c | CD8 |
| CD83 | CD27 | b2c | CD3ζ |
| CD83 | CD27 | b2c | CD3δ |
| CD83 | CD27 | b2c | CD3γ |
| CD83 | CD27 | b2c | CD3ε |
| CD83 | CD27 | b2c | FcγRI-γ |

TABLE 3-continued

Third Generation CARs

| ScFv | Co-stimulatory Signal | Co-stimulatory Signal | Signal Domain |
|---|---|---|---|
| CD83 | CD27 | b2c | FcγRIII-γ |
| CD83 | CD27 | b2c | FcεRIβ |
| CD83 | CD27 | b2c | FcεRIγ |
| CD83 | CD27 | b2c | DAP10 |
| CD83 | CD27 | b2c | DAP12 |
| CD83 | CD27 | b2c | CD32 |
| CD83 | CD27 | b2c | CD79a |
| CD83 | CD27 | b2c | CD79b |
| CD83 | CD27 | CD137/41BB | CD8 |
| CD83 | CD27 | CD137/41BB | CD3ζ |
| CD83 | CD27 | CD137/41BB | CD3δ |
| CD83 | CD27 | CD137/41BB | CD3γ |
| CD83 | CD27 | CD137/41BB | CD3ε |
| CD83 | CD27 | CD137/41BB | FcγRI-γ |
| CD83 | CD27 | CD137/41BB | FcγRIII-γ |
| CD83 | CD27 | CD137/41BB | FcεRIβ |
| CD83 | CD27 | CD137/41BB | FcεRIγ |
| CD83 | CD27 | CD137/41BB | DAP10 |
| CD83 | CD27 | CD137/41BB | DAP12 |
| CD83 | CD27 | CD137/41BB | CD32 |
| CD83 | CD27 | CD137/41BB | CD79a |
| CD83 | CD27 | CD137/41BB | CD79b |
| CD83 | CD27 | ICOS | CD8 |
| CD83 | CD27 | ICOS | CD3ζ |
| CD83 | CD27 | ICOS | CD3δ |
| CD83 | CD27 | ICOS | CD3γ |
| CD83 | CD27 | ICOS | CD3ε |
| CD83 | CD27 | ICOS | FcγRI-γ |
| CD83 | CD27 | ICOS | FcγRIII-γ |
| CD83 | CD27 | ICOS | FcεRIβ |
| CD83 | CD27 | ICOS | FcεRIγ |
| CD83 | CD27 | ICOS | DAP10 |
| CD83 | CD27 | ICOS | DAP12 |
| CD83 | CD27 | ICOS | CD32 |
| CD83 | CD27 | ICOS | CD79a |
| CD83 | CD27 | ICOS | CD79b |
| CD83 | CD27 | CD27 | CD8 |
| CD83 | CD27 | CD27 | CD3ζ |
| CD83 | CD27 | CD27 | CD3δ |
| CD83 | CD27 | CD27 | CD3γ |
| CD83 | CD27 | CD27 | CD3ε |
| CD83 | CD27 | CD27 | FcγRI-γ |
| CD83 | CD27 | CD27 | FcγRIII-γ |
| CD83 | CD27 | CD27 | FcεRIβ |
| CD83 | CD27 | CD27 | FcεRIγ |
| CD83 | CD27 | CD27 | DAP10 |
| CD83 | CD27 | CD27 | DAP12 |
| CD83 | CD27 | CD27 | CD32 |
| CD83 | CD27 | CD27 | CD79a |
| CD83 | CD27 | CD27 | CD79b |
| CD83 | CD27 | CD28δ | CD8 |
| CD83 | CD27 | CD28δ | CD3ζ |
| CD83 | CD27 | CD28δ | CD3δ |
| CD83 | CD27 | CD28δ | CD3γ |
| CD83 | CD27 | CD28δ | CD3ε |
| CD83 | CD27 | CD28δ | FcγRI-γ |
| CD83 | CD27 | CD28δ | FcγRIII-γ |
| CD83 | CD27 | CD28δ | FcεRIβ |
| CD83 | CD27 | CD28δ | FcεRIγ |
| CD83 | CD27 | CD28δ | DAP10 |
| CD83 | CD27 | CD28δ | DAP12 |
| CD83 | CD27 | CD28δ | CD32 |
| CD83 | CD27 | CD28δ | CD79a |
| CD83 | CD27 | CD28δ | CD79b |
| CD83 | CD27 | CD80 | CD8 |
| CD83 | CD27 | CD80 | CD3ζ |
| CD83 | CD27 | CD80 | CD3δ |
| CD83 | CD27 | CD80 | CD3γ |
| CD83 | CD27 | CD80 | CD3ε |
| CD83 | CD27 | CD80 | FcγRI-γ |
| CD83 | CD27 | CD80 | FcγRIII-γ |
| CD83 | CD27 | CD80 | FcεRIβ |
| CD83 | CD27 | CD80 | FcεRIγ |
| CD83 | CD27 | CD80 | DAP10 |
| CD83 | CD27 | CD80 | DAP12 |

TABLE 3-continued

Third Generation CARs

| ScFv | Co-stimulatory Signal | Co-stimulatory Signal | Signal Domain |
|---|---|---|---|
| CD83 | CD27 | CD80 | CD32 |
| CD83 | CD27 | CD80 | CD79a |
| CD83 | CD27 | CD80 | CD79b |
| CD83 | CD27 | CD86 | CD8 |
| CD83 | CD27 | CD86 | CD3ζ |
| CD83 | CD27 | CD86 | CD3δ |
| CD83 | CD27 | CD86 | CD3γ |
| CD83 | CD27 | CD86 | CD3ε |
| CD83 | CD27 | CD86 | FcγRI-γ |
| CD83 | CD27 | CD86 | FcγRIII-γ |
| CD83 | CD27 | CD86 | FcεRIβ |
| CD83 | CD27 | CD86 | FcεRIγ |
| CD83 | CD27 | CD86 | DAP10 |
| CD83 | CD27 | CD86 | DAP12 |
| CD83 | CD27 | CD86 | CD32 |
| CD83 | CD27 | CD86 | CD79a |
| CD83 | CD27 | CD86 | CD79b |
| CD83 | CD27 | OX40 | CD8 |
| CD83 | CD27 | OX40 | CD3ζ |
| CD83 | CD27 | OX40 | CD3δ |
| CD83 | CD27 | OX40 | CD3γ |
| CD83 | CD27 | OX40 | CD3ε |
| CD83 | CD27 | OX40 | FcγRI-γ |
| CD83 | CD27 | OX40 | FcγRIII-γ |
| CD83 | CD27 | OX40 | FcεRIβ |
| CD83 | CD27 | OX40 | FcεRIγ |
| CD83 | CD27 | OX40 | DAP10 |
| CD83 | CD27 | OX40 | DAP12 |
| CD83 | CD27 | OX40 | CD32 |
| CD83 | CD27 | OX40 | CD79a |
| CD83 | CD27 | OX40 | CD79b |
| CD83 | CD27 | DAP10 | CD8 |
| CD83 | CD27 | DAP10 | CD3ζ |
| CD83 | CD27 | DAP10 | CD3δ |
| CD83 | CD27 | DAP10 | CD3γ |
| CD83 | CD27 | DAP10 | CD3ε |
| CD83 | CD27 | DAP10 | FcγRI-γ |
| CD83 | CD27 | DAP10 | FcγRIII-γ |
| CD83 | CD27 | DAP10 | FcεRIβ |
| CD83 | CD27 | DAP10 | FcεRIγ |
| CD83 | CD27 | DAP10 | DAP10 |
| CD83 | CD27 | DAP10 | DAP12 |
| CD83 | CD27 | DAP10 | CD32 |
| CD83 | CD27 | DAP10 | CD79a |
| CD83 | CD27 | DAP10 | CD79b |
| CD83 | CD27 | DAP12 | CD8 |
| CD83 | CD27 | DAP12 | CD3ζ |
| CD83 | CD27 | DAP12 | CD3δ |
| CD83 | CD27 | DAP12 | CD3γ |
| CD83 | CD27 | DAP12 | CD3ε |
| CD83 | CD27 | DAP12 | FcγRI-γ |
| CD83 | CD27 | DAP12 | FcγRIII-γ |
| CD83 | CD27 | DAP12 | FcεRIβ |
| CD83 | CD27 | DAP12 | FcεRIγ |
| CD83 | CD27 | DAP12 | DAP10 |
| CD83 | CD27 | DAP12 | DAP12 |
| CD83 | CD27 | DAP12 | CD32 |
| CD83 | CD27 | DAP12 | CD79a |
| CD83 | CD27 | DAP12 | CD79b |
| CD83 | CD27 | MyD88 | CD8 |
| CD83 | CD27 | MyD88 | CD3ζ |
| CD83 | CD27 | MyD88 | CD3δ |
| CD83 | CD27 | MyD88 | CD3γ |
| CD83 | CD27 | MyD88 | CD3ε |
| CD83 | CD27 | MyD88 | FcγRI-γ |
| CD83 | CD27 | MyD88 | FcγRIII-γ |
| CD83 | CD27 | MyD88 | FcεRIβ |
| CD83 | CD27 | MyD88 | FcεRIγ |
| CD83 | CD27 | MyD88 | DAP10 |
| CD83 | CD27 | MyD88 | DAP12 |
| CD83 | CD27 | MyD88 | CD32 |
| CD83 | CD27 | MyD88 | CD79a |
| CD83 | CD27 | MyD88 | CD79b |
| CD83 | CD27 | CD7 | CD8 |
| CD83 | CD27 | CD7 | CD3ζ |
| CD83 | CD27 | CD7 | CD3δ |
| CD83 | CD27 | CD7 | CD3γ |
| CD83 | CD27 | CD7 | CD3ε |
| CD83 | CD27 | CD7 | FcγRI-γ |
| CD83 | CD27 | CD7 | FcγRIII-γ |
| CD83 | CD27 | CD7 | FcγRIβ |
| CD83 | CD27 | CD7 | FcεRIγ |
| CD83 | CD27 | CD7 | DAP10 |
| CD83 | CD27 | CD7 | DAP12 |
| CD83 | CD27 | CD7 | CD32 |
| CD83 | CD27 | CD7 | CD79a |
| CD83 | CD27 | CD7 | CD79b |
| CD83 | CD27 | BTNL3 | CD8 |
| CD83 | CD27 | BTNL3 | CD3ζ |
| CD83 | CD27 | BTNL3 | CD3δ |
| CD83 | CD27 | BTNL3 | CD3γ |
| CD83 | CD27 | BTNL3 | CD3ε |
| CD83 | CD27 | BTNL3 | FcγRI-γ |
| CD83 | CD27 | BTNL3 | FcγRIII-γ |
| CD83 | CD27 | BTNL3 | FcεRIβ |
| CD83 | CD27 | BTNL3 | FcεRIγ |
| CD83 | CD27 | BTNL3 | DAP10 |
| CD83 | CD27 | BTNL3 | DAP12 |
| CD83 | CD27 | BTNL3 | CD32 |
| CD83 | CD27 | BTNL3 | CD79a |
| CD83 | CD27 | BTNL3 | CD79b |
| CD83 | CD27 | NKG2D | CD8 |
| CD83 | CD27 | NKG2D | CD3ζ |
| CD83 | CD27 | NKG2D | CD3δ |
| CD83 | CD27 | NKG2D | CD3γ |
| CD83 | CD27 | NKG2D | CD3ε |
| CD83 | CD27 | NKG2D | FcγRI-γ |
| CD83 | CD27 | NKG2D | FcγRIII-γ |
| CD83 | CD27 | NKG2D | FcεRIβ |
| CD83 | CD27 | NKG2D | FcεRIγ |
| CD83 | CD27 | NKG2D | DAP10 |
| CD83 | CD27 | NKG2D | DAP12 |
| CD83 | CD27 | NKG2D | CD32 |
| CD83 | CD27 | NKG2D | CD79a |
| CD83 | CD27 | NKG2D | CD79b |
| CD83 | CD28δ | CD28 | CD8 |
| CD83 | CD28δ | CD28 | CD3ζ |
| CD83 | CD28δ | CD28 | CD3δ |
| CD83 | CD28δ | CD28 | CD3γ |
| CD83 | CD28δ | CD28 | CD3ε |
| CD83 | CD28δ | CD28 | FcγRI-γ |
| CD83 | CD28δ | CD28 | FcγRIII-γ |
| CD83 | CD28δ | CD28 | FcεRIβ |
| CD83 | CD28δ | CD28 | FcεRIγ |
| CD83 | CD28δ | CD28 | DAP10 |
| CD83 | CD28δ | CD28 | DAP12 |
| CD83 | CD28δ | CD28 | CD32 |
| CD83 | CD28δ | CD28 | CD79a |
| CD83 | CD28δ | CD28 | CD79b |
| CD83 | CD28δ | CD8 | CD8 |
| CD83 | CD28δ | CD8 | CD3ζ |
| CD83 | CD28δ | CD8 | CD3δ |
| CD83 | CD28δ | CD8 | CD3γ |
| CD83 | CD28δ | CD8 | CD3ε |
| CD83 | CD28δ | CD8 | FcγRI-γ |
| CD83 | CD28δ | CD8 | FcγRIII-γ |
| CD83 | CD28δ | CD8 | FcεRIβ |
| CD83 | CD28δ | CD8 | FcεRIγ |
| CD83 | CD28δ | CD8 | DAP10 |
| CD83 | CD28δ | CD8 | DAP12 |
| CD83 | CD28δ | CD8 | CD32 |
| CD83 | CD28δ | CD8 | CD79a |
| CD83 | CD28δ | CD8 | CD79b |
| CD83 | CD28δ | CD4 | CD8 |
| CD83 | CD28δ | CD4 | CD3ζ |
| CD83 | CD28δ | CD4 | CD3δ |
| CD83 | CD28δ | CD4 | CD3γ |
| CD83 | CD28δ | CD4 | CD3ε |
| CD83 | CD28δ | CD4 | FcγRI-γ |
| CD83 | CD28δ | CD4 | FcγRIII-γ |

TABLE 3-continued

Third Generation CARs

| ScFv | Co-stimulatory Signal | Co-stimulatory Signal | Signal Domain |
|---|---|---|---|
| CD83 | CD28δ | CD4 | FcεRIβ |
| CD83 | CD28δ | CD4 | FcεRIγ |
| CD83 | CD28δ | CD4 | DAP10 |
| CD83 | CD28δ | CD4 | DAP12 |
| CD83 | CD28δ | CD4 | CD32 |
| CD83 | CD28δ | CD4 | CD79a |
| CD83 | CD28δ | CD4 | CD79b |
| CD83 | CD28δ | b2c | CD8 |
| CD83 | CD28δ | b2c | CD3ζ |
| CD83 | CD28δ | b2c | CD3δ |
| CD83 | CD28δ | b2c | CD3γ |
| CD83 | CD28δ | b2c | CD3ε |
| CD83 | CD28δ | b2c | FcγRI-γ |
| CD83 | CD28δ | b2c | FcγRIII-γ |
| CD83 | CD28δ | b2c | FcεRIβ |
| CD83 | CD28δ | b2c | FcεRIγ |
| CD83 | CD28δ | b2c | DAP10 |
| CD83 | CD28δ | b2c | DAP12 |
| CD83 | CD28δ | b2c | CD32 |
| CD83 | CD28δ | b2c | CD79a |
| CD83 | CD28δ | b2c | CD79b |
| CD83 | CD28δ | CD137/41BB | CD8 |
| CD83 | CD28δ | CD137/41BB | CD3ζ |
| CD83 | CD28δ | CD137/41BB | CD3δ |
| CD83 | CD28δ | CD137/41BB | CD3γ |
| CD83 | CD28δ | CD137/41BB | CD3ε |
| CD83 | CD28δ | CD137/41BB | FcγRI-γ |
| CD83 | CD28δ | CD137/41BB | FcγRIII-γ |
| CD83 | CD28δ | CD137/41BB | FcεRIβ |
| CD83 | CD28δ | CD137/41BB | FcεRIγ |
| CD83 | CD28δ | CD137/41BB | DAP10 |
| CD83 | CD28δ | CD137/41BB | DAP12 |
| CD83 | CD28δ | CD137/41BB | CD32 |
| CD83 | CD28δ | CD137/41BB | CD79a |
| CD83 | CD28δ | CD137/41BB | CD79b |
| CD83 | CD28δ | ICOS | CD8 |
| CD83 | CD28δ | ICOS | CD3ζ |
| CD83 | CD28δ | ICOS | CD3δ |
| CD83 | CD28δ | ICOS | CD3γ |
| CD83 | CD28δ | ICOS | CD3ε |
| CD83 | CD28δ | ICOS | FcγRI-γ |
| CD83 | CD28δ | ICOS | FcγRIII-γ |
| CD83 | CD28δ | ICOS | FcεRIβ |
| CD83 | CD28δ | ICOS | FcεRIγ |
| CD83 | CD28δ | ICOS | DAP10 |
| CD83 | CD28δ | ICOS | DAP12 |
| CD83 | CD28δ | ICOS | CD32 |
| CD83 | CD28δ | ICOS | CD79a |
| CD83 | CD28δ | ICOS | CD79b |
| CD83 | CD28δ | CD27 | CD8 |
| CD83 | CD28δ | CD27 | CD3ζ |
| CD83 | CD28δ | CD27 | CD3δ |
| CD83 | CD28δ | CD27 | CD3γ |
| CD83 | CD28δ | CD27 | CD3ε |
| CD83 | CD28δ | CD27 | FcγRI-γ |
| CD83 | CD28δ | CD27 | FcγRIII-γ |
| CD83 | CD28δ | CD27 | FcεRIβ |
| CD83 | CD28δ | CD27 | FcεRIγ |
| CD83 | CD28δ | CD27 | DAP10 |
| CD83 | CD28δ | CD27 | DAP12 |
| CD83 | CD28δ | CD27 | CD32 |
| CD83 | CD28δ | CD27 | CD79a |
| CD83 | CD28δ | CD27 | CD79b |
| CD83 | CD28δ | CD28δ | CD8 |
| CD83 | CD28δ | CD28δ | CD3ζ |
| CD83 | CD28δ | CD28δ | CD3δ |
| CD83 | CD28δ | CD28δ | CD3γ |
| CD83 | CD28δ | CD28δ | CD3ε |
| CD83 | CD28δ | CD28δ | FcγRI-γ |
| CD83 | CD28δ | CD28δ | FcγRIII-γ |
| CD83 | CD28δ | CD28δ | FcεRIβ |
| CD83 | CD28δ | CD28δ | FcεRIγ |
| CD83 | CD28δ | CD28δ | DAP10 |
| CD83 | CD28δ | CD28δ | DAP12 |
| CD83 | CD28δ | CD28δ | CD32 |

TABLE 3-continued

Third Generation CARs

| ScFv | Co-stimulatory Signal | Co-stimulatory Signal | Signal Domain |
|---|---|---|---|
| CD83 | CD28δ | CD28δ | CD79a |
| CD83 | CD28δ | CD28δ | CD79b |
| CD83 | CD28δ | CD80 | CD8 |
| CD83 | CD28δ | CD80 | CD3ζ |
| CD83 | CD28δ | CD80 | CD3δ |
| CD83 | CD28δ | CD80 | CD3γ |
| CD83 | CD28δ | CD80 | CD3ε |
| CD83 | CD28δ | CD80 | FcγRI-γ |
| CD83 | CD28δ | CD80 | FcγRIII-γ |
| CD83 | CD28δ | CD80 | FcεRIβ |
| CD83 | CD28δ | CD80 | FcεRIγ |
| CD83 | CD28δ | CD80 | DAP10 |
| CD83 | CD28δ | CD80 | DAP12 |
| CD83 | CD28δ | CD80 | CD32 |
| CD83 | CD28δ | CD80 | CD79a |
| CD83 | CD28δ | CD80 | CD79b |
| CD83 | CD28δ | CD86 | CD8 |
| CD83 | CD28δ | CD86 | CD3ζ |
| CD83 | CD28δ | CD86 | CD3δ |
| CD83 | CD28δ | CD86 | CD3γ |
| CD83 | CD28δ | CD86 | CD3ε |
| CD83 | CD28δ | CD86 | FcγRI-γ |
| CD83 | CD28δ | CD86 | FcγRIII-γ |
| CD83 | CD28δ | CD86 | FcεRIβ |
| CD83 | CD28δ | CD86 | FcεRIγ |
| CD83 | CD28δ | CD86 | DAP10 |
| CD83 | CD28δ | CD86 | DAP12 |
| CD83 | CD28δ | CD86 | CD32 |
| CD83 | CD28δ | CD86 | CD79a |
| CD83 | CD28δ | CD86 | CD79b |
| CD83 | CD28δ | OX40 | CD8 |
| CD83 | CD28δ | OX40 | CD3ζ |
| CD83 | CD28δ | OX40 | CD3δ |
| CD83 | CD28δ | OX40 | CD3γ |
| CD83 | CD28δ | OX40 | CD3ε |
| CD83 | CD28δ | OX40 | FcγRI-γ |
| CD83 | CD28δ | OX40 | FcγRIII-γ |
| CD83 | CD28δ | OX40 | FcεRIβ |
| CD83 | CD28δ | OX40 | FcεRIγ |
| CD83 | CD28δ | OX40 | DAP10 |
| CD83 | CD28δ | OX40 | DAP12 |
| CD83 | CD28δ | OX40 | CD32 |
| CD83 | CD28δ | OX40 | CD79a |
| CD83 | CD28δ | OX40 | CD79b |
| CD83 | CD28δ | DAP10 | CD8 |
| CD83 | CD28δ | DAP10 | CD3ζ |
| CD83 | CD28δ | DAP10 | CD3δ |
| CD83 | CD28δ | DAP10 | CD3γ |
| CD83 | CD28δ | DAP10 | CD3ε |
| CD83 | CD28δ | DAP10 | FcγRI-γ |
| CD83 | CD28δ | DAP10 | FcγRIII-γ |
| CD83 | CD28δ | DAP10 | FcεRIβ |
| CD83 | CD28δ | DAP10 | FcεRIγ |
| CD83 | CD28δ | DAP10 | DAP10 |
| CD83 | CD28δ | DAP10 | DAP12 |
| CD83 | CD28δ | DAP10 | CD32 |
| CD83 | CD28δ | DAP10 | CD79a |
| CD83 | CD28δ | DAP10 | CD79b |
| CD83 | CD28δ | DAP12 | CD8 |
| CD83 | CD28δ | DAP12 | CD3ζ |
| CD83 | CD28δ | DAP12 | CD3δ |
| CD83 | CD28δ | DAP12 | CD3γ |
| CD83 | CD28δ | DAP12 | CD3ε |
| CD83 | CD28δ | DAP12 | FcγRI-γ |
| CD83 | CD28δ | DAP12 | FcγRIII-γ |
| CD83 | CD28δ | DAP12 | FcεRIβ |
| CD83 | CD28δ | DAP12 | FcεRIγ |
| CD83 | CD28δ | DAP12 | DAP10 |
| CD83 | CD28δ | DAP12 | DAP12 |
| CD83 | CD28δ | DAP12 | CD32 |
| CD83 | CD28δ | DAP12 | CD79a |
| CD83 | CD28δ | DAP12 | CD79b |
| CD83 | CD28δ | MyD88 | CD8 |
| CD83 | CD28δ | MyD88 | CD3ζ |
| CD83 | CD28δ | MyD88 | CD3δ |

TABLE 3-continued

Third Generation CARs

| ScFv | Co-stimulatory Signal | Co-stimulatory Signal | Signal Domain |
|---|---|---|---|
| CD83 | CD28δ | MyD88 | CD3γ |
| CD83 | CD28δ | MyD88 | CD3ε |
| CD83 | CD28δ | MyD88 | FcγRI-γ |
| CD83 | CD28δ | MyD88 | FcγRIII-γ |
| CD83 | CD28δ | MyD88 | FcεRIβ |
| CD83 | CD28δ | MyD88 | FcεRIγ |
| CD83 | CD28δ | MyD88 | DAP10 |
| CD83 | CD28δ | MyD88 | DAP12 |
| CD83 | CD28δ | MyD88 | CD32 |
| CD83 | CD28δ | MyD88 | CD79a |
| CD83 | CD28δ | MyD88 | CD79b |
| CD83 | CD28δ | CD7 | CD8 |
| CD83 | CD28δ | CD7 | CD3ζ |
| CD83 | CD28δ | CD7 | CD3δ |
| CD83 | CD28δ | CD7 | CD3γ |
| CD83 | CD28δ | CD7 | CD3ε |
| CD83 | CD28δ | CD7 | FcγRI-γ |
| CD83 | CD28δ | CD7 | FcγRIII-γ |
| CD83 | CD28δ | CD7 | FcεRIβ |
| CD83 | CD28δ | CD7 | FcεRIγ |
| CD83 | CD28δ | CD7 | DAP10 |
| CD83 | CD28δ | CD7 | DAP12 |
| CD83 | CD28δ | CD7 | CD32 |
| CD83 | CD28δ | CD7 | CD79a |
| CD83 | CD28δ | CD7 | CD79b |
| CD83 | CD28δ | BTNL3 | CD8 |
| CD83 | CD28δ | BTNL3 | CD3ζ |
| CD83 | CD28δ | BTNL3 | CD3δ |
| CD83 | CD28δ | BTNL3 | CD3γ |
| CD83 | CD28δ | BTNL3 | CD3ε |
| CD83 | CD28δ | BTNL3 | FcγRI-γ |
| CD83 | CD28δ | BTNL3 | FcγRIII-γ |
| CD83 | CD28δ | BTNL3 | FcεRIβ |
| CD83 | CD28δ | BTNL3 | FcεRIγ |
| CD83 | CD28δ | BTNL3 | DAP10 |
| CD83 | CD28δ | BTNL3 | DAP12 |
| CD83 | CD28δ | BTNL3 | CD32 |
| CD83 | CD28δ | BTNL3 | CD79a |
| CD83 | CD28δ | BTNL3 | CD79b |
| CD83 | CD28δ | NKG2D | CD8 |
| CD83 | CD28δ | NKG2D | CD3ζ |
| CD83 | CD28δ | NKG2D | CD3δ |
| CD83 | CD28δ | NKG2D | CD3γ |
| CD83 | CD28δ | NKG2D | CD3ε |
| CD83 | CD28δ | NKG2D | FcγRI-γ |
| CD83 | CD28δ | NKG2D | FcγRIII-γ |
| CD83 | CD28δ | NKG2D | FcεRIβ |
| CD83 | CD28δ | NKG2D | FcεRIγ |
| CD83 | CD28δ | NKG2D | DAP10 |
| CD83 | CD28δ | NKG2D | DAP12 |
| CD83 | CD28δ | NKG2D | CD32 |
| CD83 | CD28δ | NKG2D | CD79a |
| CD83 | CD28δ | NKG2D | CD79b |
| CD83 | CD80 | CD28 | CD8 |
| CD83 | CD80 | CD28 | CD3ζ |
| CD83 | CD80 | CD28 | CD3δ |
| CD83 | CD80 | CD28 | CD3γ |
| CD83 | CD80 | CD28 | CD3ε |
| CD83 | CD80 | CD28 | FcγRI-γ |
| CD83 | CD80 | CD28 | FcγRIII-γ |
| CD83 | CD80 | CD28 | FcεRIβ |
| CD83 | CD80 | CD28 | FcεRIγ |
| CD83 | CD80 | CD28 | DAP10 |
| CD83 | CD80 | CD28 | DAP12 |
| CD83 | CD80 | CD28 | CD32 |
| CD83 | CD80 | CD28 | CD79a |
| CD83 | CD80 | CD28 | CD79b |
| CD83 | CD80 | CD8 | CD8 |
| CD83 | CD80 | CD8 | CD3ζ |
| CD83 | CD80 | CD8 | CD3δ |
| CD83 | CD80 | CD8 | CD3γ |
| CD83 | CD80 | CD8 | CD3ε |
| CD83 | CD80 | CD8 | FcγRI-γ |
| CD83 | CD80 | CD8 | FcγRIII-γ |
| CD83 | CD80 | CD8 | FcεRIβ |

TABLE 3-continued

Third Generation CARs

| ScFv | Co-stimulatory Signal | Co-stimulatory Signal | Signal Domain |
|---|---|---|---|
| CD83 | CD80 | CD8 | FcεRIγ |
| CD83 | CD80 | CD8 | DAP10 |
| CD83 | CD80 | CD8 | DAP12 |
| CD83 | CD80 | CD8 | CD32 |
| CD83 | CD80 | CD8 | CD79a |
| CD83 | CD80 | CD8 | CD79b |
| CD83 | CD80 | CD4 | CD8 |
| CD83 | CD80 | CD4 | CD3ζ |
| CD83 | CD80 | CD4 | CD3δ |
| CD83 | CD80 | CD4 | CD3γ |
| CD83 | CD80 | CD4 | CD3ε |
| CD83 | CD80 | CD4 | FcγRI-γ |
| CD83 | CD80 | CD4 | FcγRIII-γ |
| CD83 | CD80 | CD4 | FcεRIβ |
| CD83 | CD80 | CD4 | FcεRIγ |
| CD83 | CD80 | CD4 | DAP10 |
| CD83 | CD80 | CD4 | DAP12 |
| CD83 | CD80 | CD4 | CD32 |
| CD83 | CD80 | CD4 | CD79a |
| CD83 | CD80 | CD4 | CD79b |
| CD83 | CD80 | b2c | CD8 |
| CD83 | CD80 | b2c | CD3ζ |
| CD83 | CD80 | b2c | CD3δ |
| CD83 | CD80 | b2c | CD3γ |
| CD83 | CD80 | b2c | CD3ε |
| CD83 | CD80 | b2c | FcγRI-γ |
| CD83 | CD80 | b2c | FcγRIII-γ |
| CD83 | CD80 | b2c | FcεRIβ |
| CD83 | CD80 | b2c | FcεRIγ |
| CD83 | CD80 | b2c | DAP10 |
| CD83 | CD80 | b2c | DAP12 |
| CD83 | CD80 | b2c | CD32 |
| CD83 | CD80 | b2c | CD79a |
| CD83 | CD80 | b2c | CD79b |
| CD83 | CD80 | CD137/41BB | CD8 |
| CD83 | CD80 | CD137/41BB | CD3ζ |
| CD83 | CD80 | CD137/41BB | CD3δ |
| CD83 | CD80 | CD137/41BB | CD3γ |
| CD83 | CD80 | CD137/41BB | CD3ε |
| CD83 | CD80 | CD137/41BB | FcγRI-γ |
| CD83 | CD80 | CD137/41BB | FcγRIII-γ |
| CD83 | CD80 | CD137/41BB | FcεRIβ |
| CD83 | CD80 | CD137/41BB | FcεRIγ |
| CD83 | CD80 | CD137/41BB | DAP10 |
| CD83 | CD80 | CD137/41BB | DAP12 |
| CD83 | CD80 | CD137/41BB | CD32 |
| CD83 | CD80 | CD137/41BB | CD79a |
| CD83 | CD80 | CD137/41BB | CD79b |
| CD83 | CD80 | ICOS | CD8 |
| CD83 | CD80 | ICOS | CD3ζ |
| CD83 | CD80 | ICOS | CD3δ |
| CD83 | CD80 | ICOS | CD3γ |
| CD83 | CD80 | ICOS | CD3ε |
| CD83 | CD80 | ICOS | FcγRI-γ |
| CD83 | CD80 | ICOS | FcγRIII-γ |
| CD83 | CD80 | ICOS | FcεRIβ |
| CD83 | CD80 | ICOS | FcεRIγ |
| CD83 | CD80 | ICOS | DAP10 |
| CD83 | CD80 | ICOS | DAP12 |
| CD83 | CD80 | ICOS | CD32 |
| CD83 | CD80 | ICOS | CD79a |
| CD83 | CD80 | ICOS | CD79b |
| CD83 | CD80 | CD27 | CD8 |
| CD83 | CD80 | CD27 | CD3ζ |
| CD83 | CD80 | CD27 | CD3δ |
| CD83 | CD80 | CD27 | CD3γ |
| CD83 | CD80 | CD27 | CD3ε |
| CD83 | CD80 | CD27 | FcγRI-γ |
| CD83 | CD80 | CD27 | FcγRIII-γ |
| CD83 | CD80 | CD27 | FcεRIβ |
| CD83 | CD80 | CD27 | FcεRIγ |
| CD83 | CD80 | CD27 | DAP10 |
| CD83 | CD80 | CD27 | DAP12 |
| CD83 | CD80 | CD27 | CD32 |
| CD83 | CD80 | CD27 | CD79a |

TABLE 3-continued

Third Generation CARs

| ScFv | Co-stimulatory Signal | Co-stimulatory Signal | Signal Domain |
|---|---|---|---|
| CD83 | CD80 | CD27 | CD79b |
| CD83 | CD80 | CD28δ | CD8 |
| CD83 | CD80 | CD28δ | CD3ζ |
| CD83 | CD80 | CD28δ | CD3δ |
| CD83 | CD80 | CD28δ | CD3γ |
| CD83 | CD80 | CD28δ | CD3ε |
| CD83 | CD80 | CD28δ | FcγRI-γ |
| CD83 | CD80 | CD28δ | FcγRIII-γ |
| CD83 | CD80 | CD28δ | FcεRIβ |
| CD83 | CD80 | CD28δ | FcεRIγ |
| CD83 | CD80 | CD28δ | DAP10 |
| CD83 | CD80 | CD28δ | DAP12 |
| CD83 | CD80 | CD28δ | CD32 |
| CD83 | CD80 | CD28δ | CD79a |
| CD83 | CD80 | CD28δ | CD79b |
| CD83 | CD80 | CD80 | CD8 |
| CD83 | CD80 | CD80 | CD3ζ |
| CD83 | CD80 | CD80 | CD3δ |
| CD83 | CD80 | CD80 | CD3γ |
| CD83 | CD80 | CD80 | CD3ε |
| CD83 | CD80 | CD80 | FcγRI-γ |
| CD83 | CD80 | CD80 | FcγRIII-γ |
| CD83 | CD80 | CD80 | FcεRIβ |
| CD83 | CD80 | CD80 | FcεRIγ |
| CD83 | CD80 | CD80 | DAP10 |
| CD83 | CD80 | CD80 | DAP12 |
| CD83 | CD80 | CD80 | CD32 |
| CD83 | CD80 | CD80 | CD79a |
| CD83 | CD80 | CD80 | CD79b |
| CD83 | CD80 | CD86 | CD8 |
| CD83 | CD80 | CD86 | CD3ζ |
| CD83 | CD80 | CD86 | CD3δ |
| CD83 | CD80 | CD86 | CD3γ |
| CD83 | CD80 | CD86 | CD3ε |
| CD83 | CD80 | CD86 | FcγRI-γ |
| CD83 | CD80 | CD86 | FcγRIII-γ |
| CD83 | CD80 | CD86 | FcεRIβ |
| CD83 | CD80 | CD86 | FcεRIγ |
| CD83 | CD80 | CD86 | DAP10 |
| CD83 | CD80 | CD86 | DAP12 |
| CD83 | CD80 | CD86 | CD32 |
| CD83 | CD80 | CD86 | CD79a |
| CD83 | CD80 | CD86 | CD79b |
| CD83 | CD80 | OX40 | CD8 |
| CD83 | CD80 | OX40 | CD3ζ |
| CD83 | CD80 | OX40 | CD3δ |
| CD83 | CD80 | OX40 | CD3γ |
| CD83 | CD80 | OX40 | CD3ε |
| CD83 | CD80 | OX40 | FcγRI-γ |
| CD83 | CD80 | OX40 | FcγRIII-γ |
| CD83 | CD80 | OX40 | FcεRIβ |
| CD83 | CD80 | OX40 | FcεRIγ |
| CD83 | CD80 | OX40 | DAP10 |
| CD83 | CD80 | OX40 | DAP12 |
| CD83 | CD80 | OX40 | CD32 |
| CD83 | CD80 | OX40 | CD79a |
| CD83 | CD80 | OX40 | CD79b |
| CD83 | CD80 | DAP10 | CD8 |
| CD83 | CD80 | DAP10 | CD3ζ |
| CD83 | CD80 | DAP10 | CD3δ |
| CD83 | CD80 | DAP10 | CD3γ |
| CD83 | CD80 | DAP10 | CD3ε |
| CD83 | CD80 | DAP10 | FcγRI-γ |
| CD83 | CD80 | DAP10 | FcγRIII-γ |
| CD83 | CD80 | DAP10 | FcεRIβ |
| CD83 | CD80 | DAP10 | FcεRIγ |
| CD83 | CD80 | DAP10 | DAP10 |
| CD83 | CD80 | DAP10 | DAP12 |
| CD83 | CD80 | DAP10 | CD32 |
| CD83 | CD80 | DAP10 | CD79a |
| CD83 | CD80 | DAP10 | CD79b |
| CD83 | CD80 | DAP12 | CD8 |
| CD83 | CD80 | DAP12 | CD3ζ |
| CD83 | CD80 | DAP12 | CD3δ |
| CD83 | CD80 | DAP12 | CD3γ |

TABLE 3-continued

Third Generation CARs

| ScFv | Co-stimulatory Signal | Co-stimulatory Signal | Signal Domain |
|---|---|---|---|
| CD83 | CD80 | DAP12 | CD3ε |
| CD83 | CD80 | DAP12 | FcγRI-γ |
| CD83 | CD80 | DAP12 | FcγRIII-γ |
| CD83 | CD80 | DAP12 | FcεRIβ |
| CD83 | CD80 | DAP12 | FcεRIγ |
| CD83 | CD80 | DAP12 | DAP10 |
| CD83 | CD80 | DAP12 | DAP12 |
| CD83 | CD80 | DAP12 | CD32 |
| CD83 | CD80 | DAP12 | CD79a |
| CD83 | CD80 | DAP12 | CD79b |
| CD83 | CD80 | MyD88 | CD8 |
| CD83 | CD80 | MyD88 | CD3ζ |
| CD83 | CD80 | MyD88 | CD3δ |
| CD83 | CD80 | MyD88 | CD3γ |
| CD83 | CD80 | MyD88 | CD3ε |
| CD83 | CD80 | MyD88 | FcγRI-γ |
| CD83 | CD80 | MyD88 | FcγRIII-γ |
| CD83 | CD80 | MyD88 | FcεRIβ |
| CD83 | CD80 | MyD88 | FcεRIγ |
| CD83 | CD80 | MyD88 | DAP10 |
| CD83 | CD80 | MyD88 | DAP12 |
| CD83 | CD80 | MyD88 | CD32 |
| CD83 | CD80 | MyD88 | CD79a |
| CD83 | CD80 | MyD88 | CD79b |
| CD83 | CD80 | CD7 | CD8 |
| CD83 | CD80 | CD7 | CD3ζ |
| CD83 | CD80 | CD7 | CD3δ |
| CD83 | CD80 | CD7 | CD3γ |
| CD83 | CD80 | CD7 | CD3ε |
| CD83 | CD80 | CD7 | FcγRI-γ |
| CD83 | CD80 | CD7 | FcγRIII-γ |
| CD83 | CD80 | CD7 | FcεRIβ |
| CD83 | CD80 | CD7 | FcεRIγ |
| CD83 | CD80 | CD7 | DAP10 |
| CD83 | CD80 | CD7 | DAP12 |
| CD83 | CD80 | CD7 | CD32 |
| CD83 | CD80 | CD7 | CD79a |
| CD83 | CD80 | CD7 | CD79b |
| CD83 | CD80 | BTNL3 | CD8 |
| CD83 | CD80 | BTNL3 | CD3ζ |
| CD83 | CD80 | BTNL3 | CD3δ |
| CD83 | CD80 | BTNL3 | CD3γ |
| CD83 | CD80 | BTNL3 | CD3ε |
| CD83 | CD80 | BTNL3 | FcγRI-γ |
| CD83 | CD80 | BTNL3 | FcγRIII-γ |
| CD83 | CD80 | BTNL3 | FcεRIβ |
| CD83 | CD80 | BTNL3 | FcεRIγ |
| CD83 | CD80 | BTNL3 | DAP10 |
| CD83 | CD80 | BTNL3 | DAP12 |
| CD83 | CD80 | BTNL3 | CD32 |
| CD83 | CD80 | BTNL3 | CD79a |
| CD83 | CD80 | BTNL3 | CD79b |
| CD83 | CD80 | NKG2D | CD8 |
| CD83 | CD80 | NKG2D | CD3ζ |
| CD83 | CD80 | NKG2D | CD3δ |
| CD83 | CD80 | NKG2D | CD3γ |
| CD83 | CD80 | NKG2D | CD3ε |
| CD83 | CD80 | NKG2D | FcγRI-γ |
| CD83 | CD80 | NKG2D | FcγRIII-γ |
| CD83 | CD80 | NKG2D | FcεRIβ |
| CD83 | CD80 | NKG2D | FcεRIγ |
| CD83 | CD80 | NKG2D | DAP10 |
| CD83 | CD80 | NKG2D | DAP12 |
| CD83 | CD80 | NKG2D | CD32 |
| CD83 | CD80 | NKG2D | CD79a |
| CD83 | CD80 | NKG2D | CD79b |
| CD83 | CD86 | CD28 | CD8 |
| CD83 | CD86 | CD28 | CD3ζ |
| CD83 | CD86 | CD28 | CD3δ |
| CD83 | CD86 | CD28 | CD3γ |
| CD83 | CD86 | CD28 | CD3ε |
| CD83 | CD86 | CD28 | FcγRI-γ |
| CD83 | CD86 | CD28 | FcγRIII-γ |
| CD83 | CD86 | CD28 | FcεRIβ |
| CD83 | CD86 | CD28 | FcεRIγ |

TABLE 3-continued

Third Generation CARs

| ScFv | Co-stimulatory Signal | Co-stimulatory Signal | Signal Domain |
|---|---|---|---|
| CD83 | CD86 | CD28 | DAP10 |
| CD83 | CD86 | CD28 | DAP12 |
| CD83 | CD86 | CD28 | CD32 |
| CD83 | CD86 | CD28 | CD79a |
| CD83 | CD86 | CD28 | CD79b |
| CD83 | CD86 | CD8 | CD8 |
| CD83 | CD86 | CD8 | CD3ζ |
| CD83 | CD86 | CD8 | CD3δ |
| CD83 | CD86 | CD8 | CD3γ |
| CD83 | CD86 | CD8 | CD3ε |
| CD83 | CD86 | CD8 | FcγRI-γ |
| CD83 | CD86 | CD8 | FcγRIII-γ |
| CD83 | CD86 | CD8 | FcεRIβ |
| CD83 | CD86 | CD8 | FcεRIγ |
| CD83 | CD86 | CD8 | DAP10 |
| CD83 | CD86 | CD8 | DAP12 |
| CD83 | CD86 | CD8 | CD32 |
| CD83 | CD86 | CD8 | CD79a |
| CD83 | CD86 | CD8 | CD79b |
| CD83 | CD86 | CD4 | CD8 |
| CD83 | CD86 | CD4 | CD3ζ |
| CD83 | CD86 | CD4 | CD3δ |
| CD83 | CD86 | CD4 | CD3γ |
| CD83 | CD86 | CD4 | CD3ε |
| CD83 | CD86 | CD4 | FcγRI-γ |
| CD83 | CD86 | CD4 | FcγRIII-γ |
| CD83 | CD86 | CD4 | FcεRIβ |
| CD83 | CD86 | CD4 | FcεRIγ |
| CD83 | CD86 | CD4 | DAP10 |
| CD83 | CD86 | CD4 | DAP12 |
| CD83 | CD86 | CD4 | CD32 |
| CD83 | CD86 | CD4 | CD79a |
| CD83 | CD86 | CD4 | CD79b |
| CD83 | CD86 | b2c | CD8 |
| CD83 | CD86 | b2c | CD3ζ |
| CD83 | CD86 | b2c | CD3δ |
| CD83 | CD86 | b2c | CD3γ |
| CD83 | CD86 | b2c | CD3ε |
| CD83 | CD86 | b2c | FcγRI-γ |
| CD83 | CD86 | b2c | FcγRIII-γ |
| CD83 | CD86 | b2c | FcεRIβ |
| CD83 | CD86 | b2c | FcεRIγ |
| CD83 | CD86 | b2c | DAP10 |
| CD83 | CD86 | b2c | DAP12 |
| CD83 | CD86 | b2c | CD32 |
| CD83 | CD86 | b2c | CD79a |
| CD83 | CD86 | b2c | CD79b |
| CD83 | CD86 | CD137/41BB | CD8 |
| CD83 | CD86 | CD137/41BB | CD3ζ |
| CD83 | CD86 | CD137/41BB | CD3δ |
| CD83 | CD86 | CD137/41BB | CD3γ |
| CD83 | CD86 | CD137/41BB | CD3ε |
| CD83 | CD86 | CD137/41BB | FcγRI-γ |
| CD83 | CD86 | CD137/41BB | FcγRIII-γ |
| CD83 | CD86 | CD137/41BB | FcεRIβ |
| CD83 | CD86 | CD137/41BB | FcεRIγ |
| CD83 | CD86 | CD137/41BB | DAP10 |
| CD83 | CD86 | CD137/41BB | DAP12 |
| CD83 | CD86 | CD137/41BB | CD32 |
| CD83 | CD86 | CD137/41BB | CD79a |
| CD83 | CD86 | CD137/41BB | CD79b |
| CD83 | CD86 | ICOS | CD8 |
| CD83 | CD86 | ICOS | CD3ζ |
| CD83 | CD86 | ICOS | CD3δ |
| CD83 | CD86 | ICOS | CD3γ |
| CD83 | CD86 | ICOS | CD3ε |
| CD83 | CD86 | ICOS | FcγRI-γ |
| CD83 | CD86 | ICOS | FcγRIII-γ |
| CD83 | CD86 | ICOS | FcεRIβ |
| CD83 | CD86 | ICOS | FcεRIγ |
| CD83 | CD86 | ICOS | DAP10 |
| CD83 | CD86 | ICOS | DAP12 |
| CD83 | CD86 | ICOS | CD32 |
| CD83 | CD86 | ICOS | CD79a |
| CD83 | CD86 | ICOS | CD79b |

TABLE 3-continued

Third Generation CARs

| ScFv | Co-stimulatory Signal | Co-stimulatory Signal | Signal Domain |
|---|---|---|---|
| CD83 | CD86 | CD27 | CD8 |
| CD83 | CD86 | CD27 | CD3ζ |
| CD83 | CD86 | CD27 | CD3δ |
| CD83 | CD86 | CD27 | CD3γ |
| CD83 | CD86 | CD27 | CD3ε |
| CD83 | CD86 | CD27 | FcγRI-γ |
| CD83 | CD86 | CD27 | FcγRIII-γ |
| CD83 | CD86 | CD27 | FcεRIβ |
| CD83 | CD86 | CD27 | FcεRIγ |
| CD83 | CD86 | CD27 | DAP10 |
| CD83 | CD86 | CD27 | DAP12 |
| CD83 | CD86 | CD27 | CD32 |
| CD83 | CD86 | CD27 | CD79a |
| CD83 | CD86 | CD27 | CD79b |
| CD83 | CD86 | CD28δ | CD8 |
| CD83 | CD86 | CD28δ | CD3ζ |
| CD83 | CD86 | CD28δ | CD3δ |
| CD83 | CD86 | CD28δ | CD3γ |
| CD83 | CD86 | CD28δ | CD3ε |
| CD83 | CD86 | CD28δ | FcγRI-γ |
| CD83 | CD86 | CD28δ | FcγRIII-γ |
| CD83 | CD86 | CD28δ | FcεRIβ |
| CD83 | CD86 | CD28δ | FcεRIγ |
| CD83 | CD86 | CD28δ | DAP10 |
| CD83 | CD86 | CD28δ | DAP12 |
| CD83 | CD86 | CD28δ | CD32 |
| CD83 | CD86 | CD28δ | CD79a |
| CD83 | CD86 | CD28δ | CD79b |
| CD83 | CD86 | CD80 | CD8 |
| CD83 | CD86 | CD80 | CD3ζ |
| CD83 | CD86 | CD80 | CD3δ |
| CD83 | CD86 | CD80 | CD3γ |
| CD83 | CD86 | CD80 | CD3ε |
| CD83 | CD86 | CD80 | FcγRI-γ |
| CD83 | CD86 | CD80 | FcγRIII-γ |
| CD83 | CD86 | CD80 | FcεRIβ |
| CD83 | CD86 | CD80 | FcεRIγ |
| CD83 | CD86 | CD80 | DAP10 |
| CD83 | CD86 | CD80 | DAP12 |
| CD83 | CD86 | CD80 | CD32 |
| CD83 | CD86 | CD80 | CD79a |
| CD83 | CD86 | CD80 | CD79b |
| CD83 | CD86 | CD86 | CD8 |
| CD83 | CD86 | CD86 | CD3ζ |
| CD83 | CD86 | CD86 | CD3δ |
| CD83 | CD86 | CD86 | CD3γ |
| CD83 | CD86 | CD86 | CD3ε |
| CD83 | CD86 | CD86 | FcγRI-γ |
| CD83 | CD86 | CD86 | FcγRIII-γ |
| CD83 | CD86 | CD86 | FcεRIβ |
| CD83 | CD86 | CD86 | FcεRIγ |
| CD83 | CD86 | CD86 | DAP10 |
| CD83 | CD86 | CD86 | DAP12 |
| CD83 | CD86 | CD86 | CD32 |
| CD83 | CD86 | CD86 | CD79a |
| CD83 | CD86 | CD86 | CD79b |
| CD83 | CD86 | OX40 | CD8 |
| CD83 | CD86 | OX40 | CD3ζ |
| CD83 | CD86 | OX40 | CD3δ |
| CD83 | CD86 | OX40 | CD3γ |
| CD83 | CD86 | OX40 | CD3ε |
| CD83 | CD86 | OX40 | FcγRI-γ |
| CD83 | CD86 | OX40 | FcγRIII-γ |
| CD83 | CD86 | OX40 | FcεRIβ |
| CD83 | CD86 | OX40 | FcεRIγ |
| CD83 | CD86 | OX40 | DAP10 |
| CD83 | CD86 | OX40 | DAP12 |
| CD83 | CD86 | OX40 | CD32 |
| CD83 | CD86 | OX40 | CD79a |
| CD83 | CD86 | OX40 | CD79b |
| CD83 | CD86 | DAP10 | CD8 |
| CD83 | CD86 | DAP10 | CD3ζ |
| CD83 | CD86 | DAP10 | CD3δ |
| CD83 | CD86 | DAP10 | CD3γ |
| CD83 | CD86 | DAP10 | CD3ε |

TABLE 3-continued

| Third Generation CARs | | | |
|---|---|---|---|
| ScFv | Co-stimulatory Signal | Co-stimulatory Signal | Signal Domain |
| CD83 | CD86 | DAP10 | FcγRI-γ |
| CD83 | CD86 | DAP10 | FcγRIII-γ |
| CD83 | CD86 | DAP10 | FcεRIβ |
| CD83 | CD86 | DAP10 | FcεRIγ |
| CD83 | CD86 | DAP10 | DAP10 |
| CD83 | CD86 | DAP10 | DAP12 |
| CD83 | CD86 | DAP10 | CD32 |
| CD83 | CD86 | DAP10 | CD79a |
| CD83 | CD86 | DAP10 | CD79b |
| CD83 | CD86 | DAP12 | CD8 |
| CD83 | CD86 | DAP12 | CD3ζ |
| CD83 | CD86 | DAP12 | CD3δ |
| CD83 | CD86 | DAP12 | CD3γ |
| CD83 | CD86 | DAP12 | CD3ε |
| CD83 | CD86 | DAP12 | FcγRI-γ |
| CD83 | CD86 | DAP12 | FcγRIII-γ |
| CD83 | CD86 | DAP12 | FcεRIβ |
| CD83 | CD86 | DAP12 | FcεRIγ |
| CD83 | CD86 | DAP12 | DAP10 |
| CD83 | CD86 | DAP12 | DAP12 |
| CD83 | CD86 | DAP12 | CD32 |
| CD83 | CD86 | DAP12 | CD79a |
| CD83 | CD86 | DAP12 | CD79b |
| CD83 | CD86 | MyD88 | CD8 |
| CD83 | CD86 | MyD88 | CD3ζ |
| CD83 | CD86 | MyD88 | CD3δ |
| CD83 | CD86 | MyD88 | CD3γ |
| CD83 | CD86 | MyD88 | CD3ε |
| CD83 | CD86 | MyD88 | FcγRI-γ |
| CD83 | CD86 | MyD88 | FcγRIII-γ |
| CD83 | CD86 | MyD88 | FcεRIβ |
| CD83 | CD86 | MyD88 | FcεRIγ |
| CD83 | CD86 | MyD88 | DAP10 |
| CD83 | CD86 | MyD88 | DAP12 |
| CD83 | CD86 | MyD88 | CD32 |
| CD83 | CD86 | MyD88 | CD79a |
| CD83 | CD86 | MyD88 | CD79b |
| CD83 | CD86 | CD7 | CD8 |
| CD83 | CD86 | CD7 | CD3ζ |
| CD83 | CD86 | CD7 | CD3δ |
| CD83 | CD86 | CD7 | CD3γ |
| CD83 | CD86 | CD7 | CD3ε |
| CD83 | CD86 | CD7 | FcγRI-γ |
| CD83 | CD86 | CD7 | FcγRIII-γ |
| CD83 | CD86 | CD7 | FcεRIβ |
| CD83 | CD86 | CD7 | FcεRIγ |
| CD83 | CD86 | CD7 | DAP10 |
| CD83 | CD86 | CD7 | DAP12 |
| CD83 | CD86 | CD7 | CD32 |
| CD83 | CD86 | CD7 | CD79a |
| CD83 | CD86 | CD7 | CD79b |
| CD83 | CD86 | BTNL3 | CD8 |
| CD83 | CD86 | BTNL3 | CD3ζ |
| CD83 | CD86 | BTNL3 | CD3δ |
| CD83 | CD86 | BTNL3 | CD3γ |
| CD83 | CD86 | BTNL3 | CD3ε |
| CD83 | CD86 | BTNL3 | FcγRI-γ |
| CD83 | CD86 | BTNL3 | FcγRIII-γ |
| CD83 | CD86 | BTNL3 | FcεRIβ |
| CD83 | CD86 | BTNL3 | FcεRIγ |
| CD83 | CD86 | BTNL3 | DAP10 |
| CD83 | CD86 | BTNL3 | DAP12 |
| CD83 | CD86 | BTNL3 | CD32 |
| CD83 | CD86 | BTNL3 | CD79a |
| CD83 | CD86 | BTNL3 | CD79b |
| CD83 | CD86 | NKG2D | CD8 |
| CD83 | CD86 | NKG2D | CD3ζ |
| CD83 | CD86 | NKG2D | CD3δ |
| CD83 | CD86 | NKG2D | CD3γ |
| CD83 | CD86 | NKG2D | CD3ε |
| CD83 | CD86 | NKG2D | FcγRI-γ |
| CD83 | CD86 | NKG2D | FcγRIII-γ |
| CD83 | CD86 | NKG2D | FcεRIβ |
| CD83 | CD86 | NKG2D | FcεRIγ |
| CD83 | CD86 | NKG2D | DAP10 |

TABLE 3-continued

| Third Generation CARs | | | |
|---|---|---|---|
| ScFv | Co-stimulatory Signal | Co-stimulatory Signal | Signal Domain |
| CD83 | CD86 | NKG2D | DAP12 |
| CD83 | CD86 | NKG2D | CD32 |
| CD83 | CD86 | NKG2D | CD79a |
| CD83 | CD86 | NKG2D | CD79b |
| CD83 | OX40 | CD28 | CD8 |
| CD83 | OX40 | CD28 | CD3ζ |
| CD83 | OX40 | CD28 | CD3δ |
| CD83 | OX40 | CD28 | CD3γ |
| CD83 | OX40 | CD28 | CD3ε |
| CD83 | OX40 | CD28 | FcγRI-γ |
| CD83 | OX40 | CD28 | FcγRIII-γ |
| CD83 | OX40 | CD28 | FcεRIβ |
| CD83 | OX40 | CD28 | FcεRIγ |
| CD83 | OX40 | CD28 | DAP10 |
| CD83 | OX40 | CD28 | DAP12 |
| CD83 | OX40 | CD28 | CD32 |
| CD83 | OX40 | CD28 | CD79a |
| CD83 | OX40 | CD28 | CD79b |
| CD83 | OX40 | CD8 | CD8 |
| CD83 | OX40 | CD8 | CD3ζ |
| CD83 | OX40 | CD8 | CD3δ |
| CD83 | OX40 | CD8 | CD3γ |
| CD83 | OX40 | CD8 | CD3ε |
| CD83 | OX40 | CD8 | FcγRI-γ |
| CD83 | OX40 | CD8 | FcγRIII-γ |
| CD83 | OX40 | CD8 | FcεRIβ |
| CD83 | OX40 | CD8 | FcεRIγ |
| CD83 | OX40 | CD8 | DAP10 |
| CD83 | OX40 | CD8 | DAP12 |
| CD83 | OX40 | CD8 | CD32 |
| CD83 | OX40 | CD8 | CD79a |
| CD83 | OX40 | CD8 | CD79b |
| CD83 | OX40 | CD4 | CD8 |
| CD83 | OX40 | CD4 | CD3ζ |
| CD83 | OX40 | CD4 | CD3δ |
| CD83 | OX40 | CD4 | CD3γ |
| CD83 | OX40 | CD4 | CD3ε |
| CD83 | OX40 | CD4 | FcγRI-γ |
| CD83 | OX40 | CD4 | FcγRIII-γ |
| CD83 | OX40 | CD4 | FcεRIβ |
| CD83 | OX40 | CD4 | FcεRIγ |
| CD83 | OX40 | CD4 | DAP10 |
| CD83 | OX40 | CD4 | DAP12 |
| CD83 | OX40 | CD4 | CD32 |
| CD83 | OX40 | CD4 | CD79a |
| CD83 | OX40 | CD4 | CD79b |
| CD83 | OX40 | b2c | CD8 |
| CD83 | OX40 | b2c | CD3ζ |
| CD83 | OX40 | b2c | CD3δ |
| CD83 | OX40 | b2c | CD3γ |
| CD83 | OX40 | b2c | CD3ε |
| CD83 | OX40 | b2c | FcγRI-γ |
| CD83 | OX40 | b2c | FcγRIII-γ |
| CD83 | OX40 | b2c | FcεRIβ |
| CD83 | OX40 | b2c | FcεRIγ |
| CD83 | OX40 | b2c | DAP10 |
| CD83 | OX40 | b2c | DAP12 |
| CD83 | OX40 | b2c | CD32 |
| CD83 | OX40 | b2c | CD79a |
| CD83 | OX40 | b2c | CD79b |
| CD83 | OX40 | CD137/41BB | CD8 |
| CD83 | OX40 | CD137/41BB | CD3ζ |
| CD83 | OX40 | CD137/41BB | CD3δ |
| CD83 | OX40 | CD137/41BB | CD3γ |
| CD83 | OX40 | CD137/41BB | CD3ε |
| CD83 | OX40 | CD137/41BB | FcγRI-γ |
| CD83 | OX40 | CD137/41BB | FcγRIII-γ |
| CD83 | OX40 | CD137/41BB | FcεRIβ |
| CD83 | OX40 | CD137/41BB | FcεRIγ |
| CD83 | OX40 | CD137/41BB | DAP10 |
| CD83 | OX40 | CD137/41BB | DAP12 |
| CD83 | OX40 | CD137/41BB | CD32 |
| CD83 | OX40 | CD137/41BB | CD79a |
| CD83 | OX40 | CD137/41BB | CD79b |
| CD83 | OX40 | ICOS | CD8 |

TABLE 3-continued

| Third Generation CARs | | | |
|---|---|---|---|
| ScFv | Co-stimulatory Signal | Co-stimulatory Signal | Signal Domain |
| CD83 | OX40 | ICOS | CD3ζ |
| CD83 | OX40 | ICOS | CD3δ |
| CD83 | OX40 | ICOS | CD3γ |
| CD83 | OX40 | ICOS | CD3ε |
| CD83 | OX40 | ICOS | FcγRI-γ |
| CD83 | OX40 | ICOS | FcγRIII-γ |
| CD83 | OX40 | ICOS | FcεRIβ |
| CD83 | OX40 | ICOS | FcεRIγ |
| CD83 | OX40 | ICOS | DAP10 |
| CD83 | OX40 | ICOS | DAP12 |
| CD83 | OX40 | ICOS | CD32 |
| CD83 | OX40 | ICOS | CD79a |
| CD83 | OX40 | ICOS | CD79b |
| CD83 | OX40 | CD27 | CD8 |
| CD83 | OX40 | CD27 | CD3ζ |
| CD83 | OX40 | CD27 | CD3δ |
| CD83 | OX40 | CD27 | CD3γ |
| CD83 | OX40 | CD27 | CD3ε |
| CD83 | OX40 | CD27 | FcγRI-γ |
| CD83 | OX40 | CD27 | FcγRIII-γ |
| CD83 | OX40 | CD27 | FcεRIβ |
| CD83 | OX40 | CD27 | FcεRIγ |
| CD83 | OX40 | CD27 | DAP10 |
| CD83 | OX40 | CD27 | DAP12 |
| CD83 | OX40 | CD27 | CD32 |
| CD83 | OX40 | CD27 | CD79a |
| CD83 | OX40 | CD27 | CD79b |
| CD83 | OX40 | CD28δ | CD8 |
| CD83 | OX40 | CD28δ | CD3ζ |
| CD83 | OX40 | CD28δ | CD3δ |
| CD83 | OX40 | CD28δ | CD3γ |
| CD83 | OX40 | CD28δ | CD3ε |
| CD83 | OX40 | CD28δ | FcγRI-γ |
| CD83 | OX40 | CD28δ | FcγRIII-γ |
| CD83 | OX40 | CD28δ | FcεRIβ |
| CD83 | OX40 | CD28δ | FcεRIγ |
| CD83 | OX40 | CD28δ | DAP10 |
| CD83 | OX40 | CD28δ | DAP12 |
| CD83 | OX40 | CD28δ | CD32 |
| CD83 | OX40 | CD28δ | CD79a |
| CD83 | OX40 | CD28δ | CD79b |
| CD83 | OX40 | CD80 | CD8 |
| CD83 | OX40 | CD80 | CD3ζ |
| CD83 | OX40 | CD80 | CD3δ |
| CD83 | OX40 | CD80 | CD3γ |
| CD83 | OX40 | CD80 | CD3ε |
| CD83 | OX40 | CD80 | FcγRI-γ |
| CD83 | OX40 | CD80 | FcγRIII-γ |
| CD83 | OX40 | CD80 | FcεRIβ |
| CD83 | OX40 | CD80 | FcεRIγ |
| CD83 | OX40 | CD80 | DAP10 |
| CD83 | OX40 | CD80 | DAP12 |
| CD83 | OX40 | CD80 | CD32 |
| CD83 | OX40 | CD80 | CD79a |
| CD83 | OX40 | CD80 | CD79b |
| CD83 | OX40 | CD86 | CD8 |
| CD83 | OX40 | CD86 | CD3ζ |
| CD83 | OX40 | CD86 | CD3δ |
| CD83 | OX40 | CD86 | CD3γ |
| CD83 | OX40 | CD86 | CD3ε |
| CD83 | OX40 | CD86 | FcγRI-γ |
| CD83 | OX40 | CD86 | FcγRIII-γ |
| CD83 | OX40 | CD86 | FcεRIβ |
| CD83 | OX40 | CD86 | FcεRIγ |
| CD83 | OX40 | CD86 | DAP10 |
| CD83 | OX40 | CD86 | DAP12 |
| CD83 | OX40 | CD86 | CD32 |
| CD83 | OX40 | CD86 | CD79a |
| CD83 | OX40 | CD86 | CD79b |
| CD83 | OX40 | OX40 | CD8 |
| CD83 | OX40 | OX40 | CD3ζ |
| CD83 | OX40 | OX40 | CD3δ |
| CD83 | OX40 | OX40 | CD3γ |
| CD83 | OX40 | OX40 | CD3ε |
| CD83 | OX40 | OX40 | FcγRI-γ |

TABLE 3-continued

| Third Generation CARs | | | |
|---|---|---|---|
| ScFv | Co-stimulatory Signal | Co-stimulatory Signal | Signal Domain |
| CD83 | OX40 | OX40 | FcγRIII-γ |
| CD83 | OX40 | OX40 | FcεRIβ |
| CD83 | OX40 | OX40 | FcεRIγ |
| CD83 | OX40 | OX40 | DAP10 |
| CD83 | OX40 | OX40 | DAP12 |
| CD83 | OX40 | OX40 | CD32 |
| CD83 | OX40 | OX40 | CD79a |
| CD83 | OX40 | OX40 | CD79b |
| CD83 | OX40 | DAP10 | CD8 |
| CD83 | OX40 | DAP10 | CD3ζ |
| CD83 | OX40 | DAP10 | CD3δ |
| CD83 | OX40 | DAP10 | CD3γ |
| CD83 | OX40 | DAP10 | CD3ε |
| CD83 | OX40 | DAP10 | FcγRI-γ |
| CD83 | OX40 | DAP10 | FcγRIII-γ |
| CD83 | OX40 | DAP10 | FcεRIβ |
| CD83 | OX40 | DAP10 | FcεRIγ |
| CD83 | OX40 | DAP10 | DAP10 |
| CD83 | OX40 | DAP10 | DAP12 |
| CD83 | OX40 | DAP10 | CD32 |
| CD83 | OX40 | DAP10 | CD79a |
| CD83 | OX40 | DAP10 | CD79b |
| CD83 | OX40 | DAP12 | CD8 |
| CD83 | OX40 | DAP12 | CD3ζ |
| CD83 | OX40 | DAP12 | CD3δ |
| CD83 | OX40 | DAP12 | CD3γ |
| CD83 | OX40 | DAP12 | CD3ε |
| CD83 | OX40 | DAP12 | FcγRI-γ |
| CD83 | OX40 | DAP12 | FcγRIII-γ |
| CD83 | OX40 | DAP12 | FcεRIβ |
| CD83 | OX40 | DAP12 | FcεRIγ |
| CD83 | OX40 | DAP12 | DAP10 |
| CD83 | OX40 | DAP12 | DAP12 |
| CD83 | OX40 | DAP12 | CD32 |
| CD83 | OX40 | DAP12 | CD79a |
| CD83 | OX40 | DAP12 | CD79b |
| CD83 | OX40 | MyD88 | CD8 |
| CD83 | OX40 | MyD88 | CD3ζ |
| CD83 | OX40 | MyD88 | CD3δ |
| CD83 | OX40 | MyD88 | CD3γ |
| CD83 | OX40 | MyD88 | CD3ε |
| CD83 | OX40 | MyD88 | FcγRI-γ |
| CD83 | OX40 | MyD88 | FcγRIII-γ |
| CD83 | OX40 | MyD88 | FcεRIβ |
| CD83 | OX40 | MyD88 | FcεRIγ |
| CD83 | OX40 | MyD88 | DAP10 |
| CD83 | OX40 | MyD88 | DAP12 |
| CD83 | OX40 | MyD88 | CD32 |
| CD83 | OX40 | MyD88 | CD79a |
| CD83 | OX40 | MyD88 | CD79b |
| CD83 | OX40 | CD7 | CD8 |
| CD83 | OX40 | CD7 | CD3ζ |
| CD83 | OX40 | CD7 | CD3δ |
| CD83 | OX40 | CD7 | CD3γ |
| CD83 | OX40 | CD7 | CD3ε |
| CD83 | OX40 | CD7 | FcγRI-γ |
| CD83 | OX40 | CD7 | FcγRIII-γ |
| CD83 | OX40 | CD7 | FcεRIβ |
| CD83 | OX40 | CD7 | FcεRIγ |
| CD83 | OX40 | CD7 | DAP10 |
| CD83 | OX40 | CD7 | DAP12 |
| CD83 | OX40 | CD7 | CD32 |
| CD83 | OX40 | CD7 | CD79a |
| CD83 | OX40 | CD7 | CD79b |
| CD83 | OX40 | BTNL3 | CD8 |
| CD83 | OX40 | BTNL3 | CD3ζ |
| CD83 | OX40 | BTNL3 | CD3δ |
| CD83 | OX40 | BTNL3 | CD3γ |
| CD83 | OX40 | BTNL3 | CD3ε |
| CD83 | OX40 | BTNL3 | FcγRI-γ |
| CD83 | OX40 | BTNL3 | FcγRIII-γ |
| CD83 | OX40 | BTNL3 | FcεRIβ |
| CD83 | OX40 | BTNL3 | FcεRIγ |
| CD83 | OX40 | BTNL3 | DAP10 |
| CD83 | OX40 | BTNL3 | DAP12 |

TABLE 3-continued

Third Generation CARs

| ScFv | Co-stimulatory Signal | Co-stimulatory Signal | Signal Domain |
|---|---|---|---|
| CD83 | OX40 | BTNL3 | CD32 |
| CD83 | OX40 | BTNL3 | CD79a |
| CD83 | OX40 | BTNL3 | CD79b |
| CD83 | OX40 | NKG2D | CD8 |
| CD83 | OX40 | NKG2D | CD3ζ |
| CD83 | OX40 | NKG2D | CD3δ |
| CD83 | OX40 | NKG2D | CD3γ |
| CD83 | OX40 | NKG2D | CD3ε |
| CD83 | OX40 | NKG2D | FcγRI-γ |
| CD83 | OX40 | NKG2D | FcγRIII-γ |
| CD83 | OX40 | NKG2D | FcεRIβ |
| CD83 | OX40 | NKG2D | FcεRIγ |
| CD83 | OX40 | NKG2D | DAP10 |
| CD83 | OX40 | NKG2D | DAP12 |
| CD83 | OX40 | NKG2D | CD32 |
| CD83 | OX40 | NKG2D | CD79a |
| CD83 | OX40 | NKG2D | CD79b |
| CD83 | DAP10 | CD28 | CD8 |
| CD83 | DAP10 | CD28 | CD3ζ |
| CD83 | DAP10 | CD28 | CD3δ |
| CD83 | DAP10 | CD28 | CD3γ |
| CD83 | DAP10 | CD28 | CD3ε |
| CD83 | DAP10 | CD28 | FcγRI-γ |
| CD83 | DAP10 | CD28 | FcγRIII-γ |
| CD83 | DAP10 | CD28 | FcεRIβ |
| CD83 | DAP10 | CD28 | FcεRIγ |
| CD83 | DAP10 | CD28 | DAP10 |
| CD83 | DAP10 | CD28 | DAP12 |
| CD83 | DAP10 | CD28 | CD32 |
| CD83 | DAP10 | CD28 | CD79a |
| CD83 | DAP10 | CD28 | CD79b |
| CD83 | DAP10 | CD8 | CD8 |
| CD83 | DAP10 | CD8 | CD3ζ |
| CD83 | DAP10 | CD8 | CD3δ |
| CD83 | DAP10 | CD8 | CD3γ |
| CD83 | DAP10 | CD8 | CD3ε |
| CD83 | DAP10 | CD8 | FcγRI-γ |
| CD83 | DAP10 | CD8 | FcγRIII-γ |
| CD83 | DAP10 | CD8 | FcεRIβ |
| CD83 | DAP10 | CD8 | FcεRIγ |
| CD83 | DAP10 | CD8 | DAP10 |
| CD83 | DAP10 | CD8 | DAP12 |
| CD83 | DAP10 | CD8 | CD32 |
| CD83 | DAP10 | CD8 | CD79a |
| CD83 | DAP10 | CD8 | CD79b |
| CD83 | DAP10 | CD4 | CD8 |
| CD83 | DAP10 | CD4 | CD3ζ |
| CD83 | DAP10 | CD4 | CD3δ |
| CD83 | DAP10 | CD4 | CD3γ |
| CD83 | DAP10 | CD4 | CD3ε |
| CD83 | DAP10 | CD4 | FcγRI-γ |
| CD83 | DAP10 | CD4 | FcγRIII-γ |
| CD83 | DAP10 | CD4 | FcεRIβ |
| CD83 | DAP10 | CD4 | FcεRIγ |
| CD83 | DAP10 | CD4 | DAP10 |
| CD83 | DAP10 | CD4 | DAP12 |
| CD83 | DAP10 | CD4 | CD32 |
| CD83 | DAP10 | CD4 | CD79a |
| CD83 | DAP10 | CD4 | CD79b |
| CD83 | DAP10 | b2c | CD8 |
| CD83 | DAP10 | b2c | CD3ζ |
| CD83 | DAP10 | b2c | CD3δ |
| CD83 | DAP10 | b2c | CD3γ |
| CD83 | DAP10 | b2c | CD3ε |
| CD83 | DAP10 | b2c | FcγRI-γ |
| CD83 | DAP10 | b2c | FcγRIII-γ |
| CD83 | DAP10 | b2c | FcεRIβ |
| CD83 | DAP10 | b2c | FcεRIγ |
| CD83 | DAP10 | b2c | DAP10 |
| CD83 | DAP10 | b2c | DAP12 |
| CD83 | DAP10 | b2c | CD32 |
| CD83 | DAP10 | b2c | CD79a |
| CD83 | DAP10 | b2c | CD79b |
| CD83 | DAP10 | CD137/41BB | CD8 |
| CD83 | DAP10 | CD137/41BB | CD3ζ |

TABLE 3-continued

Third Generation CARs

| ScFv | Co-stimulatory Signal | Co-stimulatory Signal | Signal Domain |
|---|---|---|---|
| CD83 | DAP10 | CD137/41BB | CD3δ |
| CD83 | DAP10 | CD137/41BB | CD3γ |
| CD83 | DAP10 | CD137/41BB | CD3ε |
| CD83 | DAP10 | CD137/41BB | FcγRI-γ |
| CD83 | DAP10 | CD137/41BB | FcγRIII-γ |
| CD83 | DAP10 | CD137/41BB | FcεRIβ |
| CD83 | DAP10 | CD137/41BB | FcεRIγ |
| CD83 | DAP10 | CD137/41BB | DAP10 |
| CD83 | DAP10 | CD137/41BB | DAP12 |
| CD83 | DAP10 | CD137/41BB | CD32 |
| CD83 | DAP10 | CD137/41BB | CD79a |
| CD83 | DAP10 | CD137/41BB | CD79b |
| CD83 | DAP10 | ICOS | CD8 |
| CD83 | DAP10 | ICOS | CD3ζ |
| CD83 | DAP10 | ICOS | CD3δ |
| CD83 | DAP10 | ICOS | CD3γ |
| CD83 | DAP10 | ICOS | CD3ε |
| CD83 | DAP10 | ICOS | FcγRI-γ |
| CD83 | DAP10 | ICOS | FcγRIII-γ |
| CD83 | DAP10 | ICOS | FcεRIβ |
| CD83 | DAP10 | ICOS | FcεRIγ |
| CD83 | DAP10 | ICOS | DAP10 |
| CD83 | DAP10 | ICOS | DAP12 |
| CD83 | DAP10 | ICOS | CD32 |
| CD83 | DAP10 | ICOS | CD79a |
| CD83 | DAP10 | ICOS | CD79b |
| CD83 | DAP10 | CD27 | CD8 |
| CD83 | DAP10 | CD27 | CD3ζ |
| CD83 | DAP10 | CD27 | CD3δ |
| CD83 | DAP10 | CD27 | CD3γ |
| CD83 | DAP10 | CD27 | CD3ε |
| CD83 | DAP10 | CD27 | FcγRI-γ |
| CD83 | DAP10 | CD27 | FcγRIII-γ |
| CD83 | DAP10 | CD27 | FcεRIβ |
| CD83 | DAP10 | CD27 | FcεRIγ |
| CD83 | DAP10 | CD27 | DAP10 |
| CD83 | DAP10 | CD27 | DAP12 |
| CD83 | DAP10 | CD27 | CD32 |
| CD83 | DAP10 | CD27 | CD79a |
| CD83 | DAP10 | CD27 | CD79b |
| CD83 | DAP10 | CD28δ | CD8 |
| CD83 | DAP10 | CD28δ | CD3ζ |
| CD83 | DAP10 | CD28δ | CD3δ |
| CD83 | DAP10 | CD28δ | CD3γ |
| CD83 | DAP10 | CD28δ | CD3ε |
| CD83 | DAP10 | CD28δ | FcγRI-γ |
| CD83 | DAP10 | CD28δ | FcγRIII-γ |
| CD83 | DAP10 | CD28δ | FcεRIβ |
| CD83 | DAP10 | CD28δ | FcεRIγ |
| CD83 | DAP10 | CD28δ | DAP10 |
| CD83 | DAP10 | CD28δ | DAP12 |
| CD83 | DAP10 | CD28δ | CD32 |
| CD83 | DAP10 | CD28δ | CD79a |
| CD83 | DAP10 | CD28δ | CD79b |
| CD83 | DAP10 | CD80 | CD8 |
| CD83 | DAP10 | CD80 | CD3ζ |
| CD83 | DAP10 | CD80 | CD3δ |
| CD83 | DAP10 | CD80 | CD3γ |
| CD83 | DAP10 | CD80 | CD3ε |
| CD83 | DAP10 | CD80 | FcγRI-γ |
| CD83 | DAP10 | CD80 | FcγRIII-γ |
| CD83 | DAP10 | CD80 | FcεRIβ |
| CD83 | DAP10 | CD80 | FcεRIγ |
| CD83 | DAP10 | CD80 | DAP10 |
| CD83 | DAP10 | CD80 | DAP12 |
| CD83 | DAP10 | CD80 | CD32 |
| CD83 | DAP10 | CD80 | CD79a |
| CD83 | DAP10 | CD80 | CD79b |
| CD83 | DAP10 | CD86 | CD8 |
| CD83 | DAP10 | CD86 | CD3ζ |
| CD83 | DAP10 | CD86 | CD3δ |
| CD83 | DAP10 | CD86 | CD3γ |
| CD83 | DAP10 | CD86 | CD3ε |
| CD83 | DAP10 | CD86 | FcγRI-γ |
| CD83 | DAP10 | CD86 | FcγRIII-γ |

TABLE 3-continued

Third Generation CARs

| ScFv | Co-stimulatory Signal | Co-stimulatory Signal | Signal Domain |
|---|---|---|---|
| CD83 | DAP10 | CD86 | FcεRIβ |
| CD83 | DAP10 | CD86 | FcεRIγ |
| CD83 | DAP10 | CD86 | DAP10 |
| CD83 | DAP10 | CD86 | DAP12 |
| CD83 | DAP10 | CD86 | CD32 |
| CD83 | DAP10 | CD86 | CD79a |
| CD83 | DAP10 | CD86 | CD79b |
| CD83 | DAP10 | OX40 | CD8 |
| CD83 | DAP10 | OX40 | CD3ζ |
| CD83 | DAP10 | OX40 | CD3δ |
| CD83 | DAP10 | OX40 | CD3γ |
| CD83 | DAP10 | OX40 | CD3ε |
| CD83 | DAP10 | OX40 | FcγRI-γ |
| CD83 | DAP10 | OX40 | FcγRIII-γ |
| CD83 | DAP10 | OX40 | FcεRIβ |
| CD83 | DAP10 | OX40 | FcεRIγ |
| CD83 | DAP10 | OX40 | DAP10 |
| CD83 | DAP10 | OX40 | DAP12 |
| CD83 | DAP10 | OX40 | CD32 |
| CD83 | DAP10 | OX40 | CD79a |
| CD83 | DAP10 | OX40 | CD79b |
| CD83 | DAP10 | DAP10 | CD8 |
| CD83 | DAP10 | DAP10 | CD3ζ |
| CD83 | DAP10 | DAP10 | CD3δ |
| CD83 | DAP10 | DAP10 | CD3γ |
| CD83 | DAP10 | DAP10 | CD3ε |
| CD83 | DAP10 | DAP10 | FcγRI-γ |
| CD83 | DAP10 | DAP10 | FcγRIII-γ |
| CD83 | DAP10 | DAP10 | FcεRIβ |
| CD83 | DAP10 | DAP10 | FcεRIγ |
| CD83 | DAP10 | DAP10 | DAP10 |
| CD83 | DAP10 | DAP10 | DAP12 |
| CD83 | DAP10 | DAP10 | CD32 |
| CD83 | DAP10 | DAP10 | CD79a |
| CD83 | DAP10 | DAP10 | CD79b |
| CD83 | DAP10 | DAP12 | CD8 |
| CD83 | DAP10 | DAP12 | CD3ζ |
| CD83 | DAP10 | DAP12 | CD3δ |
| CD83 | DAP10 | DAP12 | CD3γ |
| CD83 | DAP10 | DAP12 | CD3ε |
| CD83 | DAP10 | DAP12 | FcγRI-γ |
| CD83 | DAP10 | DAP12 | FcγRIII-γ |
| CD83 | DAP10 | DAP12 | FcεRIβ |
| CD83 | DAP10 | DAP12 | FcεRIγ |
| CD83 | DAP10 | DAP12 | DAP10 |
| CD83 | DAP10 | DAP12 | DAP12 |
| CD83 | DAP10 | DAP12 | CD32 |
| CD83 | DAP10 | DAP12 | CD79a |
| CD83 | DAP10 | DAP12 | CD79b |
| CD83 | DAP10 | MyD88 | CD8 |
| CD83 | DAP10 | MyD88 | CD3ζ |
| CD83 | DAP10 | MyD88 | CD3δ |
| CD83 | DAP10 | MyD88 | CD3γ |
| CD83 | DAP10 | MyD88 | CD3ε |
| CD83 | DAP10 | MyD88 | FcγRI-γ |
| CD83 | DAP10 | MyD88 | FcγRIII-γ |
| CD83 | DAP10 | MyD88 | FcεRIβ |
| CD83 | DAP10 | MyD88 | FcεRIγ |
| CD83 | DAP10 | MyD88 | DAP10 |
| CD83 | DAP10 | MyD88 | DAP12 |
| CD83 | DAP10 | MyD88 | CD32 |
| CD83 | DAP10 | MyD88 | CD79a |
| CD83 | DAP10 | MyD88 | CD79b |
| CD83 | DAP10 | CD7 | CD8 |
| CD83 | DAP10 | CD7 | CD3ζ |
| CD83 | DAP10 | CD7 | CD3δ |
| CD83 | DAP10 | CD7 | CD3γ |
| CD83 | DAP10 | CD7 | CD3ε |
| CD83 | DAP10 | CD7 | FcγRI-γ |
| CD83 | DAP10 | CD7 | FcγRIII-γ |
| CD83 | DAP10 | CD7 | FcεRIβ |
| CD83 | DAP10 | CD7 | FcεRIγ |
| CD83 | DAP10 | CD7 | DAP10 |
| CD83 | DAP10 | CD7 | DAP12 |
| CD83 | DAP10 | CD7 | CD32 |
| CD83 | DAP10 | CD7 | CD79a |
| CD83 | DAP10 | CD7 | CD79b |
| CD83 | DAP10 | BTNL3 | CD8 |
| CD83 | DAP10 | BTNL3 | CD3ζ |
| CD83 | DAP10 | BTNL3 | CD3δ |
| CD83 | DAP10 | BTNL3 | CD3γ |
| CD83 | DAP10 | BTNL3 | CD3ε |
| CD83 | DAP10 | BTNL3 | FcγRI-γ |
| CD83 | DAP10 | BTNL3 | FcγRIII-γ |
| CD83 | DAP10 | BTNL3 | FcεRIβ |
| CD83 | DAP10 | BTNL3 | FcεRIγ |
| CD83 | DAP10 | BTNL3 | DAP10 |
| CD83 | DAP10 | BTNL3 | DAP12 |
| CD83 | DAP10 | BTNL3 | CD32 |
| CD83 | DAP10 | BTNL3 | CD79a |
| CD83 | DAP10 | BTNL3 | CD79b |
| CD83 | DAP10 | NKG2D | CD8 |
| CD83 | DAP10 | NKG2D | CD3ζ |
| CD83 | DAP10 | NKG2D | CD3δ |
| CD83 | DAP10 | NKG2D | CD3γ |
| CD83 | DAP10 | NKG2D | CD3ε |
| CD83 | DAP10 | NKG2D | FcγRI-γ |
| CD83 | DAP10 | NKG2D | FcγRIII-γ |
| CD83 | DAP10 | NKG2D | FcεRIβ |
| CD83 | DAP10 | NKG2D | FcεRIγ |
| CD83 | DAP10 | NKG2D | DAP10 |
| CD83 | DAP10 | NKG2D | DAP12 |
| CD83 | DAP10 | NKG2D | CD32 |
| CD83 | DAP10 | NKG2D | CD79a |
| CD83 | DAP10 | NKG2D | CD79b |
| CD83 | DAP12 | CD28 | CD8 |
| CD83 | DAP12 | CD28 | CD3ζ |
| CD83 | DAP12 | CD28 | CD3δ |
| CD83 | DAP12 | CD28 | CD3γ |
| CD83 | DAP12 | CD28 | CD3ε |
| CD83 | DAP12 | CD28 | FcγRI-γ |
| CD83 | DAP12 | CD28 | FcγRIII-γ |
| CD83 | DAP12 | CD28 | FcεRIβ |
| CD83 | DAP12 | CD28 | FcεRIγ |
| CD83 | DAP12 | CD28 | DAP10 |
| CD83 | DAP12 | CD28 | DAP12 |
| CD83 | DAP12 | CD28 | CD32 |
| CD83 | DAP12 | CD28 | CD79a |
| CD83 | DAP12 | CD28 | CD79b |
| CD83 | DAP12 | CD8 | CD8 |
| CD83 | DAP12 | CD8 | CD3ζ |
| CD83 | DAP12 | CD8 | CD3δ |
| CD83 | DAP12 | CD8 | CD3γ |
| CD83 | DAP12 | CD8 | CD3ε |
| CD83 | DAP12 | CD8 | FcγRI-γ |
| CD83 | DAP12 | CD8 | FcγRIII-γ |
| CD83 | DAP12 | CD8 | FcεRIβ |
| CD83 | DAP12 | CD8 | FcεRIγ |
| CD83 | DAP12 | CD8 | DAP10 |
| CD83 | DAP12 | CD8 | DAP12 |
| CD83 | DAP12 | CD8 | CD32 |
| CD83 | DAP12 | CD8 | CD79a |
| CD83 | DAP12 | CD8 | CD79b |
| CD83 | DAP12 | CD4 | CD8 |
| CD83 | DAP12 | CD4 | CD3ζ |
| CD83 | DAP12 | CD4 | CD3δ |
| CD83 | DAP12 | CD4 | CD3γ |
| CD83 | DAP12 | CD4 | CD3ε |
| CD83 | DAP12 | CD4 | FcγRI-γ |
| CD83 | DAP12 | CD4 | FcγRIII-γ |
| CD83 | DAP12 | CD4 | FcεRIβ |
| CD83 | DAP12 | CD4 | FcεRIγ |
| CD83 | DAP12 | CD4 | DAP10 |
| CD83 | DAP12 | CD4 | DAP12 |
| CD83 | DAP12 | CD4 | CD32 |
| CD83 | DAP12 | CD4 | CD79a |
| CD83 | DAP12 | CD4 | CD79b |
| CD83 | DAP12 | b2c | CD8 |
| CD83 | DAP12 | b2c | CD3ζ |
| CD83 | DAP12 | b2c | CD3δ |

TABLE 3-continued

| Third Generation CARs | | | |
|---|---|---|---|
| ScFv | Co-stimulatory Signal | Co-stimulatory Signal | Signal Domain |
| CD83 | DAP12 | b2c | CD3γ |
| CD83 | DAP12 | b2c | CD3ε |
| CD83 | DAP12 | b2c | FcγRI-γ |
| CD83 | DAP12 | b2c | FcγRIII-γ |
| CD83 | DAP12 | b2c | FcεRIβ |
| CD83 | DAP12 | b2c | FcεRIγ |
| CD83 | DAP12 | b2c | DAP10 |
| CD83 | DAP12 | b2c | DAP12 |
| CD83 | DAP12 | b2c | CD32 |
| CD83 | DAP12 | b2c | CD79a |
| CD83 | DAP12 | b2c | CD79b |
| CD83 | DAP12 | CD137/41BB | CD8 |
| CD83 | DAP12 | CD137/41BB | CD3ζ |
| CD83 | DAP12 | CD137/41BB | CD3δ |
| CD83 | DAP12 | CD137/41BB | CD3γ |
| CD83 | DAP12 | CD137/41BB | CD3ε |
| CD83 | DAP12 | CD137/41BB | FcγRI-γ |
| CD83 | DAP12 | CD137/41BB | FcγRIII-γ |
| CD83 | DAP12 | CD137/41BB | FcεRIβ |
| CD83 | DAP12 | CD137/41BB | FcεRIγ |
| CD83 | DAP12 | CD137/41BB | DAP10 |
| CD83 | DAP12 | CD137/41BB | DAP12 |
| CD83 | DAP12 | CD137/41BB | CD32 |
| CD83 | DAP12 | CD137/41BB | CD79a |
| CD83 | DAP12 | CD137/41BB | CD79b |
| CD83 | DAP12 | ICOS | CD8 |
| CD83 | DAP12 | ICOS | CD3ζ |
| CD83 | DAP12 | ICOS | CD3δ |
| CD83 | DAP12 | ICOS | CD3γ |
| CD83 | DAP12 | ICOS | CD3ε |
| CD83 | DAP12 | ICOS | FcγRI-γ |
| CD83 | DAP12 | ICOS | FcγRIII-γ |
| CD83 | DAP12 | ICOS | FcεRIβ |
| CD83 | DAP12 | ICOS | FcεRIγ |
| CD83 | DAP12 | ICOS | DAP10 |
| CD83 | DAP12 | ICOS | DAP12 |
| CD83 | DAP12 | ICOS | CD32 |
| CD83 | DAP12 | ICOS | CD79a |
| CD83 | DAP12 | ICOS | CD79b |
| CD83 | DAP12 | CD27 | CD8 |
| CD83 | DAP12 | CD27 | CD3ζ |
| CD83 | DAP12 | CD27 | CD3δ |
| CD83 | DAP12 | CD27 | CD3γ |
| CD83 | DAP12 | CD27 | CD3ε |
| CD83 | DAP12 | CD27 | FcγRI-γ |
| CD83 | DAP12 | CD27 | FcγRIII-γ |
| CD83 | DAP12 | CD27 | FcεRIβ |
| CD83 | DAP12 | CD27 | FcεRIγ |
| CD83 | DAP12 | CD27 | DAP10 |
| CD83 | DAP12 | CD27 | DAP12 |
| CD83 | DAP12 | CD27 | CD32 |
| CD83 | DAP12 | CD27 | CD79a |
| CD83 | DAP12 | CD27 | CD79b |
| CD83 | DAP12 | CD28δ | CD8 |
| CD83 | DAP12 | CD28δ | CD3ζ |
| CD83 | DAP12 | CD28δ | CD3δ |
| CD83 | DAP12 | CD28δ | CD3γ |
| CD83 | DAP12 | CD28δ | CD3ε |
| CD83 | DAP12 | CD28δ | FcγRI-γ |
| CD83 | DAP12 | CD28δ | FcγRIII-γ |
| CD83 | DAP12 | CD28δ | FcεRIβ |
| CD83 | DAP12 | CD28δ | FcεRIγ |
| CD83 | DAP12 | CD28δ | DAP10 |
| CD83 | DAP12 | CD28δ | DAP12 |
| CD83 | DAP12 | CD28δ | CD32 |
| CD83 | DAP12 | CD28δ | CD79a |
| CD83 | DAP12 | CD28δ | CD79b |
| CD83 | DAP12 | CD80 | CD8 |
| CD83 | DAP12 | CD80 | CD3ζ |
| CD83 | DAP12 | CD80 | CD3δ |
| CD83 | DAP12 | CD80 | CD3γ |
| CD83 | DAP12 | CD80 | CD3ε |
| CD83 | DAP12 | CD80 | FcγRI-γ |
| CD83 | DAP12 | CD80 | FcγRIII-γ |
| CD83 | DAP12 | CD80 | FcεRIβ |

TABLE 3-continued

| Third Generation CARs | | | |
|---|---|---|---|
| ScFv | Co-stimulatory Signal | Co-stimulatory Signal | Signal Domain |
| CD83 | DAP12 | CD80 | FcεRIγ |
| CD83 | DAP12 | CD80 | DAP10 |
| CD83 | DAP12 | CD80 | DAP12 |
| CD83 | DAP12 | CD80 | CD32 |
| CD83 | DAP12 | CD80 | CD79a |
| CD83 | DAP12 | CD80 | CD79b |
| CD83 | DAP12 | CD86 | CD8 |
| CD83 | DAP12 | CD86 | CD3ζ |
| CD83 | DAP12 | CD86 | CD3δ |
| CD83 | DAP12 | CD86 | CD3γ |
| CD83 | DAP12 | CD86 | CD3ε |
| CD83 | DAP12 | CD86 | FcγRI-γ |
| CD83 | DAP12 | CD86 | FcγRIII-γ |
| CD83 | DAP12 | CD86 | FcεRIβ |
| CD83 | DAP12 | CD86 | FcεRIγ |
| CD83 | DAP12 | CD86 | DAP10 |
| CD83 | DAP12 | CD86 | DAP12 |
| CD83 | DAP12 | CD86 | CD32 |
| CD83 | DAP12 | CD86 | CD79a |
| CD83 | DAP12 | CD86 | CD79b |
| CD83 | DAP12 | OX40 | CD8 |
| CD83 | DAP12 | OX40 | CD3ζ |
| CD83 | DAP12 | OX40 | CD3δ |
| CD83 | DAP12 | OX40 | CD3γ |
| CD83 | DAP12 | OX40 | CD3ε |
| CD83 | DAP12 | OX40 | FcγRI-γ |
| CD83 | DAP12 | OX40 | FcγRIII-γ |
| CD83 | DAP12 | OX40 | FcεRIβ |
| CD83 | DAP12 | OX40 | FcεRIγ |
| CD83 | DAP12 | OX40 | DAP10 |
| CD83 | DAP12 | OX40 | DAP12 |
| CD83 | DAP12 | OX40 | CD32 |
| CD83 | DAP12 | OX40 | CD79a |
| CD83 | DAP12 | OX40 | CD79b |
| CD83 | DAP12 | DAP10 | CD8 |
| CD83 | DAP12 | DAP10 | CD3ζ |
| CD83 | DAP12 | DAP10 | CD3δ |
| CD83 | DAP12 | DAP10 | CD3γ |
| CD83 | DAP12 | DAP10 | CD3ε |
| CD83 | DAP12 | DAP10 | FcγRI-γ |
| CD83 | DAP12 | DAP10 | FcγRIII-γ |
| CD83 | DAP12 | DAP10 | FcεRIβ |
| CD83 | DAP12 | DAP10 | FcεRIγ |
| CD83 | DAP12 | DAP10 | DAP10 |
| CD83 | DAP12 | DAP10 | DAP12 |
| CD83 | DAP12 | DAP10 | CD32 |
| CD83 | DAP12 | DAP10 | CD79a |
| CD83 | DAP12 | DAP10 | CD79b |
| CD83 | DAP12 | DAP12 | CD8 |
| CD83 | DAP12 | DAP12 | CD3ζ |
| CD83 | DAP12 | DAP12 | CD3δ |
| CD83 | DAP12 | DAP12 | CD3γ |
| CD83 | DAP12 | DAP12 | CD3ε |
| CD83 | DAP12 | DAP12 | FcγRI-γ |
| CD83 | DAP12 | DAP12 | FcγRIII-γ |
| CD83 | DAP12 | DAP12 | FcεRIβ |
| CD83 | DAP12 | DAP12 | FcεRIγ |
| CD83 | DAP12 | DAP12 | DAP10 |
| CD83 | DAP12 | DAP12 | DAP12 |
| CD83 | DAP12 | DAP12 | CD32 |
| CD83 | DAP12 | DAP12 | CD79a |
| CD83 | DAP12 | DAP12 | CD79b |
| CD83 | DAP12 | MyD88 | CD8 |
| CD83 | DAP12 | MyD88 | CD3ζ |
| CD83 | DAP12 | MyD88 | CD3δ |
| CD83 | DAP12 | MyD88 | CD3γ |
| CD83 | DAP12 | MyD88 | CD3ε |
| CD83 | DAP12 | MyD88 | FcγRI-γ |
| CD83 | DAP12 | MyD88 | FcγRIII-γ |
| CD83 | DAP12 | MyD88 | FcεRIβ |
| CD83 | DAP12 | MyD88 | FcεRIγ |
| CD83 | DAP12 | MyD88 | DAP10 |
| CD83 | DAP12 | MyD88 | DAP12 |
| CD83 | DAP12 | MyD88 | CD32 |
| CD83 | DAP12 | MyD88 | CD79a |

TABLE 3-continued

| Third Generation CARs | | | |
|---|---|---|---|
| ScFv | Co-stimulatory Signal | Co-stimulatory Signal | Signal Domain |
| CD83 | DAP12 | MyD88 | CD79b |
| CD83 | DAP12 | CD7 | CD8 |
| CD83 | DAP12 | CD7 | CD3ζ |
| CD83 | DAP12 | CD7 | CD3δ |
| CD83 | DAP12 | CD7 | CD3γ |
| CD83 | DAP12 | CD7 | CD3ε |
| CD83 | DAP12 | CD7 | FcγRI-γ |
| CD83 | DAP12 | CD7 | FcγRIII-γ |
| CD83 | DAP12 | CD7 | FcεRIβ |
| CD83 | DAP12 | CD7 | FcεRIγ |
| CD83 | DAP12 | CD7 | DAP10 |
| CD83 | DAP12 | CD7 | DAP12 |
| CD83 | DAP12 | CD7 | CD32 |
| CD83 | DAP12 | CD7 | CD79a |
| CD83 | DAP12 | CD7 | CD79b |
| CD83 | DAP12 | BTNL3 | CD8 |
| CD83 | DAP12 | BTNL3 | CD3ζ |
| CD83 | DAP12 | BTNL3 | CD3δ |
| CD83 | DAP12 | BTNL3 | CD3γ |
| CD83 | DAP12 | BTNL3 | CD3ε |
| CD83 | DAP12 | BTNL3 | FcγRI-γ |
| CD83 | DAP12 | BTNL3 | FcγRIII-γ |
| CD83 | DAP12 | BTNL3 | FcεRIβ |
| CD83 | DAP12 | BTNL3 | FcεRIγ |
| CD83 | DAP12 | BTNL3 | DAP10 |
| CD83 | DAP12 | BTNL3 | DAP12 |
| CD83 | DAP12 | BTNL3 | CD32 |
| CD83 | DAP12 | BTNL3 | CD79a |
| CD83 | DAP12 | BTNL3 | CD79b |
| CD83 | DAP12 | NKG2D | CD8 |
| CD83 | DAP12 | NKG2D | CD3ζ |
| CD83 | DAP12 | NKG2D | CD3δ |
| CD83 | DAP12 | NKG2D | CD3γ |
| CD83 | DAP12 | NKG2D | CD3ε |
| CD83 | DAP12 | NKG2D | FcγRI-γ |
| CD83 | DAP12 | NKG2D | FcγRIII-γ |
| CD83 | DAP12 | NKG2D | FcεRIβ |
| CD83 | DAP12 | NKG2D | FcεRIγ |
| CD83 | DAP12 | NKG2D | DAP10 |
| CD83 | DAP12 | NKG2D | DAP12 |
| CD83 | DAP12 | NKG2D | CD32 |
| CD83 | DAP12 | NKG2D | CD79a |
| CD83 | DAP12 | NKG2D | CD79b |
| CD83 | MyD88 | CD28 | CD8 |
| CD83 | MyD88 | CD28 | CD3ζ |
| CD83 | MyD88 | CD28 | CD3δ |
| CD83 | MyD88 | CD28 | CD3γ |
| CD83 | MyD88 | CD28 | CD3ε |
| CD83 | MyD88 | CD28 | FcγRI-γ |
| CD83 | MyD88 | CD28 | FcγRIII-γ |
| CD83 | MyD88 | CD28 | FcεRIβ |
| CD83 | MyD88 | CD28 | FcεRIγ |
| CD83 | MyD88 | CD28 | DAP10 |
| CD83 | MyD88 | CD28 | DAP12 |
| CD83 | MyD88 | CD28 | CD32 |
| CD83 | MyD88 | CD28 | CD79a |
| CD83 | MyD88 | CD28 | CD79b |
| CD83 | MyD88 | CD8 | CD8 |
| CD83 | MyD88 | CD8 | CD3ζ |
| CD83 | MyD88 | CD8 | CD3δ |
| CD83 | MyD88 | CD8 | CD3γ |
| CD83 | MyD88 | CD8 | CD3ε |
| CD83 | MyD88 | CD8 | FcγRI-γ |
| CD83 | MyD88 | CD8 | FcγRIII-γ |
| CD83 | MyD88 | CD8 | FcεRIβ |
| CD83 | MyD88 | CD8 | FcεRIγ |
| CD83 | MyD88 | CD8 | DAP10 |
| CD83 | MyD88 | CD8 | DAP12 |
| CD83 | MyD88 | CD8 | CD32 |
| CD83 | MyD88 | CD8 | CD79a |
| CD83 | MyD88 | CD8 | CD79b |
| CD83 | MyD88 | CD4 | CD8 |
| CD83 | MyD88 | CD4 | CD3ζ |
| CD83 | MyD88 | CD4 | CD3δ |
| CD83 | MyD88 | CD4 | CD3γ |

TABLE 3-continued

| Third Generation CARs | | | |
|---|---|---|---|
| ScFv | Co-stimulatory Signal | Co-stimulatory Signal | Signal Domain |
| CD83 | MyD88 | CD4 | CD3ε |
| CD83 | MyD88 | CD4 | FcγRI-γ |
| CD83 | MyD88 | CD4 | FcγRIII-γ |
| CD83 | MyD88 | CD4 | FcεRIβ |
| CD83 | MyD88 | CD4 | FcεRIγ |
| CD83 | MyD88 | CD4 | DAP10 |
| CD83 | MyD88 | CD4 | DAP12 |
| CD83 | MyD88 | CD4 | CD32 |
| CD83 | MyD88 | CD4 | CD79a |
| CD83 | MyD88 | CD4 | CD79b |
| CD83 | MyD88 | b2c | CD8 |
| CD83 | MyD88 | b2c | CD3ζ |
| CD83 | MyD88 | b2c | CD3δ |
| CD83 | MyD88 | b2c | CD3γ |
| CD83 | MyD88 | b2c | CD3ε |
| CD83 | MyD88 | b2c | FcγRI-γ |
| CD83 | MyD88 | b2c | FcγRIII-γ |
| CD83 | MyD88 | b2c | FcεRIβ |
| CD83 | MyD88 | b2c | FcεRIγ |
| CD83 | MyD88 | b2c | DAP10 |
| CD83 | MyD88 | b2c | DAP12 |
| CD83 | MyD88 | b2c | CD32 |
| CD83 | MyD88 | b2c | CD79a |
| CD83 | MyD88 | b2c | CD79b |
| CD83 | MyD88 | CD137/41BB | CD8 |
| CD83 | MyD88 | CD137/41BB | CD3ζ |
| CD83 | MyD88 | CD137/41BB | CD3δ |
| CD83 | MyD88 | CD137/41BB | CD3γ |
| CD83 | MyD88 | CD137/41BB | CD3ε |
| CD83 | MyD88 | CD137/41BB | FcγRI-γ |
| CD83 | MyD88 | CD137/41BB | FcγRIII-γ |
| CD83 | MyD88 | CD137/41BB | FcεRIβ |
| CD83 | MyD88 | CD137/41BB | FcεRIγ |
| CD83 | MyD88 | CD137/41BB | DAP10 |
| CD83 | MyD88 | CD137/41BB | DAP12 |
| CD83 | MyD88 | CD137/41BB | CD32 |
| CD83 | MyD88 | CD137/41BB | CD79a |
| CD83 | MyD88 | CD137/41BB | CD79b |
| CD83 | MyD88 | ICOS | CD8 |
| CD83 | MyD88 | ICOS | CD3ζ |
| CD83 | MyD88 | ICOS | CD3δ |
| CD83 | MyD88 | ICOS | CD3γ |
| CD83 | MyD88 | ICOS | CD3ε |
| CD83 | MyD88 | ICOS | FcγRI-γ |
| CD83 | MyD88 | ICOS | FcγRIII-γ |
| CD83 | MyD88 | ICOS | FcεRIβ |
| CD83 | MyD88 | ICOS | FcεRIγ |
| CD83 | MyD88 | ICOS | DAP10 |
| CD83 | MyD88 | ICOS | DAP12 |
| CD83 | MyD88 | ICOS | CD32 |
| CD83 | MyD88 | ICOS | CD79a |
| CD83 | MyD88 | ICOS | CD79b |
| CD83 | MyD88 | CD27 | CD8 |
| CD83 | MyD88 | CD27 | CD3ζ |
| CD83 | MyD88 | CD27 | CD3δ |
| CD83 | MyD88 | CD27 | CD3γ |
| CD83 | MyD88 | CD27 | CD3ε |
| CD83 | MyD88 | CD27 | FcγRI-γ |
| CD83 | MyD88 | CD27 | FcγRIII-γ |
| CD83 | MyD88 | CD27 | FcεRIβ |
| CD83 | MyD88 | CD27 | FcεRIγ |
| CD83 | MyD88 | CD27 | DAP10 |
| CD83 | MyD88 | CD27 | DAP12 |
| CD83 | MyD88 | CD27 | CD32 |
| CD83 | MyD88 | CD27 | CD79a |
| CD83 | MyD88 | CD27 | CD79b |
| CD83 | MyD88 | CD28δ | CD8 |
| CD83 | MyD88 | CD28δ | CD3ζ |
| CD83 | MyD88 | CD28δ | CD3δ |
| CD83 | MyD88 | CD28δ | CD3γ |
| CD83 | MyD88 | CD28δ | CD3ε |
| CD83 | MyD88 | CD28δ | FcγRI-γ |
| CD83 | MyD88 | CD28δ | FcγRIII-γ |
| CD83 | MyD88 | CD28δ | FcεRIβ |
| CD83 | MyD88 | CD28δ | FcεRIγ |

TABLE 3-continued

Third Generation CARs

| ScFv | Co-stimulatory Signal | Co-stimulatory Signal | Signal Domain |
|---|---|---|---|
| CD83 | MyD88 | CD28δ | DAP10 |
| CD83 | MyD88 | CD28δ | DAP12 |
| CD83 | MyD88 | CD28δ | CD32 |
| CD83 | MyD88 | CD28δ | CD79a |
| CD83 | MyD88 | CD28δ | CD79b |
| CD83 | MyD88 | CD80 | CD8 |
| CD83 | MyD88 | CD80 | CD3ζ |
| CD83 | MyD88 | CD80 | CD3δ |
| CD83 | MyD88 | CD80 | CD3γ |
| CD83 | MyD88 | CD80 | CD3ε |
| CD83 | MyD88 | CD80 | FcγRI-γ |
| CD83 | MyD88 | CD80 | FcγRIII-γ |
| CD83 | MyD88 | CD80 | FcεRIβ |
| CD83 | MyD88 | CD80 | FcεRIγ |
| CD83 | MyD88 | CD80 | DAP10 |
| CD83 | MyD88 | CD80 | DAP12 |
| CD83 | MyD88 | CD80 | CD32 |
| CD83 | MyD88 | CD80 | CD79a |
| CD83 | MyD88 | CD80 | CD79b |
| CD83 | MyD88 | CD86 | CD8 |
| CD83 | MyD88 | CD86 | CD3ζ |
| CD83 | MyD88 | CD86 | CD3δ |
| CD83 | MyD88 | CD86 | CD3γ |
| CD83 | MyD88 | CD86 | CD3ε |
| CD83 | MyD88 | CD86 | FcγRI-γ |
| CD83 | MyD88 | CD86 | FcγRIII-γ |
| CD83 | MyD88 | CD86 | FcεRIβ |
| CD83 | MyD88 | CD86 | FcεRIγ |
| CD83 | MyD88 | CD86 | DAP10 |
| CD83 | MyD88 | CD86 | DAP12 |
| CD83 | MyD88 | CD86 | CD32 |
| CD83 | MyD88 | CD86 | CD79a |
| CD83 | MyD88 | CD86 | CD79b |
| CD83 | MyD88 | OX40 | CD8 |
| CD83 | MyD88 | OX40 | CD3ζ |
| CD83 | MyD88 | OX40 | CD3δ |
| CD83 | MyD88 | OX40 | CD3γ |
| CD83 | MyD88 | OX40 | CD3ε |
| CD83 | MyD88 | OX40 | FcγRI-γ |
| CD83 | MyD88 | OX40 | FcγRIII-γ |
| CD83 | MyD88 | OX40 | FcεRIβ |
| CD83 | MyD88 | OX40 | FcεRIγ |
| CD83 | MyD88 | OX40 | DAP10 |
| CD83 | MyD88 | OX40 | DAP12 |
| CD83 | MyD88 | OX40 | CD32 |
| CD83 | MyD88 | OX40 | CD79a |
| CD83 | MyD88 | OX40 | CD79b |
| CD83 | MyD88 | DAP10 | CD8 |
| CD83 | MyD88 | DAP10 | CD3ζ |
| CD83 | MyD88 | DAP10 | CD3δ |
| CD83 | MyD88 | DAP10 | CD3γ |
| CD83 | MyD88 | DAP10 | CD3ε |
| CD83 | MyD88 | DAP10 | FcγRI-γ |
| CD83 | MyD88 | DAP10 | FcγRIII-γ |
| CD83 | MyD88 | DAP10 | FcεRIβ |
| CD83 | MyD88 | DAP10 | FcεRIγ |
| CD83 | MyD88 | DAP10 | DAP10 |
| CD83 | MyD88 | DAP10 | DAP12 |
| CD83 | MyD88 | DAP10 | CD32 |
| CD83 | MyD88 | DAP10 | CD79a |
| CD83 | MyD88 | DAP10 | CD79b |
| CD83 | MyD88 | DAP12 | CD8 |
| CD83 | MyD88 | DAP12 | CD3ζ |
| CD83 | MyD88 | DAP12 | CD3δ |
| CD83 | MyD88 | DAP12 | CD3γ |
| CD83 | MyD88 | DAP12 | CD3ε |
| CD83 | MyD88 | DAP12 | FcγRI-γ |
| CD83 | MyD88 | DAP12 | FcγRIII-γ |
| CD83 | MyD88 | DAP12 | FcεRIβ |
| CD83 | MyD88 | DAP12 | FcεRIγ |
| CD83 | MyD88 | DAP12 | DAP10 |
| CD83 | MyD88 | DAP12 | DAP12 |
| CD83 | MyD88 | DAP12 | CD32 |
| CD83 | MyD88 | DAP12 | CD79a |
| CD83 | MyD88 | DAP12 | CD79b |

TABLE 3-continued

Third Generation CARs

| ScFv | Co-stimulatory Signal | Co-stimulatory Signal | Signal Domain |
|---|---|---|---|
| CD83 | MyD88 | MyD88 | CD8 |
| CD83 | MyD88 | MyD88 | CD3ζ |
| CD83 | MyD88 | MyD88 | CD3δ |
| CD83 | MyD88 | MyD88 | CD3γ |
| CD83 | MyD88 | MyD88 | CD3ε |
| CD83 | MyD88 | MyD88 | FcγRI-γ |
| CD83 | MyD88 | MyD88 | FcγRIII-γ |
| CD83 | MyD88 | MyD88 | FcεRIβ |
| CD83 | MyD88 | MyD88 | FcεRIγ |
| CD83 | MyD88 | MyD88 | DAP10 |
| CD83 | MyD88 | MyD88 | DAP12 |
| CD83 | MyD88 | MyD88 | CD32 |
| CD83 | MyD88 | MyD88 | CD79a |
| CD83 | MyD88 | MyD88 | CD79b |
| CD83 | MyD88 | CD7 | CD8 |
| CD83 | MyD88 | CD7 | CD3ζ |
| CD83 | MyD88 | CD7 | CD3δ |
| CD83 | MyD88 | CD7 | CD3γ |
| CD83 | MyD88 | CD7 | CD3ε |
| CD83 | MyD88 | CD7 | FcγRI-γ |
| CD83 | MyD88 | CD7 | FcγRIII-γ |
| CD83 | MyD88 | CD7 | FcεRIβ |
| CD83 | MyD88 | CD7 | FcεRIγ |
| CD83 | MyD88 | CD7 | DAP10 |
| CD83 | MyD88 | CD7 | DAP12 |
| CD83 | MyD88 | CD7 | CD32 |
| CD83 | MyD88 | CD7 | CD79a |
| CD83 | MyD88 | CD7 | CD79b |
| CD83 | MyD88 | BTNL3 | CD8 |
| CD83 | MyD88 | BTNL3 | CD3ζ |
| CD83 | MyD88 | BTNL3 | CD3δ |
| CD83 | MyD88 | BTNL3 | CD3γ |
| CD83 | MyD88 | BTNL3 | CD3ε |
| CD83 | MyD88 | BTNL3 | FcγRI-γ |
| CD83 | MyD88 | BTNL3 | FcγRIII-γ |
| CD83 | MyD88 | BTNL3 | FcεRIβ |
| CD83 | MyD88 | BTNL3 | FcεRIγ |
| CD83 | MyD88 | BTNL3 | DAP10 |
| CD83 | MyD88 | BTNL3 | DAP12 |
| CD83 | MyD88 | BTNL3 | CD32 |
| CD83 | MyD88 | BTNL3 | CD79a |
| CD83 | MyD88 | BTNL3 | CD79b |
| CD83 | MyD88 | NKG2D | CD8 |
| CD83 | MyD88 | NKG2D | CD3ζ |
| CD83 | MyD88 | NKG2D | CD3δ |
| CD83 | MyD88 | NKG2D | CD3γ |
| CD83 | MyD88 | NKG2D | CD3ε |
| CD83 | MyD88 | NKG2D | FcγRI-γ |
| CD83 | MyD88 | NKG2D | FcγRIII-γ |
| CD83 | MyD88 | NKG2D | FcεRIβ |
| CD83 | MyD88 | NKG2D | FcεRIγ |
| CD83 | MyD88 | NKG2D | DAP10 |
| CD83 | MyD88 | NKG2D | DAP12 |
| CD83 | MyD88 | NKG2D | CD32 |
| CD83 | MyD88 | NKG2D | CD79a |
| CD83 | MyD88 | NKG2D | CD79b |
| CD83 | CD7 | CD28 | CD8 |
| CD83 | CD7 | CD28 | CD3ζ |
| CD83 | CD7 | CD28 | CD3δ |
| CD83 | CD7 | CD28 | CD3γ |
| CD83 | CD7 | CD28 | CD3ε |
| CD83 | CD7 | CD28 | FcγRI-γ |
| CD83 | CD7 | CD28 | FcγRIII-γ |
| CD83 | CD7 | CD28 | FcεRIβ |
| CD83 | CD7 | CD28 | FcεRIγ |
| CD83 | CD7 | CD28 | DAP10 |
| CD83 | CD7 | CD28 | DAP12 |
| CD83 | CD7 | CD28 | CD32 |
| CD83 | CD7 | CD28 | CD79a |
| CD83 | CD7 | CD28 | CD79b |
| CD83 | CD7 | CD8 | CD8 |
| CD83 | CD7 | CD8 | CD3ζ |
| CD83 | CD7 | CD8 | CD3δ |
| CD83 | CD7 | CD8 | CD3γ |
| CD83 | CD7 | CD8 | CD3ε |

TABLE 3-continued

Third Generation CARs

| ScFv | Co-stimulatory Signal | Co-stimulatory Signal | Signal Domain |
|---|---|---|---|
| CD83 | CD7 | CD8 | FcγRI-γ |
| CD83 | CD7 | CD8 | FcγRIII-γ |
| CD83 | CD7 | CD8 | FcεRIβ |
| CD83 | CD7 | CD8 | FcεRIγ |
| CD83 | CD7 | CD8 | DAP10 |
| CD83 | CD7 | CD8 | DAP12 |
| CD83 | CD7 | CD8 | CD32 |
| CD83 | CD7 | CD8 | CD79a |
| CD83 | CD7 | CD8 | CD79b |
| CD83 | CD7 | CD4 | CD8 |
| CD83 | CD7 | CD4 | CD3ζ |
| CD83 | CD7 | CD4 | CD3δ |
| CD83 | CD7 | CD4 | CD3γ |
| CD83 | CD7 | CD4 | CD3ε |
| CD83 | CD7 | CD4 | FcγRI-γ |
| CD83 | CD7 | CD4 | FcγRIII-γ |
| CD83 | CD7 | CD4 | FcεRIβ |
| CD83 | CD7 | CD4 | FcεRIγ |
| CD83 | CD7 | CD4 | DAP10 |
| CD83 | CD7 | CD4 | DAP12 |
| CD83 | CD7 | CD4 | CD32 |
| CD83 | CD7 | CD4 | CD79a |
| CD83 | CD7 | CD4 | CD79b |
| CD83 | CD7 | b2c | CD8 |
| CD83 | CD7 | b2c | CD3ζ |
| CD83 | CD7 | b2c | CD3δ |
| CD83 | CD7 | b2c | CD3γ |
| CD83 | CD7 | b2c | CD3ε |
| CD83 | CD7 | b2c | FcγRI-γ |
| CD83 | CD7 | b2c | FcγRIII-γ |
| CD83 | CD7 | b2c | FcεRIβ |
| CD83 | CD7 | b2c | FcεRIγ |
| CD83 | CD7 | b2c | DAP10 |
| CD83 | CD7 | b2c | DAP12 |
| CD83 | CD7 | b2c | CD32 |
| CD83 | CD7 | b2c | CD79a |
| CD83 | CD7 | b2c | CD79b |
| CD83 | CD7 | CD137/41BB | CD8 |
| CD83 | CD7 | CD137/41BB | CD3ζ |
| CD83 | CD7 | CD137/41BB | CD3δ |
| CD83 | CD7 | CD137/41BB | CD3γ |
| CD83 | CD7 | CD137/41BB | CD3ε |
| CD83 | CD7 | CD137/41BB | FcγRI-γ |
| CD83 | CD7 | CD137/41BB | FcγRIII-γ |
| CD83 | CD7 | CD137/41BB | FcεRIβ |
| CD83 | CD7 | CD137/41BB | FcεRIγ |
| CD83 | CD7 | CD137/41BB | DAP10 |
| CD83 | CD7 | CD137/41BB | DAP12 |
| CD83 | CD7 | CD137/41BB | CD32 |
| CD83 | CD7 | CD137/41BB | CD79a |
| CD83 | CD7 | CD137/41BB | CD79b |
| CD83 | CD7 | ICOS | CD8 |
| CD83 | CD7 | ICOS | CD3ζ |
| CD83 | CD7 | ICOS | CD3δ |
| CD83 | CD7 | ICOS | CD3γ |
| CD83 | CD7 | ICOS | CD3ε |
| CD83 | CD7 | ICOS | FcγRI-γ |
| CD83 | CD7 | ICOS | FcγRIII-γ |
| CD83 | CD7 | ICOS | FcεRIβ |
| CD83 | CD7 | ICOS | FcεRIγ |
| CD83 | CD7 | ICOS | DAP10 |
| CD83 | CD7 | ICOS | DAP12 |
| CD83 | CD7 | ICOS | CD32 |
| CD83 | CD7 | ICOS | CD79a |
| CD83 | CD7 | ICOS | CD79b |
| CD83 | CD7 | CD27 | CD8 |
| CD83 | CD7 | CD27 | CD3ζ |
| CD83 | CD7 | CD27 | CD3δ |
| CD83 | CD7 | CD27 | CD3γ |
| CD83 | CD7 | CD27 | CD3ε |
| CD83 | CD7 | CD27 | FcγRI-γ |
| CD83 | CD7 | CD27 | FcγRIII-γ |
| CD83 | CD7 | CD27 | FcεRIβ |
| CD83 | CD7 | CD27 | FcεRIγ |
| CD83 | CD7 | CD27 | DAP10 |

TABLE 3-continued

Third Generation CARs

| ScFv | Co-stimulatory Signal | Co-stimulatory Signal | Signal Domain |
|---|---|---|---|
| CD83 | CD7 | CD27 | DAP12 |
| CD83 | CD7 | CD27 | CD32 |
| CD83 | CD7 | CD27 | CD79a |
| CD83 | CD7 | CD27 | CD79b |
| CD83 | CD7 | CD28δ | CD8 |
| CD83 | CD7 | CD28δ | CD3ζ |
| CD83 | CD7 | CD28δ | CD3δ |
| CD83 | CD7 | CD28δ | CD3γ |
| CD83 | CD7 | CD28δ | CD3ε |
| CD83 | CD7 | CD28δ | FcγRI-γ |
| CD83 | CD7 | CD28δ | FcγRIII-γ |
| CD83 | CD7 | CD28δ | FcεRIβ |
| CD83 | CD7 | CD28δ | FcεRIγ |
| CD83 | CD7 | CD28δ | DAP10 |
| CD83 | CD7 | CD28δ | DAP12 |
| CD83 | CD7 | CD28δ | CD32 |
| CD83 | CD7 | CD28δ | CD79a |
| CD83 | CD7 | CD28δ | CD79b |
| CD83 | CD7 | CD80 | CD8 |
| CD83 | CD7 | CD80 | CD3ζ |
| CD83 | CD7 | CD80 | CD3δ |
| CD83 | CD7 | CD80 | CD3γ |
| CD83 | CD7 | CD80 | CD3ε |
| CD83 | CD7 | CD80 | FcγRI-γ |
| CD83 | CD7 | CD80 | FcγRIII-γ |
| CD83 | CD7 | CD80 | FcεRIβ |
| CD83 | CD7 | CD80 | FcεRIγ |
| CD83 | CD7 | CD80 | DAP10 |
| CD83 | CD7 | CD80 | DAP12 |
| CD83 | CD7 | CD80 | CD32 |
| CD83 | CD7 | CD80 | CD79a |
| CD83 | CD7 | CD80 | CD79b |
| CD83 | CD7 | CD86 | CD8 |
| CD83 | CD7 | CD86 | CD3ζ |
| CD83 | CD7 | CD86 | CD3δ |
| CD83 | CD7 | CD86 | CD3γ |
| CD83 | CD7 | CD86 | CD3ε |
| CD83 | CD7 | CD86 | FcγRI-γ |
| CD83 | CD7 | CD86 | FcγRIII-γ |
| CD83 | CD7 | CD86 | FcεRIβ |
| CD83 | CD7 | CD86 | FcεRIγ |
| CD83 | CD7 | CD86 | DAP10 |
| CD83 | CD7 | CD86 | DAP12 |
| CD83 | CD7 | CD86 | CD32 |
| CD83 | CD7 | CD86 | CD79a |
| CD83 | CD7 | CD86 | CD79b |
| CD83 | CD7 | OX40 | CD8 |
| CD83 | CD7 | OX40 | CD3ζ |
| CD83 | CD7 | OX40 | CD3δ |
| CD83 | CD7 | OX40 | CD3γ |
| CD83 | CD7 | OX40 | CD3ε |
| CD83 | CD7 | OX40 | FcγRI-γ |
| CD83 | CD7 | OX40 | FcγRIII-γ |
| CD83 | CD7 | OX40 | FcεRIβ |
| CD83 | CD7 | OX40 | FcεRIγ |
| CD83 | CD7 | OX40 | DAP10 |
| CD83 | CD7 | OX40 | DAP12 |
| CD83 | CD7 | OX40 | CD32 |
| CD83 | CD7 | OX40 | CD79a |
| CD83 | CD7 | OX40 | CD79b |
| CD83 | CD7 | DAP10 | CD8 |
| CD83 | CD7 | DAP10 | CD3ζ |
| CD83 | CD7 | DAP10 | CD3δ |
| CD83 | CD7 | DAP10 | CD3γ |
| CD83 | CD7 | DAP10 | CD3ε |
| CD83 | CD7 | DAP10 | FcγRI-γ |
| CD83 | CD7 | DAP10 | FcγRIII-γ |
| CD83 | CD7 | DAP10 | FcεRIβ |
| CD83 | CD7 | DAP10 | FcεRIγ |
| CD83 | CD7 | DAP10 | DAP10 |
| CD83 | CD7 | DAP10 | DAP12 |
| CD83 | CD7 | DAP10 | CD32 |
| CD83 | CD7 | DAP10 | CD79a |
| CD83 | CD7 | DAP10 | CD79b |
| CD83 | CD7 | DAP12 | CD8 |

TABLE 3-continued

| Third Generation CARs | | | |
|---|---|---|---|
| ScFv | Co-stimulatory Signal | Co-stimulatory Signal | Signal Domain |
| CD83 | CD7 | DAP12 | CD3ζ |
| CD83 | CD7 | DAP12 | CD3δ |
| CD83 | CD7 | DAP12 | CD3γ |
| CD83 | CD7 | DAP12 | CD3ε |
| CD83 | CD7 | DAP12 | FcγRI-γ |
| CD83 | CD7 | DAP12 | FcγRIII-γ |
| CD83 | CD7 | DAP12 | FcεRIβ |
| CD83 | CD7 | DAP12 | FcεRIγ |
| CD83 | CD7 | DAP12 | DAP10 |
| CD83 | CD7 | DAP12 | DAP12 |
| CD83 | CD7 | DAP12 | CD32 |
| CD83 | CD7 | DAP12 | CD79a |
| CD83 | CD7 | DAP12 | CD79b |
| CD83 | CD7 | MyD88 | CD8 |
| CD83 | CD7 | MyD88 | CD3ζ |
| CD83 | CD7 | MyD88 | CD3δ |
| CD83 | CD7 | MyD88 | CD3γ |
| CD83 | CD7 | MyD88 | CD3ε |
| CD83 | CD7 | MyD88 | FcγRI-γ |
| CD83 | CD7 | MyD88 | FcγRIII-γ |
| CD83 | CD7 | MyD88 | FcεRIβ |
| CD83 | CD7 | MyD88 | FcεRIγ |
| CD83 | CD7 | MyD88 | DAP10 |
| CD83 | CD7 | MyD88 | DAP12 |
| CD83 | CD7 | MyD88 | CD32 |
| CD83 | CD7 | MyD88 | CD79a |
| CD83 | CD7 | MyD88 | CD79b |
| CD83 | CD7 | CD7 | CD8 |
| CD83 | CD7 | CD7 | CD3ζ |
| CD83 | CD7 | CD7 | CD3δ |
| CD83 | CD7 | CD7 | CD3γ |
| CD83 | CD7 | CD7 | CD3ε |
| CD83 | CD7 | CD7 | FcγRI-γ |
| CD83 | CD7 | CD7 | FcγRIII-γ |
| CD83 | CD7 | CD7 | FcεRIβ |
| CD83 | CD7 | CD7 | FcεRIγ |
| CD83 | CD7 | CD7 | DAP10 |
| CD83 | CD7 | CD7 | DAP12 |
| CD83 | CD7 | CD7 | CD32 |
| CD83 | CD7 | CD7 | CD79a |
| CD83 | CD7 | CD7 | CD79b |
| CD83 | CD7 | BTNL3 | CD8 |
| CD83 | CD7 | BTNL3 | CD3ζ |
| CD83 | CD7 | BTNL3 | CD3δ |
| CD83 | CD7 | BTNL3 | CD3γ |
| CD83 | CD7 | BTNL3 | CD3ε |
| CD83 | CD7 | BTNL3 | FcγRI-γ |
| CD83 | CD7 | BTNL3 | FcγRIII-γ |
| CD83 | CD7 | BTNL3 | FcεRIβ |
| CD83 | CD7 | BTNL3 | FcεRIγ |
| CD83 | CD7 | BTNL3 | DAP10 |
| CD83 | CD7 | BTNL3 | DAP12 |
| CD83 | CD7 | BTNL3 | CD32 |
| CD83 | CD7 | BTNL3 | CD79a |
| CD83 | CD7 | BTNL3 | CD79b |
| CD83 | CD7 | NKG2D | CD8 |
| CD83 | CD7 | NKG2D | CD3ζ |
| CD83 | CD7 | NKG2D | CD3δ |
| CD83 | CD7 | NKG2D | CD3γ |
| CD83 | CD7 | NKG2D | CD3ε |
| CD83 | CD7 | NKG2D | FcγRI-γ |
| CD83 | CD7 | NKG2D | FcγRIII-γ |
| CD83 | CD7 | NKG2D | FcεRIβ |
| CD83 | CD7 | NKG2D | FcεRIγ |
| CD83 | CD7 | NKG2D | DAP10 |
| CD83 | CD7 | NKG2D | DAP12 |
| CD83 | CD7 | NKG2D | CD32 |
| CD83 | CD7 | NKG2D | CD79a |
| CD83 | CD7 | NKG2D | CD79b |
| CD83 | BTNL3 | CD28 | CD8 |
| CD83 | BTNL3 | CD28 | CD3ζ |
| CD83 | BTNL3 | CD28 | CD3δ |
| CD83 | BTNL3 | CD28 | CD3γ |
| CD83 | BTNL3 | CD28 | CD3ε |
| CD83 | BTNL3 | CD28 | FcγRI-γ |

TABLE 3-continued

| Third Generation CARs | | | |
|---|---|---|---|
| ScFv | Co-stimulatory Signal | Co-stimulatory Signal | Signal Domain |
| CD83 | BTNL3 | CD28 | FcγRIII-γ |
| CD83 | BTNL3 | CD28 | FcεRIβ |
| CD83 | BTNL3 | CD28 | FcεRIγ |
| CD83 | BTNL3 | CD28 | DAP10 |
| CD83 | BTNL3 | CD28 | DAP12 |
| CD83 | BTNL3 | CD28 | CD32 |
| CD83 | BTNL3 | CD28 | CD79a |
| CD83 | BTNL3 | CD28 | CD79b |
| CD83 | BTNL3 | CD8 | CD8 |
| CD83 | BTNL3 | CD8 | CD3ζ |
| CD83 | BTNL3 | CD8 | CD3δ |
| CD83 | BTNL3 | CD8 | CD3γ |
| CD83 | BTNL3 | CD8 | CD3ε |
| CD83 | BTNL3 | CD8 | FcγRI-γ |
| CD83 | BTNL3 | CD8 | FcγRIII-γ |
| CD83 | BTNL3 | CD8 | FcεRIβ |
| CD83 | BTNL3 | CD8 | FcεRIγ |
| CD83 | BTNL3 | CD8 | DAP10 |
| CD83 | BTNL3 | CD8 | DAP12 |
| CD83 | BTNL3 | CD8 | CD32 |
| CD83 | BTNL3 | CD8 | CD79a |
| CD83 | BTNL3 | CD8 | CD79b |
| CD83 | BTNL3 | CD4 | CD8 |
| CD83 | BTNL3 | CD4 | CD3ζ |
| CD83 | BTNL3 | CD4 | CD3δ |
| CD83 | BTNL3 | CD4 | CD3γ |
| CD83 | BTNL3 | CD4 | CD3ε |
| CD83 | BTNL3 | CD4 | FcγRI-γ |
| CD83 | BTNL3 | CD4 | FcγRIII-γ |
| CD83 | BTNL3 | CD4 | FcεRIβ |
| CD83 | BTNL3 | CD4 | FcεRIγ |
| CD83 | BTNL3 | CD4 | DAP10 |
| CD83 | BTNL3 | CD4 | DAP12 |
| CD83 | BTNL3 | CD4 | CD32 |
| CD83 | BTNL3 | CD4 | CD79a |
| CD83 | BTNL3 | CD4 | CD79b |
| CD83 | BTNL3 | b2c | CD8 |
| CD83 | BTNL3 | b2c | CD3ζ |
| CD83 | BTNL3 | b2c | CD3δ |
| CD83 | BTNL3 | b2c | CD3γ |
| CD83 | BTNL3 | b2c | CD3ε |
| CD83 | BTNL3 | b2c | FcγRI-γ |
| CD83 | BTNL3 | b2c | FcγRIII-γ |
| CD83 | BTNL3 | b2c | FcεRIβ |
| CD83 | BTNL3 | b2c | FcεRIγ |
| CD83 | BTNL3 | b2c | DAP10 |
| CD83 | BTNL3 | b2c | DAP12 |
| CD83 | BTNL3 | b2c | CD32 |
| CD83 | BTNL3 | b2c | CD79a |
| CD83 | BTNL3 | b2c | CD79b |
| CD83 | BTNL3 | CD137/41BB | CD8 |
| CD83 | BTNL3 | CD137/41BB | CD3ζ |
| CD83 | BTNL3 | CD137/41BB | CD3δ |
| CD83 | BTNL3 | CD137/41BB | CD3γ |
| CD83 | BTNL3 | CD137/41BB | CD3ε |
| CD83 | BTNL3 | CD137/41BB | FcγRI-γ |
| CD83 | BTNL3 | CD137/41BB | FcγRIII-γ |
| CD83 | BTNL3 | CD137/41BB | FcεRIβ |
| CD83 | BTNL3 | CD137/41BB | FcεRIγ |
| CD83 | BTNL3 | CD137/41BB | DAP10 |
| CD83 | BTNL3 | CD137/41BB | DAP12 |
| CD83 | BTNL3 | CD137/41BB | CD32 |
| CD83 | BTNL3 | CD137/41BB | CD79a |
| CD83 | BTNL3 | CD137/41BB | CD79b |
| CD83 | BTNL3 | ICOS | CD8 |
| CD83 | BTNL3 | ICOS | CD3ζ |
| CD83 | BTNL3 | ICOS | CD3δ |
| CD83 | BTNL3 | ICOS | CD3γ |
| CD83 | BTNL3 | ICOS | CD3ε |
| CD83 | BTNL3 | ICOS | FcγRI-γ |
| CD83 | BTNL3 | ICOS | FcγRIII-γ |
| CD83 | BTNL3 | ICOS | FcεRIβ |
| CD83 | BTNL3 | ICOS | FcεRIγ |
| CD83 | BTNL3 | ICOS | DAP10 |
| CD83 | BTNL3 | ICOS | DAP12 |

TABLE 3-continued

Third Generation CARs

| ScFv | Co-stimulatory Signal | Co-stimulatory Signal | Signal Domain |
|---|---|---|---|
| CD83 | BTNL3 | ICOS | CD32 |
| CD83 | BTNL3 | ICOS | CD79a |
| CD83 | BTNL3 | ICOS | CD79b |
| CD83 | BTNL3 | CD27 | CD8 |
| CD83 | BTNL3 | CD27 | CD3ζ |
| CD83 | BTNL3 | CD27 | CD3δ |
| CD83 | BTNL3 | CD27 | CD3γ |
| CD83 | BTNL3 | CD27 | CD3ε |
| CD83 | BTNL3 | CD27 | FcγRI-γ |
| CD83 | BTNL3 | CD27 | FcγRIII-γ |
| CD83 | BTNL3 | CD27 | FcεRIβ |
| CD83 | BTNL3 | CD27 | FcεRIγ |
| CD83 | BTNL3 | CD27 | DAP10 |
| CD83 | BTNL3 | CD27 | DAP12 |
| CD83 | BTNL3 | CD27 | CD32 |
| CD83 | BTNL3 | CD27 | CD79a |
| CD83 | BTNL3 | CD27 | CD79b |
| CD83 | BTNL3 | CD28δ | CD8 |
| CD83 | BTNL3 | CD28δ | CD3ζ |
| CD83 | BTNL3 | CD28δ | CD3δ |
| CD83 | BTNL3 | CD28δ | CD3γ |
| CD83 | BTNL3 | CD28δ | CD3ε |
| CD83 | BTNL3 | CD28δ | FcγRI-γ |
| CD83 | BTNL3 | CD28δ | FcγRIII-γ |
| CD83 | BTNL3 | CD28δ | FcεRIβ |
| CD83 | BTNL3 | CD28δ | FcεRIγ |
| CD83 | BTNL3 | CD28δ | DAP10 |
| CD83 | BTNL3 | CD28δ | DAP12 |
| CD83 | BTNL3 | CD28δ | CD32 |
| CD83 | BTNL3 | CD28δ | CD79a |
| CD83 | BTNL3 | CD28δ | CD79b |
| CD83 | BTNL3 | CD80 | CD8 |
| CD83 | BTNL3 | CD80 | CD3ζ |
| CD83 | BTNL3 | CD80 | CD3δ |
| CD83 | BTNL3 | CD80 | CD3γ |
| CD83 | BTNL3 | CD80 | CD3ε |
| CD83 | BTNL3 | CD80 | FcγRI-γ |
| CD83 | BTNL3 | CD80 | FcγRIII-γ |
| CD83 | BTNL3 | CD80 | FcεRIβ |
| CD83 | BTNL3 | CD80 | FcεRIγ |
| CD83 | BTNL3 | CD80 | DAP10 |
| CD83 | BTNL3 | CD80 | DAP12 |
| CD83 | BTNL3 | CD80 | CD32 |
| CD83 | BTNL3 | CD80 | CD79a |
| CD83 | BTNL3 | CD80 | CD79b |
| CD83 | BTNL3 | CD86 | CD8 |
| CD83 | BTNL3 | CD86 | CD3ζ |
| CD83 | BTNL3 | CD86 | CD3δ |
| CD83 | BTNL3 | CD86 | CD3γ |
| CD83 | BTNL3 | CD86 | CD3ε |
| CD83 | BTNL3 | CD86 | FcγRI-γ |
| CD83 | BTNL3 | CD86 | FcγRIII-γ |
| CD83 | BTNL3 | CD86 | FcεRIβ |
| CD83 | BTNL3 | CD86 | FcεRIγ |
| CD83 | BTNL3 | CD86 | DAP10 |
| CD83 | BTNL3 | CD86 | DAP12 |
| CD83 | BTNL3 | CD86 | CD32 |
| CD83 | BTNL3 | CD86 | CD79a |
| CD83 | BTNL3 | CD86 | CD79b |
| CD83 | BTNL3 | OX40 | CD8 |
| CD83 | BTNL3 | OX40 | CD3ζ |
| CD83 | BTNL3 | OX40 | CD3δ |
| CD83 | BTNL3 | OX40 | CD3γ |
| CD83 | BTNL3 | OX40 | CD3ε |
| CD83 | BTNL3 | OX40 | FcγRI-γ |
| CD83 | BTNL3 | OX40 | FcγRIII-γ |
| CD83 | BTNL3 | OX40 | FcεRIβ |
| CD83 | BTNL3 | OX40 | FcεRIγ |
| CD83 | BTNL3 | OX40 | DAP10 |
| CD83 | BTNL3 | OX40 | DAP12 |
| CD83 | BTNL3 | OX40 | CD32 |
| CD83 | BTNL3 | OX40 | CD79a |
| CD83 | BTNL3 | OX40 | CD79b |
| CD83 | BTNL3 | DAP10 | CD8 |
| CD83 | BTNL3 | DAP10 | CD3ζ |

TABLE 3-continued

Third Generation CARs

| ScFv | Co-stimulatory Signal | Co-stimulatory Signal | Signal Domain |
|---|---|---|---|
| CD83 | BTNL3 | DAP10 | CD3δ |
| CD83 | BTNL3 | DAP10 | CD3γ |
| CD83 | BTNL3 | DAP10 | CD3ε |
| CD83 | BTNL3 | DAP10 | FcγRI-γ |
| CD83 | BTNL3 | DAP10 | FcγRIII-γ |
| CD83 | BTNL3 | DAP10 | FcεRIβ |
| CD83 | BTNL3 | DAP10 | FcεRIγ |
| CD83 | BTNL3 | DAP10 | DAP10 |
| CD83 | BTNL3 | DAP10 | DAP12 |
| CD83 | BTNL3 | DAP10 | CD32 |
| CD83 | BTNL3 | DAP10 | CD79a |
| CD83 | BTNL3 | DAP10 | CD79b |
| CD83 | BTNL3 | DAP12 | CD8 |
| CD83 | BTNL3 | DAP12 | CD3ζ |
| CD83 | BTNL3 | DAP12 | CD3δ |
| CD83 | BTNL3 | DAP12 | CD3γ |
| CD83 | BTNL3 | DAP12 | CD3ε |
| CD83 | BTNL3 | DAP12 | FcγRI-γ |
| CD83 | BTNL3 | DAP12 | FcγRIII-γ |
| CD83 | BTNL3 | DAP12 | FcεRIβ |
| CD83 | BTNL3 | DAP12 | FcεRIγ |
| CD83 | BTNL3 | DAP12 | DAP10 |
| CD83 | BTNL3 | DAP12 | DAP12 |
| CD83 | BTNL3 | DAP12 | CD32 |
| CD83 | BTNL3 | DAP12 | CD79a |
| CD83 | BTNL3 | DAP12 | CD79b |
| CD83 | BTNL3 | MyD88 | CD8 |
| CD83 | BTNL3 | MyD88 | CD3ζ |
| CD83 | BTNL3 | MyD88 | CD3δ |
| CD83 | BTNL3 | MyD88 | CD3γ |
| CD83 | BTNL3 | MyD88 | CD3ε |
| CD83 | BTNL3 | MyD88 | FcγRI-γ |
| CD83 | BTNL3 | MyD88 | FcγRIII-γ |
| CD83 | BTNL3 | MyD88 | FcεRIβ |
| CD83 | BTNL3 | MyD88 | FcεRIγ |
| CD83 | BTNL3 | MyD88 | DAP10 |
| CD83 | BTNL3 | MyD88 | DAP12 |
| CD83 | BTNL3 | MyD88 | CD32 |
| CD83 | BTNL3 | MyD88 | CD79a |
| CD83 | BTNL3 | MyD88 | CD79b |
| CD83 | BTNL3 | CD7 | CD8 |
| CD83 | BTNL3 | CD7 | CD3ζ |
| CD83 | BTNL3 | CD7 | CD3δ |
| CD83 | BTNL3 | CD7 | CD3γ |
| CD83 | BTNL3 | CD7 | CD3ε |
| CD83 | BTNL3 | CD7 | FcγRI-γ |
| CD83 | BTNL3 | CD7 | FcγRIII-γ |
| CD83 | BTNL3 | CD7 | FcεRIβ |
| CD83 | BTNL3 | CD7 | FcεRIγ |
| CD83 | BTNL3 | CD7 | DAP10 |
| CD83 | BTNL3 | CD7 | DAP12 |
| CD83 | BTNL3 | CD7 | CD32 |
| CD83 | BTNL3 | CD7 | CD79a |
| CD83 | BTNL3 | CD7 | CD79b |
| CD83 | BTNL3 | BTNL3 | CD8 |
| CD83 | BTNL3 | BTNL3 | CD3ζ |
| CD83 | BTNL3 | BTNL3 | CD3δ |
| CD83 | BTNL3 | BTNL3 | CD3γ |
| CD83 | BTNL3 | BTNL3 | CD3ε |
| CD83 | BTNL3 | BTNL3 | FcγRI-γ |
| CD83 | BTNL3 | BTNL3 | FcγRIII-γ |
| CD83 | BTNL3 | BTNL3 | FcεRIβ |
| CD83 | BTNL3 | BTNL3 | FcεRIγ |
| CD83 | BTNL3 | BTNL3 | DAP10 |
| CD83 | BTNL3 | BTNL3 | DAP12 |
| CD83 | BTNL3 | BTNL3 | CD32 |
| CD83 | BTNL3 | BTNL3 | CD79a |
| CD83 | BTNL3 | BTNL3 | CD79b |
| CD83 | BTNL3 | NKG2D | CD8 |
| CD83 | BTNL3 | NKG2D | CD3ζ |
| CD83 | BTNL3 | NKG2D | CD3δ |
| CD83 | BTNL3 | NKG2D | CD3γ |
| CD83 | BTNL3 | NKG2D | CD3ε |
| CD83 | BTNL3 | NKG2D | FcγRI-γ |
| CD83 | BTNL3 | NKG2D | FcγRIII-γ |

TABLE 3-continued

| Third Generation CARs | | | |
|---|---|---|---|
| ScFv | Co-stimulatory Signal | Co-stimulatory Signal | Signal Domain |
| CD83 | BTNL3 | NKG2D | FcεRIβ |
| CD83 | BTNL3 | NKG2D | FcεRIγ |
| CD83 | BTNL3 | NKG2D | DAP10 |
| CD83 | BTNL3 | NKG2D | DAP12 |
| CD83 | BTNL3 | NKG2D | CD32 |
| CD83 | BTNL3 | NKG2D | CD79a |
| CD83 | BTNL3 | NKG2D | CD79b |
| CD83 | NKG2D | CD28 | CD8 |
| CD83 | NKG2D | CD28 | CD3ζ |
| CD83 | NKG2D | CD28 | CD3δ |
| CD83 | NKG2D | CD28 | CD3γ |
| CD83 | NKG2D | CD28 | CD3ε |
| CD83 | NKG2D | CD28 | FcγRI-γ |
| CD83 | NKG2D | CD28 | FcγRIII-γ |
| CD83 | NKG2D | CD28 | FcεRIβ |
| CD83 | NKG2D | CD28 | FcεRIγ |
| CD83 | NKG2D | CD28 | DAP10 |
| CD83 | NKG2D | CD28 | DAP12 |
| CD83 | NKG2D | CD28 | CD32 |
| CD83 | NKG2D | CD28 | CD79a |
| CD83 | NKG2D | CD28 | CD79b |
| CD83 | NKG2D | CD8 | CD8 |
| CD83 | NKG2D | CD8 | CD3ζ |
| CD83 | NKG2D | CD8 | CD3δ |
| CD83 | NKG2D | CD8 | CD3γ |
| CD83 | NKG2D | CD8 | CD3ε |
| CD83 | NKG2D | CD8 | FcγRI-γ |
| CD83 | NKG2D | CD8 | FcγRIII-γ |
| CD83 | NKG2D | CD8 | FcεRIβ |
| CD83 | NKG2D | CD8 | FcεRIγ |
| CD83 | NKG2D | CD8 | DAP10 |
| CD83 | NKG2D | CD8 | DAP12 |
| CD83 | NKG2D | CD8 | CD32 |
| CD83 | NKG2D | CD8 | CD79a |
| CD83 | NKG2D | CD8 | CD79b |
| CD83 | NKG2D | CD4 | CD8 |
| CD83 | NKG2D | CD4 | CD3ζ |
| CD83 | NKG2D | CD4 | CD3δ |
| CD83 | NKG2D | CD4 | CD3γ |
| CD83 | NKG2D | CD4 | CD3ε |
| CD83 | NKG2D | CD4 | FcγRI-γ |
| CD83 | NKG2D | CD4 | FcγRIII-γ |
| CD83 | NKG2D | CD4 | FcεRIβ |
| CD83 | NKG2D | CD4 | FcεRIγ |
| CD83 | NKG2D | CD4 | DAP10 |
| CD83 | NKG2D | CD4 | DAP12 |
| CD83 | NKG2D | CD4 | CD32 |
| CD83 | NKG2D | CD4 | CD79a |
| CD83 | NKG2D | CD4 | CD79b |
| CD83 | NKG2D | b2c | CD8 |
| CD83 | NKG2D | b2c | CD3ζ |
| CD83 | NKG2D | b2c | CD3δ |
| CD83 | NKG2D | b2c | CD3γ |
| CD83 | NKG2D | b2c | CD3ε |
| CD83 | NKG2D | b2c | FcγRI-γ |
| CD83 | NKG2D | b2c | FcγRIII-γ |
| CD83 | NKG2D | b2c | FcεRIβ |
| CD83 | NKG2D | b2c | FcεRIγ |
| CD83 | NKG2D | b2c | DAP10 |
| CD83 | NKG2D | b2c | DAP12 |
| CD83 | NKG2D | b2c | CD32 |
| CD83 | NKG2D | b2c | CD79a |
| CD83 | NKG2D | b2c | CD79b |
| CD83 | NKG2D | CD137/41BB | CD8 |
| CD83 | NKG2D | CD137/41BB | CD3ζ |
| CD83 | NKG2D | CD137/41BB | CD3δ |
| CD83 | NKG2D | CD137/41BB | CD3γ |
| CD83 | NKG2D | CD137/41BB | CD3ε |
| CD83 | NKG2D | CD137/41BB | FcγRI-γ |
| CD83 | NKG2D | CD137/41BB | FcγRIII-γ |
| CD83 | NKG2D | CD137/41BB | FcεRIβ |
| CD83 | NKG2D | CD137/41BB | FcεRIγ |
| CD83 | NKG2D | CD137/41BB | DAP10 |
| CD83 | NKG2D | CD137/41BB | DAP12 |
| CD83 | NKG2D | CD137/41BB | CD32 |

TABLE 3-continued

| Third Generation CARs | | | |
|---|---|---|---|
| ScFv | Co-stimulatory Signal | Co-stimulatory Signal | Signal Domain |
| CD83 | NKG2D | CD137/41BB | CD79a |
| CD83 | NKG2D | CD137/41BB | CD79b |
| CD83 | NKG2D | ICOS | CD8 |
| CD83 | NKG2D | ICOS | CD3ζ |
| CD83 | NKG2D | ICOS | CD3δ |
| CD83 | NKG2D | ICOS | CD3γ |
| CD83 | NKG2D | ICOS | CD3ε |
| CD83 | NKG2D | ICOS | FcγRI-γ |
| CD83 | NKG2D | ICOS | FcγRIII-γ |
| CD83 | NKG2D | ICOS | FcεRIβ |
| CD83 | NKG2D | ICOS | FcεRIγ |
| CD83 | NKG2D | ICOS | DAP10 |
| CD83 | NKG2D | ICOS | DAP12 |
| CD83 | NKG2D | ICOS | CD32 |
| CD83 | NKG2D | ICOS | CD79a |
| CD83 | NKG2D | ICOS | CD79b |
| CD83 | NKG2D | CD27 | CD8 |
| CD83 | NKG2D | CD27 | CD3ζ |
| CD83 | NKG2D | CD27 | CD3δ |
| CD83 | NKG2D | CD27 | CD3γ |
| CD83 | NKG2D | CD27 | CD3ε |
| CD83 | NKG2D | CD27 | FcγRI-γ |
| CD83 | NKG2D | CD27 | FcγRIII-γ |
| CD83 | NKG2D | CD27 | FcεRIβ |
| CD83 | NKG2D | CD27 | FcεRIγ |
| CD83 | NKG2D | CD27 | DAP10 |
| CD83 | NKG2D | CD27 | DAP12 |
| CD83 | NKG2D | CD27 | CD32 |
| CD83 | NKG2D | CD27 | CD79a |
| CD83 | NKG2D | CD27 | CD79b |
| CD83 | NKG2D | CD28δ | CD8 |
| CD83 | NKG2D | CD28δ | CD3ζ |
| CD83 | NKG2D | CD28δ | CD3δ |
| CD83 | NKG2D | CD28δ | CD3γ |
| CD83 | NKG2D | CD28δ | CD3ε |
| CD83 | NKG2D | CD28δ | FcγRI-γ |
| CD83 | NKG2D | CD28δ | FcγRIII-γ |
| CD83 | NKG2D | CD28δ | FcεRIβ |
| CD83 | NKG2D | CD28δ | FcεRIγ |
| CD83 | NKG2D | CD28δ | DAP10 |
| CD83 | NKG2D | CD28δ | DAP12 |
| CD83 | NKG2D | CD28δ | CD32 |
| CD83 | NKG2D | CD28δ | CD79a |
| CD83 | NKG2D | CD28δ | CD79b |
| CD83 | NKG2D | CD80 | CD8 |
| CD83 | NKG2D | CD80 | CD3ζ |
| CD83 | NKG2D | CD80 | CD3δ |
| CD83 | NKG2D | CD80 | CD3γ |
| CD83 | NKG2D | CD80 | CD3ε |
| CD83 | NKG2D | CD80 | FcγRI-γ |
| CD83 | NKG2D | CD80 | FcγRIII-γ |
| CD83 | NKG2D | CD80 | FcεRIβ |
| CD83 | NKG2D | CD80 | FcεRIγ |
| CD83 | NKG2D | CD80 | DAP10 |
| CD83 | NKG2D | CD80 | DAP12 |
| CD83 | NKG2D | CD80 | CD32 |
| CD83 | NKG2D | CD80 | CD79a |
| CD83 | NKG2D | CD80 | CD79b |
| CD83 | NKG2D | CD86 | CD8 |
| CD83 | NKG2D | CD86 | CD3ζ |
| CD83 | NKG2D | CD86 | CD3δ |
| CD83 | NKG2D | CD86 | CD3γ |
| CD83 | NKG2D | CD86 | CD3ε |
| CD83 | NKG2D | CD86 | FcγRI-γ |
| CD83 | NKG2D | CD86 | FcγRIII-γ |
| CD83 | NKG2D | CD86 | FcεRIβ |
| CD83 | NKG2D | CD86 | FcεRIγ |
| CD83 | NKG2D | CD86 | DAP10 |
| CD83 | NKG2D | CD86 | DAP12 |
| CD83 | NKG2D | CD86 | CD32 |
| CD83 | NKG2D | CD86 | CD79a |
| CD83 | NKG2D | CD86 | CD79b |
| CD83 | NKG2D | OX40 | CD8 |
| CD83 | NKG2D | OX40 | CD3ζ |
| CD83 | NKG2D | OX40 | CD3δ |

TABLE 3-continued

| Third Generation CARs | | | |
|---|---|---|---|
| ScFv | Co-stimulatory Signal | Co-stimulatory Signal | Signal Domain |
| CD83 | NKG2D | OX40 | CD3γ |
| CD83 | NKG2D | OX40 | CD3ε |
| CD83 | NKG2D | OX40 | FcγRI-γ |
| CD83 | NKG2D | OX40 | FcγRIII-γ |
| CD83 | NKG2D | OX40 | FcεRIβ |
| CD83 | NKG2D | OX40 | FcεRIγ |
| CD83 | NKG2D | OX40 | DAP10 |
| CD83 | NKG2D | OX40 | DAP12 |
| CD83 | NKG2D | OX40 | CD32 |
| CD83 | NKG2D | OX40 | CD79a |
| CD83 | NKG2D | OX40 | CD79b |
| CD83 | NKG2D | DAP10 | CD8 |
| CD83 | NKG2D | DAP10 | CD3ζ |
| CD83 | NKG2D | DAP10 | CD3δ |
| CD83 | NKG2D | DAP10 | CD3γ |
| CD83 | NKG2D | DAP10 | CD3ε |
| CD83 | NKG2D | DAP10 | FcγRI-γ |
| CD83 | NKG2D | DAP10 | FcγRIII-γ |
| CD83 | NKG2D | DAP10 | FcεRIβ |
| CD83 | NKG2D | DAP10 | FcεRIγ |
| CD83 | NKG2D | DAP10 | DAP10 |
| CD83 | NKG2D | DAP10 | DAP12 |
| CD83 | NKG2D | DAP10 | CD32 |
| CD83 | NKG2D | DAP10 | CD79a |
| CD83 | NKG2D | DAP10 | CD79b |
| CD83 | NKG2D | DAP12 | CD8 |
| CD83 | NKG2D | DAP12 | CD3ζ |
| CD83 | NKG2D | DAP12 | CD3δ |
| CD83 | NKG2D | DAP12 | CD3γ |
| CD83 | NKG2D | DAP12 | CD3ε |
| CD83 | NKG2D | DAP12 | FcγRI-γ |
| CD83 | NKG2D | DAP12 | FcγRIII-γ |
| CD83 | NKG2D | DAP12 | FcεRIβ |
| CD83 | NKG2D | DAP12 | FcεRIγ |
| CD83 | NKG2D | DAP12 | DAP10 |
| CD83 | NKG2D | DAP12 | DAP12 |
| CD83 | NKG2D | DAP12 | CD32 |
| CD83 | NKG2D | DAP12 | CD79a |
| CD83 | NKG2D | DAP12 | CD79b |
| CD83 | NKG2D | MyD88 | CD8 |
| CD83 | NKG2D | MyD88 | CD3ζ |
| CD83 | NKG2D | MyD88 | CD3δ |
| CD83 | NKG2D | MyD88 | CD3γ |
| CD83 | NKG2D | MyD88 | CD3ε |
| CD83 | NKG2D | MyD88 | FcγRI-γ |
| CD83 | NKG2D | MyD88 | FcγRIII-γ |
| CD83 | NKG2D | MyD88 | FcεRIβ |
| CD83 | NKG2D | MyD88 | FcεRIγ |
| CD83 | NKG2D | MyD88 | DAP10 |
| CD83 | NKG2D | MyD88 | DAP12 |
| CD83 | NKG2D | MyD88 | CD32 |
| CD83 | NKG2D | MyD88 | CD79a |
| CD83 | NKG2D | MyD88 | CD79b |
| CD83 | NKG2D | CD7 | CD8 |
| CD83 | NKG2D | CD7 | CD3ζ |
| CD83 | NKG2D | CD7 | CD3δ |
| CD83 | NKG2D | CD7 | CD3γ |
| CD83 | NKG2D | CD7 | CD3ε |
| CD83 | NKG2D | CD7 | FcγRI-γ |
| CD83 | NKG2D | CD7 | FcγRIII-γ |
| CD83 | NKG2D | CD7 | FcεRIβ |
| CD83 | NKG2D | CD7 | FcεRIγ |
| CD83 | NKG2D | CD7 | DAP10 |
| CD83 | NKG2D | CD7 | DAP12 |
| CD83 | NKG2D | CD7 | CD32 |
| CD83 | NKG2D | CD7 | CD79a |
| CD83 | NKG2D | CD7 | CD79b |
| CD83 | NKG2D | BTNL3 | CD8 |
| CD83 | NKG2D | BTNL3 | CD3ζ |
| CD83 | NKG2D | BTNL3 | CD3δ |
| CD83 | NKG2D | BTNL3 | CD3γ |
| CD83 | NKG2D | BTNL3 | CD3ε |
| CD83 | NKG2D | BTNL3 | FcγRI-γ |
| CD83 | NKG2D | BTNL3 | FcγRIII-γ |
| CD83 | NKG2D | BTNL3 | FcεRIβ |

TABLE 3-continued

| Third Generation CARs | | | |
|---|---|---|---|
| ScFv | Co-stimulatory Signal | Co-stimulatory Signal | Signal Domain |
| CD83 | NKG2D | BTNL3 | FcεRIγ |
| CD83 | NKG2D | BTNL3 | DAP10 |
| CD83 | NKG2D | BTNL3 | DAP12 |
| CD83 | NKG2D | BTNL3 | CD32 |
| CD83 | NKG2D | BTNL3 | CD79a |
| CD83 | NKG2D | BTNL3 | CD79b |
| CD83 | NKG2D | NKG2D | CD8 |
| CD83 | NKG2D | NKG2D | CD3ζ |
| CD83 | NKG2D | NKG2D | CD3δ |
| CD83 | NKG2D | NKG2D | CD3γ |
| CD83 | NKG2D | NKG2D | CD3ε |
| CD83 | NKG2D | NKG2D | FcγRI-γ |
| CD83 | NKG2D | NKG2D | FcγRIII-γ |
| CD83 | NKG2D | NKG2D | FcεRIβ |
| CD83 | NKG2D | NKG2D | FcεRIγ |
| CD83 | NKG2D | NKG2D | DAP10 |
| CD83 | NKG2D | NKG2D | DAP12 |
| CD83 | NKG2D | NKG2D | CD32 |
| CD83 | NKG2D | NKG2D | CD79a |
| CD83 | NKG2D | NKG2D | CD79b |

TABLE 4

| CARs lacking Co-Simulatory Signal (for dual CAR approach) | | |
|---|---|---|
| ScFv | Co-stimulatory Signal | Signal Domain |
| CD83 or CD19 | none | CD8 |
| CD83 or CD19 | none | CD3ζ |
| CD83 or CD19 | none | CD3δ |
| CD83 or CD19 | none | CD3γ |
| CD83 or CD19 | none | CD3ε |
| CD83 or CD19 | none | FcγRI-γ |
| CD83 or CD19 | none | FcγRIII-γ |
| CD83 or CD19 | none | FcεRIβ |
| CD83 or CD19 | none | FcεRIγ |
| CD83 or CD19 | none | DAP10 |
| CD83 or CD19 | none | DAP12 |
| CD83 or CD19 | none | CD32 |
| CD83 or CD19 | none | CD79a |
| CD83 or CD19 | none | CD8 |
| CD83 or CD19 | none | CD3ζ |
| CD83 or CD19 | none | CD3δ |
| CD83 or CD19 | none | CD3γ |
| CD83 or CD19 | none | CD3ε |
| CD83 or CD19 | none | FcγRI-γ |

TABLE 5

| CARs lacking Signal Domain (for dual CAR approach) | | |
|---|---|---|
| ScFv | Co-stimulatory Signal | Signal Domain |
| CD83 or CD19 | CD28 | none |
| CD83 or CD19 | CD8 | none |
| CD83 or CD19 | CD4 | none |
| CD83 or CD19 | b2c | none |
| CD83 or CD19 | CD137/41BB | none |
| CD83 or CD19 | ICOS | none |
| CD83 or CD19 | CD27 | none |
| CD83 or CD19 | CD28δ | none |
| CD83 or CD19 | CD80 | none |
| CD83 or CD19 | CD86 | none |
| CD83 or CD19 | OX40 | none |
| CD83 or CD19 | DAP10 | none |
| CD83 or CD19 | MyD88 | none |
| CD83 or CD19 | CD7 | none |
| CD83 or CD19 | DAP12 | none |
| CD83 or CD19 | MyD88 | none |
| CD83 or CD19 | CD7 | none |

TABLE 5-continued

| CARs lacking Signal Domain (for dual CAR approach) | | |
|---|---|---|
| ScFv | Co-stimulatory Signal | Signal Domain |
| CD83 or CD19 | BTNL3 | none |
| CD83 or CD19 | NKG2D | none |

TABLE 6

| Third Generation CARs lacking Signal Domain (for dual CAR approach) | | | |
|---|---|---|---|
| ScFv | Co-stimulatory Signal | Co-stimulatory Signal | Signal Domain |
| CD83 or CD19 | CD28 | CD28 | none |
| CD83 or CD19 | CD28 | CD8 | none |
| CD83 or CD19 | CD28 | CD4 | none |
| CD83 or CD19 | CD28 | b2c | none |
| CD83 or CD19 | CD28 | CD137/41BB | none |
| CD83 or CD19 | CD28 | ICOS | none |
| CD83 or CD19 | CD28 | CD27 | none |
| CD83 or CD19 | CD28 | CD28δ | none |
| CD83 or CD19 | CD28 | CD80 | none |
| CD83 or CD19 | CD28 | CD86 | none |
| CD83 or CD19 | CD28 | OX40 | none |
| CD83 or CD19 | CD28 | DAP10 | none |
| CD83 or CD19 | CD28 | MyD88 | none |
| CD83 or CD19 | CD28 | CD7 | none |
| CD83 or CD19 | CD28 | DAP12 | none |
| CD83 or CD19 | CD28 | MyD88 | none |
| CD83 or CD19 | CD28 | CD7 | none |
| CD83 or CD19 | CD8 | CD28 | none |
| CD83 or CD19 | CD8 | CD8 | none |
| CD83 or CD19 | CD8 | CD4 | none |
| CD83 or CD19 | CD8 | b2c | none |
| CD83 or CD19 | CD8 | CD137/41BB | none |
| CD83 or CD19 | CD8 | ICOS | none |
| CD83 or CD19 | CD8 | CD27 | none |
| CD83 or CD19 | CD8 | CD28δ | none |
| CD83 or CD19 | CD8 | CD80 | none |
| CD83 or CD19 | CD8 | CD86 | none |
| CD83 or CD19 | CD8 | OX40 | none |
| CD83 or CD19 | CD8 | DAP10 | none |
| CD83 or CD19 | CD8 | MyD88 | none |
| CD83 or CD19 | CD8 | CD7 | none |
| CD83 or CD19 | CD8 | DAP12 | none |
| CD83 or CD19 | CD8 | MyD88 | none |
| CD83 or CD19 | CD8 | CD7 | none |
| CD83 or CD19 | CD4 | CD28 | none |
| CD83 or CD19 | CD4 | CD8 | none |
| CD83 or CD19 | CD4 | CD4 | none |
| CD83 or CD19 | CD4 | b2c | none |
| CD83 or CD19 | CD4 | CD137/41BB | none |
| CD83 or CD19 | CD4 | ICOS | none |
| CD83 or CD19 | CD4 | CD27 | none |
| CD83 or CD19 | CD4 | CD28δ | none |
| CD83 or CD19 | CD4 | CD80 | none |
| CD83 or CD19 | CD4 | CD86 | none |
| CD83 or CD19 | CD4 | OX40 | none |
| CD83 or CD19 | CD4 | DAP10 | none |
| CD83 or CD19 | CD4 | MyD88 | none |
| CD83 or CD19 | CD4 | CD7 | none |
| CD83 or CD19 | CD4 | DAP12 | none |
| CD83 or CD19 | CD4 | MyD88 | none |
| CD83 or CD19 | CD4 | CD7 | none |
| CD83 or CD19 | b2c | CD28 | none |
| CD83 or CD19 | b2c | CD8 | none |
| CD83 or CD19 | b2c | CD4 | none |
| CD83 or CD19 | b2c | b2c | none |
| CD83 or CD19 | b2c | CD137/41BB | none |
| CD83 or CD19 | b2c | ICOS | none |
| CD83 or CD19 | b2c | CD27 | none |
| CD83 or CD19 | b2c | CD28δ | none |
| CD83 or CD19 | b2c | CD80 | none |
| CD83 or CD19 | b2c | CD86 | none |
| CD83 or CD19 | b2c | OX40 | none |

TABLE 6-continued

| Third Generation CARs lacking Signal Domain (for dual CAR approach) | | | |
|---|---|---|---|
| ScFv | Co-stimulatory Signal | Co-stimulatory Signal | Signal Domain |
| CD83 or CD19 | b2c | DAP10 | none |
| CD83 or CD19 | b2c | MyD88 | none |
| CD83 or CD19 | b2c | CD7 | none |
| CD83 or CD19 | b2c | DAP12 | none |
| CD83 or CD19 | b2c | MyD88 | none |
| CD83 or CD19 | b2c | CD7 | none |
| CD83 or CD19 | CD137/41BB | CD28 | none |
| CD83 or CD19 | CD137/41BB | CD8 | none |
| CD83 or CD19 | CD137/41BB | CD4 | none |
| CD83 or CD19 | CD137/41BB | b2c | none |
| CD83 or CD19 | CD137/41BB | CD137/41BB | none |
| CD83 or CD19 | CD137/41BB | ICOS | none |
| CD83 or CD19 | CD137/41BB | CD27 | none |
| CD83 or CD19 | CD137/41BB | CD28δ | none |
| CD83 or CD19 | CD137/41BB | CD80 | none |
| CD83 or CD19 | CD137/41BB | CD86 | none |
| CD83 or CD19 | CD137/41BB | OX40 | none |
| CD83 or CD19 | CD137/41BB | DAP10 | none |
| CD83 or CD19 | CD137/41BB | MyD88 | none |
| CD83 or CD19 | CD137/41BB | CD7 | none |
| CD83 or CD19 | CD137/41BB | DAP12 | none |
| CD83 or CD19 | CD137/41BB | MyD88 | none |
| CD83 or CD19 | CD137/41BB | CD7 | none |
| CD83 or CD19 | ICOS | CD28 | none |
| CD83 or CD19 | ICOS | CD8 | none |
| CD83 or CD19 | ICOS | CD4 | none |
| CD83 or CD19 | ICOS | b2c | none |
| CD83 or CD19 | ICOS | CD137/41BB | none |
| CD83 or CD19 | ICOS | ICOS | none |
| CD83 or CD19 | ICOS | CD27 | none |
| CD83 or CD19 | ICOS | CD28δ | none |
| CD83 or CD19 | ICOS | CD80 | none |
| CD83 or CD19 | ICOS | CD86 | none |
| CD83 or CD19 | ICOS | OX40 | none |
| CD83 or CD19 | ICOS | DAP10 | none |
| CD83 or CD19 | ICOS | MyD88 | none |
| CD83 or CD19 | ICOS | CD7 | none |
| CD83 or CD19 | ICOS | DAP12 | none |
| CD83 or CD19 | ICOS | MyD88 | none |
| CD83 or CD19 | ICOS | CD7 | none |
| CD83 or CD19 | ICOS | CD28 | none |
| CD83 or CD19 | ICOS | CD8 | none |
| CD83 or CD19 | ICOS | CD4 | none |
| CD83 or CD19 | ICOS | b2c | none |
| CD83 or CD19 | ICOS | CD137/41BB | none |
| CD83 or CD19 | ICOS | ICOS | none |
| CD83 or CD19 | ICOS | CD27 | none |
| CD83 or CD19 | ICOS | CD28δ | none |
| CD83 or CD19 | ICOS | CD80 | none |
| CD83 or CD19 | ICOS | CD86 | none |
| CD83 or CD19 | ICOS | OX40 | none |
| CD83 or CD19 | ICOS | DAP10 | none |
| CD83 or CD19 | ICOS | MyD88 | none |
| CD83 or CD19 | ICOS | CD7 | none |
| CD83 or CD19 | ICOS | DAP12 | none |
| CD83 or CD19 | ICOS | MyD88 | none |
| CD83 or CD19 | ICOS | CD7 | none |
| CD83 or CD19 | CD27 | CD28 | none |
| CD83 or CD19 | CD27 | CD8 | none |
| CD83 or CD19 | CD27 | CD4 | none |
| CD83 or CD19 | CD27 | b2c | none |
| CD83 or CD19 | CD27 | CD137/41BB | none |
| CD83 or CD19 | CD27 | ICOS | none |
| CD83 or CD19 | CD27 | CD27 | none |
| CD83 or CD19 | CD27 | CD28δ | none |
| CD83 or CD19 | CD27 | CD80 | none |
| CD83 or CD19 | CD27 | CD86 | none |
| CD83 or CD19 | CD27 | OX40 | none |
| CD83 or CD19 | CD27 | DAP10 | none |
| CD83 or CD19 | CD27 | MyD88 | none |
| CD83 or CD19 | CD27 | CD7 | none |
| CD83 or CD19 | CD27 | DAP12 | none |
| CD83 or CD19 | CD27 | MyD88 | none |
| CD83 or CD19 | CD27 | CD7 | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| CD83 or CD19 | CD28δ | CD28 | none |
| CD83 or CD19 | CD28δ | CD8 | none |
| CD83 or CD19 | CD28δ | CD4 | none |
| CD83 or CD19 | CD28δ | b2c | none |
| CD83 or CD19 | CD28δ | CD137/41BB | none |
| CD83 or CD19 | CD28δ | ICOS | none |
| CD83 or CD19 | CD28δ | CD27 | none |
| CD83 or CD19 | CD28δ | CD28δ | none |
| CD83 or CD19 | CD28δ | CD80 | none |
| CD83 or CD19 | CD28δ | CD86 | none |
| CD83 or CD19 | CD28δ | OX40 | none |
| CD83 or CD19 | CD28δ | DAP10 | none |
| CD83 or CD19 | CD28δ | MyD88 | none |
| CD83 or CD19 | CD28δ | CD7 | none |
| CD83 or CD19 | CD28δ | DAP12 | none |
| CD83 or CD19 | CD28δ | MyD88 | none |
| CD83 or CD19 | CD28δ | CD7 | none |
| CD83 or CD19 | CD80 | CD28 | none |
| CD83 or CD19 | CD80 | CD8 | none |
| CD83 or CD19 | CD80 | CD4 | none |
| CD83 or CD19 | CD80 | b2c | none |
| CD83 or CD19 | CD80 | CD137/41BB | none |
| CD83 or CD19 | CD80 | ICOS | none |
| CD83 or CD19 | CD80 | CD27 | none |
| CD83 or CD19 | CD80 | CD28δ | none |
| CD83 or CD19 | CD80 | CD80 | none |
| CD83 or CD19 | CD80 | CD86 | none |
| CD83 or CD19 | CD80 | OX40 | none |
| CD83 or CD19 | CD80 | DAP10 | none |
| CD83 or CD19 | CD80 | MyD88 | none |
| CD83 or CD19 | CD80 | CD7 | none |
| CD83 or CD19 | CD80 | DAP12 | none |
| CD83 or CD19 | CD80 | MyD88 | none |
| CD83 or CD19 | CD80 | CD7 | none |
| CD83 or CD19 | CD86 | CD28 | none |
| CD83 or CD19 | CD86 | CD8 | none |
| CD83 or CD19 | CD86 | CD4 | none |
| CD83 or CD19 | CD86 | b2c | none |
| CD83 or CD19 | CD86 | CD137/41BB | none |
| CD83 or CD19 | CD86 | ICOS | none |
| CD83 or CD19 | CD86 | CD27 | none |
| CD83 or CD19 | CD86 | CD28δ | none |
| CD83 or CD19 | CD86 | CD80 | none |
| CD83 or CD19 | CD86 | CD86 | none |
| CD83 or CD19 | CD86 | OX40 | none |
| CD83 or CD19 | CD86 | DAP10 | none |
| CD83 or CD19 | CD86 | MyD88 | none |
| CD83 or CD19 | CD86 | CD7 | none |
| CD83 or CD19 | CD86 | DAP12 | none |
| CD83 or CD19 | CD86 | MyD88 | none |
| CD83 or CD19 | CD86 | CD7 | none |
| CD83 or CD19 | OX40 | CD28 | none |
| CD83 or CD19 | OX40 | CD8 | none |
| CD83 or CD19 | OX40 | CD4 | none |
| CD83 or CD19 | OX40 | b2c | none |
| CD83 or CD19 | OX40 | CD137/41BB | none |
| CD83 or CD19 | OX40 | ICOS | none |
| CD83 or CD19 | OX40 | CD27 | none |
| CD83 or CD19 | OX40 | CD28δ | none |
| CD83 or CD19 | OX40 | CD80 | none |
| CD83 or CD19 | OX40 | CD86 | none |
| CD83 or CD19 | OX40 | OX40 | none |
| CD83 or CD19 | OX40 | DAP10 | none |
| CD83 or CD19 | OX40 | MyD88 | none |
| CD83 or CD19 | OX40 | CD7 | none |
| CD83 or CD19 | OX40 | DAP12 | none |
| CD83 or CD19 | OX40 | MyD88 | none |
| CD83 or CD19 | OX40 | CD7 | none |
| CD83 or CD19 | DAP10 | CD28 | none |
| CD83 or CD19 | DAP10 | CD8 | none |
| CD83 or CD19 | DAP10 | CD4 | none |
| CD83 or CD19 | DAP10 | b2c | none |
| CD83 or CD19 | DAP10 | CD137/41BB | none |
| CD83 or CD19 | DAP10 | ICOS | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| CD83 or CD19 | DAP10 | CD27 | none |
| CD83 or CD19 | DAP10 | CD28δ | none |
| CD83 or CD19 | DAP10 | CD80 | none |
| CD83 or CD19 | DAP10 | CD86 | none |
| CD83 or CD19 | DAP10 | OX40 | none |
| CD83 or CD19 | DAP10 | DAP10 | none |
| CD83 or CD19 | DAP10 | MyD88 | none |
| CD83 or CD19 | DAP10 | CD7 | none |
| CD83 or CD19 | DAP10 | DAP12 | none |
| CD83 or CD19 | DAP10 | MyD88 | none |
| CD83 or CD19 | DAP10 | CD7 | none |
| CD83 or CD19 | DAP12 | CD28 | none |
| CD83 or CD19 | DAP12 | CD8 | none |
| CD83 or CD19 | DAP12 | CD4 | none |
| CD83 or CD19 | DAP12 | b2c | none |
| CD83 or CD19 | DAP12 | CD137/41BB | none |
| CD83 or CD19 | DAP12 | ICOS | none |
| CD83 or CD19 | DAP12 | CD27 | none |
| CD83 or CD19 | DAP12 | CD28δ | none |
| CD83 or CD19 | DAP12 | CD80 | none |
| CD83 or CD19 | DAP12 | CD86 | none |
| CD83 or CD19 | DAP12 | OX40 | none |
| CD83 or CD19 | DAP12 | DAP10 | none |
| CD83 or CD19 | DAP12 | MyD88 | none |
| CD83 or CD19 | DAP12 | CD7 | none |
| CD83 or CD19 | DAP12 | DAP12 | none |
| CD83 or CD19 | DAP12 | MyD88 | none |
| CD83 or CD19 | DAP12 | CD7 | none |
| CD83 or CD19 | MyD88 | CD28 | none |
| CD83 or CD19 | MyD88 | CD8 | none |
| CD83 or CD19 | MyD88 | CD4 | none |
| CD83 or CD19 | MyD88 | b2c | none |
| CD83 or CD19 | MyD88 | CD137/41BB | none |
| CD83 or CD19 | MyD88 | ICOS | none |
| CD83 or CD19 | MyD88 | CD27 | none |
| CD83 or CD19 | MyD88 | CD28δ | none |
| CD83 or CD19 | MyD88 | CD80 | none |
| CD83 or CD19 | MyD88 | CD86 | none |
| CD83 or CD19 | MyD88 | OX40 | none |
| CD83 or CD19 | MyD88 | DAP10 | none |
| CD83 or CD19 | MyD88 | MyD88 | none |
| CD83 or CD19 | MyD88 | CD7 | none |
| CD83 or CD19 | MyD88 | DAP12 | none |
| CD83 or CD19 | MyD88 | MyD88 | none |
| CD83 or CD19 | MyD88 | CD7 | none |
| CD83 or CD19 | CD7 | CD28 | none |
| CD83 or CD19 | CD7 | CD8 | none |
| CD83 or CD19 | CD7 | CD4 | none |
| CD83 or CD19 | CD7 | b2c | none |
| CD83 or CD19 | CD7 | CD137/41BB | none |
| CD83 or CD19 | CD7 | ICOS | none |
| CD83 or CD19 | CD7 | CD27 | none |
| CD83 or CD19 | CD7 | CD28δ | none |
| CD83 or CD19 | CD7 | CD80 | none |
| CD83 or CD19 | CD7 | CD86 | none |
| CD83 or CD19 | CD7 | OX40 | none |
| CD83 or CD19 | CD7 | DAP10 | none |
| CD83 or CD19 | CD7 | MyD88 | none |
| CD83 or CD19 | CD7 | CD7 | none |
| CD83 or CD19 | CD7 | DAP12 | none |
| CD83 or CD19 | CD7 | MyD88 | none |
| CD83 or CD19 | CD7 | CD7 | none |
| CD83 or CD19 | BTNL3 | CD28 | none |
| CD83 or CD19 | BTNL3 | CD8 | none |
| CD83 or CD19 | BTNL3 | CD4 | none |
| CD83 or CD19 | BTNL3 | b2c | none |
| CD83 or CD19 | BTNL3 | CD137/41BB | none |
| CD83 or CD19 | BTNL3 | ICOS | none |
| CD83 or CD19 | BTNL3 | CD27 | none |
| CD83 or CD19 | BTNL3 | CD28δ | none |
| CD83 or CD19 | BTNL3 | CD80 | none |
| CD83 or CD19 | BTNL3 | CD86 | none |
| CD83 or CD19 | BTNL3 | OX40 | none |
| CD83 or CD19 | BTNL3 | DAP10 | none |

TABLE 6-continued

| Third Generation CARs lacking Signal Domain (for dual CAR approach) | | | |
|---|---|---|---|
| ScFv | Co-stimulatory Signal | Co-stimulatory Signal | Signal Domain |
| CD83 or CD19 | BTNL3 | MyD88 | none |
| CD83 or CD19 | BTNL3 | CD7 | none |
| CD83 or CD19 | BTNL3 | DAP12 | none |
| CD83 or CD19 | BTNL3 | MyD88 | none |
| CD83 or CD19 | BTNL3 | CD7 | none |
| CD83 or CD19 | NKG2D | CD28 | none |
| CD83 or CD19 | NKG2D | CD8 | none |
| CD83 or CD19 | NKG2D | CD4 | none |
| CD83 or CD19 | NKG2D | b2c | none |
| CD83 or CD19 | NKG2D | CD137/41BB | none |
| CD83 or CD19 | NKG2D | ICOS | none |
| CD83 or CD19 | NKG2D | CD27 | none |
| CD83 or CD19 | NKG2D | CD28δ | none |
| CD83 or CD19 | NKG2D | CD80 | none |
| CD83 or CD19 | NKG2D | CD86 | none |
| CD83 or CD19 | NKG2D | OX40 | none |
| CD83 or CD19 | NKG2D | DAP10 | none |
| CD83 or CD19 | NKG2D | MyD88 | none |
| CD83 or CD19 | NKG2D | CD7 | none |
| CD83 or CD19 | NKG2D | DAP12 | none |
| CD83 or CD19 | NKG2D | MyD88 | none |
| CD83 or CD19 | NKG2D | CD7 | none |

In some embodiments, the anti-CD83 and/or anti-CD19 binding agent is single chain variable fragment (scFv) antibody. The affinity/specificity of an scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the anti-CD83 binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs (AND-gated or OR-gated) that target CD83 and at least one additional antigen, such as CD5 (e.g. T cell leukemia and lymphoma), CD7 (e.g. T cell leukemia and lymphoma), CD19 (e.g. B cell malignancies), CD30 (e.g. T cell leukemia and lymphoma; Hodgkin lymphoma), CD38 (e.g. hematological malignancies), CD79b (e.g. B cell malignancies), or BCMA (e.g. multiple myeloma).

In some embodiments, the anti-BCMA scFv can comprise a variable heavy ($V_H$) domain having CDR1, CDR2 and CDR3 sequences and a variable light ($V_L$) domain having CDR1, CDR2 and CDR3 sequences. For example, anti-BCMA scFvs are described in US20200360431A1, which is incorporated by reference in its entirety for the description of these scFvs and their sequences.

In some embodiments, the anti-CD5 scFv can comprise a variable heavy ($V_H$) domain having CDR1, CDR2 and CDR3 sequences and a variable light ($V_L$) domain having CDR1, CDR2 and CDR3 sequences. For example, anti-CD5 scFvs are described in US20180104308A1, which is incorporated by reference in its entirety for the description of these scFvs and their sequences.

In some embodiments, the anti-CD7 scFv can comprise a variable heavy ($V_H$) domain having CDR1, CDR2 and CDR3 sequences and a variable light ($V_L$) domain having CDR1, CDR2 and CDR3 sequences. For example, anti-CD7 scFvs are described in US20180179280A1, which is incorporated by reference in its entirety for the description of these scFvs and their sequences.

In some embodiments, the anti-CD30 scFv can comprise a variable heavy ($V_H$) domain having CDR1, CDR2 and CDR3 sequences and a variable light ($V_L$) domain having CDR1, CDR2 and CDR3 sequences. For example, anti-CD30 scFvs are described in WO2020135426A1, which is incorporated by reference in its entirety for the description of these scFvs and their sequences.

In some embodiments, the anti-CD79b scFv can comprise a variable heavy ($V_H$) domain having CDR1, CDR2 and CDR3 sequences and a variable light ($V_L$) domain having CDR1, CDR2 and CDR3 sequences. For example anti-CD79b are described in WO2019220110A1, which is incorporated by reference in its entirety for the description of these scFvs and their sequences.

Also disclosed are CARs designed to work only in conjunction with another CAR that binds a different antigen. For example, in these embodiments, the endodomain of the disclosed CAR can contain only a signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

Nucleic Acids and Vectors

Also disclosed are polynucleotides and polynucleotide vectors encoding the disclosed CARs. Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells (Tc cells, or CTLs) destroy virally infected cells and tumor cells, and are also implicated in transplant rejection. These cells are also known as $CD8^+$ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either $CD4^+$ or $CD8^+$. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of $CD4^+$ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic $CD8^+$ T lymphocytes. In some embodiments, the T cells comprise γδ T cells, which possess a distinct T-cell receptor (TCR) having one γ chain and one δ chain instead of a and p chains.

Natural-killer (NK) cells are $CD56^+CD3^-$ large granular lymphocytes that can kill virally infected and transformed cells, and constitute a critical cellular subset of the innate immune system (Godfrey J, et al. Leuk Lymphoma 2012 53:1666-1676). Unlike cytotoxic $CD8^+$ T lymphocytes, NK cells launch cytotoxicity against tumor cells without the requirement for prior sensitization, and can also eradicate MHC-1-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects.

Therapeutic Methods

The disclosed CAR-modified immune effector cells may be administered either alone, or as a pharmaceutical composition in combination with diluents and/or with other components such as IL-2, IL-15, or other cytokines or cell populations.

In some embodiments, the disclosed CAR-modified immune effector cells are administered in combination with ER stress blockade (compounds to target the IRE-1/XBP-1 pathway (e.g., B-I09). In some embodiments, the disclosed CAR-modified immune effector cells are administered in combination with a JAK2 inhibitor, a STAT3 inhibitor, an Aurora kinase inhibitor, an mTOR inhibitor, or any combination thereof.

Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When a "therapeutic amount" is indicated, the precise amount of the compositions of the present invention to be administered can be determined by a physician with consideration of individual differences in age, weight, extent of transplantation, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a site of transplantation.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC TAG, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a first antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tissue, and is advantageous in situations where certain normal tissues may express very low levels of a antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

Typically, CAR-T cells are created using α-β T cells, however γ-δ T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

SPECIFIC EMBODIMENTS

Embodiment 1. A method of providing an anti-cancer immunity in a subject with a CD83-expressing B and/or T cell acute lymphoblastic leukemia (ALL), the method comprising administering to the subject an effective amount of an immune effector cell genetically modified to express a first chimeric antigen receptor (CAR) polypeptide that selectively binds CD83, thereby providing an anti-tumor immunity in the mammal.

Embodiment 2. The method of embodiment 1, wherein the immune effector cells is further genetically modified to express a second CAR polypeptide that selectively binds a second antigen on the CD83-expressing cancer.

Embodiment 3. The method of embodiment 1, wherein the second antigen is CD19.

Embodiment 4. The method of embodiment 1, wherein the first CAR polypeptide is defined by the formula:

SP-CD83-HG-TM-SD, and wherein the second CAR polypeptide is defined by the formula:

SP-CD19-HG-TM-CSR; or wherein the first CAR polypeptide is defined by the formula:

SP-CD83-HG-TM-CSR, and wherein the second CAR polypeptide is defined by the formula:

SP-CD19-HG-TM-SD;

wherein "SP" represents an optional signal peptide,
wherein "CD83" represents a CD83 antigen binding region,
wherein "CD19" represents a CD19 antigen binding region,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

Embodiment 5. The method of any one of embodiments 1 to 4, wherein the first CAR polypeptide comprises a CD83 antigen binding domain, a transmembrane domain, an intracellular signaling domain, and a co-stimulatory signaling region, wherein the CD83 antigen binding domain is a single-chain variable fragment (scFv) of an antibody comprising a variable heavy ($V_H$) domain having CDR1, CDR2 and CDR3 sequences and a variable light ($V_L$) domain having CDR1, CDR2 and CDR3 sequences, and wherein the CDR1 sequence of the $V_H$ domain comprises the amino acid sequence GFSITTGGYWWT (SEQ ID NO:1), the CDR2 sequence of the $V_H$ domain comprises the amino acid sequence GYIFSSGNTNYNPSIKS (SEQ ID NO:2), the CDR3 sequence of the $V_H$ domain comprises the amino acid sequence CARAYGKLGFDY (SEQ ID NO:3), the CDR1 sequence of the $V_L$ comprises the amino acid sequence TLSSQHSTYTIG (SEQ ID NO:4), the CDR2 sequence of the $V_L$ domain comprises the amino acid sequence VNSDGSHSKGD (SEQ ID NO:5), and the CDR3 sequence of the $V_L$ domain comprises the amino acid sequence GSSDSSGYV (SEQ ID NO:6);

the CDR1 sequence of the $V_H$ domain comprises the amino acid sequence SDGIS (SEQ ID NO:7), CDR2 sequence of the $V_H$ domain comprises the amino acid sequence IISSGGNTYYASWAKG (SEQ ID NO:8), CDR3 sequence of the $V_H$ domain comprises the amino acid sequence VVGGTYSI (SEQ ID NO:9), CDR1 sequence of the $V_L$ comprises the amino acid sequence QSSQS VYNNDFLS (SEQ ID NO:10), CDR2 sequence of the $V_L$ domain comprises the amino acid sequence YASTLAS (SEQ ID NO:11), and CDR3 sequence of the $V_L$ domain comprises the amino acid sequence TGTYGNSAWYEDA (SEQ ID NO:12); or the CDR1 sequence of the $V_H$ domain comprises the amino acid sequence SNAMI (SEQ ID NO:13), CDR2 sequence of the $V_H$ domain comprises the amino acid sequence AMDSNSRTYYATWAKG (SEQ ID NO:14), CDR3 sequence of the $V_H$ domain comprises the amino acid sequence GDGGSSDYTEM (SEQ ID NO:15), CDR1 sequence of the $V_L$ comprises the amino acid sequence QSSQSVYGNNELS (SEQ ID NO:16), CDR2 sequence of the $V_L$ domain comprises the amino acid sequence QASSLAS (SEQ ID NO:17), and CDR3 sequence of the $V_L$ domain comprises the amino acid sequence LGEYSISADNH (SEQ ID NO:18).

Embodiment 6. The method of embodiment 5, wherein the anti-CD83 scFv $V_H$ domain comprises the amino acid sequence SEQ ID NO:33, SEQ ID NO:34, SEQ ID NO:35, SEQ ID NO:36, SEQ ID NO:37, or SEQ ID NO:38.

Embodiment 7. The method of embodiments 5 or 6, wherein the anti-CD83 scFv $V_L$ domain comprises the amino acid sequence SEQ ID NO:39, SEQ ID NO:40, SEQ ID NO:41, SEQ ID NO:42, or SEQ ID NO:43.

Embodiment 8. The method of any one of embodiments 4 or 7, wherein the second CAR polypeptide comprises a CD19 antigen binding domain, a transmembrane domain, an intracellular signaling domain, and a co-stimulatory signaling region, wherein the CD19 antigen binding domain is a scFv of an antibody comprising a $V_H$ domain having CDR1, CDR2 and CDR3 sequences and a $V_L$ domain having CDR1, CDR2 and CDR3 sequences, and wherein the CDR1 sequence of the VH domain comprises the amino acid sequence SYWMN (SEQ ID NO:72), CDR2 sequence of the VH domain comprises the amino acid sequence QIWPGDGDTNYNGKFKG (SEQ ID NO:73), CDR3 sequence of the VH domain comprises the amino acid sequence RETTTVGRYYYAMDY (SEQ ID NO:74), CDR1 sequence of the VL comprises the amino acid sequence KASQSVDYDGDSYLN (SEQ ID NO:75), CDR2 sequence of the VL domain comprises the amino acid sequence DASNLVS (SEQ ID NO:76), and CDR3 sequence of the VL domain comprises the amino acid sequence QQSTEDPWT (SEQ ID NO:77).

Embodiment 9. The method of any one of embodiments 1 or 8, wherein the immune effector cell is selected from the group consisting of a T cell, a Natural Killer (NK) cell, a cytotoxic T lymphocyte (CTL), and a regulatory T cell.

Embodiment 10. The method of any one of embodiments 1 or 9, further comprising administering to the subject a checkpoint inhibitor.

Embodiment 11. The method of embodiment 10, wherein the checkpoint inhibitor comprises an anti-PD-1 antibody, anti-PD-L1 antibody, anti-CTLA-4 antibody, or a combination thereof.

Embodiment 12. The method of any one of embodiments 1 or 11, wherein the cancer comprises a CD19+/CD83+ Diffuse Large B cell Lymphoma (DLBCL), a Follicular Lymphoma (FL), a Marginal Zone Lymphoma (MZL), a Chronic lymphocytic leukemia/Small lymphocytic lymphoma (CLL/SLL) a BCMA+/CD83+ or CD38+/CD83+ Multiple myeloma (MM), a CD7+/CD83+ or CD5+/CD83+ Peripheral T cell lymphoma (PTCL), a Cutaneous T cell lymphoma (CTCL), a Burkitt Lymphoma, a T cell lymphoma, or a CD30+/CD83+ non-Hodgkin lymphoma.

Embodiment 13. A chimeric antigen receptor (CAR) polypeptide, comprising a CD83 antigen binding domain, a CD19 antigen binding domain, a transmembrane domain, an intracellular signaling domain, and a co-stimulatory signaling region.

Embodiment 14. The CAR polypeptide of embodiment 13, wherein the CD83 antigen binding domain is a single-chain variable fragment (scFv) of an antibody comprising a variable heavy ($V_H$) domain having CDR1, CDR2 and CDR3 sequences and a variable light ($V_L$) domain having CDR1, CDR2 and CDR3 sequences, and the CDR1 sequence of the $V_H$ domain comprises the amino acid sequence GFSITTGGYWWT (SEQ ID NO:1), the CDR2 sequence of the $V_H$ domain comprises the amino acid sequence GYIFSSGNTNYNPSIKS (SEQ ID NO:2), the CDR3 sequence of the $V_H$ domain comprises the amino acid sequence CARAYGKLGFDY (SEQ ID NO:3), the CDR1 sequence of the $V_L$ comprises the amino acid sequence TLSSQHSTYTIG (SEQ ID NO:4), the CDR2 sequence of the $V_L$ domain comprises the amino acid sequence VNSDGSHSKGD (SEQ ID NO:5), and the CDR3 sequence of the $V_L$ domain comprises the amino acid sequence GSSDSSGYV (SEQ ID NO:6);

the CDR1 sequence of the $V_H$ domain comprises the amino acid sequence SDGIS (SEQ ID NO:7), CDR2 sequence of the $V_H$ domain comprises the amino acid sequence IISSGGNTYYASWAKG (SEQ ID NO:8), CDR3 sequence of the $V_H$ domain comprises the amino acid sequence VVGGTYSI (SEQ ID NO:9), CDR1 sequence of the $V_L$ comprises the amino acid sequence QSSQS VYNNDFLS (SEQ ID NO:10), CDR2 sequence of the $V_L$ domain comprises the amino acid sequence YASTLAS (SEQ ID NO:11), and CDR3 sequence of the $V_L$ domain comprises the amino acid sequence TGTYGNSAWYEDA (SEQ ID NO:12); or the CDR1 sequence of the $V_H$ domain comprises the amino acid sequence SNAMI (SEQ ID NO:13), CDR2 sequence of the $V_H$ domain comprises the amino acid sequence AMDSNSRTYYATWAKG (SEQ ID NO:14), CDR3 sequence of the $V_H$ domain comprises the amino acid sequence GDGGSSDYTEM (SEQ ID NO:15), CDR1 sequence of the $V_L$ comprises the amino acid sequence QSSQSVYGNNELS (SEQ ID NO:16), CDR2 sequence of the $V_L$ domain comprises the amino acid sequence QASSLAS (SEQ ID NO:17), and CDR3 sequence of the $V_L$ domain comprises the amino acid sequence LGEYSISADNH (SEQ ID NO:18).

Embodiment 15. The CAR polypeptide of embodiments 13 or 14, wherein the CD19 antigen binding domain is a scFv of an antibody comprising a $V_H$ domain having CDR1, CDR2 and CDR3 sequences and a $V_L$ domain having CDR1, CDR2 and CDR3 sequences, and wherein the CDR1 sequence of the VH domain comprises the amino acid sequence SYWMN (SEQ ID NO:72), CDR2 sequence of the VH domain comprises the amino acid sequence QIWPGDGDTNYNGKFKG (SEQ ID NO:73), CDR3 sequence of the VH domain comprises the amino acid sequence RETTTVGRYYYAMDY (SEQ ID NO:74), CDR1 sequence of the $V_L$ comprises the amino acid sequence KASQSVDYDGDSYLN (SEQ ID NO:75), CDR2 sequence of the $V_L$ domain comprises the amino acid sequence DASNLVS (SEQ ID NO:76), and CDR3 sequence of the $V_L$ domain comprises the amino acid sequence QQSTEDPWT (SEQ ID NO:77).

Embodiment 16. The CAR polypeptide of any one of embodiments 13 to 15, wherein the CAR polypeptide has a loop configuration defined by the formula:

SP-CD19$V_L$-CD83$V_H$-CD83$V_L$-CD19$V_H$-HG-TM-SD,

SP-CD19$V_L$-CD83$V_L$-CD83$V_H$-CD19$V_H$-HG-TM-SD,

SP-CD19$V_H$-CD83$V_H$-CD83$V_L$-CD19$V_L$-HG-TM-SD,

SP-CD19$V_H$-CD83$V_L$-CD83$V_H$-CD19$V_L$-HG-TM-SD,

SP-CD83$V_L$-CD19$V_H$-CD19$V_L$-CD839$V_H$-HG-TM-SD,

SP-CD83$V_L$-CD19$V_L$-CD19$V_H$-CD83$V_H$-HG-TM-SD,

SP-CD83$V_H$-CD19$V_H$-CD19$V_L$-CD83$V_L$-HG-TM-SD,

SP-CD83$V_H$-CD19$V_L$-CD19$V_H$-CD83$V_L$-HG-TM-SD, wherein "SP" represents an optional signal peptide,
wherein "CD83$V_H$" represents a CD83$V_H$ domain,
wherein "CD83$V_L$" represents a CD83$V_L$ domain,
wherein "CD19$V_H$" represents a CD83$V_H$ domain,
wherein "CD19$V_L$" represents a CD83$V_L$ domain,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

Embodiment 17. The CAR polypeptide of any one of embodiments 13 to 16, wherein the CAR polypeptide has a tandem configuration defined by the formula:

SP-CD19$V_H$-CD19$V_L$-CD83$V_L$-CD83$V_H$-HG-TM-SD,

SP-CD19$V_H$-CD19$V_L$-CD83$V_H$-CD83$V_L$-HG-TM-SD,

SP-CD19$V_L$-CD19$V_H$-CD83$V_L$-CD83$V_H$-HG-TM-SD,

SP-CD19$V_L$-CD19$V_H$-CD83$V_H$-CD83$V_L$-HG-TM-SD,

SP-CD83$V_H$-CD83$V_L$-CD19$V_L$-CD19$V_H$-HG-TM-SD,

SP-CD83$V_H$-CD83$V_L$-CD19$V_H$-CD19$V_L$-HG-TM-SD,

SP-CD83$V_L$-CD83$V_H$-CD19$V_L$-CD19$V_H$-HG-TM-SD,

SP-CD83$V_L$-CD83$V_H$-CD19$V_H$-CD19$V_L$-HG-TM-SD, wherein "SP" represents an optional signal peptide,
wherein "CD83$V_H$" represents a CD83$V_H$ domain,
wherein "CD83$V_L$" represents a CD83$V_L$ domain,
wherein "CD19$V_H$" represents a CD83$V_H$ domain,
wherein "CD19$V_L$" represents a CD83$V_L$ domain,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

Embodiment 18. A method of providing an anti-cancer immunity in a subject with a CD83-expressing B and/or T cell acute lymphoblastic leukemia (ALL), the method comprising administering to the subject an effective amount of an immune effector cell genetically modified to express the CAR polypeptide of any one of embodiments 13 to 17, thereby providing an anti-tumor immunity in the mammal.

Embodiment 19. The method of embodiment 18, wherein the immune effector cell is selected from the group consisting of a T cell, a Natural Killer (NK) cell, a cytotoxic T lymphocyte (CTL), and a regulatory T cell.

Embodiment 20. The method of embodiments 18 or 19, further comprising administering to the subject a checkpoint inhibitor.

Embodiment 21. The method of embodiment 20, wherein the checkpoint inhibitor comprises an anti-PD-1 antibody, anti-PD-L1 antibody, anti-CTLA-4 antibody, or a combination thereof.

Embodiment 22. The method of any one of embodiments 18 to 21, wherein the cancer comprises a CD19+/CD83+ Diffuse Large B cell Lymphoma (DLBCL), a Follicular Lymphoma (FL), a Marginal Zone Lymphoma (MZL), a Chronic lymphocytic leukemia/Small lymphocytic lymphoma (CLL/SLL) a BCMA+/CD83+ or CD38+/CD83+ Multiple myeloma (MM), a CD7+/CD83+ or CD5+/CD83+ Peripheral T cell lymphoma (PTCL), a Cutaneous T cell lymphoma (CTCL), a Burkitt Lymphoma, a T cell lymphoma, or a CD30+/CD83+ non-Hodgkin lymphoma.

A number of embodiments of the invention have been described. Nevertheless, it will be understood that various modifications may be made without departing from the spirit and scope of the invention. Accordingly, other embodiments are within the scope of the following claims.

EXAMPLES

Example 1

FIGS. 1A to 1D show CD83 is expressed on human B ALL and B lymphoblast cell lines, including Daudi and Raji. This is critical data, as it is evidence that once can target B ALL with a CD83 CAR T and avoid the B cell aplasia induced by CD19 CAR T.

Example 2

Figure 2A:
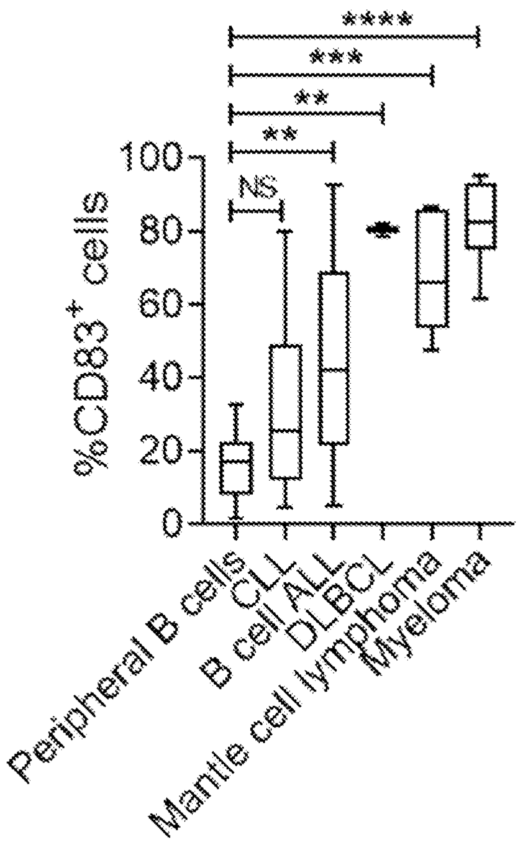
FIGS. 2A to 2C show CD83 expression among various blood cancers, co-expression of CD83 with BCMA among multiple myeloma plasma cells, and co-expression of CD5 with CD83 on T cell ALL.
Figure 2B:
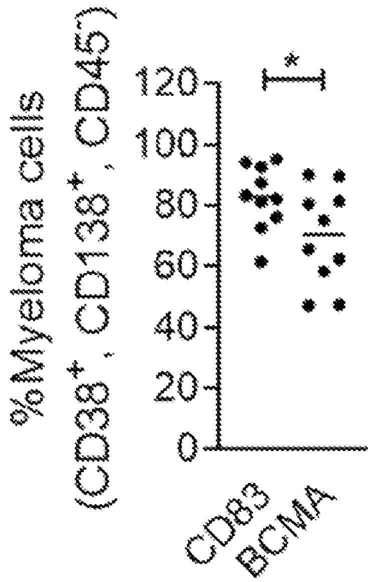
Figure 2C:
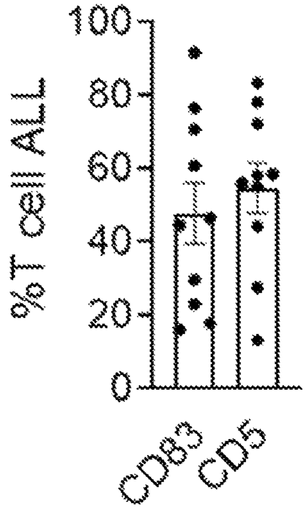

FIG. 2A shows CD83 expression on human peripheral B cells, CLL, B cell ALL, DLBCL, mantle cell lymphoma, and multiple myeloma. FIG. 2B depicts co-expression of CD83 and BCMA on multiple myeloma plasma cells. FIG. 2C shows co-expression of CD5 and CD83 on T cell ALL. These data support that CD83 can be used in coordination with other cancer target antigen to balance potency with safety to optimize overall efficacy in treating relevant malignancies.

Example 3

Figure 6:
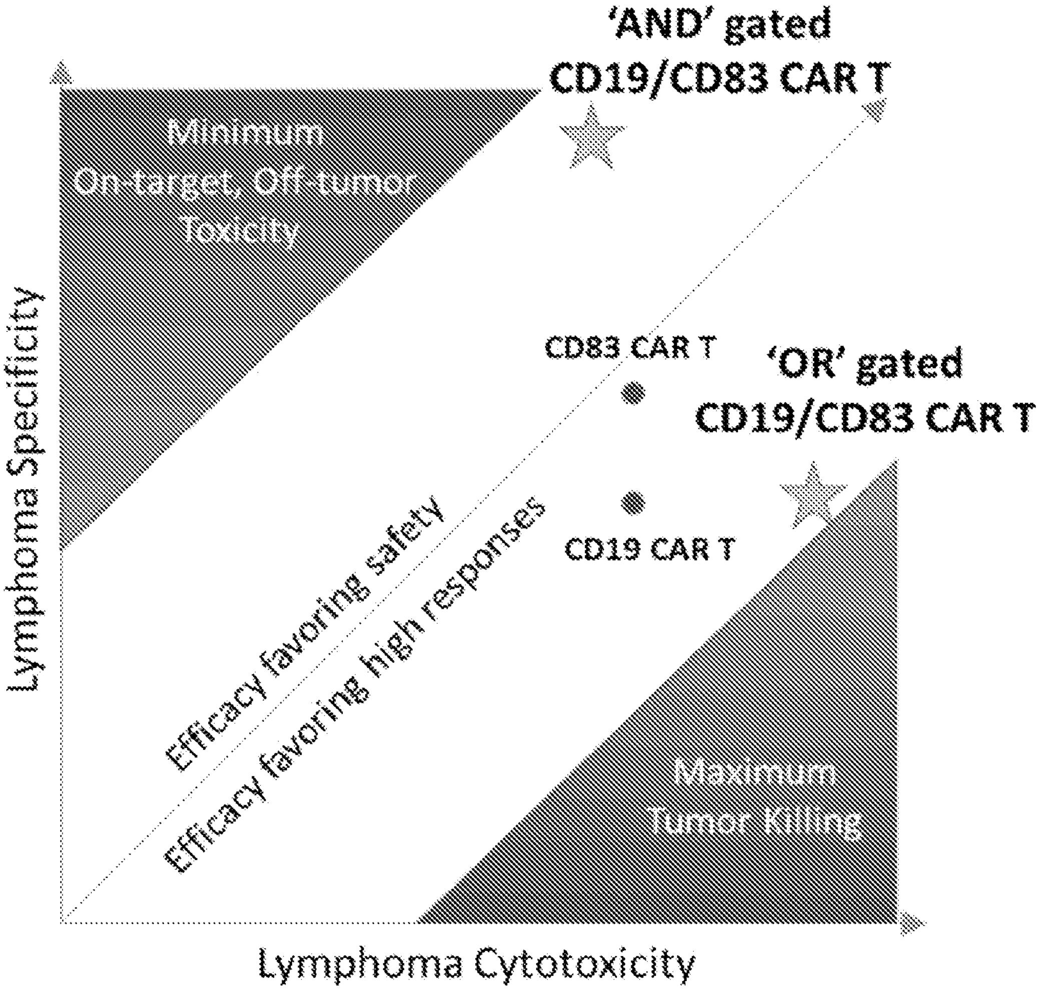
FIG. 6 shows that logic gating permits CAR T personalization. AND-gated CD19/CD83 CAR T could limit toxicity, while OR-gated CD19/CD83 CAR T could maximize opportunity for tumor killing, especially when CD19 antigen escape or loss has occurred after CD19 CAR T.

As disclosed herein, 'AND/OR' logic gated CD19/CD83 CAR T cells can achieve balance between lymphoma killing and cell product safety to maximize CAR T efficacy for patients with B cell malignancies. 'AND/OR' logic gating allows the study of preclinical strategies in vivo that stringently limit on-target, off-tumor toxicity (AND gating) versus increased opportunity for on-target lymphoma cytotoxicity (OR gating) (FIG. 6). This example investigates the performance and safety of 'OR' logic gated CD19/CD83 CAR T in relevant experimental conditions that mimic CD19 antigen escape, where the target cells either lack CD19 via genetic deletion (wild type versus CD19 knock out Raji cells) or come from patients that relapse post CD19 CAR T therapy (B cell ALL xenograft model). The objective is to establish optimal CAR T design to eradicate B cell malignancies, overcome CD19 antigen escape, and eliminate on-target/off-tumor toxicity.

Targeting CD83 in Hematologic Malignancies.

Figure 7B:
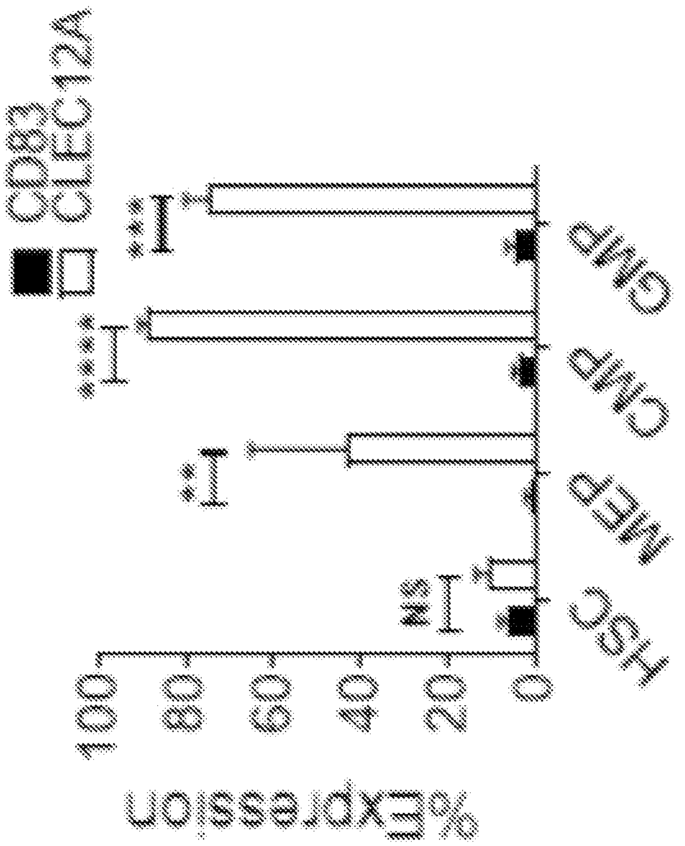
FIGS. 7A to 7D show CD83 CAR T kills AML but spares human hematopoiesis. CD83 expression (versus myeloid markers CD33, CD123, or CLEC12A) among AML blasts (FIG. 7A), marrow myeloid progenitors (FIG. 7B), and circulating myeloid cells (FIG. 7C).
Figure 7A:
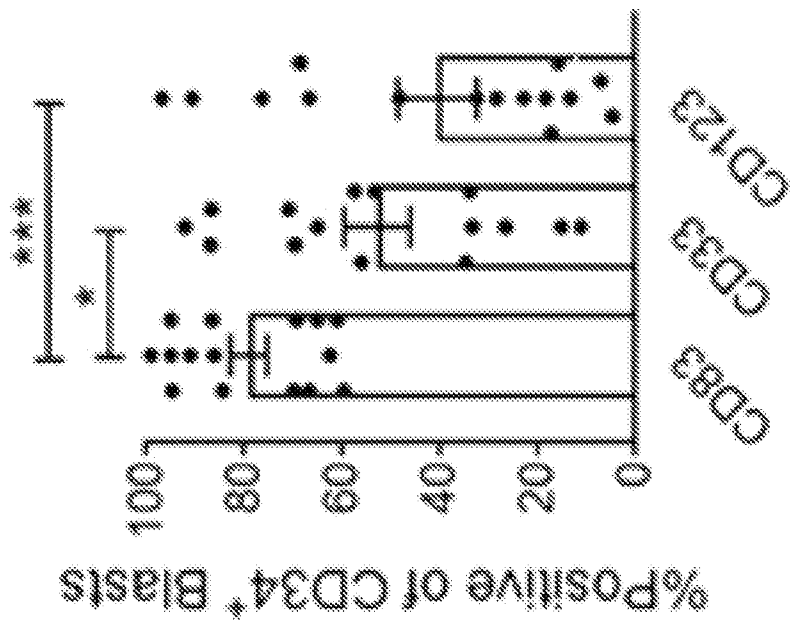
Figure 7C:
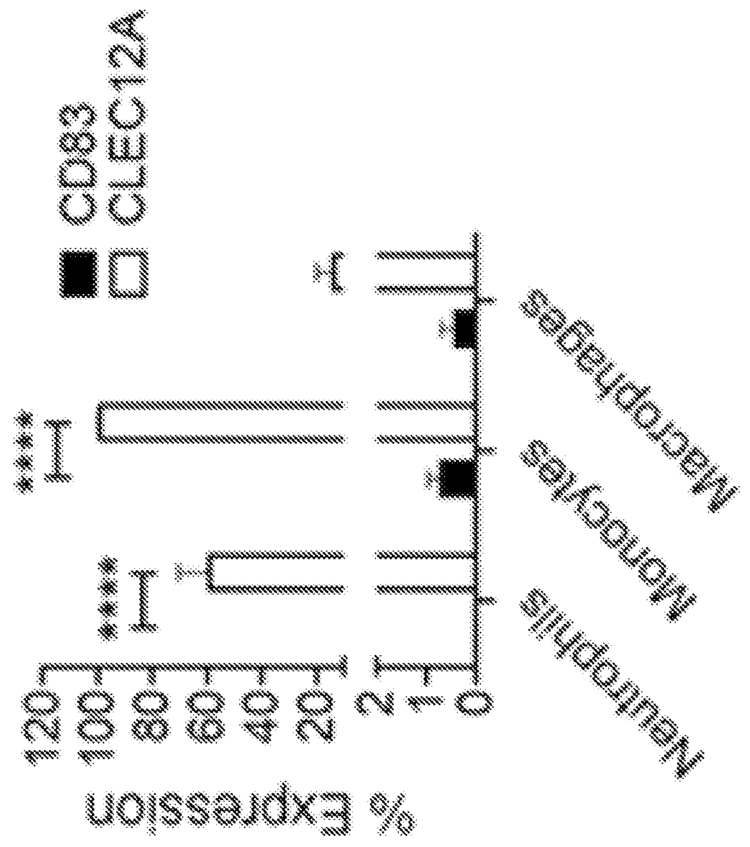
Figure 7D:
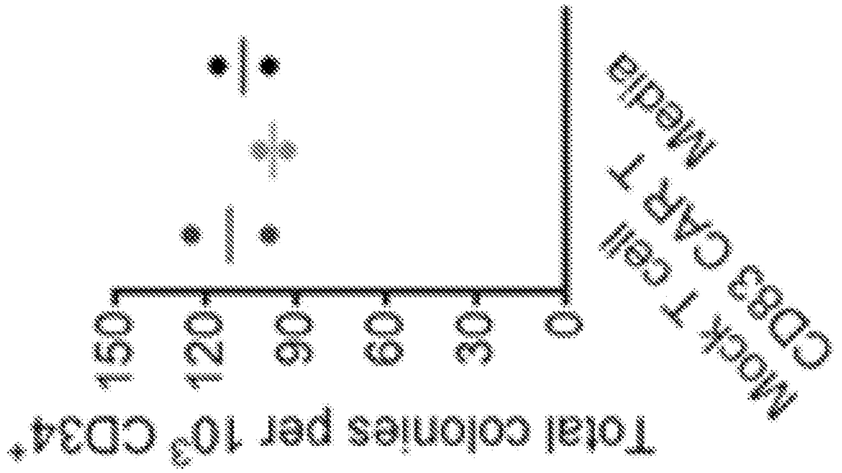

Acute Myeloid Leukemia. A CD83 CAR T construct was created that consists of an anti-CD83 scFv paired to a CD8 hinge and transmembrane domain, followed by an intracellular 41BB co-stimulatory domain and CD3ζ activation domain. This CD83 CAR T can selectively eliminate alloreactive donor T cells that cause graft-versus-host disease (GVHD) after allogeneic hematopoietic cell transplantation (AlloHCT), yet spare healthy T cells and normal immunity. Moreover, CD83 is differentially expressed on acute myeloid leukemia (AML) blasts and that CD83 CAR T potently kills AML (FIG. 7A-7E). Importantly, CD83 CAR T spares normal hematopoiesis, as HSCs and myeloid progenitors [megakaryocyte-erythroid progenitors (MEP), common myeloid progenitors (CMP), and granulocyte-monocyte progenitors (GMP)] in the bone marrow lack CD83 expression (FIG. 7B-7D). Thus, CD83 CAR T can protect patients from two major causes of death after alloHCT, leukemia relapse and GVHD, with minimal risk for myeloid aplasia or prolonged neutropenia.

Figure 8A:
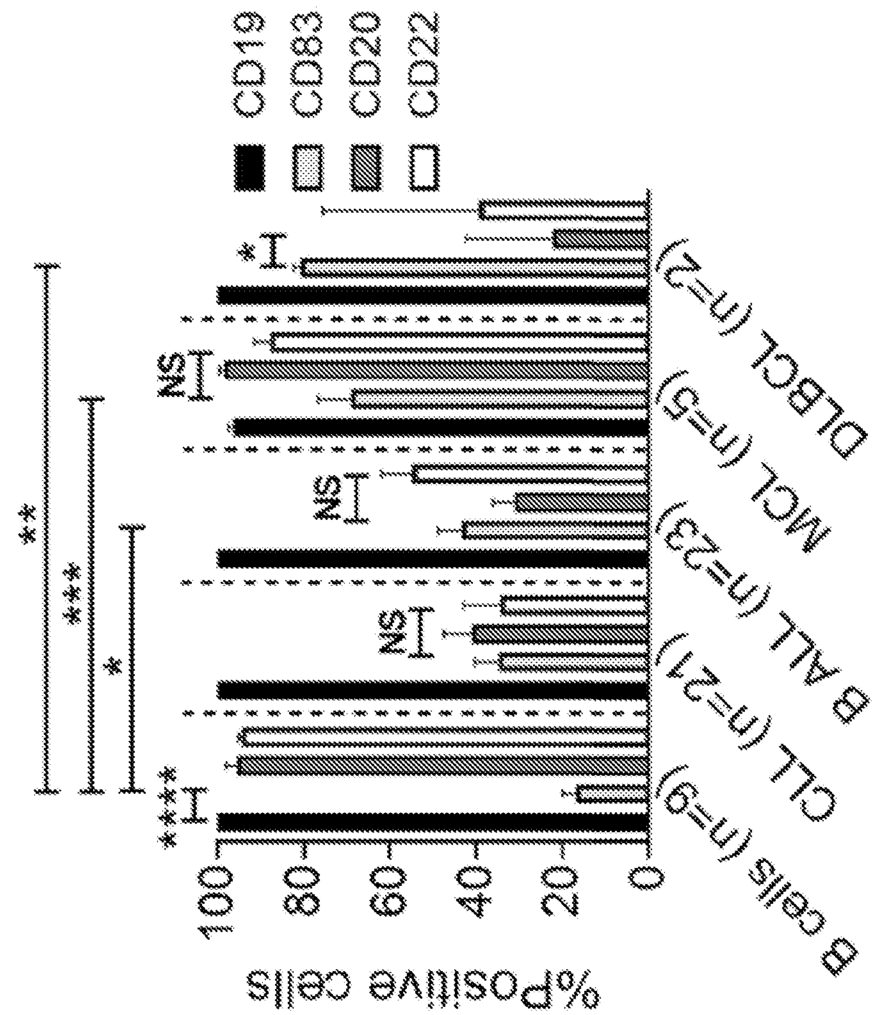
FIGS. 8A to 8D show CD83 is expressed on B cell malignancies and readily killed by CD83 CAR T. CD19, CD83, CD20, and CD22 expression is shown among healthy peripheral B cells (FIG. 8A) versus B cell malignancies Nalm6, Daudi, and Raji cell lines (FIG. 8B).
Figure 8B:
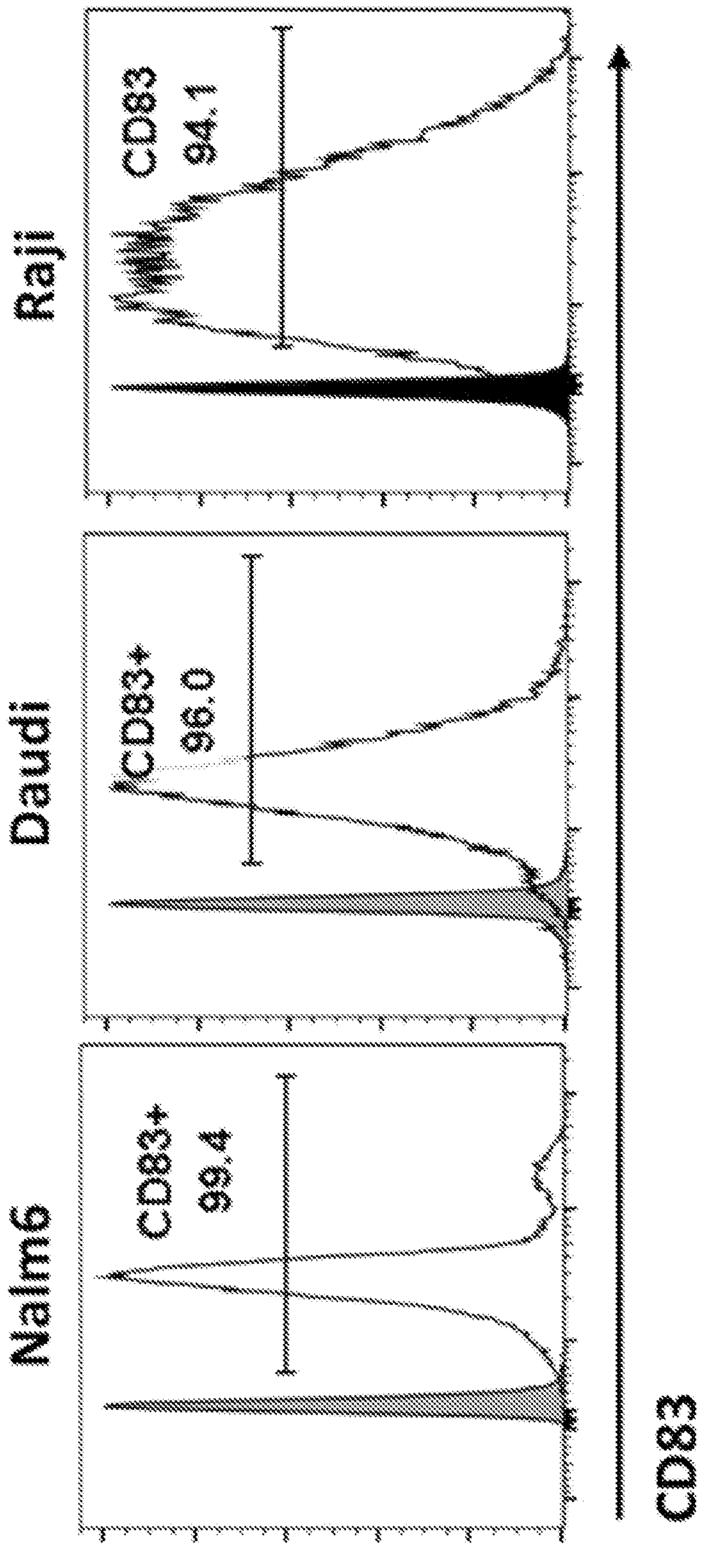
Figure 8C:
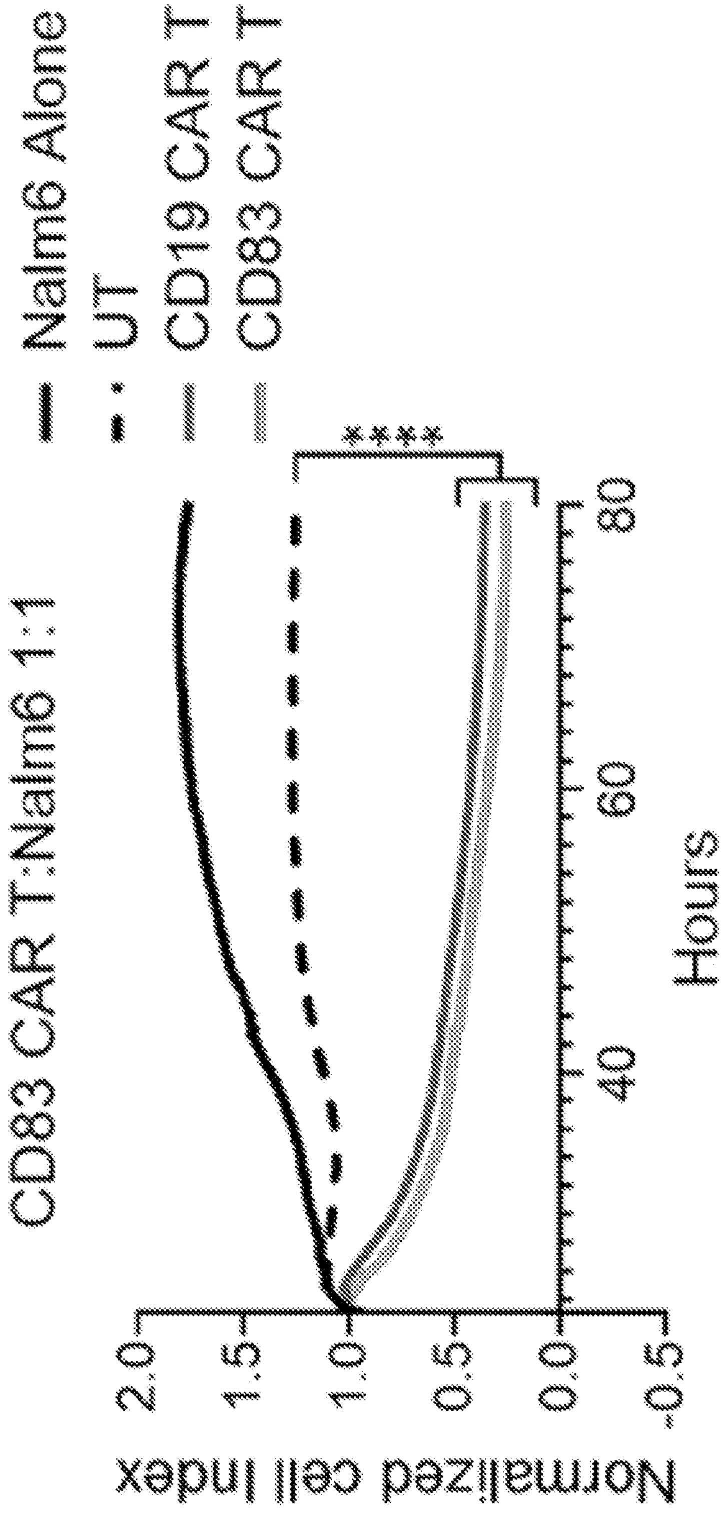
Figure 8D:
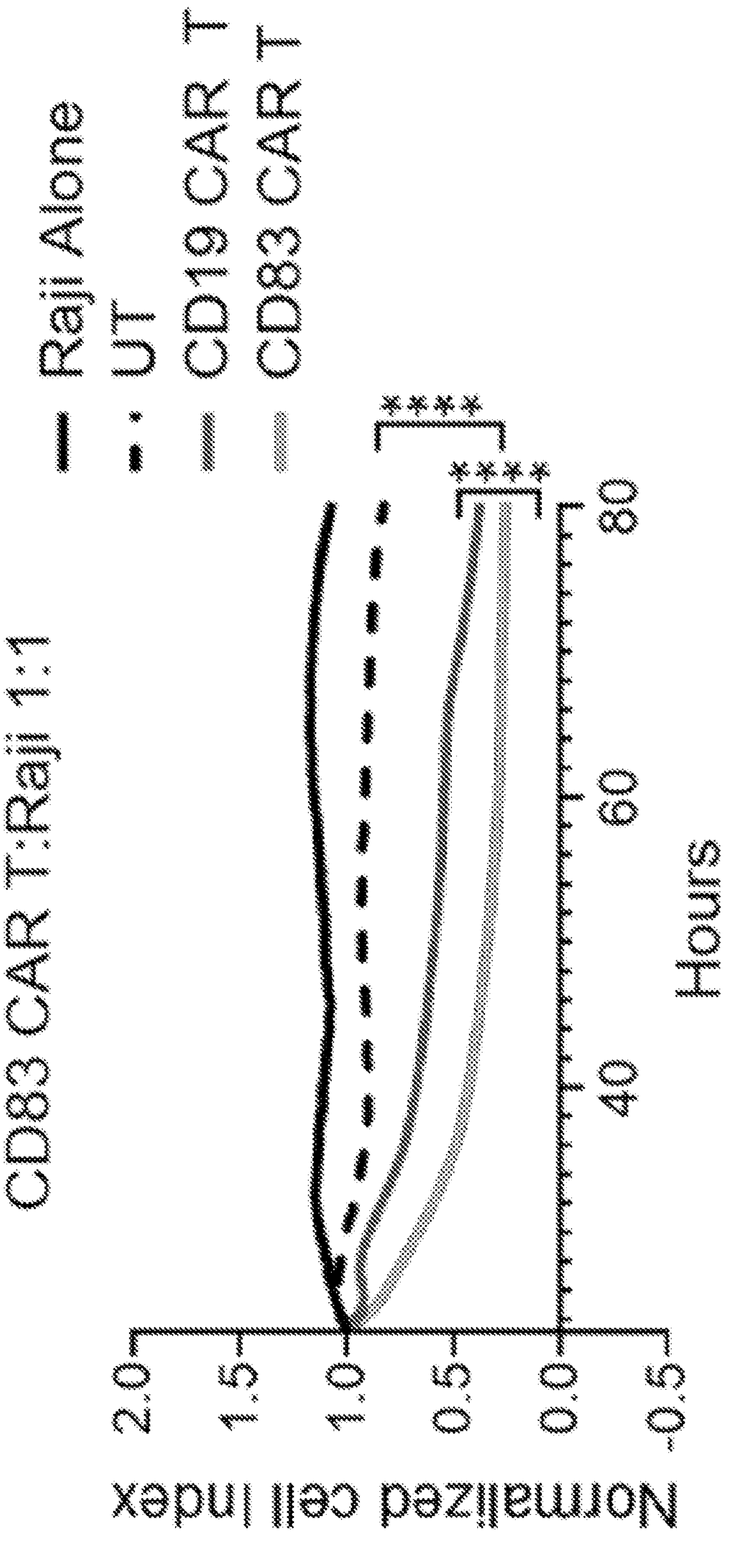

B cell Leukemia and Lymphoma. CD83 is also present on Reed-Sternberg cells in Hodgkin lymphoma. This observation led to an investigation of whether B cell malignancies may express CD83, rendering B cell leukemia and lymphoma sensitive to CD83 CAR T therapy. While CD19 CAR T are indicated for relapsed/refractor DLBCL, B cell ALL, MCL, and FL, the onset of CD19 antigen escape makes such malignancies unresponsive to CD19 CAR T. Thus, identifying novel CAR targets for B cell malignancies, such as CD83, is a critical unmet need for cancer patients who relapse after CD19 CAR T therapy. The disclosed data provides evidence that CD83 is differentially expressed on multiple B cell malignancies compared to exceptionally low expression on circulating healthy B cells (FIG. 8A). Like CD19, CD20 and CD22 also fails to distinguish healthy B cells from lymphoma (FIG. 8A). Further, CD22 is also susceptible to antigen escape. Interestingly, CD83 expression is similar to CD20 or CD22 across several B cell malignancies, despite its low expression on circulating B cells (FIG. 8A). CD83 may outperform CD20 or CD22 in targeting DLBCL (FIG. 8A). In addition to providing a target against B cell malignancies after CD19 antigen escape, targeting CD83 is expected to avoid B cell aplasia seen with CD19 CAR T. CD83 is robustly expressed on Nalm6, Raji, and Daudi B lymphoblast cell lines (FIG. 8B). Additionally, DS (DLBCL) and PF-1 (MCL) cell lines are 97.3% and 90.5% CD83+, respectively. Further, CD83 CAR T significantly kill Nalm6 and Raji cells with potency at least as effective as CD19 CAR T (FIG. 8C,8D), highlighting the relevance of CD83 in targeting B cell malignancies.

Figure 3:
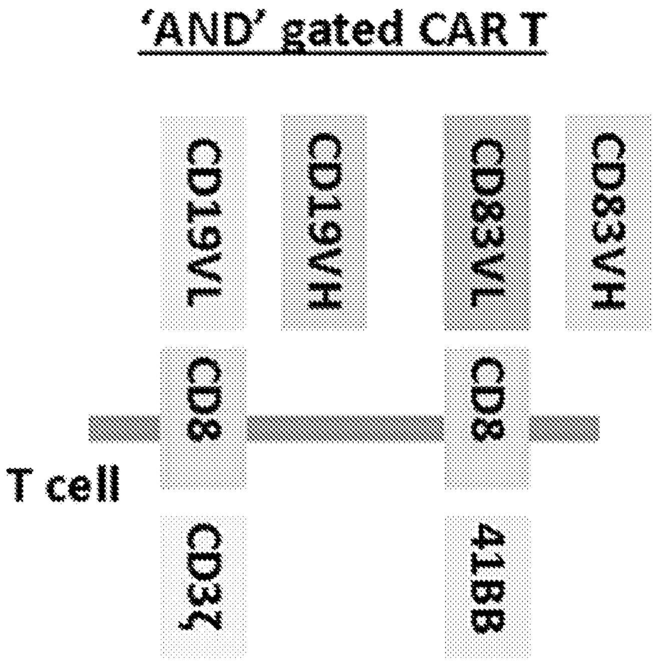
FIG. 3 illustrates an "AND-gated" CAR-T cell.
Figure 4:
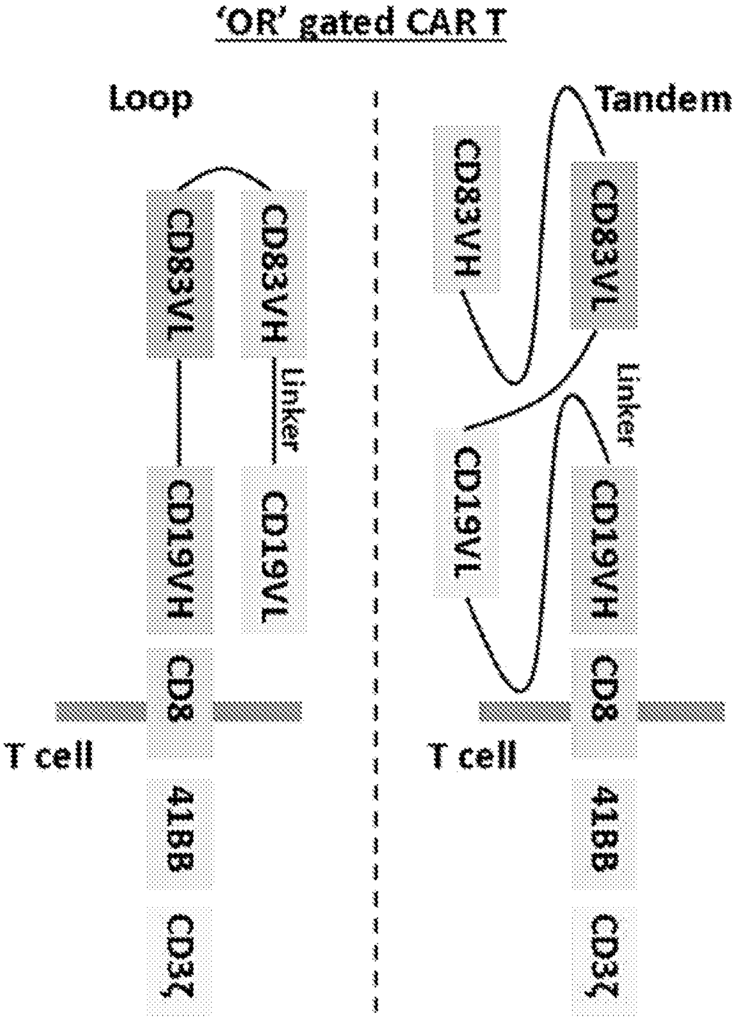
FIG. 4 illustrates an "OR-gated" CAR-T cell.
Figure 5:
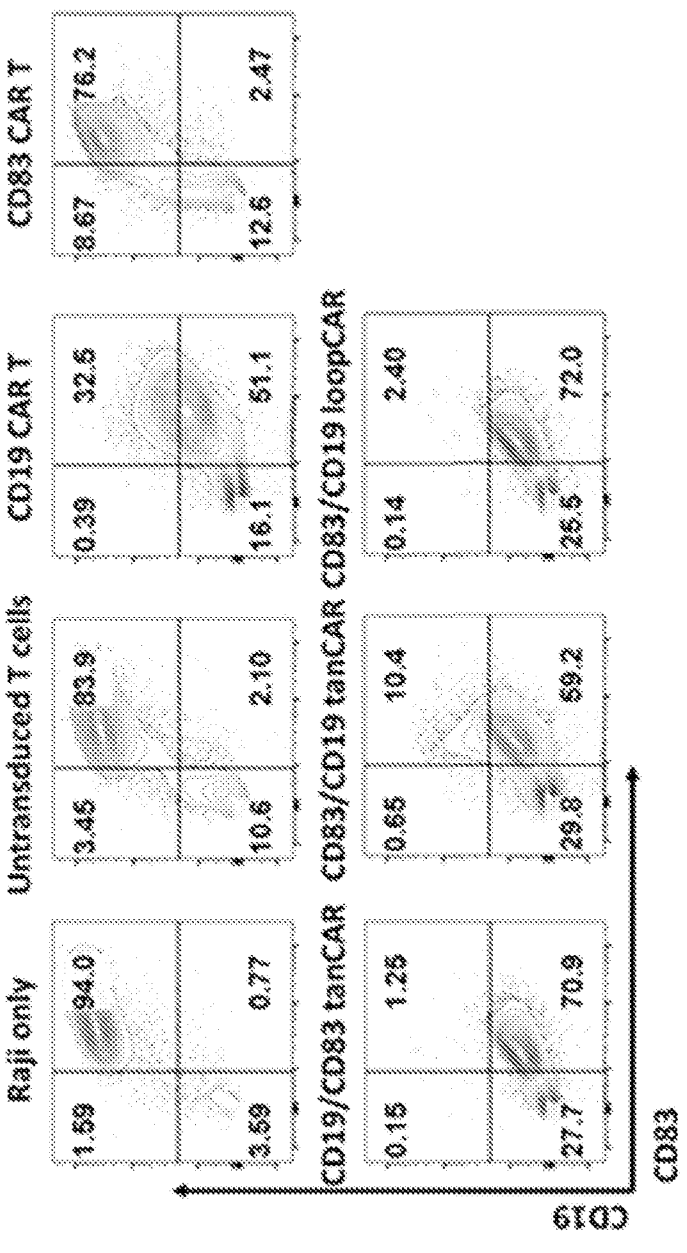
FIG. 5 shows Raji cells (express CD19 and CD83) cultured 1:1 with CAR T as overnight. Expression of CD19 or CD83 was assessed among the surviving Raji cells the following day. Note, the bispecific CARs are 'OR' gated CD19/CD83 CAR T.
Figure 9A:
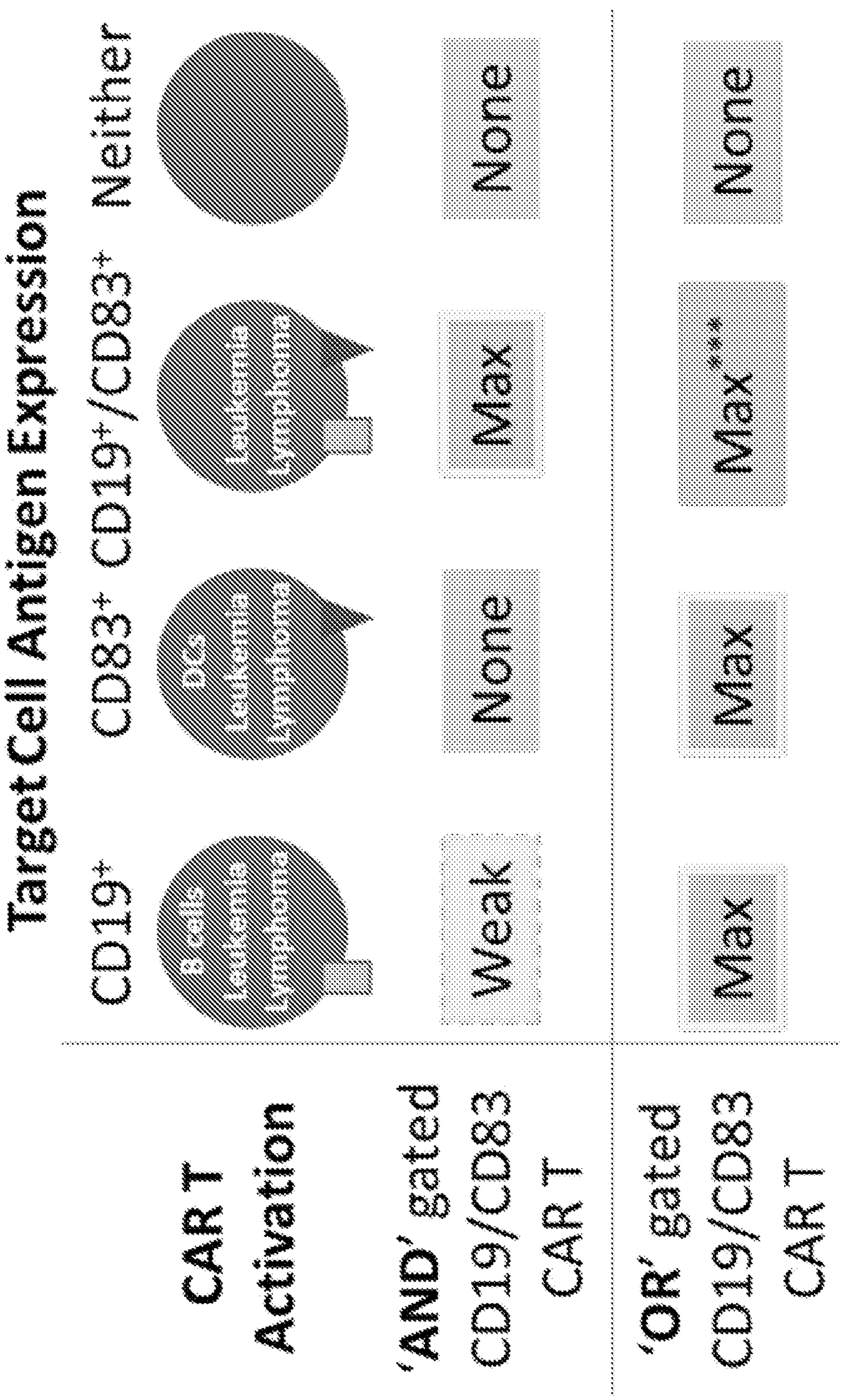
FIGS. 9A to 9C show human anti-CD19/CD83 CAR T design.
Figure 9B:
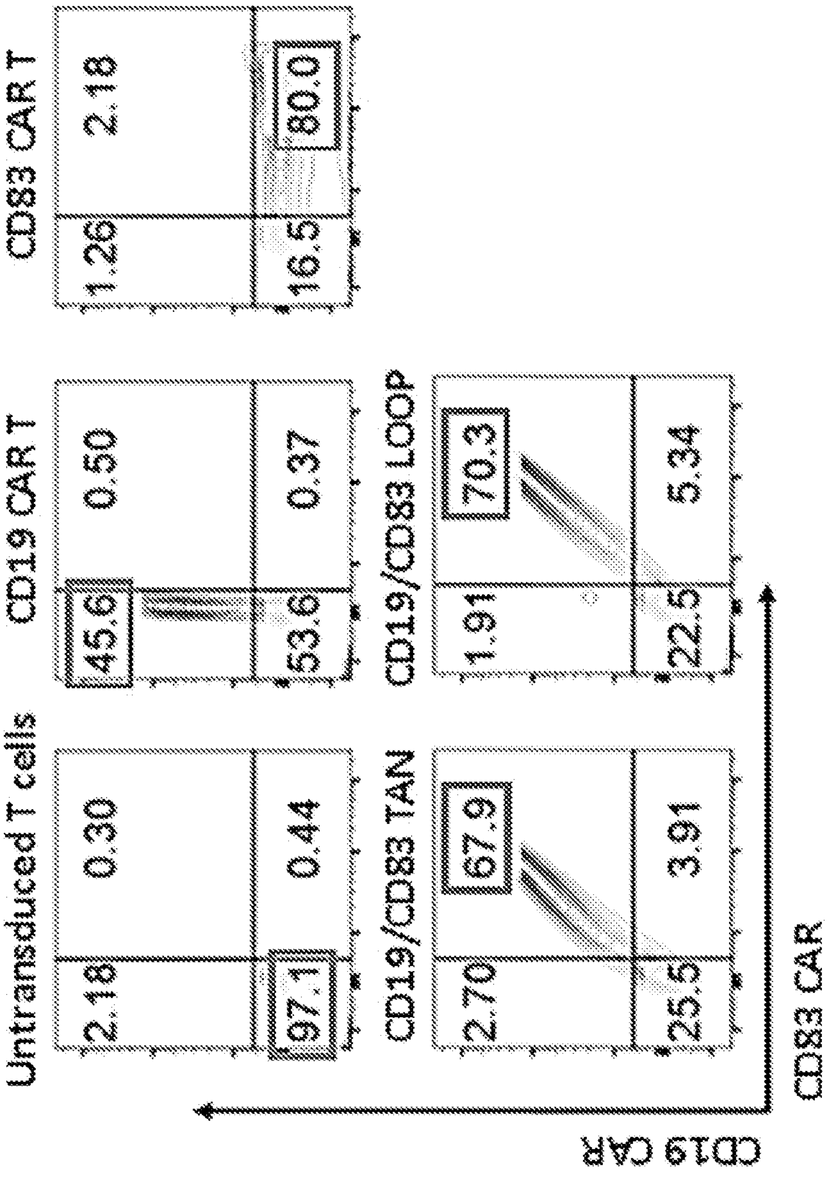
Figure 9C:
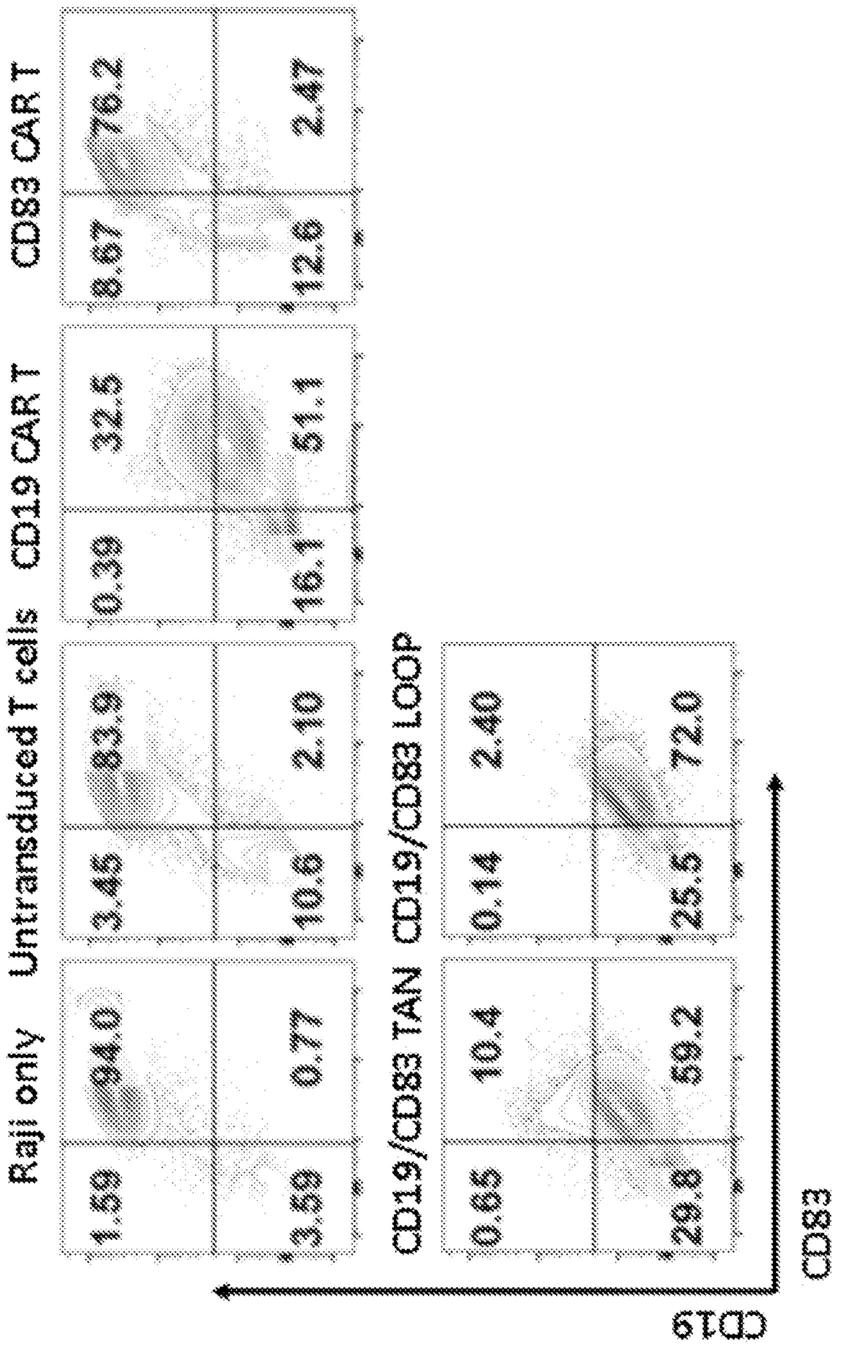

Development of 'AND/OR' logic gated CD19/CD83 CAR T. Rather than testing pooled, mono-gated CAR T, we developed bispecific 'AND/OR' logic gated CD19/CD83 CAR T to balance potency and safety. T cells require several levels of activation for optimal cytolytic function. The 'OR' gated CD19/CD83 CAR T uses a loop or tandem, dual-scFv design, where engagement of either CD19 or CD83 leads to shared CD3ζ and 41BB (signals 1 and 2) T cell activation via a single endodomain (FIG. 9A). Therefore, the 'OR' gated CD19/CD83 CAR T can potently kill target cells that express CD19 or CD83, and may achieve synergistic cytotoxicity if the antigens are co-expressed (FIG. 9A). Alternatively, the 'AND' gated CD19/CD83 CAR T can use a bicistronic construct. Two separate CARs, with unique endodomains, are expressed on the T cell via a single vector. To facilitate 'AND' logic, signal 1 of T cell activation is linked to the CD19 CAR via CD3ζ and signal 2 via 41BB is assigned to the CD83 CAR endodomain (FIG. 3). If the 'AND' gated CD19/CD83 CAR T only engages CD19 alone, very weak T cell activation will be achieved (FIG. 9A). Conversely, nothing will occur if the 'AND' gated CD19/CD83 CAR T engages CD83 alone (FIG. 9A). Only when the 'AND' gated CD19/CD83 CAR T engages target cells expressing both CD19 and CD83 will full cytolytic potency be achieved (FIG. 9A). This strategy limits on-target/off-tumor toxicity by requiring the presence of both antigens to achieve maximum CAR T cell activation. As shown with the CD83 CAR, robust gammaretroviral transduction efficacy of the CD19/CD83 CAR constructs was achieve in human T cells (FIG. 9B). CD19 CAR T leads to antigen loss, while we do not observe this phenomenon when targeting CD83 (FIG. 9C). This supports the concept that targeting CD83 can overcome CD19 antigen loss with CAR T therapy.

Figure 10A:
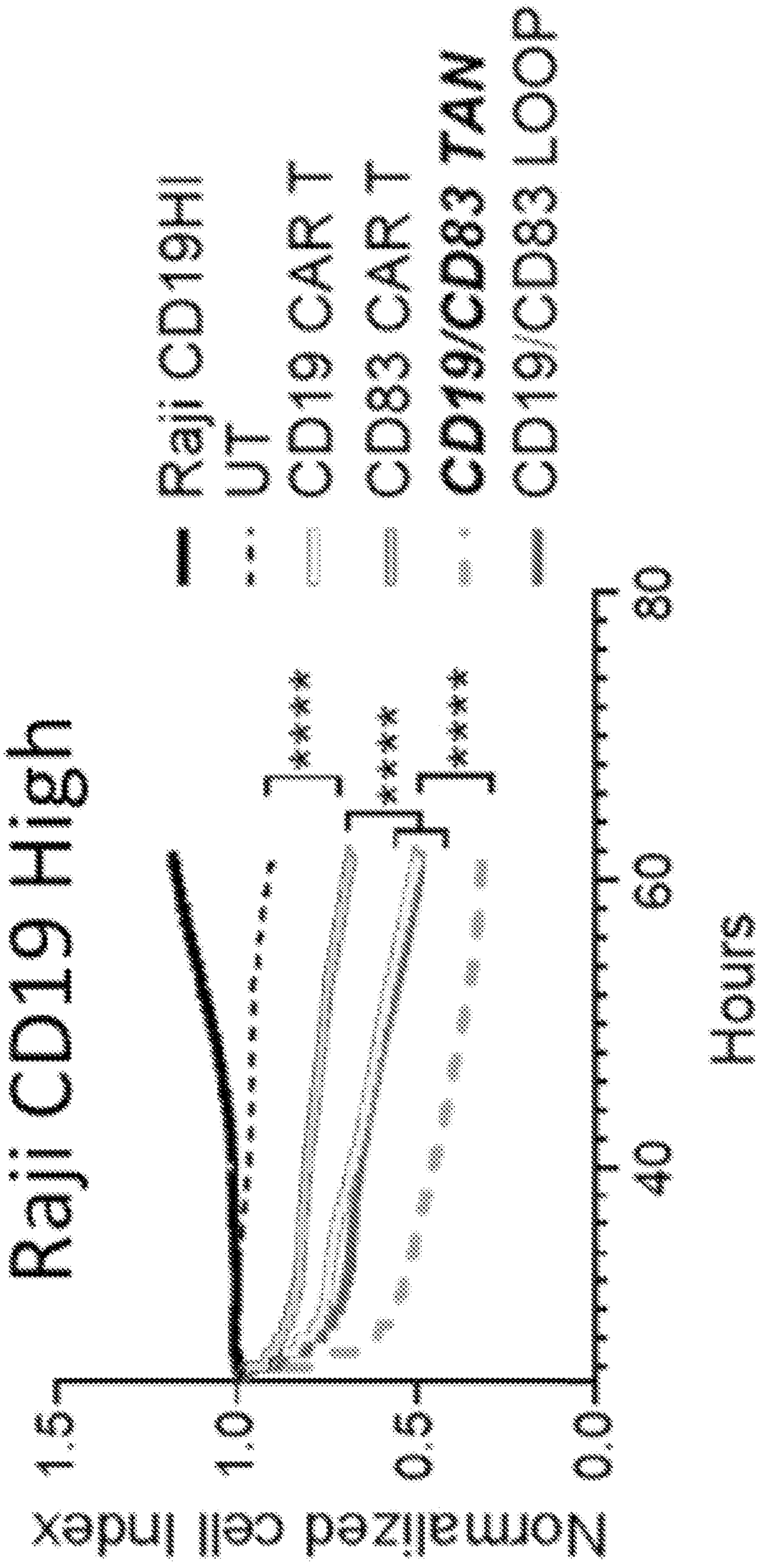
FIGS. 10A to 10H show CD19/CD83 CAR T provide enhanced anti-leukemia potency and overcome CD19 antigen escape.
Figure 10B:
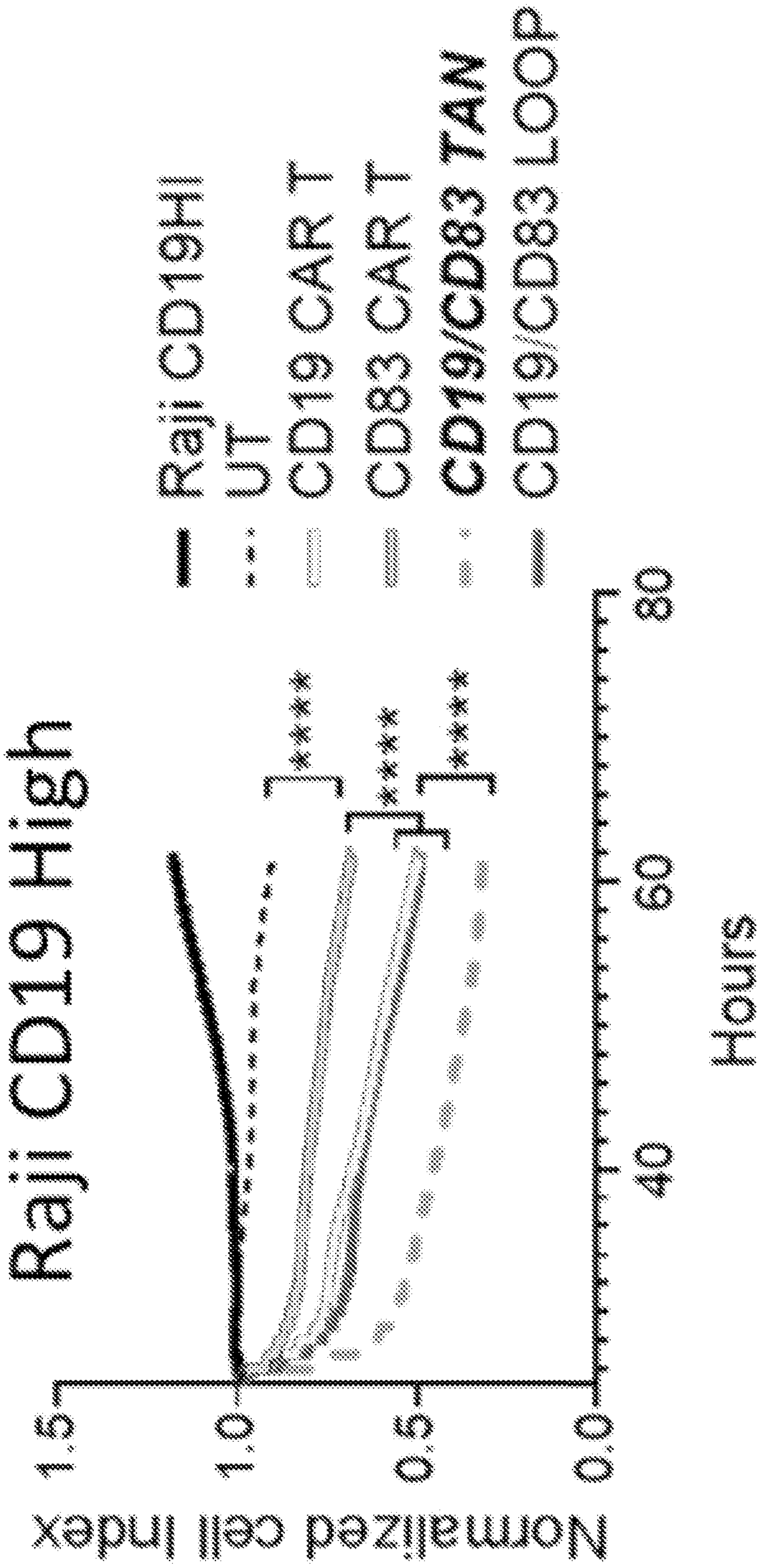
Figures 10C, 10D, 10E:
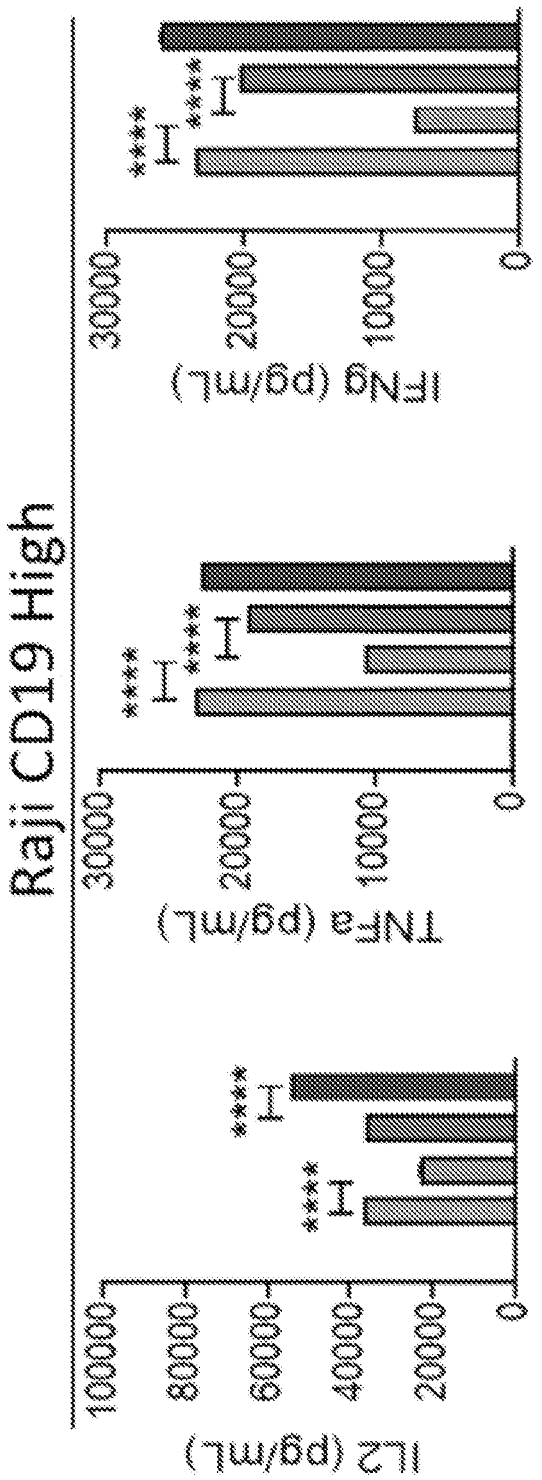
Figures 10F, 10G, 10H:
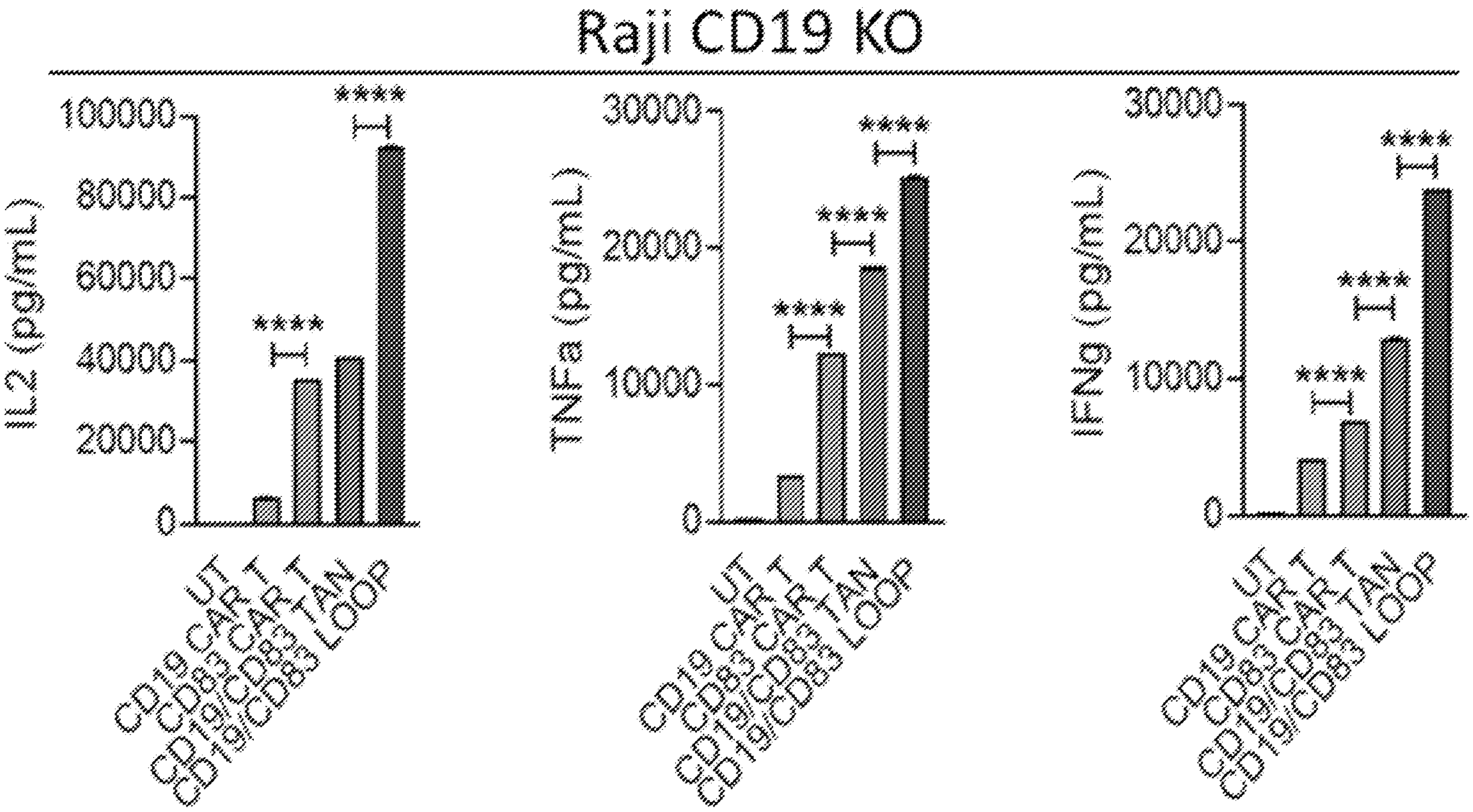

Using a Raji cell line transduced to express high levels of CD19 (MFI 1 log higher than wild type), the CD83 CAR T offers intermediate cytotoxicity compared to the CD19 CAR T (FIG. 10A). This is expected given the increased density of CD19 antigen compared to CD83. As proof-of-concept, the 'OR' gated CD19/CD83 tandem CAR T offers enhanced killing of the Raji CD19HI target cells, compared to CD19 or CD83 CAR T alone (FIG. 10A). The tandem CAR T also outperforms the loop construct (FIG. 10A), even though both constructs use identical anti-CD19 and -CD83 scFvs. This supports the concept that spatial interactions between tandem versus loop CAR constructs and their target antigens may impact resultant CAR T function. Mimicking CD19 antigen loss, CD83 CAR T was shown to significantly kill CD19 knock out Raji cells (~1% CD19+), compared to CD19 CAR T (FIG. 10B). CD19 CAR T also produce significantly less IL-2, TNFα, or IFNγ in response to CD19KO Raji target cells, compared to CD83 CAR T (FIG. 10C-10H). Moreover, the 'OR' gated CD19/CD83 CAR T (loop and tandem constructs) significantly kill Raji targets regardless of CD19 expression (FIG. 10A,10B). Further, the tandem CD19/CD83 CAR T offers enhanced cytolytic potency and cytokine production (e.g., TNFα and IFNγ) against CD19 deficient Raji cells, compared to CD83 CAR T (FIG. 10B-10H). Thus, the tandem bispecific CAR design may provide better activation than the mono-CAR, as both CAR T are targeting CD83 alone against the CD19KO Raji cells. While the loop construct produced more cytokine than the tandem CD19/CD83 CAR T in response to CD19KO targets (FIGS. 10F-10H), the cytolytic activity of the loop design was similar to the tandem against CD19KO Raji cells (FIG. 10B). This further supports the rationale to investigate and compare the tandem versus loop 'OR' gating constructs, the potential impact of spatial interactions between the CARs and their target antigens, and the activation characteristics of the bispecific CAR designs. Importantly, the proof-of-concept data (FIG. 10) support that 'OR' gated CD19/CD83 CAR T can provide enhanced cytolytic activity against lymphoma targets and overcome CD19 antigen escape.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of providing an anti-cancer immunity in a subject with a CD83-expressing B and/or T cell acute lymphoblastic leukemia (ALL), the method comprising administering to the subject an effective amount of an immune effector cell genetically modified to express a first chimeric antigen receptor (CAR) polypeptide that selectively binds CD83 and a second CAR polypeptide that selectively binds CD19, thereby providing an anti-tumor immunity in the mammal, wherein the first CAR polypeptide comprises a CD83 antigen binding domain, a transmembrane domain, an intracellular signaling domain, and a co-stimulatory signaling region, wherein the CD83 antigen binding domain is a single-chain variable fragment (scFv) of an antibody comprising a variable heavy ($V_H$) domain having CDR1, CDR2 and CDR3 sequences and a variable light ($V_L$) domain having CDR1, CDR2 and CDR3 sequences, and wherein the CDR1 sequence of the $V_H$ domain comprises the amino acid sequence GFSITTGGYWWT (SEQ ID NO:1), the CDR2 sequence of the $V_H$ domain comprises the amino acid sequence GYIFSSGNTNYNPSIKS (SEQ ID NO:2), the CDR3 sequence of the $V_H$ domain comprises the amino acid sequence CARAYGKLGFDY (SEQ ID NO:3), the CDR1 sequence of the $V_L$ comprises the amino acid sequence TLSSQHSTYTIG (SEQ ID NO:4), the CDR2 sequence of the $V_L$ domain comprises the amino acid sequence VNSDGSHSKGD (SEQ ID NO: 5), and the CDR3 sequence of the $V_L$ domain comprises the amino acid sequence GSSDSSGYV (SEQ ID NO:6);

wherein the CDR1 sequence of the $V_H$ domain comprises the amino acid sequence SDGIS (SEQ ID NO:7), CDR2 sequence of the $V_H$ domain comprises the amino acid sequence IISSGGNTYYASWAKG (SEQ ID NO:8), CDR3 sequence of the $V_H$ domain comprises the amino acid sequence VVGGTYSI (SEQ ID NO:9), CDR1 sequence of the $V_L$ comprises the amino acid sequence QSSQS VYNNDFLS (SEQ ID NO:10), CDR2 sequence of the $V_L$ domain comprises the amino acid sequence YASTLAS (SEQ ID NO:11), and CDR3 sequence of the $V_L$ domain comprises the amino acid sequence TGTYGNSAWYEDA (SEQ ID NO:12); or wherein the CDR1 sequence of the $V_H$ domain comprises the amino acid sequence SNAMI (SEQ ID NO: 13), CDR2 sequence of the $V_H$ domain comprises the amino acid sequence AMDSNSRTYYATWAKG (SEQ ID NO:14), CDR3 sequence of the $V_H$ domain comprises the amino acid sequence GDGGSSDYTEM (SEQ ID NO: 15), CDR1 sequence of the $V_L$ comprises the amino acid sequence QSSQSVYGNNELS (SEQ ID NO: 16), CDR2 sequence of the $V_L$ domain comprises the amino acid sequence QASSLAS (SEQ ID NO:17), and CDR3 sequence of the $V_L$ domain comprises the amino acid sequence LGEYSISADNH (SEQ ID NO: 18).

2. The method of claim 1, wherein the first CAR polypeptide is defined by the formula:

SP-CD83-HG-TM-SD, and wherein the second CAR polypeptide is defined by the formula:

SP-CDX-HG-TM-CSR; or wherein the first CAR polypeptide is defined by the formula:

SP-CD83-HG-TM-CSR, and wherein the second CAR polypeptide is defined by the formula:

SP-CDX-HG-TM-SD;

wherein "SP" represents an optional signal peptide, wherein "CD83" represents a CD83 antigen binding region, wherein "CDX" represents a CD19 antigen binding region, wherein "HG" represents an optional hinge domain, wherein "TM" represents a transmembrane domain, wherein "CSR" represents one or more co-stimulatory signaling regions, wherein "SD" represents a signaling domain, and wherein "-" represents a peptide bond or linker.

3. The method of claim 1, wherein the anti-CD83 scFv $V_L$ domain comprises the amino acid sequence SEQ ID NO:39, SEQ ID NO:40, SEQ ID NO:41, SEQ ID NO:42, or SEQ ID NO:43.

4. The method of claim 1, wherein the CD19 antigen binding domain is a scFv of an antibody comprising a $V_H$ domain having CDR1, CDR2 and CDR3 sequences and a $V_L$ domain having CDR1, CDR2 and CDR3 sequences, and wherein the CDR1 sequence of the $V_H$ domain comprises the amino acid sequence SYWMN (SEQ ID NO: 72), CDR2 sequence of the $V_H$ domain comprises the amino acid sequence QIWPGDGDTNYNGKFKG (SEQ ID NO:73), CDR3 sequence of the $V_H$ domain comprises the amino acid sequence RETTTVGRYYYAMDY (SEQ ID NO:74), CDR1 sequence of the $V_L$ comprises the amino acid sequence KASQSVDYDGDSYLN (SEQ ID NO:75), CDR2 sequence of the $V_L$ domain comprises the amino acid sequence DASNLVS (SEQ ID NO:76), and CDR3 sequence of the $V_L$ domain comprises the amino acid sequence QQST-EDPWT (SEQ ID NO: 77).

5. The method of claim 1, wherein the immune effector cell is selected from the group consisting of a T cell, a Natural Killer (NK) cell, a cytotoxic T lymphocyte (CTL), and a regulatory T cell.

6. The method of claim 1, further comprising administering to the subject a checkpoint inhibitor.

7. The method of claim 6, wherein the checkpoint inhibitor comprises an anti-PD-1 antibody, anti-PD-L1 antibody, anti-CTLA-4 antibody, or a combination thereof.

8. A chimeric antigen receptor (CAR) polypeptide, comprising a CD83 antigen binding domain, a CD19 antigen binding domain, a transmembrane domain, an intracellular signaling domain, and a co-stimulatory signaling region, wherein the CD83 antigen binding domain is a single-chain variable fragment (scFv) of an antibody comprising a variable heavy (VH) domain having CDR1, CDR2 and CDR3 sequences and a variable light (VL) domain having CDR1, CDR2 and CDR3 sequences, wherein the CDR1 sequence of the VH domain comprises the amino acid sequence GFSITTGGYWWT (SEQ ID NO: 1), the CDR2 sequence of the VH domain comprises the amino acid sequence GYIFSSGNTNYNPSIKS (SEQ ID NO:2), the CDR3 sequence of the VH domain comprises the amino acid sequence CARAYGKLGFDY (SEQ ID NO:3), the CDR1 sequence of the VL comprises the amino acid sequence TLSSQHSTYTIG (SEQ ID NO:4), the CDR2 sequence of the VL domain comprises the amino acid sequence VNSDGSHSKGD (SEQ ID NO: 5), and the CDR3 sequence of the VL domain comprises the amino acid sequence GSSDSSGYV (SEQ ID NO:6);

wherein the CDR1 sequence of the VH domain comprises the amino acid sequence SDGIS (SEQ ID NO:7), CDR2 sequence of the VH domain comprises the amino acid sequence IISSGGNTYYASWAKG (SEQ ID NO:8), CDR3 sequence of the VH domain comprises the amino acid sequence VVGGTYSI (SEQ ID NO:9), CDR1 sequence of the VL comprises the amino acid sequence QSSQS VYNNDFLS (SEQ ID NO:10), CDR2 sequence of the VL domain comprises the amino acid sequence YASTLAS (SEQ ID NO:11), and CDR3 sequence of the VL domain comprises the amino acid sequence TGTYGNSAWYEDA (SEQ ID NO: 12); or wherein the CDR1 sequence of the VH domain comprises the amino acid sequence SNAMI (SEQ ID NO:13), CDR2 sequence of the VH domain comprises the amino acid sequence AMDSNSRTYYATWAKG (SEQ ID NO:14), CDR3 sequence of the VH domain comprises the amino acid sequence GDGGSSDYTEM (SEQ ID NO: 15), CDR1 sequence of the VL comprises the amino acid sequence QSSQSVYGNNELS (SEQ ID NO: 16), CDR2 sequence of the VL domain comprises the amino acid sequence QASSLAS (SEQ ID NO:17), and CDR3 sequence of the VL domain comprises the amino acid sequence LGEYSISADNH (SEQ ID NO: 18).

9. The CAR polypeptide of claim 8, wherein the CD19 antigen binding domain is a scFv of an antibody comprising a VH domain having CDR1, CDR2 and CDR3 sequences and a VL domain having CDR1, CDR2 and CDR3 sequences, and wherein the CDR1 sequence of the VH domain comprises the amino acid sequence SYWMN (SEQ ID NO:72), CDR2 sequence of the VH domain comprises the amino acid sequence QIWPGDGDTNYNGKFKG (SEQ ID NO:73), CDR3 sequence of the VH domain comprises the amino acid sequence RETTTVGRYYYAMDY (SEQ ID NO:74), CDR1 sequence of the VL comprises the amino acid sequence KASQSVDYDGDSYLN (SEQ ID NO:75), CDR2 sequence of the VL domain comprises the amino acid sequence DASNLVS (SEQ ID NO:76), and CDR3 sequence of the VL domain comprises the amino acid sequence QQSTEDPWT (SEQ ID NO: 77).

10. The CAR polypeptide of claim 8, wherein the CAR polypeptide has a loop configuration defined by the formula:

SP-CD19VL-CD83VH-CD83VL-CD19VH-HG-TM-SD,

SP-CD19VL-CD83VL-CD83VH-CD19VH-HG-TM-SD,

SP-CD19VH-CD83VH-CD83VL-CD19VL-HG-TM-SD,

SP-CD19VH-CD83VL-CD83VH-CD19VL-HG-TM-SD,

SP-CD83VL-CD19VH-CD19VL-CD83VH-HG-TM-SD

SP-CD83VL-CD19VL-CD19VH-CD83VH-HG-TM-SD,

SP-CD83VH-CD19VH-CD19VL-CD83VL-HG-TM-SD, or

SP-CD83VH-CD19VL-CD19VH-CD83VL-HG-TM-SD, wherein "SP" represents an optional signal peptide,
wherein "CD83VH" represents a CD83 VH domain,
wherein "CD83VL" represents a CD83 VL domain,
wherein "CD19VH" represents a CD83 VH domain,
wherein "CD19VL" represents a CD83 VL domain,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

11. The CAR polypeptide of claim 8, wherein the CAR polypeptide has a tandem configuration defined by the formula:

SP-CD19VH-CD19VL-CD83VL-CD83VH-HG-TM-SD,

SP-CD19VH-CD19VL-CD83VH-CD83VL-HG-TM-SD,

SP-CD19VL-CD19VH-CD83VL-CD83VH-HG-TM-SD,

SP-CD19VL-CD19VH-CD83VH-CD83VL-HG-TM-SD,

SP-CD83VH-CD83VL-CD19VL-CD19VH-HG-TM-SD,

SP-CD83VH-CD83VL-CD19VH-CD19VL-HG-TM-SD,

SP-CD83VL-CD83VH-CD19VL-CD19VH-HG-TM-SD, or

SP-CD83VL-CD83VH-CD19VH-CD19VL-HG-TM-SD, wherein "SP" represents an optional signal peptide,
wherein "CD83VH" represents a CD83 VH domain,
wherein "CD83VL" represents a CD83 VL domain,
wherein "CD19VH" represents a CD83 VH domain,
wherein "CD19VL" represents a CD83 VL domain,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

12. A method of providing an anti-cancer immunity in a subject with a CD83-expressing cancer, the method comprising administering to the subject an effective amount of an immune effector cell genetically modified to express the CAR polypeptide of claim 8, thereby providing an anti-tumor immunity in the mammal.

13. The method of claim 12, wherein the immune effector cell is selected from the group consisting of a T cell, a Natural Killer (NK) cell, a cytotoxic T lymphocyte (CTL), and a regulatory T cell.

14. The method of claim 12, further comprising administering to the subject a checkpoint inhibitor.

15. The method of claim 14, wherein the checkpoint inhibitor comprises an anti-PD-1 antibody, anti-PD-L1 antibody, anti-CTLA-4 antibody, or a combination thereof.

16. The method of claim 12, wherein the cancer comprises a CD19+/CD83+ Diffuse Large B cell Lymphoma (DLBCL), a Follicular Lymphoma (FL), a Marginal Zone Lymphoma (MZL), a Chronic lymphocytic leukemia/Small lymphocytic lymphoma (CLL/SLL) a BCMA+/CD83+ or CD38+/CD83+ Multiple myeloma (MM), a CD7+/CD83+ or CD5+/CD83+ Peripheral T cell lymphoma (PTCL), a Cutaneous T cell lymphoma (CTCL), a Burkitt Lymphoma, a T cell lymphoma, or a CD30+/CD83+ non-Hodgkin lymphoma.

17. The method of claim 12, wherein the cancer comprises B and/or T cell acute lymphoblastic leukemia (ALL).

* * * * *